United States Patent
Liu et al.

(10) Patent No.: US 10,682,371 B2
(45) Date of Patent: Jun. 16, 2020

(54) SMALL MOLECULE CONJUGATES SPECIFICALLY ACTIVATED IN TUMOR MICROENVIRONMENT FOR TARGETING AND USE THEREOF

(71) Applicant: Yafei Shanghai Biolog Medicine Science & Technology Co. Ltd., Pudong, Shanghai (CN)

(72) Inventors: Chen Liu, Shanghai (CN); Yuan Liu, Shanghai (CN)

(73) Assignee: YAFEI SHANGHAI BIOLOG MEDICINE SCIENCE & TECHNOLOGY CO. LTD., Shanghai (CN)

( * ) Notice: Subject to any disclaimer, the term of this patent is extended or adjusted under 35 U.S.C. 154(b) by 0 days.

(21) Appl. No.: 15/505,861

(22) PCT Filed: Aug. 21, 2015

(86) PCT No.: PCT/CN2015/087746
§ 371 (c)(1),
(2) Date: Feb. 22, 2017

(87) PCT Pub. No.: WO2016/026458
PCT Pub. Date: Feb. 25, 2016

(65) Prior Publication Data
US 2017/0266308 A1  Sep. 21, 2017

(30) Foreign Application Priority Data

| Aug. 22, 2014 | (CN) | 2014 1 0415968 |
| Aug. 22, 2014 | (CN) | 2014 1 0415969 |
| Aug. 22, 2014 | (CN) | 2014 1 0415970 |
| Aug. 22, 2014 | (CN) | 2014 1 0417882 |
| Aug. 22, 2014 | (CN) | 2014 1 0417885 |
| Aug. 22, 2014 | (CN) | 2014 1 0417919 |

(51) Int. Cl.
| A61K 31/7072 | (2006.01) |
| A61K 47/65 | (2017.01) |
| A61K 47/54 | (2017.01) |
| A61K 31/7076 | (2006.01) |
| A61K 31/4745 | (2006.01) |
| A61K 31/7068 | (2006.01) |
| A61K 31/337 | (2006.01) |
| A61P 35/00 | (2006.01) |
| A61K 31/136 | (2006.01) |
| A61K 31/198 | (2006.01) |
| A61K 31/427 | (2006.01) |
(Continued)

(52) U.S. Cl.
CPC ........ *A61K 31/7076* (2013.01); *A61K 31/136* (2013.01); *A61K 31/198* (2013.01); *A61K 31/337* (2013.01); *A61K 31/427* (2013.01); *A61K 31/475* (2013.01); *A61K 31/4745* (2013.01); *A61K 31/505* (2013.01); *A61K 31/519* (2013.01); *A61K 31/704* (2013.01); *A61K 31/7048* (2013.01); *A61K 31/7068* (2013.01); *A61K 31/7072* (2013.01); *A61K 47/54* (2017.08); *A61K 47/65* (2017.08); *A61P 35/00* (2018.01)

(58) Field of Classification Search
CPC .... A61K 47/65; A61K 47/64; A61K 31/7076; A61K 47/54
See application file for complete search history.

(56) References Cited

U.S. PATENT DOCUMENTS 6,251,382 B1 * 6/2001 Greenwald ............ A61K 47/60
424/486
2009/0175873 A1   7/2009 Liu
(Continued)

FOREIGN PATENT DOCUMENTS

| CN | 1040593 A | 3/1990 |
| CN | 1712399 A | 12/2005 |
(Continued)

OTHER PUBLICATIONS

Li et al., Process Biochemistry, 2007, 42, 1625-1631. (Year: 2007).*
(Continued)

*Primary Examiner* — James H Alstrum-Acevedo
*Assistant Examiner* — Kaipeen E Yang
(74) *Attorney, Agent, or Firm* — Knobbe, Martens, Olson & Bear LLP

(57) ABSTRACT

Provided is an anticancer compound including a cleavable linker specifically activated in a tumor microenvironment, and use thereof. The anticancer compound is represented by the following formula, wherein, $R_1$ is a normal functional group or a protection group; $R_2$ is Ala, Thr, Val or Ile; $R_3$ is Ala, Val or Asn; $R_4$ is a drug group linked via a hydroxyl group or an amino group; and the general formula of the drug is $R_4H$. The anticancer compound is only activated at a local portion of a tumor, thus avoiding the defect of immune system damage of a traditional chemotherapeutic drug, and promoting tumor immunization by removing a tumor immunosuppression cell. The anticancer compound or pharmaceutical composition thereof is jointly used with immunotherapy, thus improving the effect of treating the tumor, and effectively inhibiting tumor metastasis and osseous metastasis.

(II)

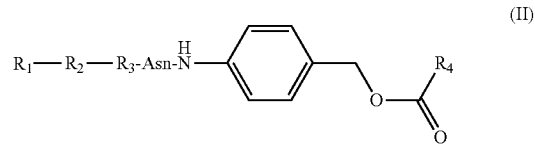

15 Claims, 4 Drawing Sheets

(51) Int. Cl.
- A61K 31/475 (2006.01)
- A61K 31/505 (2006.01)
- A61K 31/519 (2006.01)
- A61K 31/704 (2006.01)
- A61K 31/7048 (2006.01)

(56) References Cited

U.S. PATENT DOCUMENTS

| | | | |
|---|---|---|---|
| 2013/0129753 | A1 | 5/2013 | Doroski |
| 2015/0343083 | A1 | 12/2015 | Chu |

FOREIGN PATENT DOCUMENTS

| | | |
|---|---|---|
| CN | 1781932 A | 6/2006 |
| CN | 101374856 A | 2/2009 |
| CN | 101855237 A | 10/2010 |
| CN | 101935336 A | 1/2011 |
| CN | 102725001 A | 10/2012 |
| CN | 102725278 A | 10/2012 |
| CN | 103044521 A | 4/2013 |
| CN | 103945856 A | 7/2014 |
| CN | 104147612 A | 11/2014 |
| CN | 104177474 A | 12/2014 |
| CN | 104231045 A | 12/2014 |
| CN | 104231047 A | 12/2014 |
| CN | 104262455 A | 1/2015 |
| CN | 104262457 A | 1/2015 |
| WO | WO 2004111192 A2 | 12/2004 |
| WO | WO 2007/064759 A2 | 6/2007 |

OTHER PUBLICATIONS

Kumar, S.K., et al., Modulating Paclitaxel Bioavailability for Targeting Prostate Cancer, Bioorganic & Medicinal Chemistry 15(14):4973-4984, Apr. 25, 2007.

Supplementary European Search Report issued in connection with European Patent Application No. 15833275.9 dated Feb. 16, 2018.

Bajjuri, K.M., et al., The Legumain Protease-Activated Auristatin Prodrugs Suppress Tumor Growth and Metastasis Without Toxicity, CHEMMMEDCHEM 6:54-59, Dec. 10, 2010.

International Search Report received in corresponding PCT/CN2015/087746.

Stern., L., et al., A Novel Antitumor Prodrug Platform Designed to Be Cleaved by the Endoprotease Legumain, Bioconjugate Chem 20(3):500-510, May 2, 2009.

Wu, W., et al., Targeting Cell-Impermeable Prodrug Activation to Tumor Microenvironment Eradicates Multiple Drug-Resistant Neoplasms, Cancer Research 66(2):970-980, Jan. 15, 2006.

Dubowchik, G., Cathepsin B-Sensitive Dipentide Prodrugs, Models Anticancer Paclitaxel (taoIR), Mitoucin C and Doxorubicin, Biooranic Medicinal Chemistry Letters 8:3347-3352, Dec. 31, 1998.

He, M., et al., A New Facile Synthesis Method of Branched PEG, Chemical Journal of Chinese Universities 24(8):1495-1498, Sep. 15, 2003.

Jin, W., Synthesis of Polyethylene Glycol Derivatives and Their Chemical Modification to Trypsin, China Master's Theses, Full-Text Database, Engineering Technology I Series, Nov. 15, 2005, 61 pages.

Liu, X., et al., Research Progress of Polyethylene Glycol Modified Small Molecule Drugs, Chinese Journal of Pharmacology and Toxicology, Oct. 31, 2010, pp. 380-386.

Search Report received in connection with corresponding Chinese Patent Application No. 201410415968.0 dated Mar. 14, 2016.

Search Report received in connection with corresponding Chinese Patent Application No. 201410415969.5 dated Mar. 27, 2016.

Search Report received in connection with corresponding Chinese Patent Application No. 201410415970.8 dated Jun. 10, 2016.

Search Report received in connection with corresponding Chinese Patent Application No. 201410417882.1 dated Mar. 1, 2017.

Search Report received in connection with corresponding Chinese Patent Application No. 201410417885.5 dated Sep. 21, 2016.

Search Report received in connection with corresponding Chinese Patent Application No. 201410417919.0 dated May 5, 2016.

Wu Jin, Synthesis of Polyethylene Glycol Derivatives and Their Chemical Modification to Trypsin, Nov. 15, 2015.

* cited by examiner

SMALL MOLECULE CONJUGATES SPECIFICALLY ACTIVATED IN TUMOR MICROENVIRONMENT FOR TARGETING AND USE THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure belongs to a field of pharmaceutical chemistry, relating to an anti-tumor drug compound. Specifically, the present disclosure relates to a cleavable linker specifically activated in tumor microenvironment, an anti-tumor compound comprising a conjugate and use thereof.

TECHNICAL BACKGROUND

Conventional cytotoxic chemotherapy drugs have great toxicity to human normal cells and immune system. For example, Docetaxel and Paclitaxel are effective anti-tumor agents widely used at present. They are mainly used in various solid tumors, such as ovarian cancer and breast cancer, and have a certain efficacy against lung cancer, intestinal cancer, melanoma, head and neck cancer, lymphoma and cerebroma. Clinically, these two compounds have serious toxicity, such as arrest of bone marrow, and allergic reaction, and thus their doses have been restricted. Docetaxel exhibits bone marrow toxicity, resulting in reduction in neutrophilic granulocytes, and neurotoxicity and cardiovascular toxicity. Docetaxel can induce an allergic reaction, and a local inflammation, alopecia, hypodynamia, or even liver toxicity if it overflows the blood vessel. Mitomycin is another effective antitumor agent widely used at present. It is mainly used in various solid tumors, such as stomach cancer, colon cancer, liver cancer, pancreatic cancer, non-small cell lung cancer, breast cancer, and malignant ascitic fluid. However, clinically, mitomycin exhibits a serious toxicity and adverse reaction, its dose thus is restricted. Mitomycin can induce a bone marrow toxicity, resulting in reduction in leucocytes and platelets. It can also induce phlebitis, and tissue necrosis, alopecia, hypodynamia and hepatorenal damage if it overflows the blood vessel.

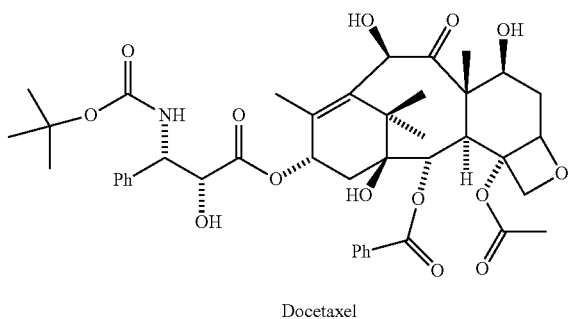

Docetaxel

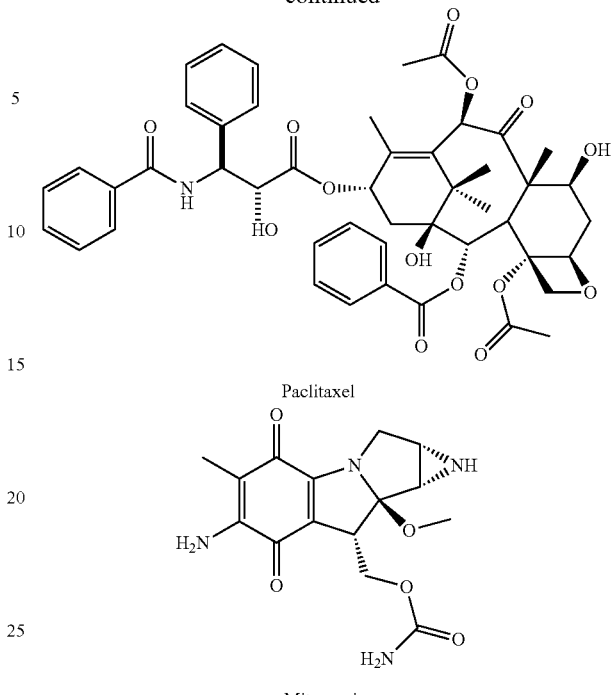

In the tumor microenvironment, the tumor cells express and secrete a great amount of asparagine endopeptidases. Expression of asparagine endopeptidase can distinguish the tumor-associated macrophage (M2 type) from the mononuclear cell and the inflammatory macrophage (M1 type). The cytokines secreted by tumor induce the mononuclear cells to transform to tumor-associated macrophages. The tumor-associated macrophages can stimulate and produce strong immunosuppression and directly help infiltration and metastasis of tumor cells. Meanwhile, a great amount of proteolytic enzymes are produced during metastasis of tumor cells to degrade intercellular matrix. Thus, new compounds can be chemically synthesized and screened based on biochemistry and pharmacological detection and screening to find a chemical conjugate that is able to be activated by asparagine endopeptidase and conjugated to drug via a secondary activated linker. The conjugate can link different groups for solubility or modification as needed to drugs for chemotherapy having specific cytotoxicity, thus producing new drugs having new functions, such as new targeting, activation, stability, solubility, metabolism, toxicity and efficacy, etc.

SUMMARY OF INVENTION

In order to develop antitumor drugs, the present disclosure creates a cleavable linker having changeable properties, such as activation by targetedly conjugating and treatment by dissolution, and provides compounds containing a cleavable linker, as shown in formulae (I) and (II). Use of the cleavable linker of the present disclosure, which can be specially activated in a tumor microenvironment, can effectively block the toxicity of the linked drug $R_4$. Then the compounds are targetedly activated by an asparagine endopeptidase in the tumor microenvironment and the 4-aminobenzyl-OC(O)— is self-released, allowing the final drugs the bring about new targeting, activation and metabolism properties.

Specifically, in the compounds containing a cleavable linker, the cleavable linker is the modified tripeptide in the brackets, —$R_2$-$R_3$-Asn-4-aminobenzyl-OC(O)—. $R_1$ and R₄ link together through the cleavable linker, wherein R₁ links to the cleavable linker through an amide bond formed by its carbonyl, and R₄ links to the cleavable linker through carbonic acid ester bond formed by its oxygen atom with the cleavable linker or through carbamate formed by its nitrogen atom with the cleavable linker:

R₁{-R₂-R₃-Asn-4-amino benzyl-OC(O)—}R₄  (I),

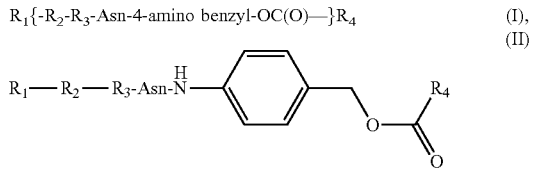

(II)

wherein
R₁ is a functional group for increasing solubility or a protective group;
R₂ is an amino acid moiety selected from the group consisting of Ala, Thr, Val and Ile, R₂ forms an amide bond with R₁ through a carbonyl group of;
R₃ is an amino acid moiety selected from the group consisting of Ala, Thr, Val and Asn;
R₂ links to R₃ through an amide bond, R₃ links to Asn through an amide bond, and Asn links to —NH— through its carbonyl;
R₄ is a drug group linking to the cleavable linker through carbonic acid ester bond or carbamate formed by its hydroxyl or amino;
the compounds containing the cleavable linker can be cleavable by contact with an asparagine endopeptidase and then is separated from R₁; and
breakage of the compound containing the cleavable linker by contact with an asparagine endopeptidase causes further cleavage of the carbonic acid ester bond or carbamate formed with R₄, resulting in that R₄ is separated from the cleavable group.

In the present disclosure, compounds containing activatable conjugates were synthesized, the compounds (formula (I),(II)) containing a cleavable linker have the following structure-efficacy relationship of structure and activation:

(1) The activatable conjugates can react with hydroxyl or amino group having proper activation grade in the toxic function related key part of R₄ via group conversion, and couple to form drugs with new structure. The resultant compounds have different activation efficiencies by asparagine endopeptidase due to their different steric hindrances. This is because the enzyme active center of asparagine endopeptidase locates at the bottom of its globular depression. The cleavage site needs to approach the active center. Thus, the polarity of the linking site becomes important as it will determine whether a steric hindrance to the cleavage site is produced by the linked compound. The extension and secondary breakage of 4-amino benzyl —OC(O)— arm effectively reduce the steric hindrance from some drugs. However, in the present disclosure S6, S20 and some unpublished compounds cannot be activated because of steric hindrance. Although they are synthesized, they cannot form functional compounds containing a cleavable linker (2) Through specific activation by asparagine endopeptidase specially expressed by tumor cells or tumor associated macrophages, the compounds containing the cleavable linker are locally activated in the tumor and thus have a targeted cytotoxicity. The drugs which could not be activated due to steric hindrance are not toxic or have low toxicity to the cells, and they cannot form anti-tumor drugs. (3) Cytotoxicity of drugs decreases greatly after connecting the conjugate, because the conjugate reacts with hydroxyl or amino group of drugs, and the active hydroxyl or amino groups on cell surface are usually key groups for drug cytotoxicity. (4) The compounds containing the cleavable linker are stable in non-tumorous environment, such as in blood, normal organs, immune system and in neutral pH, and have no toxic or low toxicity. (5) The asparagine endopeptidase cleaves the conjugate at the Asn site. According to the analysis on the metabolites, only breakage can initiate the activation between 4-amino benzyl —OC(O)— and R₄, and thus assisting the cascade activation. (6) As a linking arm, 4-amino benzyl —OC(O)— can extend the linkage, and thus can effectively reduce the steric hindrance close to the reactive center of the asparagine endopeptidase after linking to R₄. However, the activation by contacting with asparagine endopeptidase is still affected by the structure and polarity of R₄. (7) The polarity, solubility coming with R₄ are related to the activation efficiency of the conjugate, and are closely relevant to the solubility, stability and efficacy of the drugs containing the cleavable linker. In addition to the conventional linking group, R₁ can link to a special hydrophilic group or targeted group to bring a special function for the drugs containing the cleavable linker, such as improvement of solubility, and efficacy in the Examples. (8) In line with the distribution of the asparagine endopeptidase, the compounds containing the cleavable linker can be activated in many kinds of tumors. They can broaden the scope of the diseases to be treated by the drug due to the changed solubility. Therefore, antitumor drugs against various tumor or a specific tumor can be developed. (9) During metastasis of tumor cells, a great amount of asparagine endopeptidases are secreted by the cells to degrade intercellular matrix. Therefore, the targeted drugs after linking to the cleavable linker exhibit a special efficacy to tumor metastasis. (10) The compounds containing the cleavable linker have low toxicity and high efficacy, they are nontoxic to immune system and can be combined with immunotherapy at the same time, making a synergistic efficacy.

Description of the compounds and examples are as follows:

(1) Compounds S1~S43, S15', B15 and E15: Demonstrating new anti-cancer compounds can be synthesized by linking to the cleavable linker via two types of connection (Example 1-9), different anti-cancer compound shows synthetic efficiency and toxicity reduction (Example 9), different activation efficiencies (Example 10, 11) and efficacy (Example 12), providing comparative studies for the cleavable linker when used together with different R₁, R₂, R₃ (Example 13~14).

(2) Compounds S2' ~S4' and S10' ~S24', and compounds A1, A3~A4 and A10~A24: indicating that Docetaxel compounds containing the cleavable linker and different R₁, R₂ and R₃ can be synthesized (Example 16, 17, 27 and 28). The linking site, steric hindrance, connection length and variation of R₁ bring about different solubility (Example 17 and 28, improved solubility), different activation efficiency (Example 20 and 30), low toxicity, high efficacy and new indications (Example 20-26, 31-35 and 66).

(3) Compounds B1, B3~B4 and B10~B24, compounds D2~D4 and D10~D24: indicating that Docetaxel compounds containing the cleavable linker and different R₁, R₂ and R₃ can be synthesized (Example 36, 37, 46 and 47). The linking site, steric hindrance, connection length and variation of R₁ bring about different solubility (Example 37 and 47, improved solubility), different activation efficiency (Example 38 and 49), low toxicity, high efficacy and new indications (Example 40-45 and 50-54).

(4) Compounds E2~E4 and E10~E24: indicating that Mitomycin compounds containing the cleavable linker and different R₁, R₂ and R₃ can be synthesized (Example 56 and 57). The linking site, steric hindrance, connection length and variation of R₁ bring about different solubility (Example 57, improved solubility), different activation efficiency (Example 58), low toxicity, high efficacy and new indications (Example 59-65).

In one embodiment, the compound of formula (II) has a structure as set forth in any of the following formulae (IIA), (IIB), (IIC), (IID), (III), (IV), (V), (VI), (VII), (VIII), and (IX):
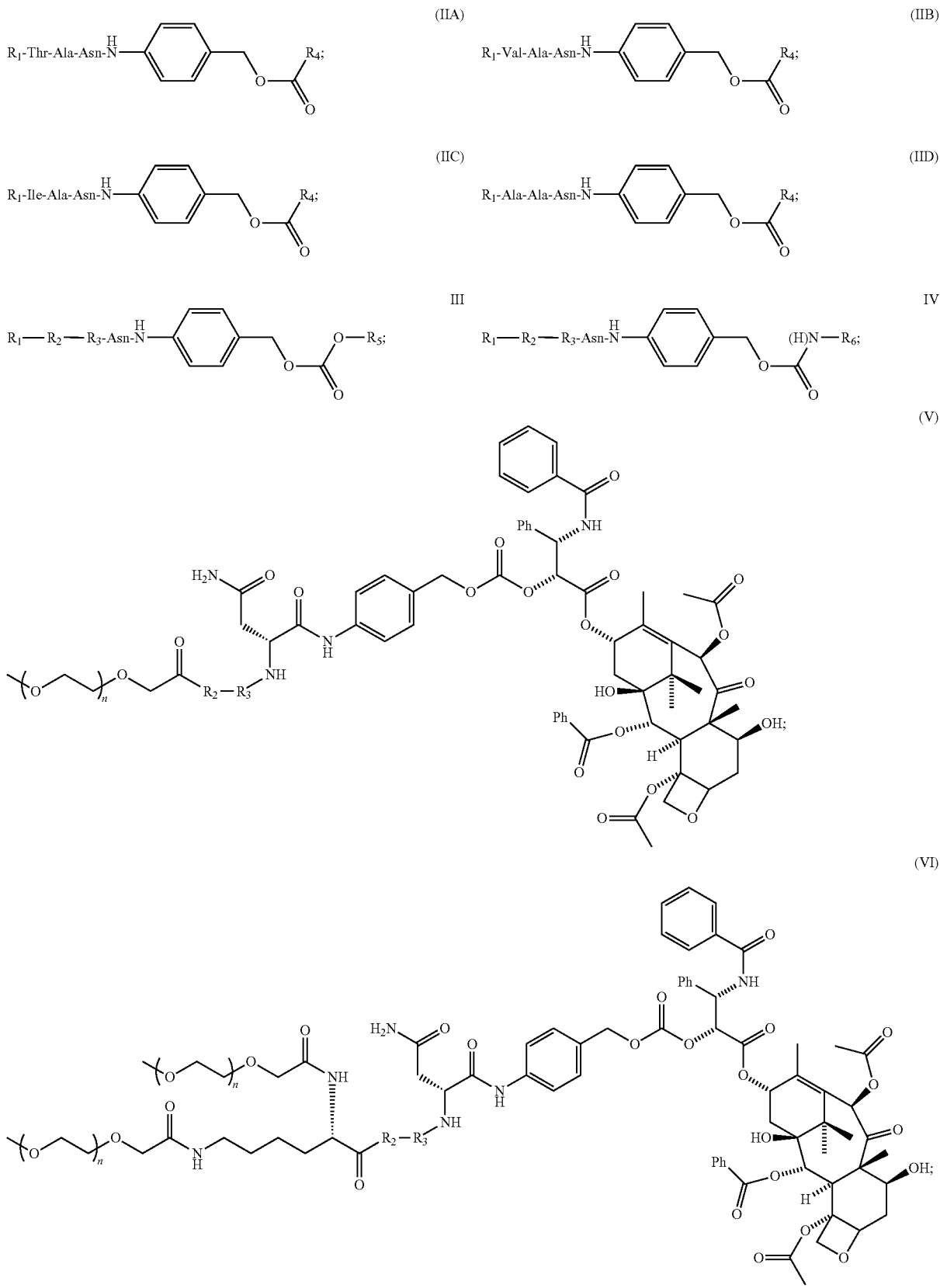

-continued
(VII)
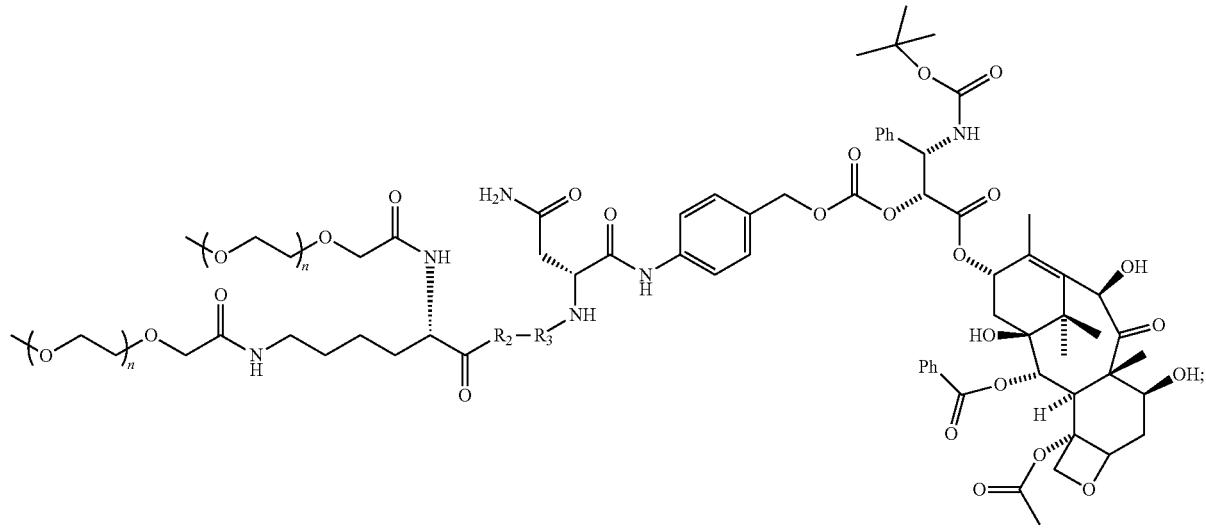
(VIII)
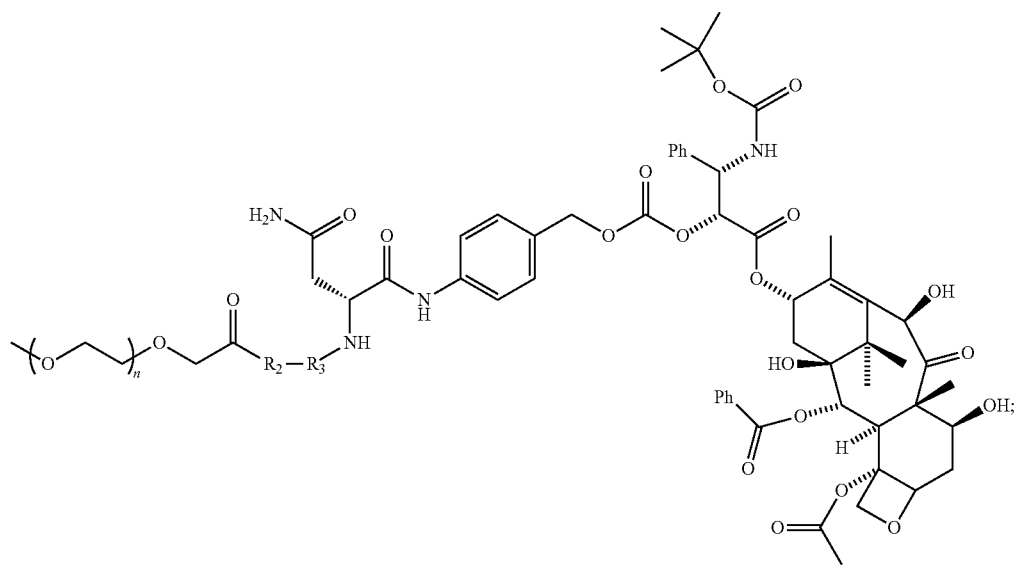
(IX)
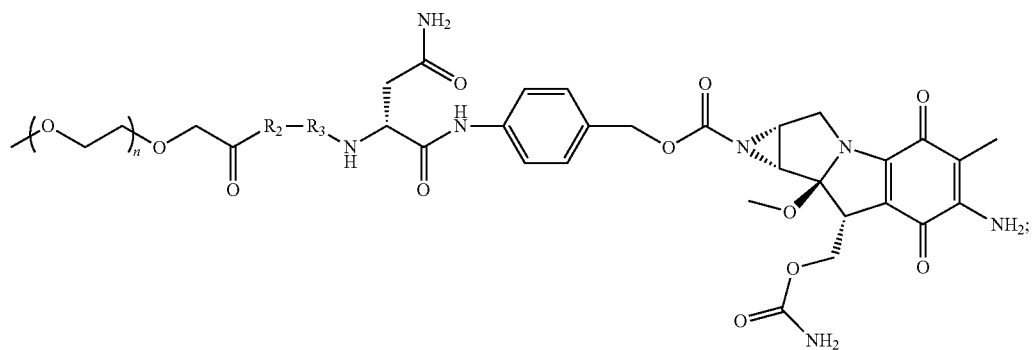

wherein

R₁ is selected from the group consisting of 6-maleimide-$C_{1-10}$ alkylcarbonyl, hydroxylaminocarbonyl-$C_{1-10}$ alkylcarbonyl, $C_{1-4}$ alkoxyl-($C_{1-4}$ alkoxyl)$_n$-$C_{1-6}$ alkylcarbonyl, or

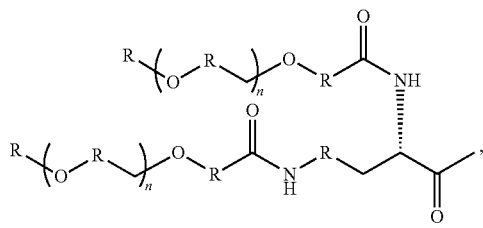

wherein each R is independently a $C_{1-4}$alkyl, and each n is independently any integer between 1-300, preferably 1-150;

R₂ is Ala, Thr, Val or Ile;

R₃ is Ala, Thr, Val or Asn;

R₅ is the active moiety of an anticancer compound containing a hydroxyl group (R₅—OH), i.e., a moiety except the hydroxyl group used for linking, wherein the anticancer compound is selected from the group consisting of Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Paclitaxel and Docetaxel; and R₆ is the active moiety of an anticancer compound containing an amino group (R₅—NH₂), i.e., a moiety except the amino group used for linking, wherein the anticancer compound is selected from the group consisting of Daunorubicin, Epirubicin, Methotrexate, Fludarabine, Gemcitabine, Cytarabine, MelphalaN, Nimustine, Mitoxantrone and Mitomycin.

The present disclosure also provides a pharmaceutical composition comprising the compound of formula (II) or a pharmaceutically acceptable salt thereof and a pharmaceutically acceptable carrier or excipient.

The present disclosure provides a method for preparing a compound of formula (III) or (IV), which is shown as follows:

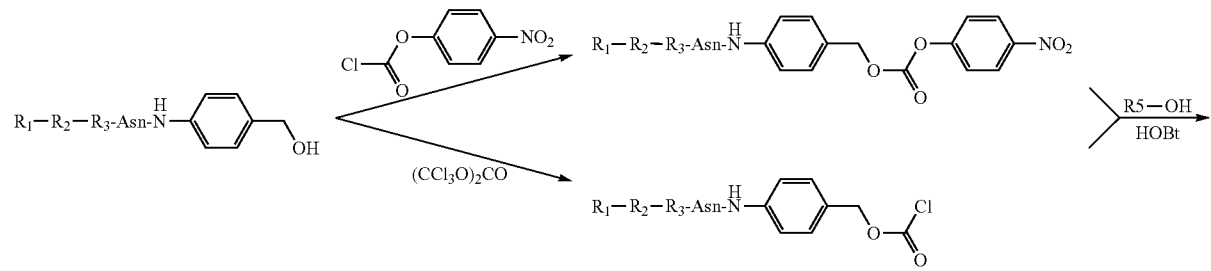

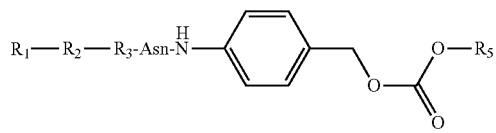

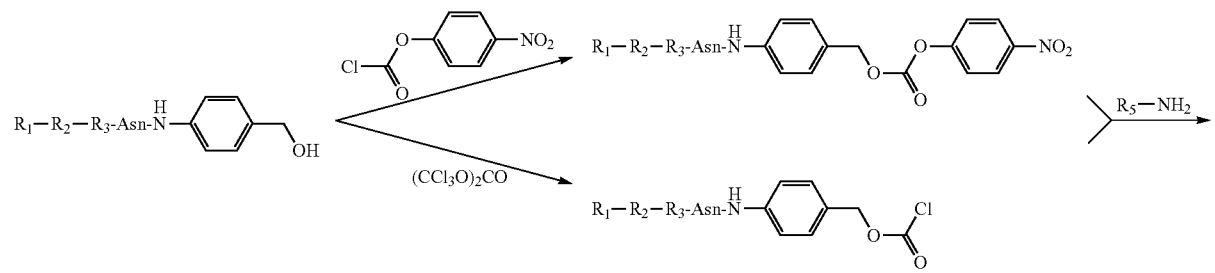

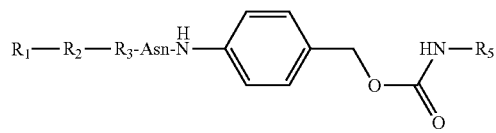

wherein the preparation of the compound of formula (III) comprises reacting $R_1$-$R_2$-$R_3$-Asn-4-amino benzyl alcohol with 4-nitrophenyl chloroformate or $(CCl_3O)_2CO$ to form an active carbonic acid ester bond or chloroformate, and then reacting the active carbonic acid ester bond or chloroformate with the drug comprising a hydroxyl group ($R_5$—OH) to form the compound of formula (III), wherein the drug is selected from the group consisting of Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Paclitaxel and Docetaxel;

the preparation of the compound of formula (IV) comprises reacting $R_1$-$R_2$-$R_3$-Asn-4-amino benzyl alcohol with 4-nitrophenyl chloroformate or $(CCl_3O)_2CO$ to form an active carbonic acid ester bond or chloroformate, and then reacting the active carbonic acid ester bond or chloroformate with the drug comprising an amino group ($R_6$—$NH_2$) to form the compound of formula (IV), wherein the drug is selected from the group consisting of Daunorubicin, Epirubicin, Methotrexate, Fludarabine, Gemcitabine, Cytarabine, Melphalan, Nimustine, Mitoxantrone and Mitomycin;

wherein $R_1$ is a conventional functional group or a protecting group; $R_2$ is Ala, Thr, Val or Ile; and $R_3$ is Ala, Thr, Val or Asn.

The present disclosure provides use of the compound of formula (II) or a pharmaceutically acceptable salt thereof or the pharmaceutical composition of the present disclosure in the manufacture of a medicament for treating or preventing a cancer.

The present disclosure provides use of a mitomycin derivative as shown in formula (IX) or a pharmaceutically acceptable salt thereof in the manufacture of a medicament for treating or preventing an ophthalmic disease.

The present disclosure provides use of the compound of formula (II) or a pharmaceutically acceptable salt thereof or the pharmaceutical composition of the present disclosure in the manufacture of a medicament for inhibiting tumor-associated macrophages, tumor growth, angiogenesis or infiltration and metastasis of tumor cells, and/or promoting anti-tumor immunization.

The present disclosure also provides a method for treating or preventing a cancer, comprising administering a subject in need thereof a therapeutically or prophylactically effective amount of the compound of formula (II) or a pharmaceutically acceptable salt thereof or the pharmaceutical composition of the present disclosure.

The present disclosure also provides a method for reducing the toxicity of an anticancer compound, comprising linking the anticancer compound to $R_1$-$R_2$-$R_3$, wherein $R_4$ is a conventional functional group or a protecting group; $R_2$ is Ala, Thr, Val or Ile; $R_3$ is Ala, Thr, Val or Asn; and the anticancer compound is selected from the group consisting of Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Daunorubicin, Epirubicin, Methotrexate, Gemcitabine, Melphalan, Nimustine, Mitoxantrone, Paclitaxel, Docetaxel and Mitomycin.

DETAILED DESCRIPTION OF THE PREFERRED EMBODIMENT

I. Compounds

Figure 1A:
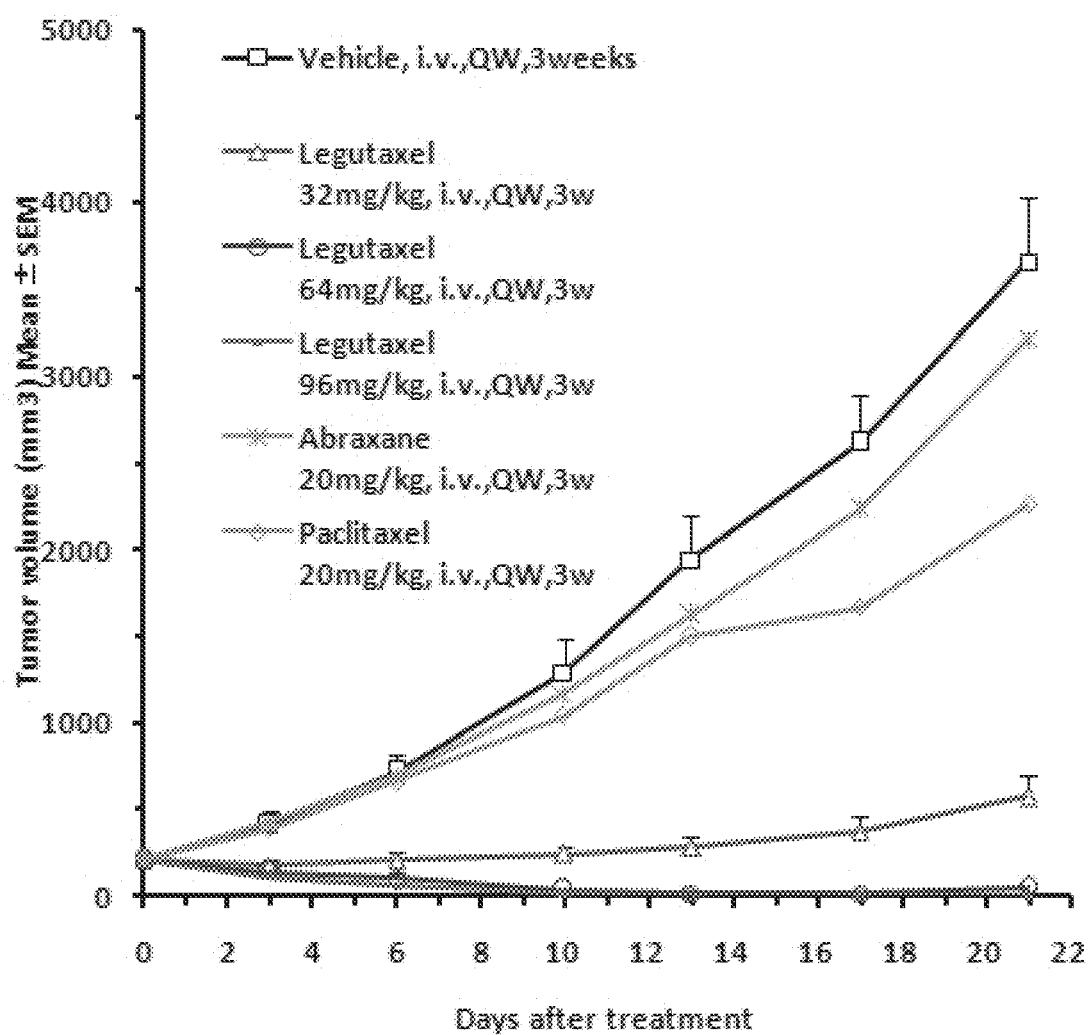
FIGS. 1A and 1B show comparative experiments performed in HT1080 model by using a high dose of Legutaxel, Capxol and Paclitaxel injections, which were used at an equal molar dose and at an equal toxic dose.

The compounds of the present disclosure comprises conjugates as shown in formula (A), and compounds of formula (II) formed by conjugating the conjugates to a drug $R_4$. The compounds of formula (II) could accumulate at the tumor site, and are specifically activated, thus releasing the antitumor compound.

The compound of formula (A) of the present disclosure has a structure as set forth below:

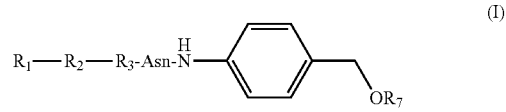

(I)

wherein, $R_1$ is a conventional functional group or a protecting group; $R_2$ is Ala, Thr, Val or Ile; $R_3$ is Ala, Thr, Val or Asn; and $R_7$ is H, XC(O)—, or optionally substituted benzyloxycarbonyl (for example, optionally substituted by 1, 2 or 3 substituents selected from the group consisting of nitro, $C_{1-4}$ alkyl, halogen, hydroxyl and amino), wherein X is halogen; wherein $R_1$ links to $R_2$ through an amide bond formed by the carbonyl of $R_1$; and amide bonds are formed between $R_2$ and $R_3$, $R_3$ and Asn, and Asn and —NH—.

The present disclosure also provides a compound of formula (II):

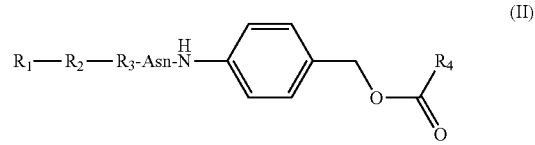

(II)

wherein $R_1$ is a conventional functional group or a protecting group; $R_2$ is Ala, Thr, Val or Ile; $R_3$ is Ala, Thr, Val or Asn; and $R_4$ is an active moiety of a drug linking through hydroxyl or amino group, and the drug is represented by formula $R_4$—H.

In some embodiments, in the compounds of the present disclosure, $R_1$ links to $R_2$ by forming an amide bond via its carbonyl, $R_2$, $R_3$ and Asn form a tripeptide, Asn links to —NH— via its carbonyl, $R_4$ links to the cleavable linker through carbonic acid ester bond formed by its oxygen atom with the cleavable linker or through carbamate formed by its nitrogen atom with the cleavable linker.

In some preferred embodiments, $R_4$ links to the cleavable linker through a carbamate formed by its nitrogen atom of the amino substituent on the aromatic ring with the cleavable linker, or through carbonic acid ester bond formed by its oxygen atom of hydroxyl substituent on the aromatic ring or heterocycle with the cleavable linker.

In some embodiments, R₃ is preferably Ala.

In the present disclosure, R₁ can be H or an amino protecting group. For example, R₁ can be a hydrophilic or hydrophobic group. Alternatively, R₁ can be selected from any of $C_{1-6}$ alkyl (such as methyl, ethyl, propyl, butyl, pentyl, hexyl), polyethylene glycol-$C_{1-5}$ alkylcarbonyl, succinyl, glucosiduronide, maleimide-$C_{1-10}$ alkylcarbonyl (such as 6-maleimide caproyl), 2-methoxyethoxy-$C_{1-6}$ alkylcarbonyl, hydroxylaminocarbonyl-$C_{1-10}$ alkylcarbonyl (such as N-hydroxylamino-1,8-octandioic acid-1-monoacyl) and caproyl ($C_{1-5}$ alkylcarbonyl).

Preferably, R₁ can be 6-maleimide-$C_{1-10}$ alkylcarbonyl, hydroxylaminocarbonyl-$C_{1-10}$ alkylcarbonyl, $C_{1-4}$ alkoxyl-($C_{1-4}$ alkoxyl)$_n$-$C_{1-6}$ alkylcarbonyl, or

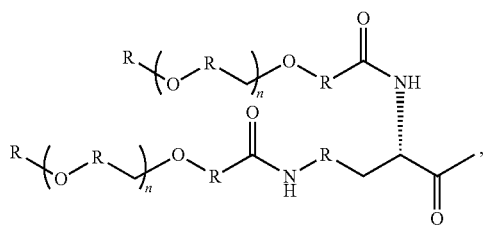

wherein each R is independently a $C_{1-4}$ alkyl, and each n is independently any integer between 1-300, preferably 1-150.

Preferably, when R₄—H is a water-insoluble drug, R₁ is preferably a PEG-type group, such as polyethylene glycol-$C_1$-$C_5$ alkylcarbonyl, or

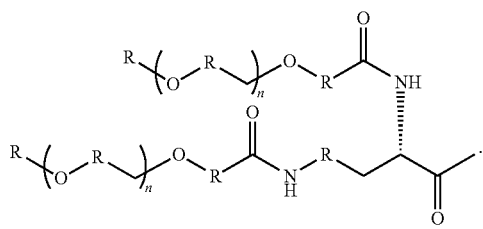

Generally, R₁ links to the amino group of R₂, and when R₁ links to R₂ via its carbonyl, an amide linkage (—CO—NH—) forms.

In the present disclosure, R₄ is the active moiety of an anticancer compound, wherein the anticancer compound includes, but is not limited to, Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Daunorubicin, Epirubicin, Methotrexate, Gemcitabine, Melphalan, Nimustine, Mitoxantrone, Paclitaxel, Docetaxel and Mitomycin.

The compounds of formula (II) may include the compounds having any of the following structures:

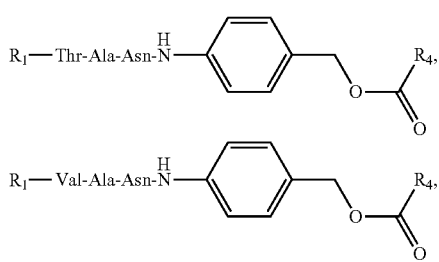

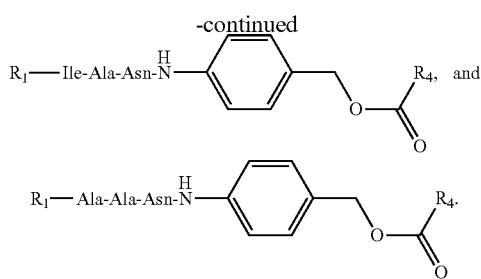

In one embodiment, R₄ is —O—R₅, and the compound of formula (II) has a structure set forth in the following formula (III):

(III)

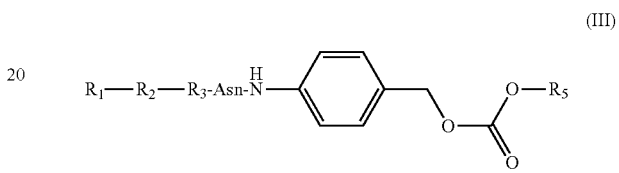

wherein R₅ is the active moiety of an anticancer compound containing a hydroxyl group (R₅—OH), i.e., a moiety except the hydroxyl group used for linking, wherein the anticancer compound is selected from the group consisting of Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Paclitaxel and Docetaxel.

In one embodiment, R₄ is R₆—NH, and the compound of formula (II) has a structure set forth in the following formula (IV):

(IV)

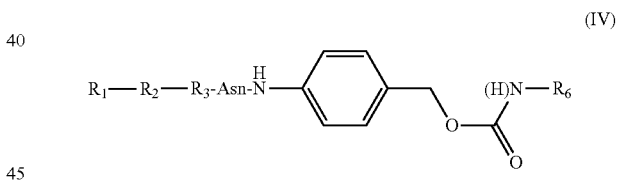

wherein R₆ is the active moiety of an anticancer compound containing an amino group (R₆—NH₂), i.e., a moiety except the amino group used for linking, wherein the anticancer compound is selected from the group consisting of Daunorubicin, Epirubicin, Methotrexate, Fludarabine, Gemcitabine, Cytarabine, Melphalan, Nimustine, Mitoxantrone and Mitomycin. In formula (IV), "(H)" represents that H is present or not present; if H is not present, N links to R₆ via a double bond.

In each structure of the present disclosure, n generally is an integer in the range of 1-300, i.e. 1, 2, 3, 4, 5, 6, 7, 8, 9, 10 . . . 100, 101, 102, 103 . . . 201, 202, 203 . . . 295, 296, 297, 298, 299 and 300. It should be understood that, although each integer between 1-300 is not specifically described, these un-described integers are obvious to the skilled artisan, and it should be constructed as that the present disclosure has literally disclosed all of the integers falling within the range. In the present disclosure, n in each structure generally is in the range of 1-250, 1-200, 1-150, 1-100, 1-50, and such as 5-10, 5-50, 5-100 and the like.

In one embodiment, compounds of formula (III) include:
(1) Compound S1 in which $R_1$ is 2-(2-methoxyethoxy) acetyl, $R_2$ is Thr, $R_3$ is Ala, and $R_4$ is 10-hydroxyl camptothecin

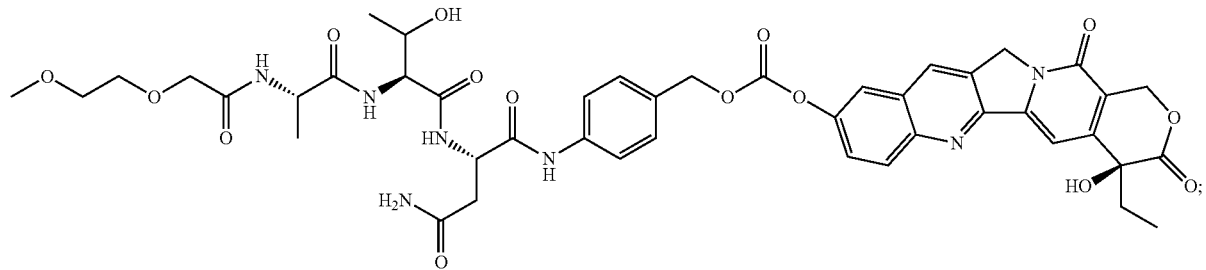 [SMILES: CC[C@@]1(O)C(=O)OCc2c1cc1n(c2=O)Cc2cc3cc(OC(=O)OCc4ccc(NC(=O)[C@H](CC(N)=O)NC(=O)[C@@H](NC(=O)[C@H](C)NC(=O)COCCOC)C(C)O)cc4)ccc3nc2-1]

(2) Compound S2 in which $R_1$ is 2-(2-methoxyethoxy) acetyl, $R_2$ is Ala, $R_3$ is Ala, and $R_4$ is camptothecin

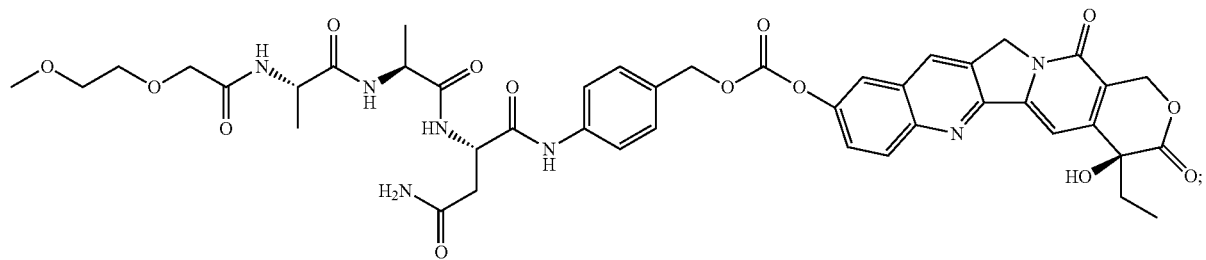 [SMILES: CC[C@@]1(O)C(=O)OCc2c1cc1n(c2=O)Cc2cc3cc(OC(=O)OCc4ccc(NC(=O)[C@H](CC(N)=O)NC(=O)[C@H](C)NC(=O)[C@H](C)NC(=O)COCCOC)cc4)ccc3nc2-1]

(3) Compound S3 in which $R_1$ is (N-hydroxylamino)-1, 8-octandioic acid-1-monoacyl, $R_2$ is Ala, $R_3$ is Ala, and $R_4$ is Capecitabine

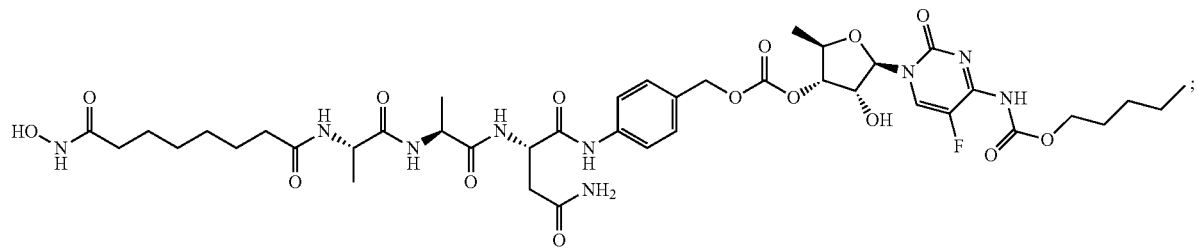 [SMILES: CCCCCOC(=O)Nc1nc(=O)n([C@@H]2O[C@H](C)[C@@H](OC(=O)OCc3ccc(NC(=O)[C@H](CC(N)=O)NC(=O)[C@H](C)NC(=O)[C@H](C)NC(=O)CCCCCCC(=O)NO)cc3)[C@H]2O)cc1F]

and (4) Compounds S7-S18, wherein $R_1$ is 2-(2-Methoxyethoxy)Acetyl, $R_2$ is Thr, $R_3$ is Ala and $R_4$ is Camptothecin (S7), 10-Hydroxyl Camptothecin (S8), Topotecan (S9), Floxuridine (S10), 5'-Deoxy-5-Fluorouridine (S11), Cytarabine (S12), Fludarabine (S13), Etoposide (S14), Capecitabine (S15), Gemcitabine (S16), Vincristine (S17), or Epothilone B (S18). The compounds and the position of the hydroxyl are as follows:

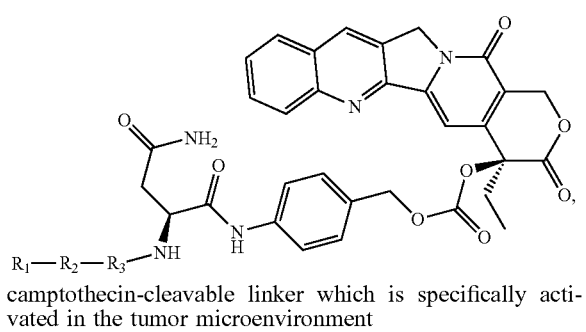

camptothecin-cleavable linker which is specifically activated in the tumor microenvironment

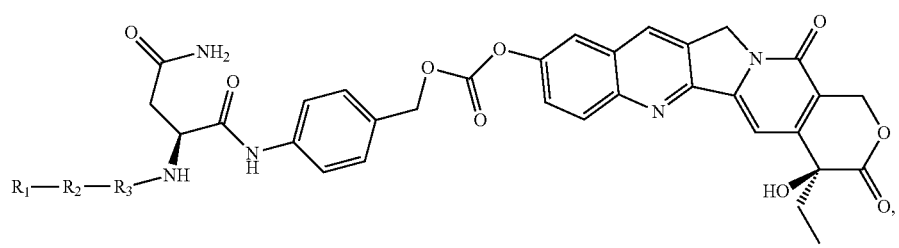

10-hydroxyl camptothecin-cleavable linker which is specifically activated in the tumor microenvironment

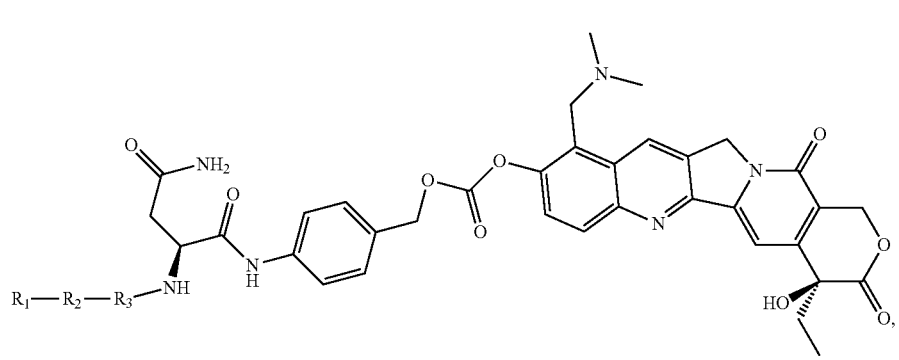

topotecan-cleavable linker which is specifically activated in the tumor microenvironment

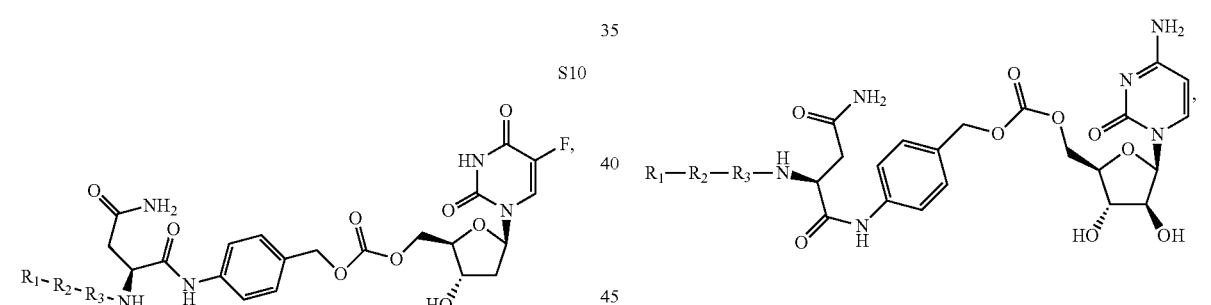

floxuridine-cleavable linker which is specifically activated in the tumor microenvironment Cytarabine-cleavable linker which is specifically activated in the tumor microenvironment

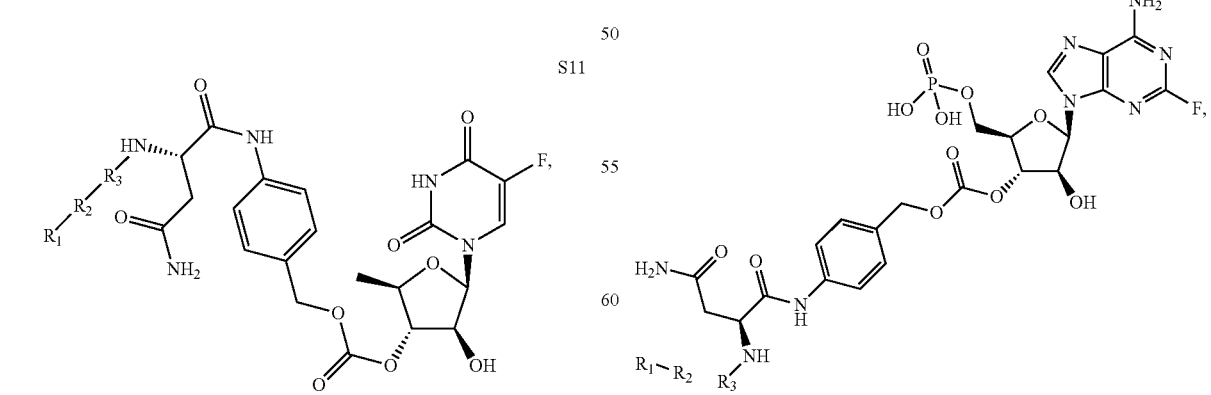

5'-Deoxy-5-Fluorouridine-cleavable linker which is specifically activated in the tumor microenvironment Fludarabine-cleavable linker which is specifically activated in the tumor microenvironment

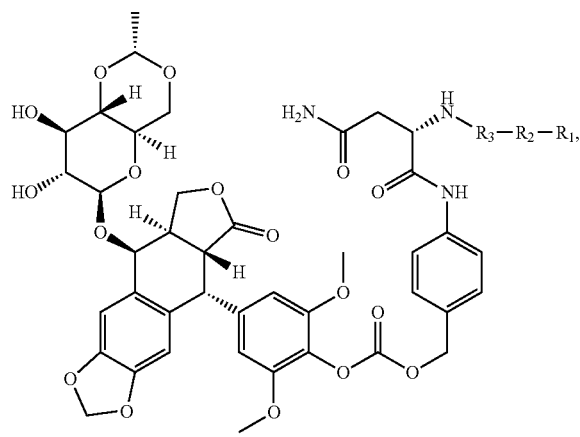

Etoposide-cleavable linker which is specifically activated in the tumor microenvironment

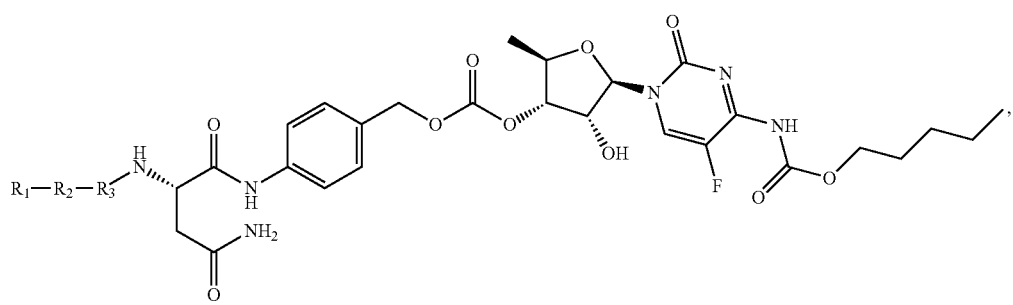

capecitabine-cleavable linker which is specifically activated in the tumor microenvironment

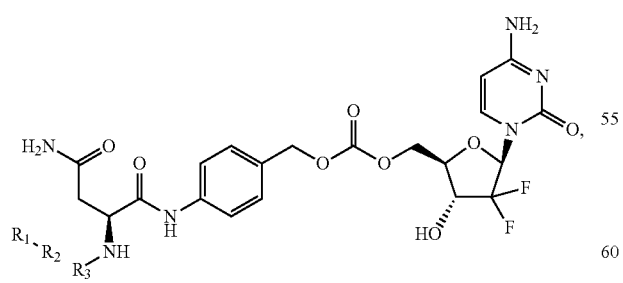

Gemcitabine-cleavable linker which is specifically activated in the tumor microenvironment

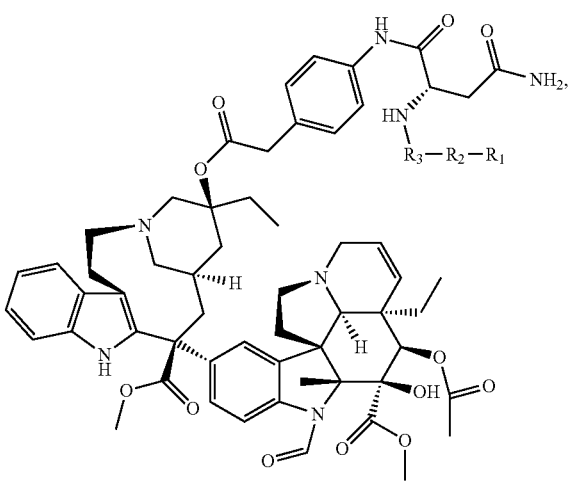

Vincristine-cleavable linker which is specifically activated in the tumor microenvironment

S18

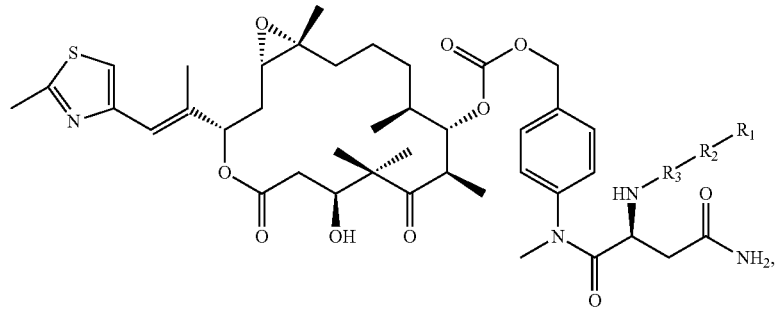

Epothilone B-cleavable linker which is specifically activated in the tumor microenvironment In one embodiment, compounds of formula (IV) include:

(1) Compound S4 in which $R_1$ is 2-(2-methoxyethoxy) acetyl, $R_2$ is Thr, $R_3$ is Ala, and $R_4$ is Daunorubicin

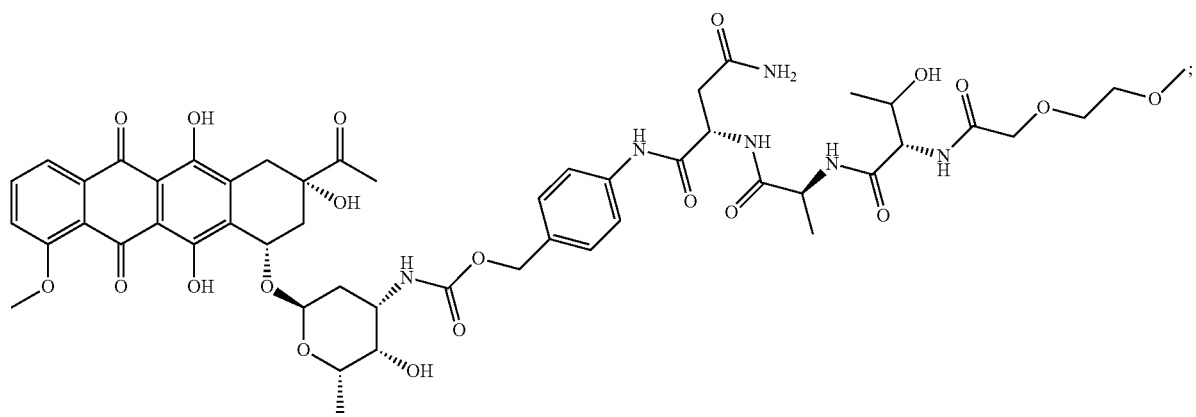 [SMILES: COCCOCC(=O)N[C@H](C(=O)N[C@@H](C)C(=O)N[C@@H](CC(N)=O)C(=O)Nc1ccc(COC(=O)N[C@H]2C[C@H](O[C@H]3C[C@](O)(C(C)=O)Cc4c(O)c5c(c(O)c43)C(=O)c3c(OC)cccc3C5=O)O[C@@H](C)[C@H]2O)cc1)C(C)O]

(2) Compound S5 in which $R_1$ is 6-maleimide caproyl, $R_2$ is Ala, $R_3$ is Ala, and $R_4$ is Daunorubicin

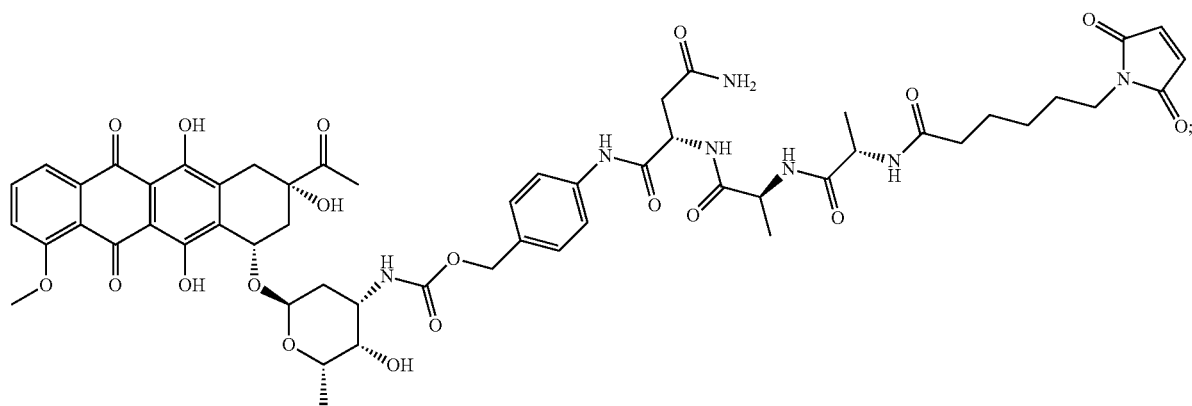 [SMILES: COc1cccc2c1C(=O)c1c(O)c3c(c(O)c1C2=O)C[C@@](O)(C(C)=O)C[C@@H]3O[C@H]1C[C@H](NC(=O)OCc2ccc(NC(=O)[C@H](CC(N)=O)NC(=O)[C@H](C)NC(=O)[C@H](C)NC(=O)CCCCCN3C(=O)C=CC3=O)cc2)[C@H](O)[C@H](C)O1]

and (3) Compounds S19-S28, wherein $R_1$ is 2-(2-Methoxyethoxy)Acetyl, $R_2$ and $R_3$ are Ala, $R_4$ is Daunorubicin (S19), Epirubicin (S20), Fludarabine (S21), Gemcitabine (S22), Nimustine (S23), Mitoxantrone (S24), Methotrexate (S25), Cytarabine (S26), Melphalan (S27) or Doxorubicin (S28). The compounds and the position of the amino group used for linking are as follows:

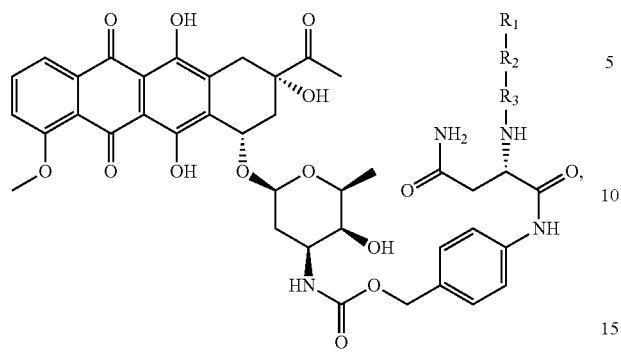
daunorubicin-cleavable linker which is specifically activated in the tumor microenvironment
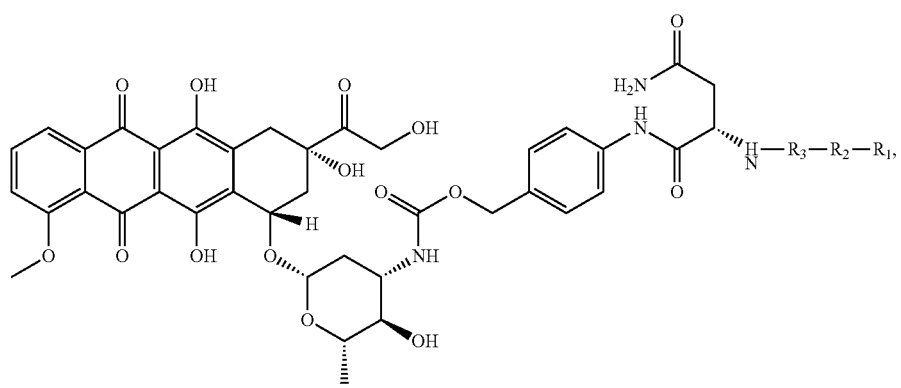
Epirubicin-cleavable linker which is specifically activated in the tumor microenvironment
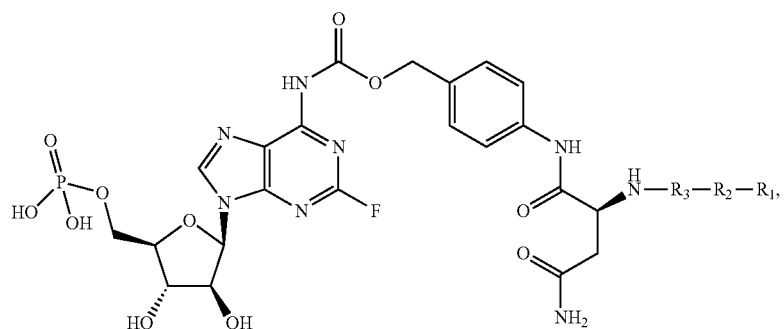
Fludarabine-cleavable linker which is specifically activated in the tumor microenvironment

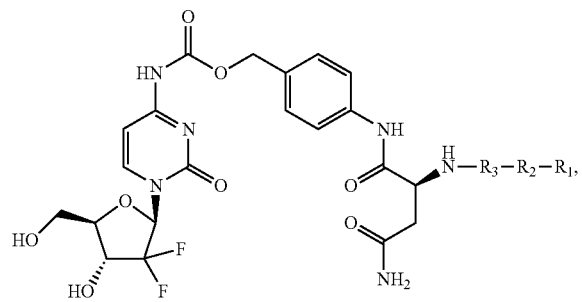

Gemcitabine-cleavable linker which is specifically activated in the tumor microenvironment

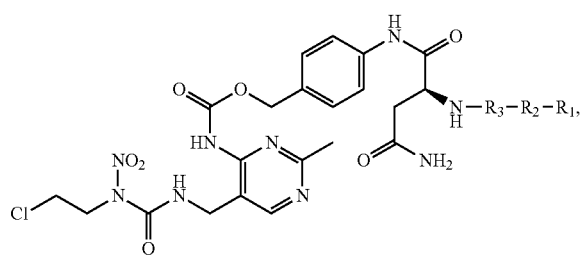

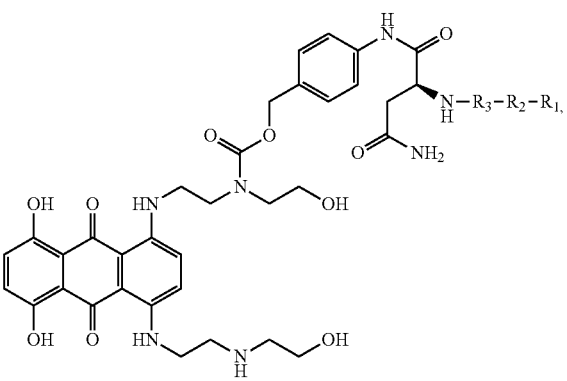

Nimustine-cleavable linker which is specifically activated in the tumor microenvironment Mitoxantrone-cleavable linker which is specifically activated in the tumor microenvironment

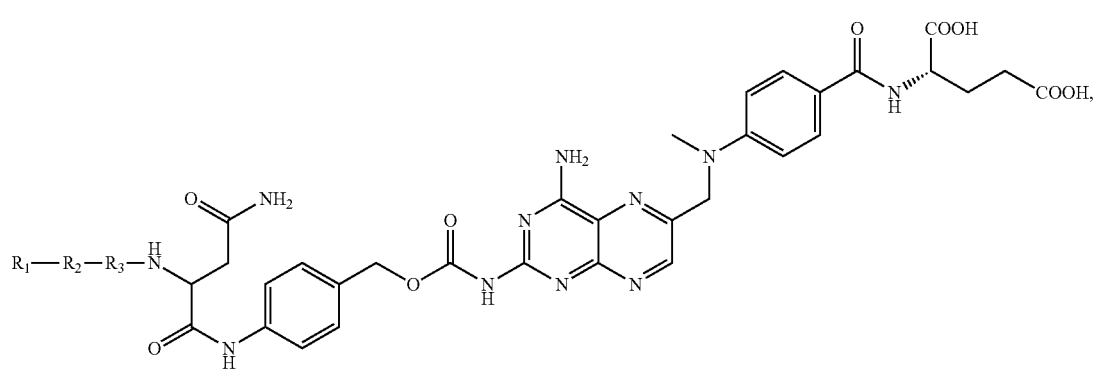

Methotrexate-cleavable linker which is specifically activated in the tumor microenvironment

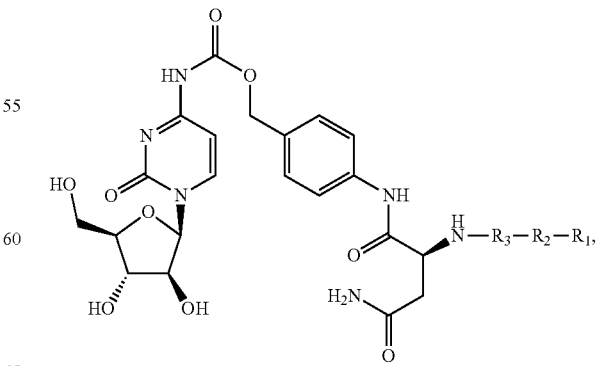

Cytarabine-cleavable linker which is specifically activated in the tumor microenvironment

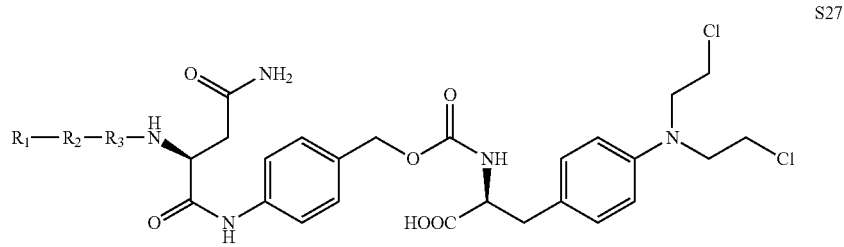

Melphalan-cleavable linker which is specifically activated in the tumor microenvironment

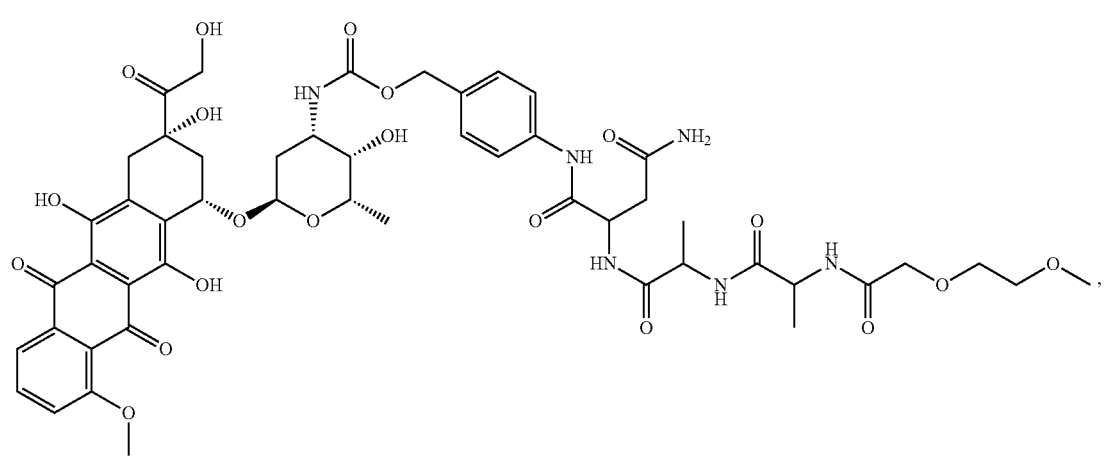

Doxorubcin-cleavable linker which is specifically activated in the tumor microenvironment In one embodiment, the present disclosure provides a paclitaxel derivative for targeted activation in the tumor microenvironment, which has a structure as set forth in the following formula (V):

wherein $R_2$ is Ala, Thr, Val or Ile; $R_3$ is Ala, Thr, Val or Asn; n is any integer between 1-300, preferably between 1-150.

Compounds of formula (V) include but is not limited to the following compounds:

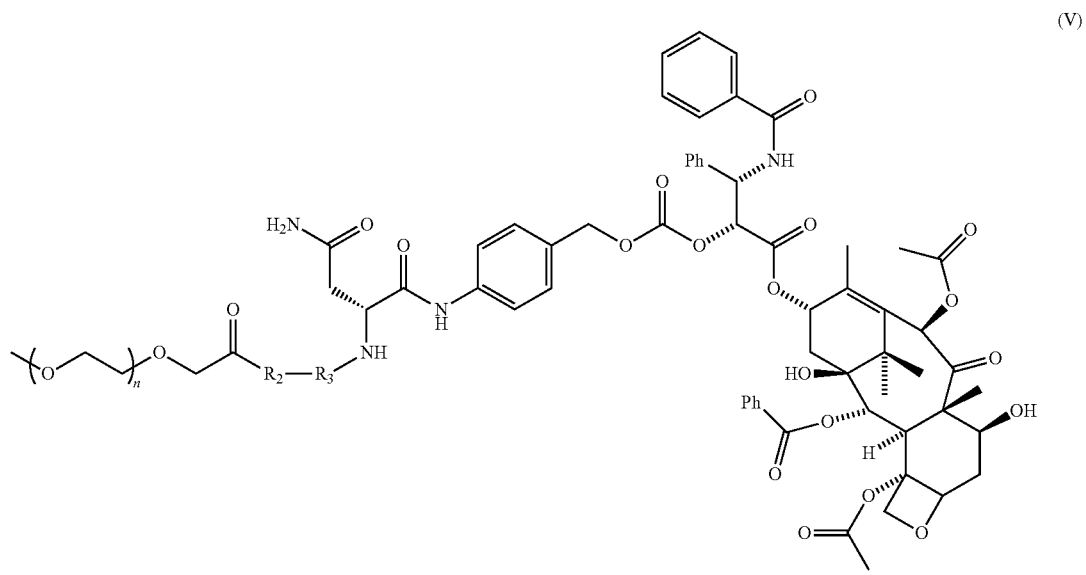

(1) Compound S1' in which n is 1, R$_2$ is Ala and R$_3$ is Ala
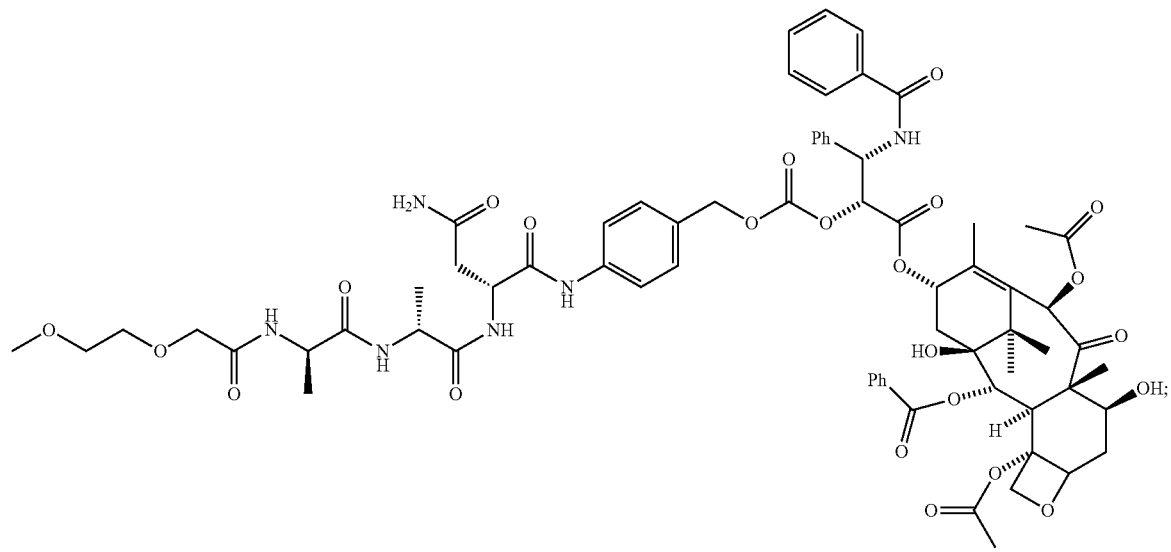
(2) Compound S2' in which n is 5, R$_2$ is Ala and R$_3$ is Ala
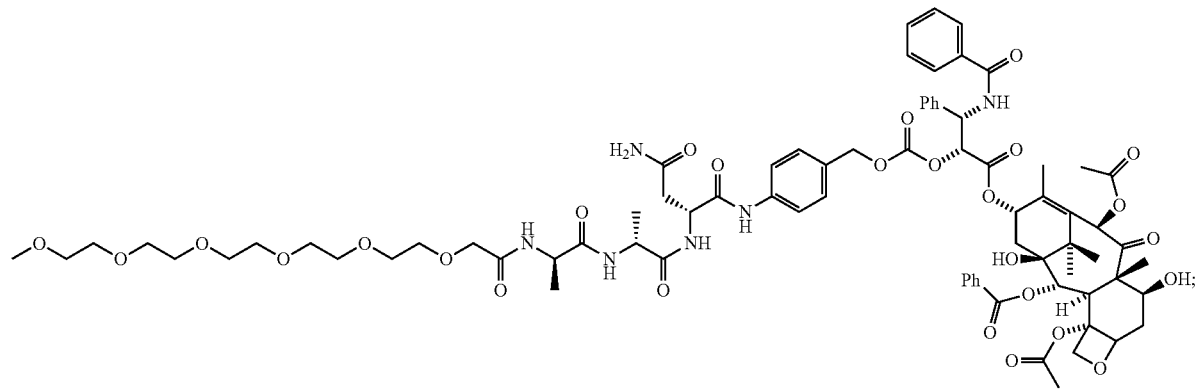
(3) Compound S3' in which n=11, R$_2$ is Ala and R$_3$ is Ala
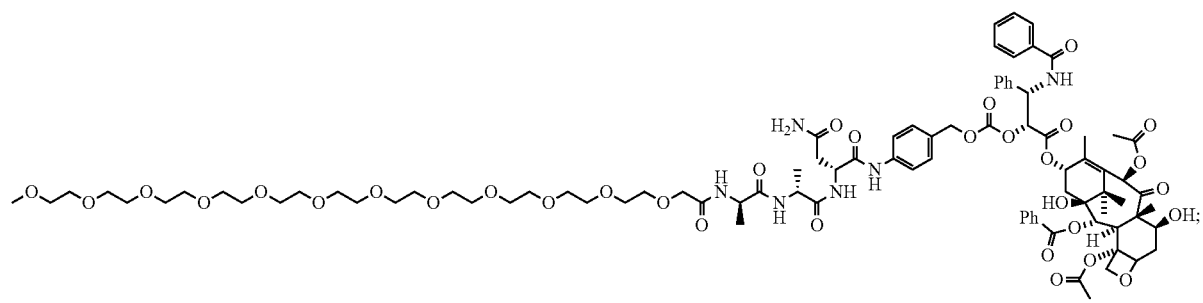

(4) Compound S4' in which n=300, $R_2$ is Ala and $R_3$ is Ala

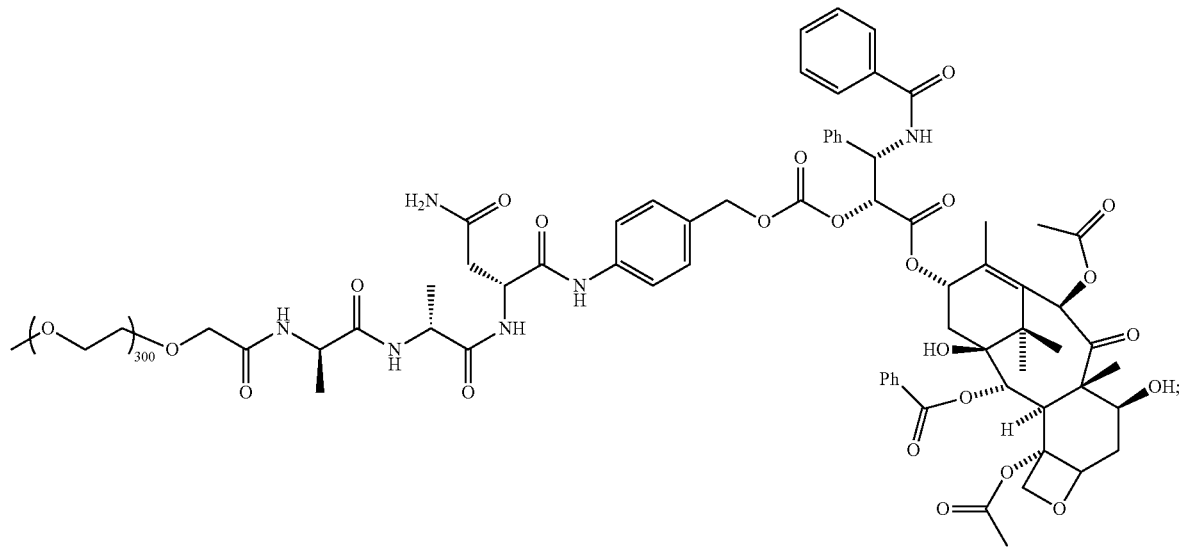

and
(5) Compounds S10'-S24' in which n is 1 and $R_2$ and $R_3$ are shown in the following table:

| No. of Compound | $R_2$ | $R_3$ | n |
|---|---|---|---|
| S10' | Ala | Thr | 1 |
| S11' | Ala | Val | 1 |
| S12' | Ala | Asn | 1 |
| S13' | Thr | Ala | 1 |
| S14' | Thr | Thr | 1 |
| S15' | Thr | Val | 1 |
| S16' | Thr | Asn | 1 |
| S17' | Val | Ala | 1 |
| S18' | Val | Thr | 1 |
| S19' | Val | Val | 1 |
| S20' | Val | Asn | 1 |
| S21' | Ile | Ala | 1 |
| S22' | Ile | Thr | 1 |
| S23' | Ile | Val | 1 |
| S24' | Ile | Asn | 1 |

In one embodiment, the present disclosure provides a water-soluble paclitaxel derivative for targeted activation, which has a structure as set forth in the following formula (VI):

(VI)

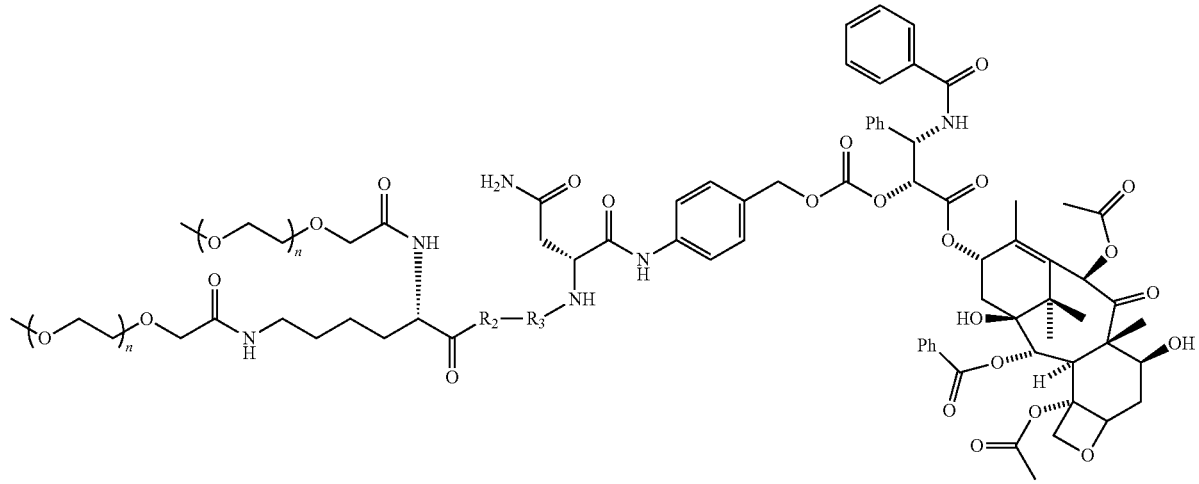

wherein $R_2$ is Ala, Thr, Val or Ile, $R_3$ is Ala, Thr, Val or Asn, and n is any integer between 1-300, preferably between 1-150.

Compounds of formula (VI) include but is not limited to the following compounds:

(1) Compound A1 in which n is 1, $R_2$ is Ala and $R_3$ is Ala
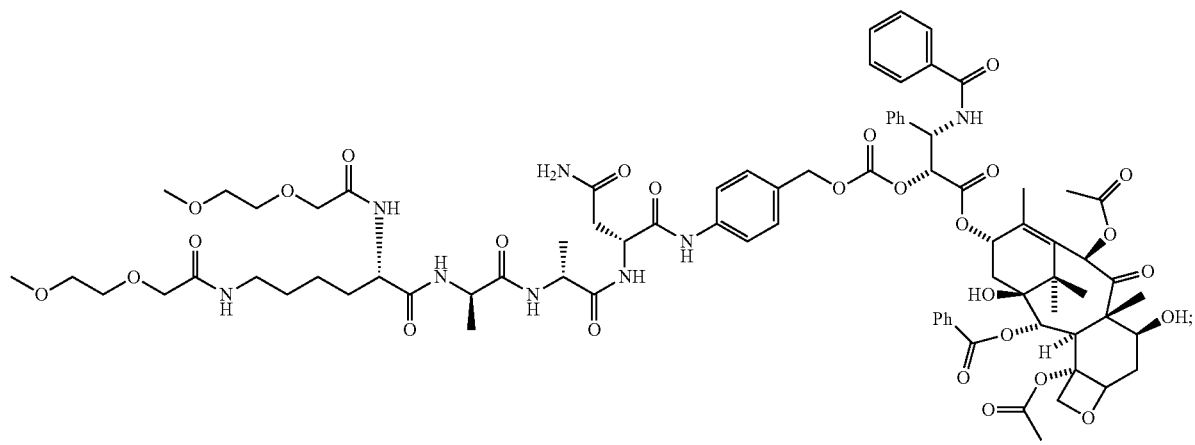
(2) Compound A2 in which n is 5, $R_2$ is Ala and $R_3$ is Ala
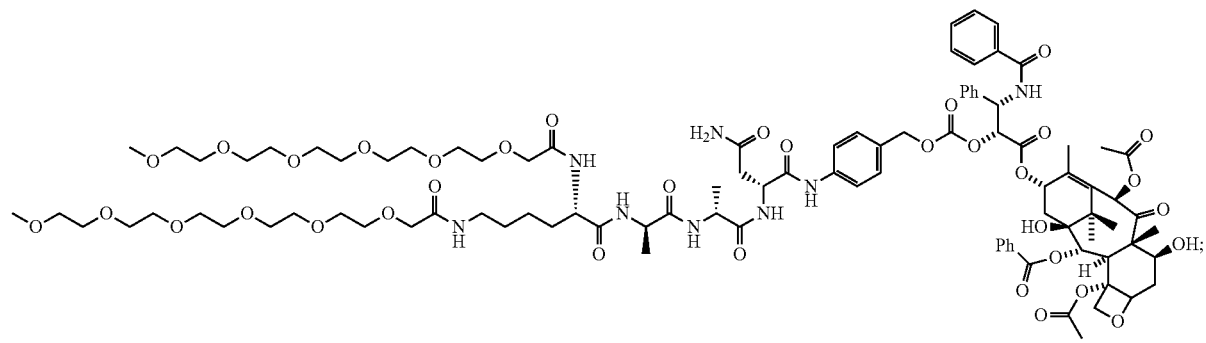
(3) Compound A3 in which n is 11, $R_2$ is Ala and $R_3$ is Ala
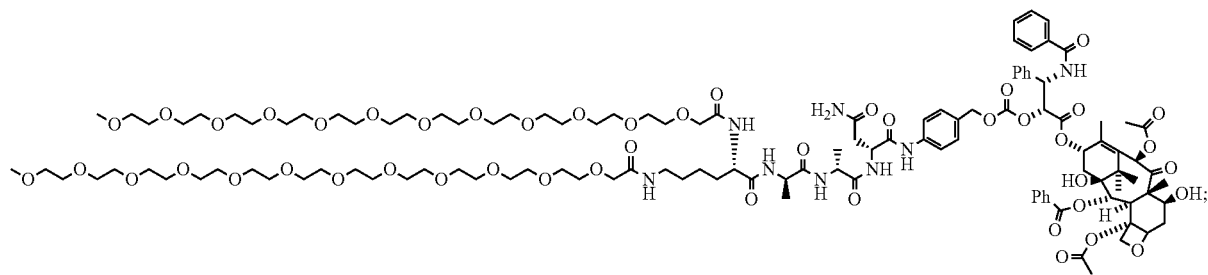
(4) Compound A4 in which n is 150, $R_2$ is Ala and $R_3$ is Ala
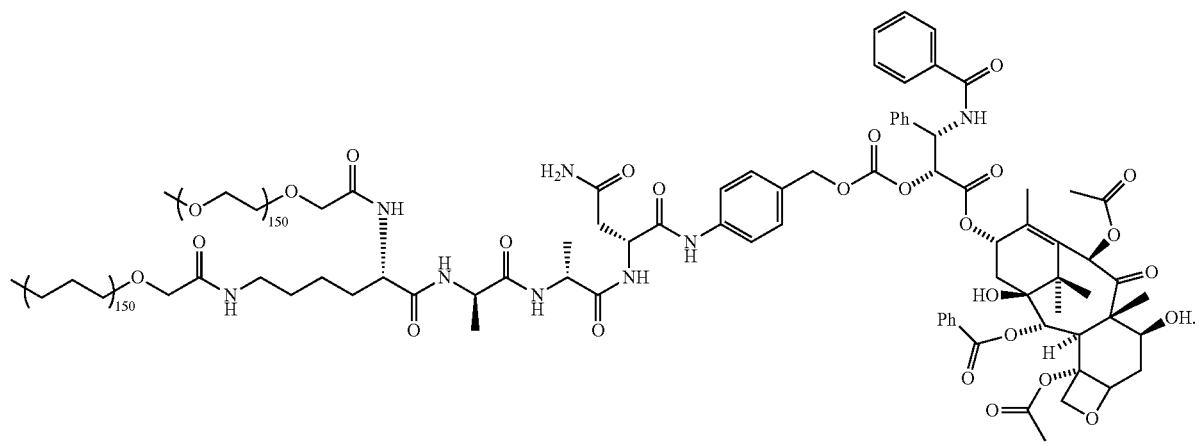

Other compounds of formula (IV) include the following compounds, in which n is 5 and $R_2$ and $R_3$ are shown in the following table:

| No. of Compound | $R_2$ | $R_3$ |
|---|---|---|
| A10 | Ala | Thr |
| A11 | Ala | Val |
| A12 | Ala | Asn |
| A13 | Thr | Ala |
| A14 | Thr | Thr |
| A15 | Thr | Val |
| A16 | Thr | Asn |
| A17 | Val | Ala |
| A18 | Val | Thr |
| A19 | Val | Val |
| A20 | Val | Asn |
| A21 | Ile | Ala |
| A22 | Ile | Thr |
| A23 | Ile | Val |
| A24 | Ile | Asn |

The present disclosure further provides a water-soluble Docetaxel derivative for targeted activation of tumor, which has a structure as set forth in the following formula (VII):

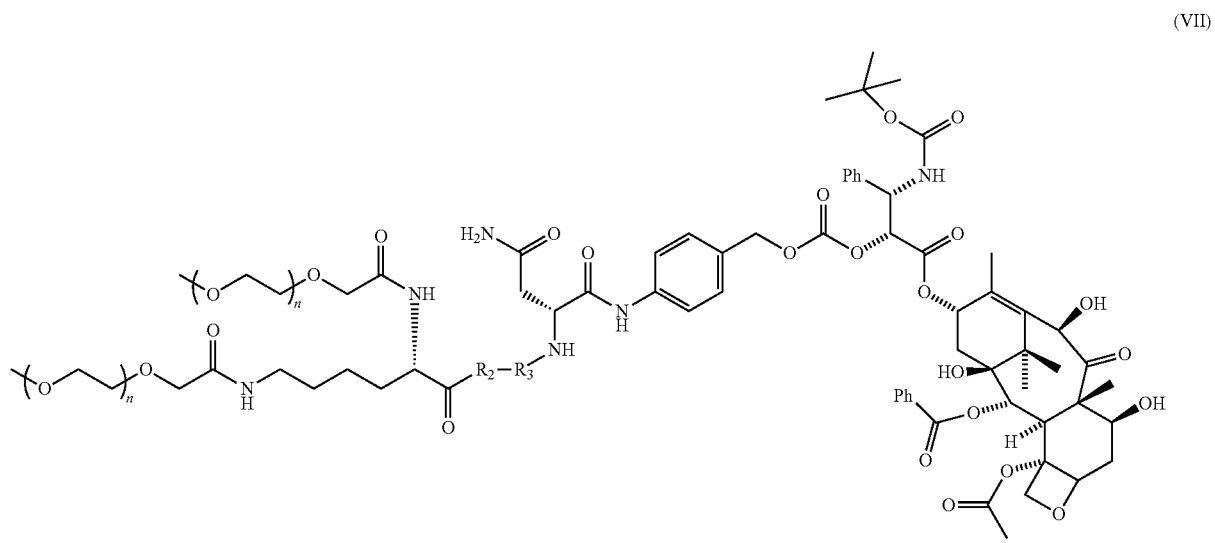

(VII)

wherein $R_2$ is any one amino acid selected from the group consisting of Ala, Thr, Val and Ile; $R_3$ is any one amino acid selected from the group consisting of Ala, Thr, Val and Asn; n is any integer between 1-300, preferably between 1-150.

Compounds of formula (VII) include but are not limited to the following compounds:

(1) Compound B1 in which n is 1, $R_2$ is Ala and $R_3$ is Ala

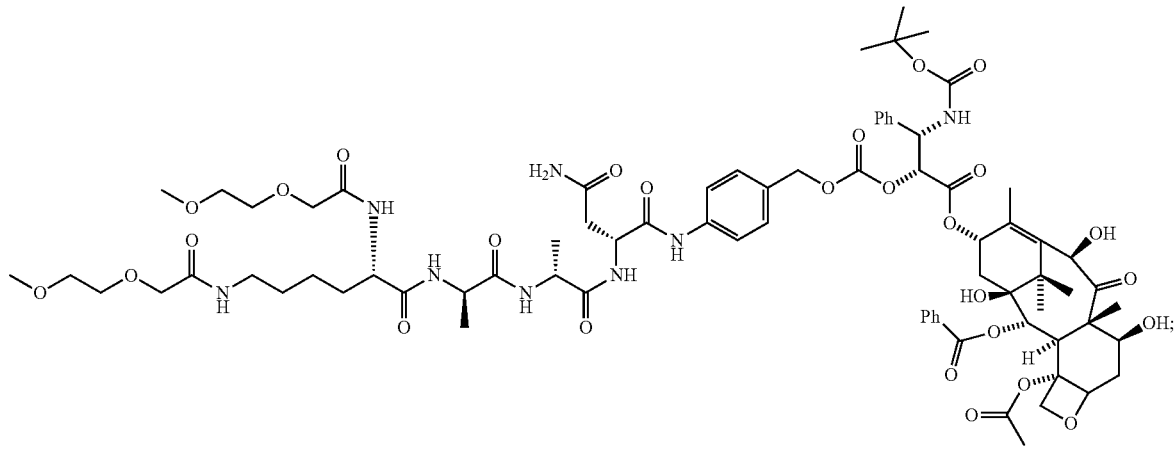

(2) Compound B2 in which n is 5, R₂ is Ala and R₃ is Ala
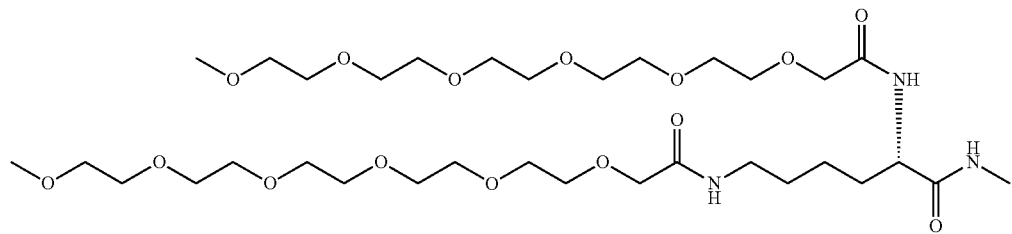
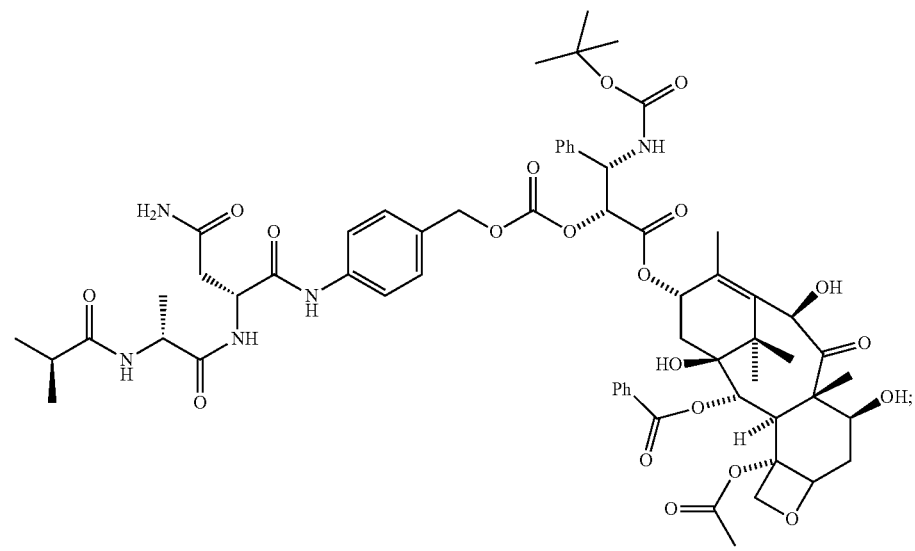
(3) Compound B3 in which n is 11, R₂ is Ala and R₃ is Ala
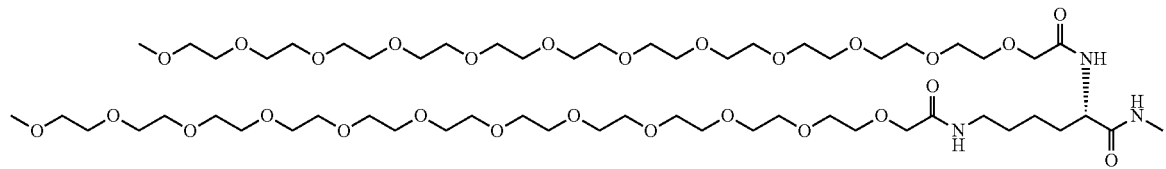
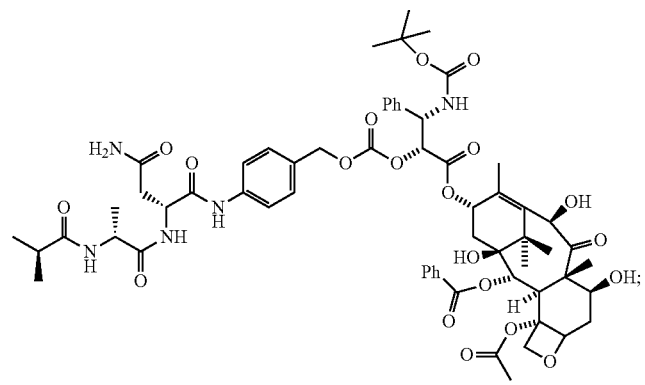

(4) Compound B4 in which n is 150, $R_2$ is Ala and $R_3$ is Ala

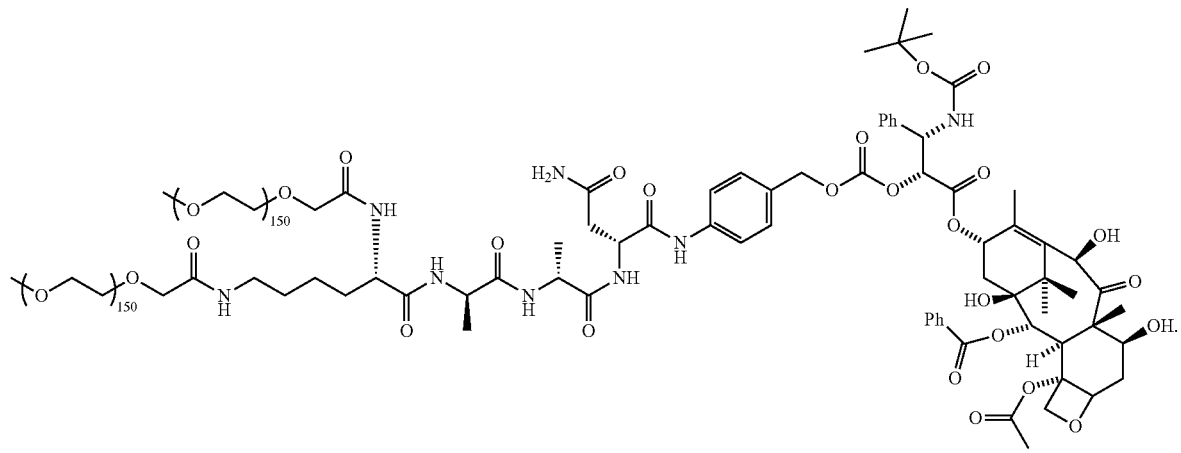

Compounds of formula (VII) further comprise the following compounds:

| No. of Compound | $R_2$ | $R_3$ | n |
|---|---|---|---|
| B10 | Ala | Thr | 5 |
| B11 | Ala | Val | 5 |
| B12 | Ala | Asn | 5 |
| B13 | Thr | Ala | 5 |
| B14 | Thr | Thr | 5 |
| B15 | Thr | Val | 5 |
| B16 | Thr | Asn | 5 |
| B17 | Val | Ala | 5 |
| B18 | Val | Thr | 5 |

-continued

| No. of Compound | $R_2$ | $R_3$ | n |
|---|---|---|---|
| B19 | Val | Val | 5 |
| B20 | Val | Asn | 5 |
| B21 | Ile | Ala | 5 |
| B22 | Ile | Thr | 5 |
| B23 | Ile | Val | 5 |
| B24 | Ile | Asn | 5 |

The present disclosure further provides a Docetaxel derivative for targeted activation of tumor microenvironment, which has a structure as set forth in the following formula (VIII):

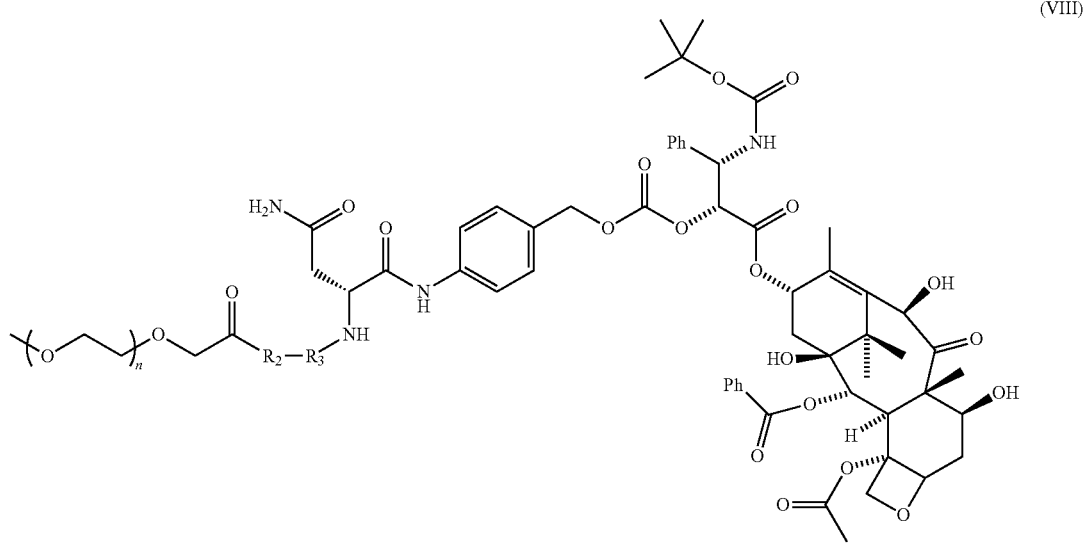

(VIII)

wherein $R_2$ is any one amino acid selected from the group consisting of Ala, Thr, Val and Ile; $R_3$ is any one amino acid selected from the group consisting of Ala, Thr, Val and Asn; n is any integer between 1-300, preferably between 1-150, more preferably between 1-20, and most preferably between 1-11.

Compounds of formula (VIII) include:
(1) Compound D1, in which n is 1, $R_2$ and $R_3$ are Ala
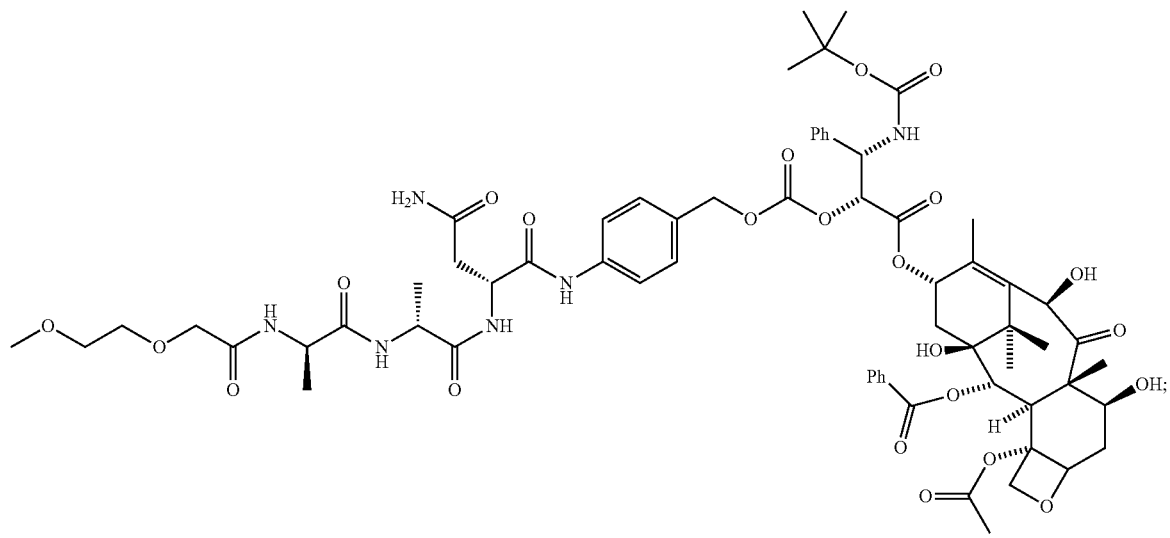
(2) Compound D2, in which n is 5, $R_2$ and $R_3$ are Ala
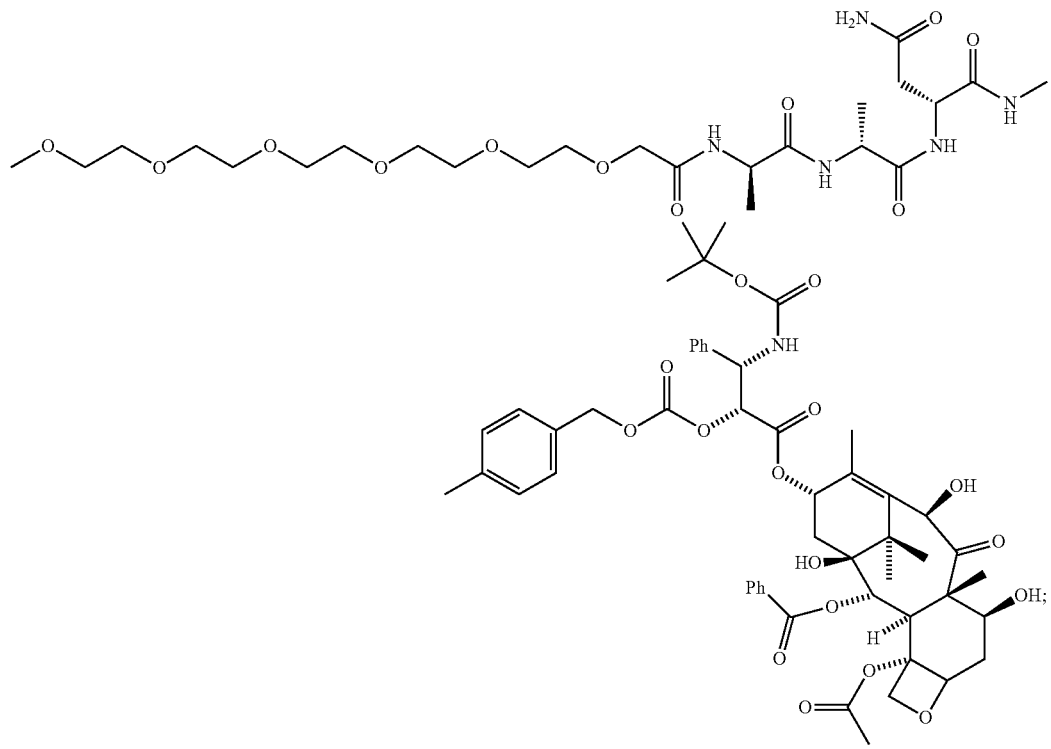
(3) Compound D3, in which n is 11, $R_2$ and $R_3$ are Ala
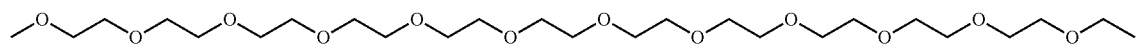

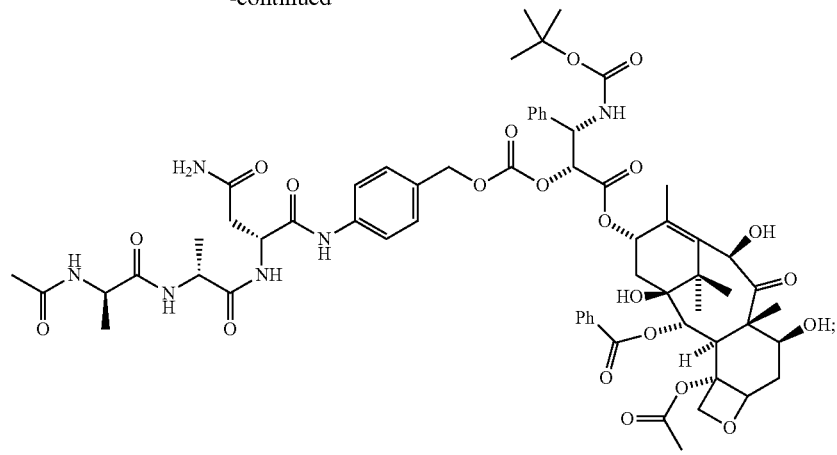

(4) Compound D4, in which n is 300, R₂ and R₃ are Ala

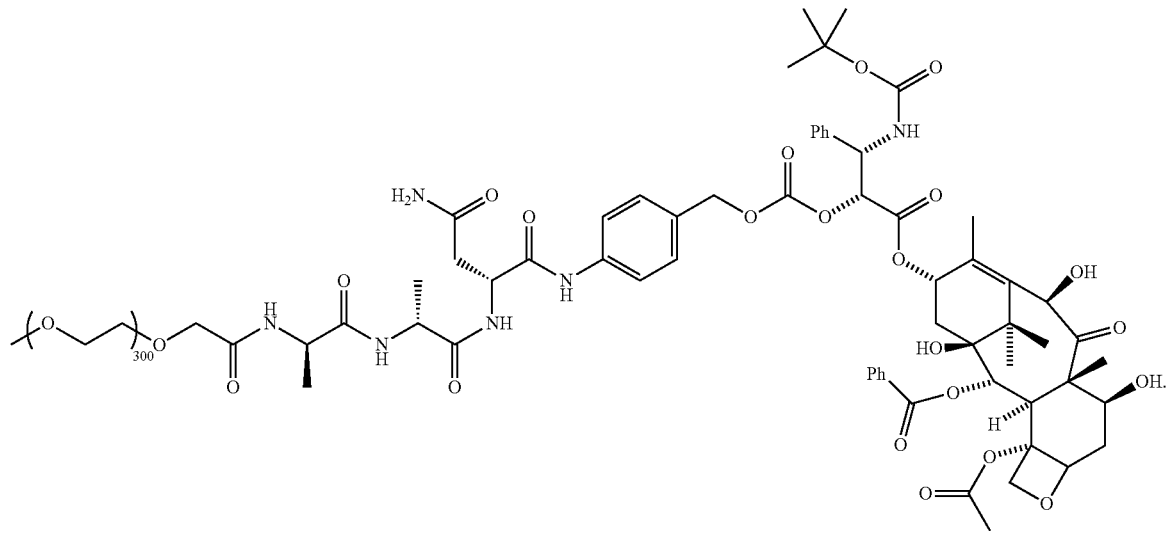

Other compounds of formula (VIII) comprise the following compounds:

| No. of Compound | R₂ | R₃ | n |
| --- | --- | --- | --- |
| D10 | Ala | Thr | 1 |
| D11 | Ala | Val | 1 |
| D12 | Ala | Asn | 1 |
| D13 | Thr | Ala | 1 |
| D14 | Thr | Thr | 1 |
| D15 | Thr | Val | 1 |
| D16 | Thr | Asn | 1 |
| D17 | Val | Ala | 1 |
| D18 | Val | Thr | 1 |
| D19 | Val | Val | 1 |
| D20 | Val | Asn | 1 |
| D21 | Ile | Ala | 1 |
| D22 | Ile | Thr | 1 |
| D23 | Ile | Val | 1 |
| D24 | Ile | Asn | 1 |

In one embodiment, the present disclosure provides a mitomycin derivative for release by targeted activation having a structure shown in the following formula (IX):

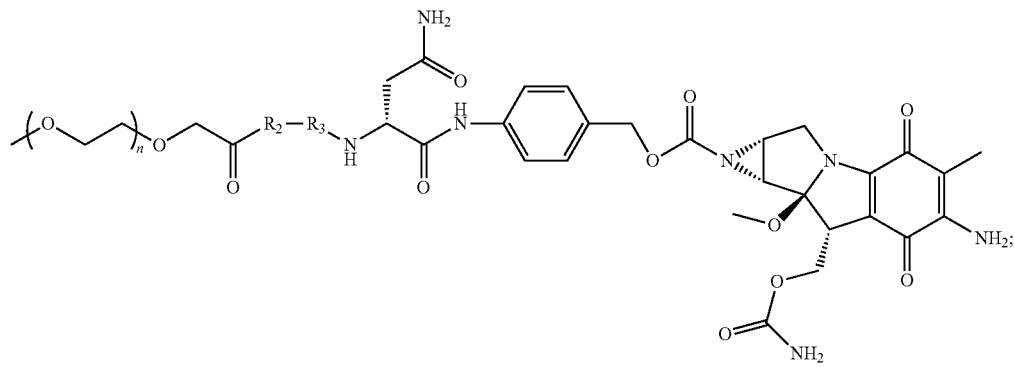

(IX)

wherein $R_2$ is any amino acid selected from the group consisting of Ala, Thr, Val and Ile; $R_3$ is any amino acid selected from the group consisting of Ala, Thr, Val and Asn; n is any integer between 1-300, preferably between 1-150, more preferably between 1-20, and most preferably between 1-11.

Examples of compounds of formula (IX) include:
(1) Compound E1, in which n is 1 and $R_2$ and $R_3$ are Ala

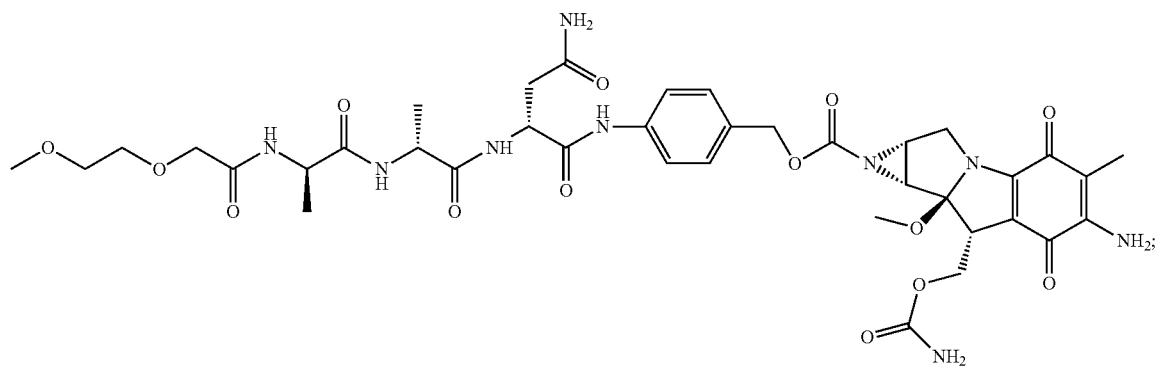 [SMILES: COCCOCC(=O)N[C@H](C)C(=O)N[C@H](C)C(=O)N[C@H](CC(N)=O)C(=O)Nc1ccc(COC(=O)N2[C@@H]3CN4C5=C(C(=O)C(N)=C(C)C5=O)[C@H](COC(N)=O)[C@]4(OC)[C@@H]32)cc1]

(2) Compound E2, in which n is 5 and $R_2$ and $R_3$ are Ala

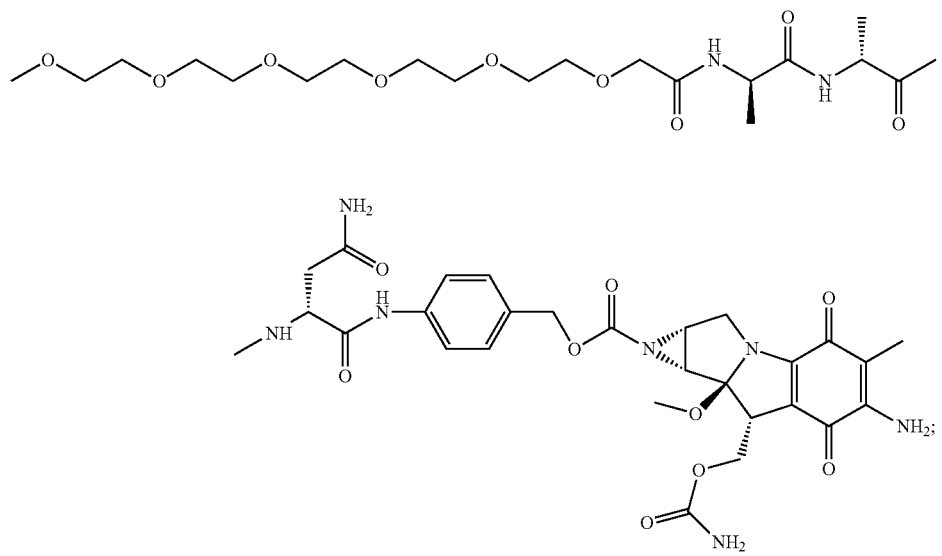

(3) Compound E3, in which n is 11 and $R_2$ and $R_3$ are Ala

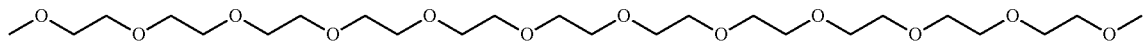

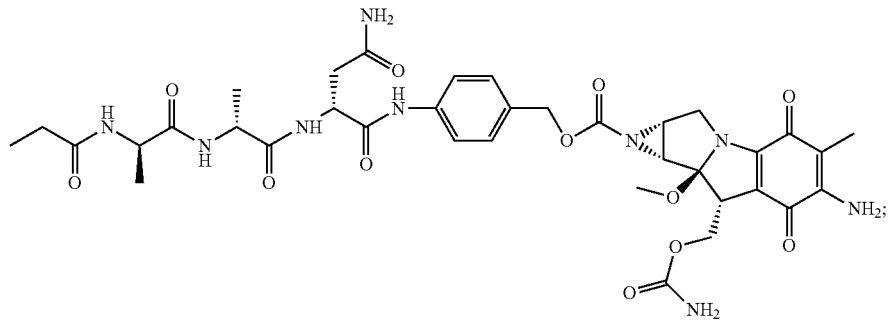

(4) Compound E4, in which n is 300 and $R_2$ and $R_3$ are Ala

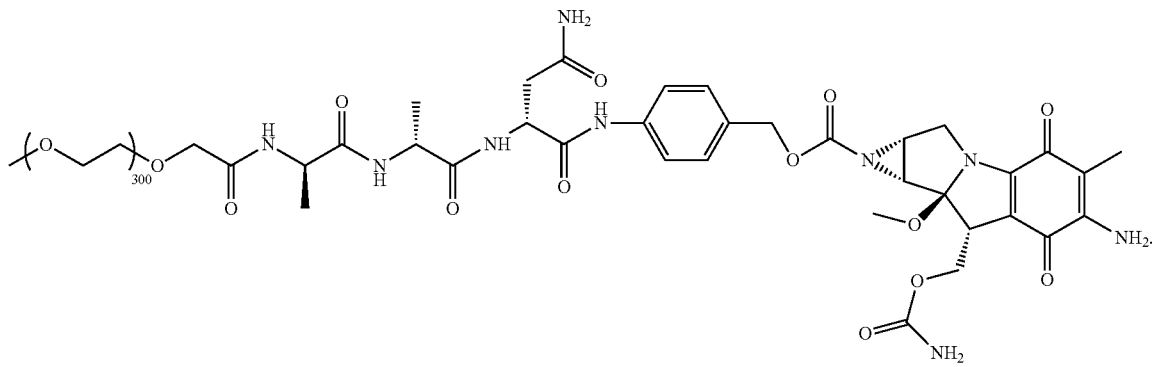

Examples of compounds of formula (XI) further comprise:

| No. of Compound | $R_2$ | $R_3$ | n |
|---|---|---|---|
| E10 | Ala | Thr | 1 |
| E11 | Ala | Val | 1 |
| E12 | Ala | Asn | 1 |
| E13 | Thr | Ala | 1 |
| E14 | Thr | Thr | 1 |
| E15 | Thr | Val | 1 |
| E16 | Thr | Asn | 1 |
| E17 | Val | Ala | 1 |
| E18 | Val | Thr | 1 |
| E19 | Val | Val | 1 |
| E20 | Val | Asn | 1 |
| E21 | Ile | Ala | 1 |
| E22 | Ile | Thr | 1 |
| E23 | Ile | Val | 1 |
| E24 | Ile | Asn | 1 |

The pharmaceutically acceptable salt of the above compounds are also included in the present disclosure. Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts with bases, such as sodium hydroxy, Tris (hydroxymethyl) aminomethane (TRIS, tromethamine) and N-methyl-glucamine.

II. Preparation of Compounds $R_1$-$R_2$-$R_3$-Asn-4-amino benzyl alcohol is used as the key intermediate in the present disclosure to prepare the present compounds. Preferably, the reaction schemes for preparing the present compound are as follows:

Scheme 1

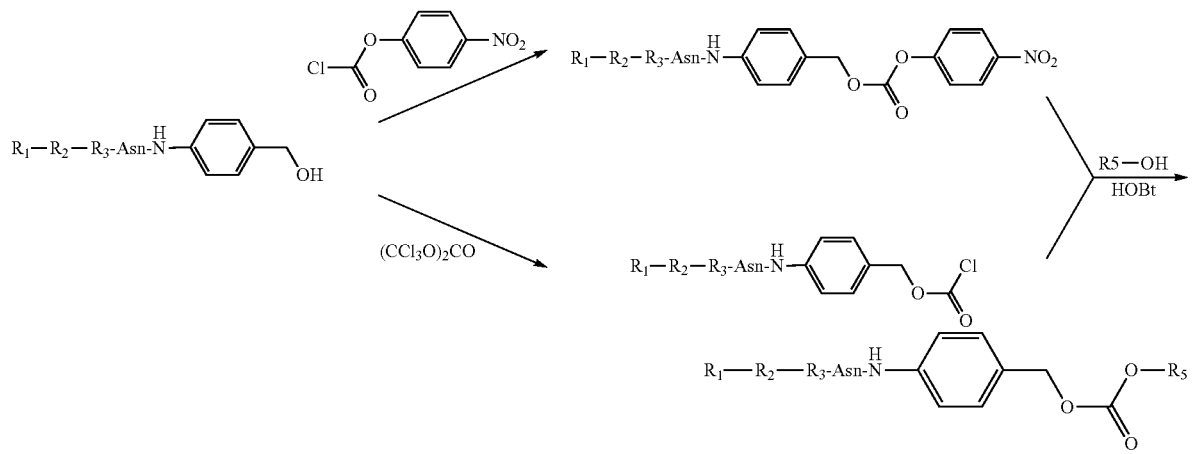

Scheme 2

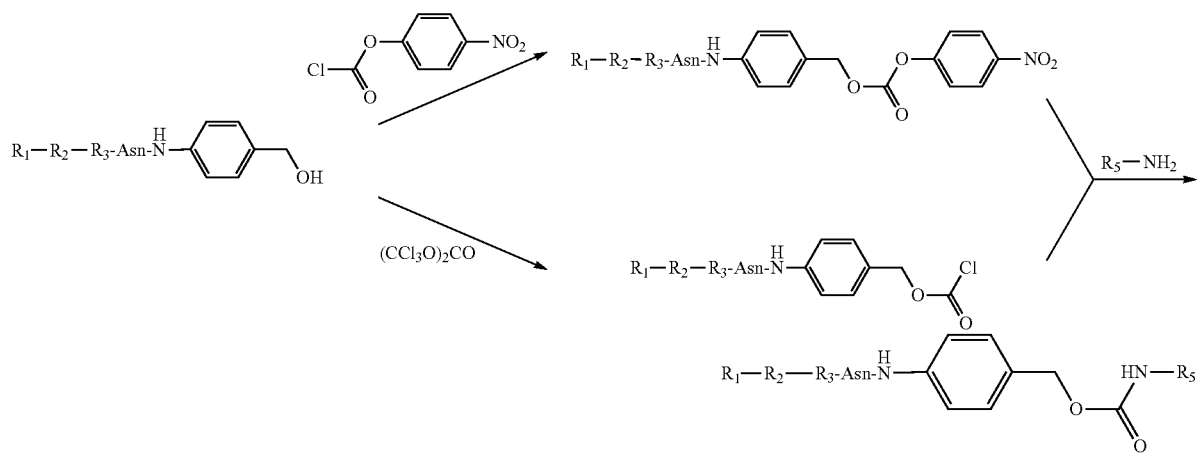

In Scheme 1, after reacting $R_1$-$R_2$-$R_3$-Asn-4-amino benzyl alcohol with 4-nitrophenyl chloroformate or $(CCl_3O)_2CO$ to form an active carbonic acid ester bond or chloroformate, the active carbonic acid ester bond or chloroformate is reacted with the drug comprising a hydroxyl group ($R_5$—OH) to form a carbonic acid diester product, which is also a conjugate. Scheme 1 can be used to prepare compounds in which $R_4$ is Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Paclitaxel or Docetaxel.

In Scheme 2, after reacting $R_4$-$R_2$-$R_3$-Asn-4-amino benzyl alcohol with 4-nitrophenyl chloroformate or $(CCl_3O)_2CO$ to form an active carbonic acid ester bond or chloroformate, the active carbonic acid ester bond or chloroformate is reacted with the drug comprising an amino group ($R_6$—$NH_2$) to form a carbonic acid diester product, which is also a conjugate. Scheme 2 can be used to prepare compounds in which $R_4$ is Daunorubicin, Epirubicin, Methotrexate, Fludarabine, Gemcitabine, Cytarabine, Melphalan, Nimustine, Mitoxantrone or Mitomycin.

Other reagents, reaction conditions, purification methods, etc., used in the above preparation methods will be apparent to the skilled artisan after reading the preparation examples disclosed herein.

III. Pharmaceutical Composition

The present disclosure comprises a pharmaceutical composition comprising a compound of any of the above structural formulae or a pharmaceutically acceptable salt thereof.

The pharmaceutical composition may further comprise a pharmaceutically acceptable carrier or excipient. The carrier or excipient may be various pharmaceutically acceptable carrier or excipient known in the art and can be varied according to the dosage form or administration route.

In one embodiment, the pharmaceutical composition may comprise one or more of solvents, solubilizer/co-solvent, pH adjustor, freeze-dried excipient and osmo-regulator.

Freeze-dried excipient suitable for use in the present disclosure includes one or more of sugars, such as lactose, maltose, dextran, glucose and fructose; amino acids, such as arginine, lysine and histine; mannitol; tartaric acid; maleic acid; citric acid; sodium chloride; and cyclodextrin, such as hydroxypropyl beta cyclodextrin and sulfobutyl beta cyclodextrin.

pH regulator suitable for use in the present disclosure includes one or more of hydrochloric acid, phosphoric acid, sulfuric acid, carbonic acid, nitric acid, acetic acid, citric acid, DL-tartaric acid, D-tartaric acid, L-tartaric acid, NaOH, KOH, meglumine, maleic acid, ethylene diamine, triethylamine, arginine, lysine, histine, $NaH_2PO_4$ and $Na_2HPO_4$.

Solvent suitable for use in the present disclosure preferably is an organic solvent, including one or more of ethanol, propylene glycol, polyethylene glycol 300, polyethylene glycol 400, t-butyl alcohol, glycerin, Tween, soybean oil, hydroxylpropyl beta cyclodextrin solution and sulfobutyl beta cyclodextrin solution.

Osmo-regulator suitable for use in the present disclosure includes one or more of glucose, sodium chloride, mannitol and sodium lactate.

Solubilizer/co-solvent suitable for use in the present disclosure includes one or more of Tween 80, Tween 60, poloxamer, hydroxypropyl beta cyclodextrin, polyethylene glycol (PEG), lithium 12-hydroxy stearate, sulfobutyl beta cyclodextrin, PVP, glycerin and polyoxyethylene castor oil.

Typically, the compound of the present disclosure or its pharmaceutically acceptable salt thereof may be administered to mammals, orally at a dose of 0.0025 to 50 mg/kg of body weight, per day, preferably, approximately 0.01 to approximately 10 mg/kg of body weight. If a known anti-cancer agent or other treatments are also administered, they are administered in an amount that is effective to achieve their intended purpose. The amounts of such known anti-cancer agents effective for cancer are well known to those skilled in the art.

The unit oral dose may comprise from approximately 0.01 mg to approximately 50 mg, preferably approximately 0.1 mg to approximately 10 mg of the compound of the invention or its pharmaceutically acceptable salt. The unit dose may be administered one or more times daily, as one or more tablets, each containing from approximately 0.1 mg to approximately 50 mg, conveniently approximately 0.25 mg to 10 mg of the compound or its pharmaceutically acceptable salt.

The pharmaceutical composition of the present disclosure may be formulated into any suitable dosage forms, including but is not limited to tablet, capsule and injection, etc. The pharmaceutical composition of the present disclosure may be administered via known routes in the art, including oral administration, intravenous injection, intramuscular injection, etc.

IV. Use of Compound and Pharmaceutical Composition

Cytokines secreted by tumor induce mononuclear cells to transform to tumor associated macrophages (TAM). Tumor associated macrophage could be stimulated to product strong immunosuppression and could directly help the tumor cells to infiltrate and metastasize. Expression of asparagine endopeptidase can distinguish the tumor-associated macrophage (M2 type) from the mononuclear cell and the inflammatory macrophage (M1 type). The compounds of the subject invention can be activated to release in the presence of asparagine endopeptidase. Since different moieties in the conjugate specifically activated by asparagine endopeptidase could greatly affect the targeting, activation, stability, toxicity and efficacy and the like of the final drug, using the conjugate specifically activated by asparagine endopeptidase of the present disclosure could effectively reduce the toxicity of the linked drug, bring new targeting, activation and metabolism properties for the final drug, increase treatment effect on tumor, produce new adaptive tumor diseases and prevent tumor from metastasis. Thus, new structure and function could be produced.

It is also found in the present disclosure that the conjugates releasable in the tumor microenvironment, such as compounds of formulae (III) to (IX) could kill tumor associated macrophage, weaken immunosuppressive cytokines in the microenvironment, and promote release of toxic CD8 cells to improve the immunization. More importantly, these compounds releasable in the tumor microenvironment could only be activated in the tumor site, which is different from the traditional chemotherapeutic drugs which impair the whole immune system. In the experiments, the compounds releasable in the tumor microenvironment and programmed death-1 (PD-1) inhibitory antibody (PDL1 antibody, which is commercially available and considered as a candidate having immunological treatment effect at present) show strong synergistic treatment and thus could solve the problem that immunological treatment is difficult to be used in combination with chemotherapeutic drug.

Therefore, the compound, its pharmaceutically acceptable salt or the pharmaceutical composition of the present disclosure could be used to treat or prevent various diseases that were known to be treated by Camptothecin, 10-Hydroxyl Camptothecin, Topotecan, Floxuridine, 5'-Deoxy-5-Fluo-rouridine, Cytarabine, Etoposide, Fludarabine, Capecitabine, Vincristine, Epothilone B, Paclitaxel, Docetaxel, Daunorubicin, Epirubicin, Methotrexate, Gemcitabine, Melphalan, Nimustine, Mitoxantrone, or Mitomycin, including cancer and ophthalmic diseases.

For example, it is known in the art that camptothecin can be used to treat or prevent malignant tumor, psoriasis, wart, acute/chronic leukaemia and hepatosplenomegaly caused by schistosomiasis; 10-hydroxyl camptothecin can be used to treat or prevent stomach cancer, liver cancer, head and neck cancer and leukaemia, etc.; paclitaxel is mainly used to treat ovarian cancer and breast cancer, and is also effective in treating lung cancer, intestinal cancer, melanoma, head and neck cancer, lymphoma, brain cancer, etc; and mitomycin can be used to chronic lymphoma, chronic myeloid leukemia, esophageal carcinoma, stomach cancer, colon cancer, rectal cancer, lung cancer, pancreatic cancer, liver cancer, cervical cancer, cancer of the uterus, ovarian cancer, breast cancer, tumor at head and neck, bladder tumor and malignant cavity effusion, etc.

Therefore, for example, diseases that can be treated or prevented by the compound, its pharmaceutically acceptable salt or the pharmaceutical composition of the present disclosure include but is not limited to cancer in bladder, brain, breast/mammary gland, cervix, colon-rectum, oesophagus, kidney, liver, lung, nasopharynx, pancreas, prostate, skin, stomach, uterus, ovary, testicle and blood. Specifically, the cancer includes bladder cancer, brain cancer, breast cancer or mammary cancer, cervical cancer, colon-rectal cancer, esophageal carcinoma, renal cancer, liver cancer, lung cancer, nasopharyngeal carcinoma, pancreatic cancer, prostate cancer, skin cancer, stomach cancer, uterus cancer, ovarian cancer, testicular cancer and blood cancer.

In one specific embodiment, the mitomycin derivative as shown in formula (IX) or a pharmaceutically acceptable thereof of the present disclosure can be used to treat or prevent an ophthalmic disease, including treating or preventing scar after healing, choroidal neovascularization, or inhibiting macrophage. In other examples, the mitomycin derivative as shown in formula (IX) can also be used to treat or prevent corneal transplantation, glaucoma, sequelae of pterygium surgery, etc.

The compound or pharmaceutical composition of the present disclosure can also be used to prevent tumor metastasis, especially metastasis of tumor to lung. In one example, the compound or pharmaceutical composition of the present disclosure can be used to prevent metastasis of mammary cancer to lung.

Therefore, the present disclosure comprises a method for treating or preventing a disease, comprising administering a subject in need thereof a therapeutically or prophylactically effective amount of the compound of the present disclosure or a pharmaceutically acceptable salt thereof, or the pharmaceutical composition comprising the compound of the present disclosure or a pharmaceutically acceptable salt thereof.

The present disclosure also comprises a method for preventing tumor metastasis, comprising administering a subject in need thereof the compound of the present disclosure or a pharmaceutically acceptable salt thereof, or the pharmaceutical composition comprising the compound of the present disclosure or a pharmaceutically acceptable salt thereof. Prevention of tumor metastasis comprising preventing tumor for metastasizing to lung and/or bone.

Tumor associated macrophage (TAM) is a key inflammatory cell, playing crucial role in tumor associated inflammation. In the tumor microenvironment, TAM promotes tumor development through affecting various biological properties of tumor. It secretes some molecules, such as EGF, to directly promote growth of tumor cell and angiogenesis, thereby promoting tumor infiltration and metastasis and inhibiting functionating of acquired immunity. Accordingly, the present invention comprises a method for inhibiting tumor associated macrophage, comprising administering a subject in need thereof the compound or a pharmaceutically acceptable salt thereof of the present disclosure, or the pharmaceutical composition comprising the compound or a pharmaceutically acceptable salt thereof of the present disclosure. By inhibiting tumor associated macrophage, tumor growth, angiogenesis, infiltration and metastasis of cancer cell can be inhibited, and anti-tumor immunization can be promoted, thus cancer can be treated and/or prevented. In one specific embodiment, the tumor associated macrophage expresses aspartate endopeptidase and is a M2 type cell.

The above-mentioned methods of the present disclosure can be used in combination with any radiotherapy or immunotherapy known in the art.

Therefore, the present disclosure also comprises compounds, their pharmaceutically acceptable salts or pharmaceutical composition of the present disclosure useful in the above-mentioned methods and uses.

The present disclosure also comprises use of the compound of the present disclosure, its pharmaceutically acceptable salt or the pharmaceutical composition of the present disclosure in the manufacture of a medicament for treating or preventing the above disease, such as cancer and cancer metastasis. The present disclosure also comprises use of the compound of the present disclosure or a pharmaceutically acceptable salt thereof or the pharmaceutical composition of the present disclosure in the manufacture of a medicament for inhibiting tumor-associated macrophages, tumor growth, angiogenesis or infiltration and metastasis of tumor cells, or promoting anti-tumor immunization.

The present disclosure further provides a method for reducing the toxicity of an anticancer compound ($R_4$—H), comprising linking the anticancer compound to $R_1$-$R_2$-$R_3$, wherein $R_1$, $R_2$ and $R_3$ are defined as above.

The method for treatment or prevention of the present disclosure comprises administering the compound or pharmaceutical composition of the present disclosure to the subject in need thereof. Administration route includes but is not limited to oral administration, intravenous inject, and intramuscular injection, etc. Subject includes mammal, especially human.

It should be understood that the "comprise" and "include" used herein also include "consist of". The sum of all weight percentages or volume percentages should be equal to 100%. Unless specifically indicated, various reagents and products used in the Examples are commercially available. And unless specifically indicated, the methods are performed according to the conventional techniques. The following Examples are not intended to limit the scope of the present disclosure.

V. Examples

The technical solutions of the present disclosure are further illustrated in connection with the following examples.

Example 1: Synthesis of Chemical Intermediates

1) Synthesis of
N—(N-benzyloxycarbonyl-L-alanyl)-L-Ala methyl ester (I)

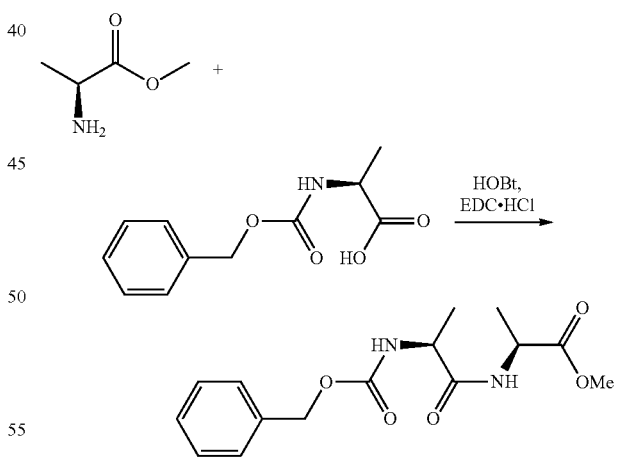

N-benzyloxycarbonyl-L Ala (100 g, 0.45 mol) were dissolved in N,N-dimethylformamide (3 L). 1-hydroxylbenzotriazole (HOBt, 72.6 g, 0.54 mol) and 1-ethyl-(3-dimethylaminopropyl) carbodiimide hydrochloride (EDC, 103.3 g, 0.54 mol) were added when stirring. After reacting for 1 hour under stirring, the mixture was cooled to 0□ in an ice bath and L-Ala methyl ester (46.2 g, 0.45 mol) and N,N-diisopropylethylamine (173.8 g, 1.34 mol) in the N,N-dimethylformamide solution (1 L) was dropped into the mixture. After dropping, the mixture was stirred under ambient temperature for 10 hours. The solvents were removed by evaporation under reduced pressure. The crude product was dissolved in dichloromethane (2 L) and washed subsequently by saturated ammonium chloride solution, water and saturated sodium chloride solution. The organic phase was dried by anhydrous sodium sulphate. After removing the solvents by evaporation under reduced pressure, the crude product was recrystallized to obtain a white solid I (101 g, Yield 73.1%).

2) Synthesis of N—(N-benzyloxycarbonyl-L-alanyl)-L-Ala (II)

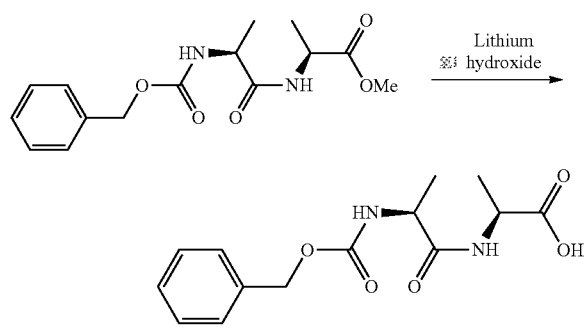

N—(N-benzyloxycarbonyl-L-alanyl)-L-Ala methyl ester (100 g, 0.34 mol) were dissolved in a mixed solution of tetrahydrofuran (2 L) and water (1 L). The mixture was cooled to 0□ and 1M lithium hydroxide solution (400 mL) were dropped into the mixture. The resultant mixture was stirred for reaction for 10 hours. Concentrated hydrochloric acid was dropped to adjust the pH to be less than 6. Most of tetrahydrofuran were removed by rotary evaporation. The residual water phase was extracted by dichloromethane (1 L×3). The organic phase was dried by anhydrous sodium sulphate. A white solid II was obtained after vaporizing and drying under reduced pressure (88 g; Yield, 92.2%).

3) Synthesis of 4-N—(N-fluorenylmethoxycarbonyl-N'-triphenylmethyl-L-asparaginyl)-amino benzyl alcohol (III)

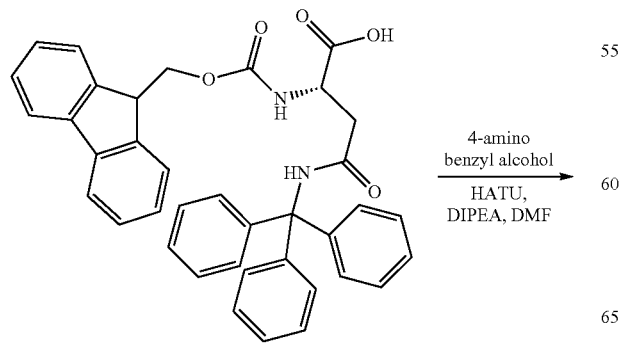

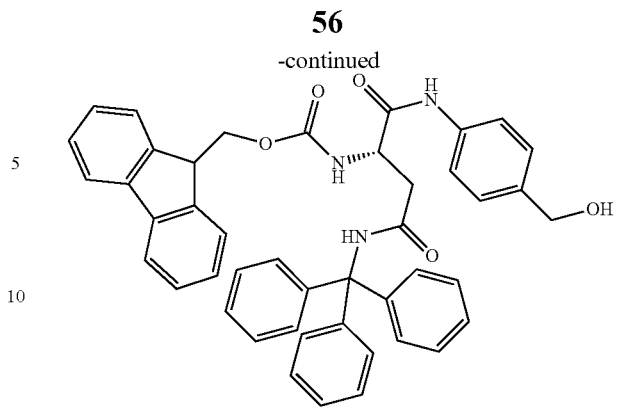

N-fluorenylmethoxycarbonyl-N'-triphenylmethyl-L-asparagine (20 g, 0.03 mol), 2-(7-azabenzotriazol)-N,N,N',N'-tetramethyluronium hexafluorophosphate (HATU) (15 g, 0.04 mol), N,N-dimethylformamide (DMF) (200 mL) were added into a three-neck flask and stirred for 30 minutes. A solution of 4-amino benzyl alcohol (4.1 g, 0.03 mol) in DMF (5 mL), and N,N-diisopropyl ethylamine (DIPEA) (8.7 g, 0.06 mol) were added separately under 0° C. and the mixture was stirred at ambient temperature for 3 hours. Most DMF were removed by rotary evaporation. The residue was dissolved in ethyl acetate (200 mL), washed subsequently by saturated ammonium chloride solution and saturated sodium chloride solution and dried by anhydrous sodium sulphate. After filtration, the solvent was removed by evaporation. The resultant crude product was pulping to obtain a white solid III (21.3 g, Yield 90%).

4) Synthesis of 4-N—(N'-triphenylmethyl-L-asparaginyl)-amino benzyl alcohol (IV)

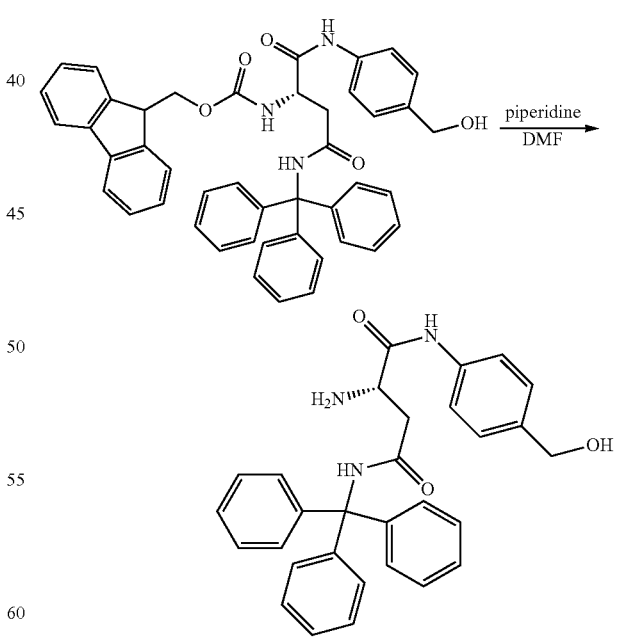

4-N—(N-fluorenylmethoxycarbonyl-N'-triphenylmethyl-L-asparaginyl)-amino benzyl alcohol (13.0 g, 18 mmol) were dissolved in N,N-dimethylformamide (80 mL). Piperidine (30 mL) was added and then stirred at ambient temperature for 2 hours. The solvents were removed by evaporation under reduced pressure. And the resultant product was dried under high vacuum within a vacuum drying oven to remove a small quantity of piperidine. A pale yellow solid IV was obtained, which could be use in the next step without purification.

5) Synthesis of 4-N—(N—(N—(N-benzyloxycarbonyl-L-alanyl)-L-alanyl)-N'-triphenylmethyl-L-asparaginyl)-amino benzyl alcohol (V)

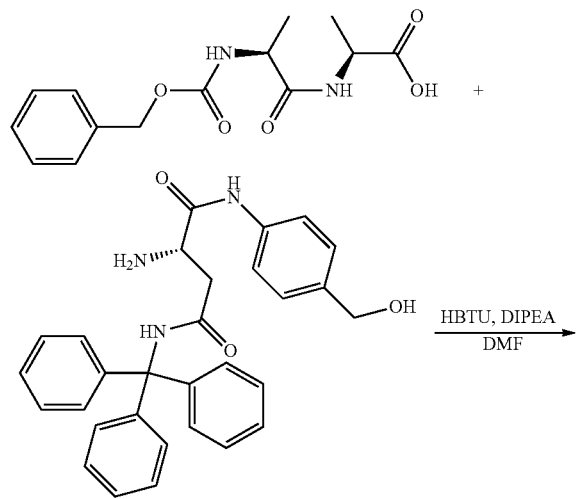

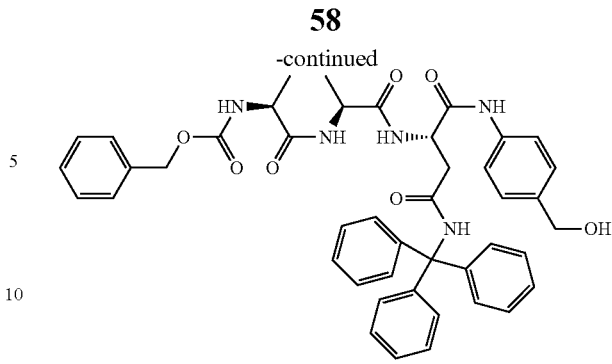

N—(N-benzyloxycarbonyl-L-alanyl)-L-Ala (6.0 g, 20.4 mmol), benzotriazol-N,N,N',N'-tetramethyluronium hexafluorophosphate (HBTU, 11.6 g, 30.6 mmol) and DMF (50 mL) were added into a three-neck flask and stirred for 30 minutes in an ice bath. A solution of 4-N—(N'-triphenylmethyl-L-asparaginyl)-amino benzyl alcohol in DMF (50 mL), and N,N-diisopropylethylamine (7.89 g, 61.2 mmol) were added separately under 0° C. The resultant mixture was stirred overnight at ambient temperature. The solvents were removed by evaporation under reduced pressure. The residue was dissolved in ethyl acetate (200 mL), washed subsequently by saturated ammonium chloride solution and saturated sodium chloride solution and dried by anhydrous sodium sulphate. After filtration, the solvent was removed by evaporation. The resultant crude product was recrystallized to obtain a white solid V (15 g, Yield 97%).

6) Synthesis of 4-N—(N-(L-alanyl)-L-alanyl)-N'-triphenylmethyl-L-asparaginyl)-amino benzyl alcohol (VI)

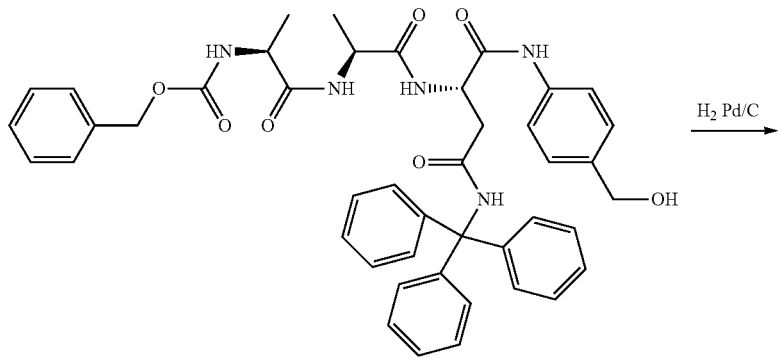

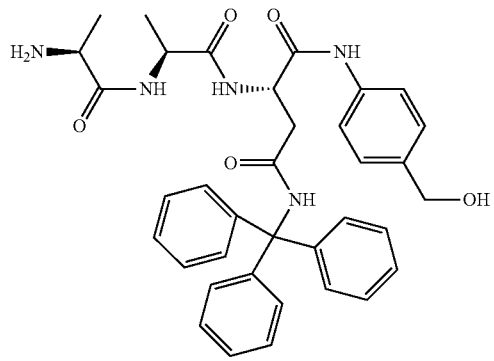

4-N—(N—(N—(N-benzyloxycarbonyl-L-alanyl)-L-alanyl)-N'-triphenylmethyl-L-asparaginyl)-amino benzyl alcohol (5.0 g, 6.61 mmol) were dissolved in THF (150 mL). 10% Pd/C (1 g) was added. After introducing hydrogen gas, the resultant mixture was stirred for reaction under normal temperature and normal pressure for 5 hours. Pd/C was removed by filtration and washed by methanol. The filtrates and the washing solutions were pooled. Most solvents were removed by rotary evaporation to obtain a crude product. After column chromatography, a white solid VI was obtained (2.0 g, Yield 49%).

7) Synthesis of 4-N—(N—N—(N-2-(2-methoxyethoxy) acetyl-L-alanyl)-L-alanyl)-N'-triphenylmethyl-L-asparaginyl)-amino benzyl alcohol (VII)

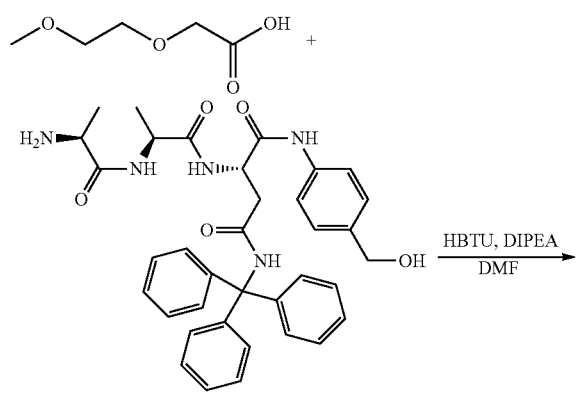

-continued

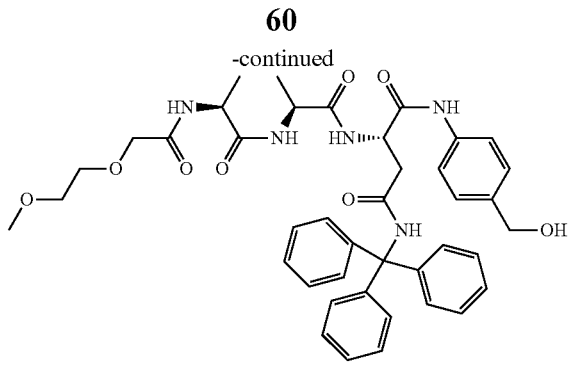

2-(2-methoxyethoxy) acetic acid (432 mg, 3.22 mmol) were dissolved in N,N-dimethylformamide (20 mL). Benzotriazol-N,N,N',N'-tetramethyluronium hexafluorophosphate (1.83 g, 4.83 mmol) were added and stirred for 30 minutes. Then 4-N—(N-(L-alanyl)-L-alanyl)-N'-triphenylmethyl-L-asparaginyl)-amino benzyl alcohol (2.0 g, 3.22 mmol) and N,N-diisopropylethylamine (1.24 g, 9.61 mmol) in N,N-dimethylformamide (20 mL) were dropped into the resultant mixture. After dropping, the temperature was slowly raised to ambient temperature and then the mixture was stirred for 10 hours. Most of DMF were removed by evaporation under reduced pressure. The residue was dissolved in acetyl acetate (200 mL), washed subsequently by saturated ammonium chloride solution and saturated sodium chloride solution and dried by anhydrous sodium sulphate. After filtration, the solvent was removed by rotary evaporation. The resultant crude product was purified by silica gel column chromatography to obtain a white solid VII (1.2 g, Yield 50%).

8) Synthesis of 4-N—(N—(N—(N-(2-(2-methoxyethoxy) acetyl-L-alanyl)-L-alanyl)-L-asparaginyl)-amino benzyl alcohol (VIII)

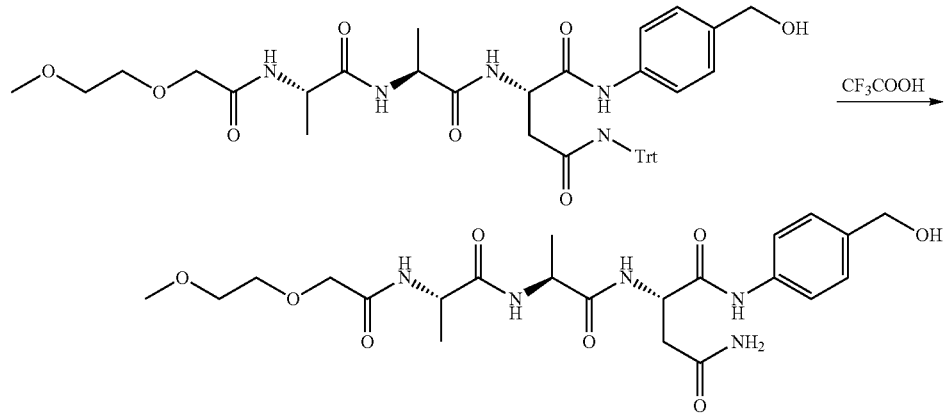

4-N—(N—N—(N-2-(2-methoxyethoxy) acetyl-L-alanyl)-L-alanyl)-N'-triphenylmethyl-L-asparaginyl)-amino benzyl alcohol (VII) (1.0 g, 1.36 mmol) were dissolved in dichloromethane (10 mL). Trifluoroacetic acid (2 mL) were added and then the resultant mixture was stirred at ambient temperature for 5 hours. The reaction solution was washed by water and separated. The organic phase was dried by anhydrous sodium sulphate and the solvents were removed by evaporation under reduced pressure. The residual trifluoroacetic acid was removed by evaporation under high vacuum. The resultant crude product was purified by column chromatography to obtain VIII (600 mg, Yield 89%).

9) Synthesis of 4-N—(N—(N—(N-(2-(2-methoxy-ethoxy) acetyl-L-alanyl)-L-alanyl)-L-asparaginyl)-amino benzyl alcohol-p-nitrophenol-carbonic acid diester

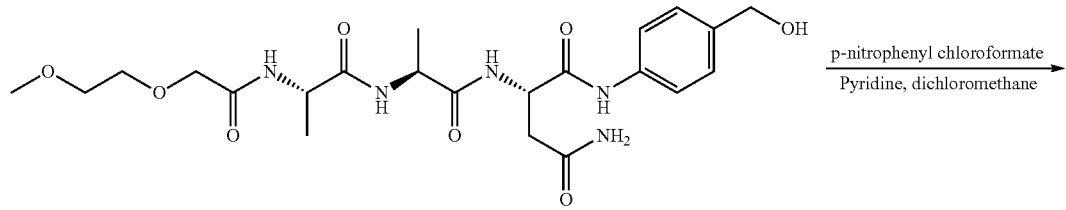

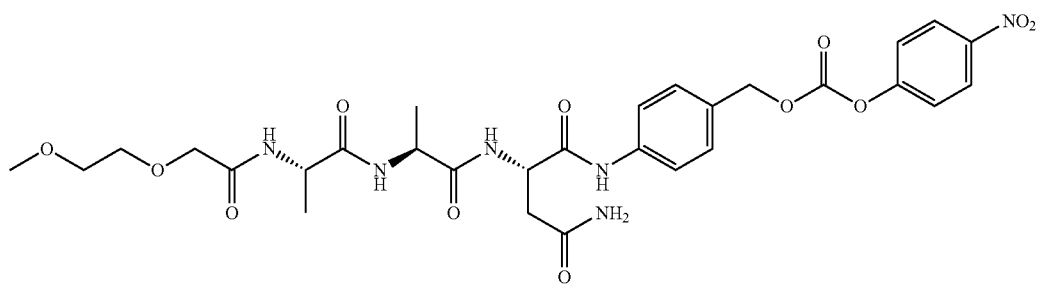

4-N—(N—(N—(N-(2-(2-methoxyethoxy) acetyl-L-alanyl)-L-alanyl)-L-asparaginyl)-amino benzyl alcohol (500 mg, 1.01 mmol) were dissolved in dichloromethane (10 mL). The resultant mixture was cooled to 5□. p-nitrophenyl chloroformate (406 mg, 2.02 mmol) in a dichloromethane solution and pyridine (160 mg, 2.03 mmol) were subsequently dropped into the mixture under protection by nitrogen gas. After dropping, the resultant mixture was stirred at ambient temperature overnight. The reaction solution was washed by water and separated. The organic phase was dried by anhydrous sodium sulphate and the solvents were removed by rotary evaporation. The resultant crude product was purified by column chromatography to obtain a pale yellow solid (450 mg, Yield 67%).

Example 2: Synthesis of 4-N—(N—(N—(N-(2-(2-methoxyethoxy) acetyl-L-threonyl)-L-alanyl)-L-asparaginyl)-amino benzyl alcohol-10-hydroxyl camptothecin-carbonic acid diester (S1)

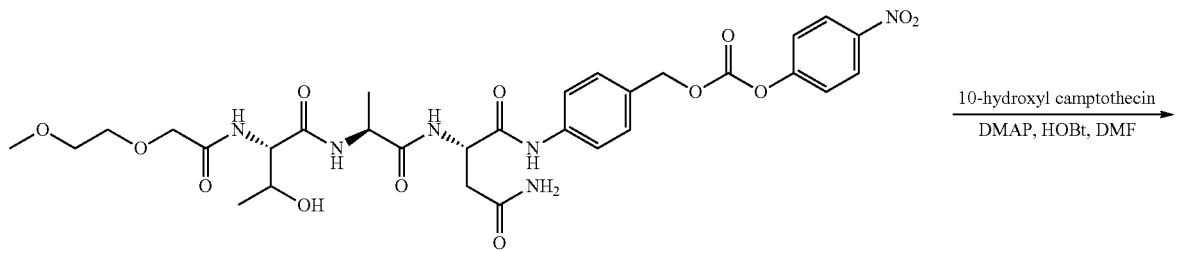

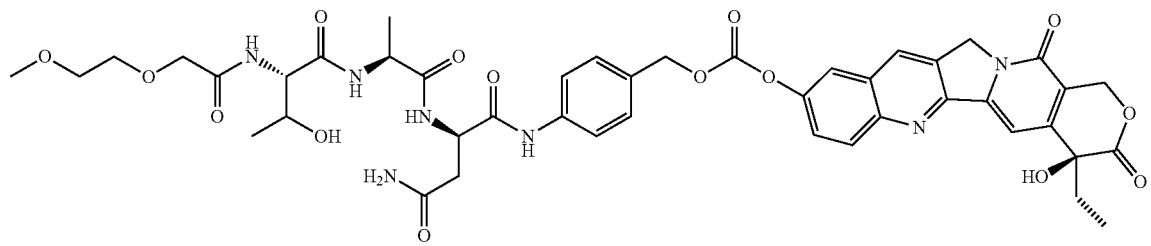

S1

4-N—(N—(N—(N-(2-(2-methoxyethoxy) acetyl-L-alanyl)-L-alanyl)-L-asparaginyl)-amino benzyl alcohol-p-nitrophenol-carbonic acid diester (330 mg, 0.5 mmol) and 10-hydroxyl camptothecin (182 mg, 0.5 mmol) were dissolved in anhydrous N,N-dimethylformamide (10 mL). The resultant mixture was cooled to 0□ and then 4-dimethyl pyridine (DMAP) (122 mg, 1.0 mmol) and 1-hydroxyl benzotriazole (27 mg, 0.2 mmol) were added. The resultant mixture was stirred at ambient temperature overnight. The reaction solution was poured into acetyl acetate (100 mL), washed subsequently by water (50 mL×3) and saturated sodium chloride (50 mL), and dried by anhydrous sodium sulphate. The solvents were removed by rotary evaporation to obtain a crude product. The crude product was purified by column chromatography to obtain the target product S1, which is a pale yellow solid (82 mg, Yield 19%).

Example 3: Synthesis of 4-N—(N—(N—(N-(2-(2-methoxyethoxy) acetyl-L-alanyl)-L-alanyl)-L-asparaginyl)-amino benzyl alcohol-camptothecin-carbonic acid diester (S2)

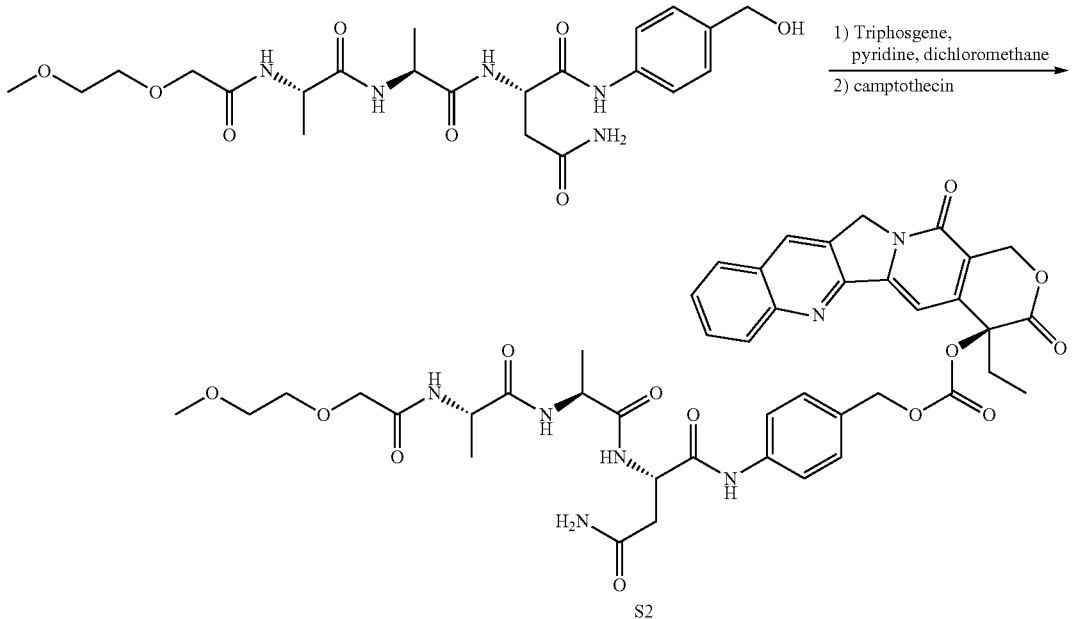

Triphosgene (600 mg, 2.02 mmol) were dissolved in anhydrous dichloromethane (10 mL). The resultant mixture was cooled to −10□ or below. 4-N—(N—(N—(N-(2-(2-methoxyethoxy) acetyl-L-alanyl)-L-alanyl)-L-asparaginyl)-amino benzyl alcohol (500 mg, 1.01 mmol) and pyridine (0.35 mL, 12.12 mmol) in dichloromethane (10 mL) were dropped into the mixture under protection by nitrogen gas and the resultant mixture was stirred at 0□ for 1 hour. The temperature of the mixture was allowed to warm up to ambient temperature naturally. After stirring for 2 hours, camptothecin (348 mg, 1 mmol) in dichloromethane (10 mL) were dropped into the mixture. Reaction was taken place at ambient temperature for 6 hours. The reaction solution was washed subsequently by water (30 mL), saturated sodium bicarbonate solution (20 mL) and saturated sodium chloride (20 mL), and dried by anhydrous sodium sulphate and then by evaporation under reduced pressure. The residue was purified by column chromatography to obtain a white solid (291 mg, Yield 53.5%).

Example 4: Synthesis of 4-N—(N—(N—(N-(8-(N-hydroxylamino)-1,8-octandioic acid-1-monoacyl)-L-alanyl)-L-alanyl)-L-asparaginyl)-amino benzyl alcohol-capecitabine-carbonic acid diester (S3)

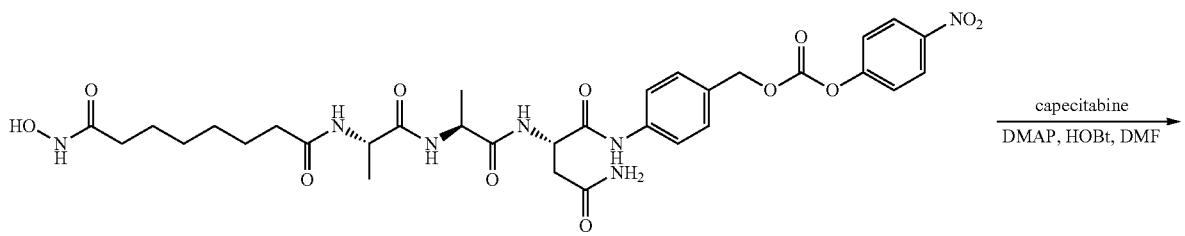

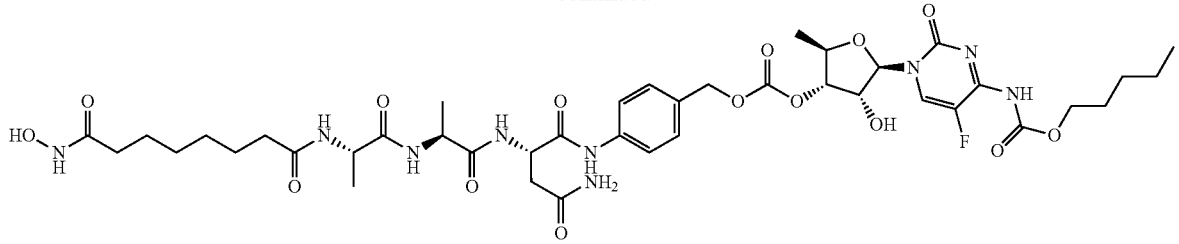

4-N—(N—(N—(N-(8-(N-hydroxylamino)-1,8-octandioic acid-1-monoacyl)-L-alanyl)-L-alanyl)-L-asparaginyl)-amino benzyl alcohol-p-nitrophenol-carbonic acid diester (715 mg, 1.0 mmol) and capecitabine (360 mg, 1.0 mmol) were dissolved by anhydrous N,N-dimethylformamide (20 mL) and cooled to 0☐ or below. Then DMAP (244 mg, 2.0 mmol) and 1-hydroxylbenzotriazole (27 mg, 0.2 mmol) were added. The resultant mixture was stirred at ambient temperature overnight. The reaction solution was poured into acetyl acetate (100 mL), washed subsequently by water (100 mL×3) and saturated sodium chloride (100 mL), and dried by anhydrous sodium sulphate. The solvents were removed by rotary evaporation to obtain a crude product. The crude product was purified by column chromatography to obtain the target product S3, which is a pale yellow solid (198 mg, Yield 21%).

Example 5: Synthesis of 4-N—(N—(N—(N-2-(2-methoxyethoxy) acetyl-L-threonyl)-L-alanyl)-L-asparaginyl)-amino benzyl alcohol-daunorubicin-carbamate (S4)

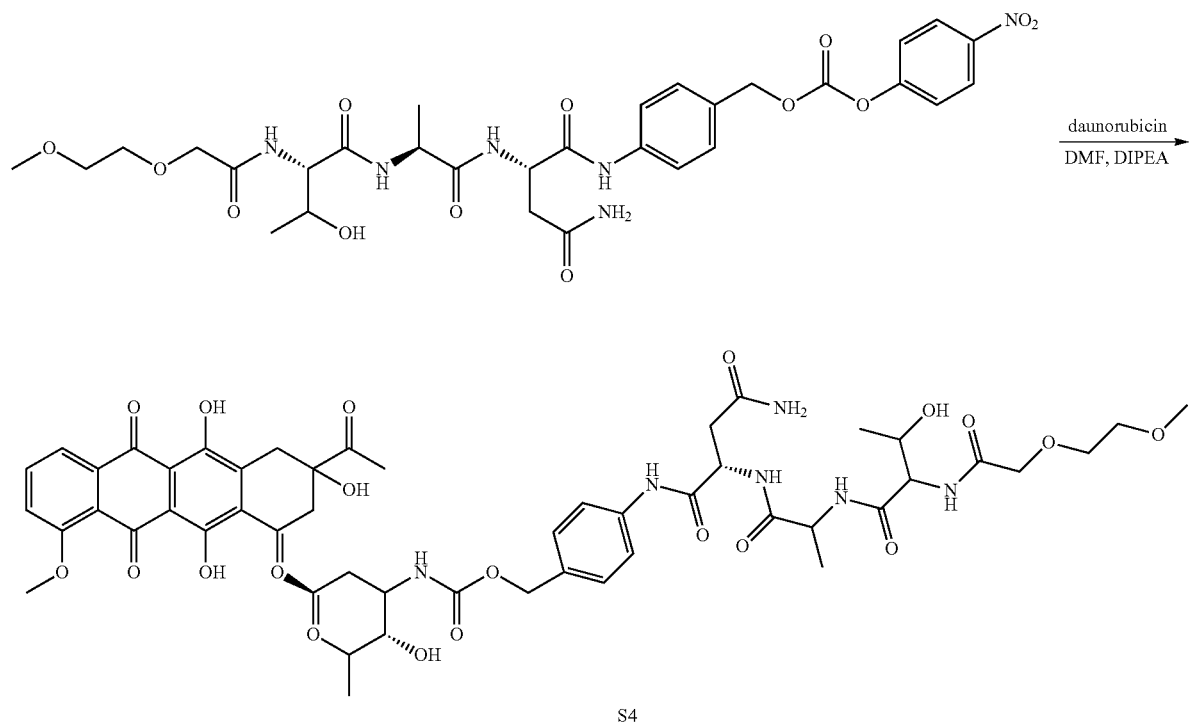

S4

4-N—(N—(N—(N-(2-(2-methoxyethoxy) acetyl-L-threonyl)-L-alanyl)-L-asparaginyl)-amino benzyl alcohol-p-nitrophenol-carbonic acid diester (264 mg, 0.4 mmol) and N,N-diisopropylethylamine (1 mL) were dissolved in N,N-dimethylformamide (10 mL). Daunorubicin (211 mg, 0.4 mmol) in a N,N-dimethylformamide (10 mL) solution were dropped into the resultant mixture at 20☐. After dropping, reaction was allowed to take place at ambient temperature for 3 hours. The reaction solution was poured into methyl tert-butyl ether, stirred for 0.5 hour and then filtered. The resultant red solid was purified by column chromatography to obtain a rid solid product S4 (177 mg, Yield 42.2%).

Example 6: Synthesis of Compound S5

1) Synthesis of 4-N—(N—(N—(N-(6-maleimido caproyl-L-alanyl)-L-alanyl)-N'-triphenylmethyl-L-asparaginyl)-amino benzyl alcohol

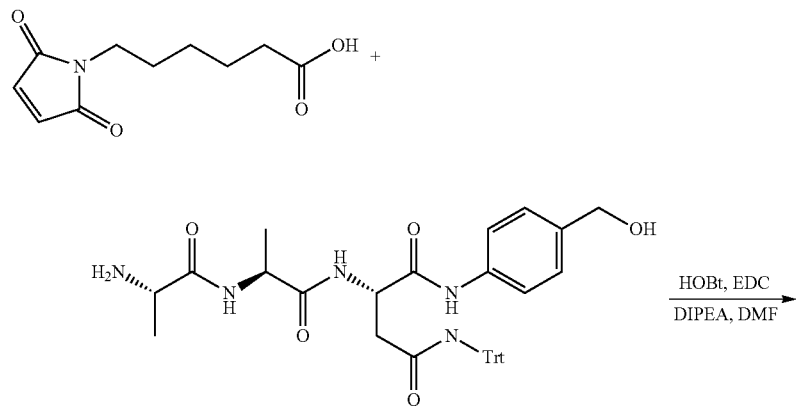

6-Maleimide caproic acid (120 mg, 0.57 mmol) were dissolved in N,N-dimethylformamide (20 mL). 1-hydroxyl-benzotriazole (92 mg, 0.68 mmol) and N,N-diisopropyl ethylamine (0.19 mL, 1.15 mmol) were added. 4-N—(N—(N-(L-alanyl)-L-alanyl)-N'-triphenylmethyl-L-asparaginyl)-amino benzyl alcohol (353 mg, 0.57 mmol) was added into under protection by nitrogen gas. The resultant mixture was stirred for 0.5 hour and then cooled to 0□ in an ice bath. Then 1-ethyl-(3-dimethylaminopropyl) carbodiimide hydrochloride (120 mg, 0.62 mmol) in a N,N-dimethylformamide (10 mL) solution were dropped into the mixture. After dropping, the resultant mixture was warmed up to ambient temperature and then stirred overnight. The reaction solution was poured into ethyl acetate (150 mL), and washed subsequently by water (100 mL×3), 5% dilute hydrochloric acid (50 mL) and 5% sodium carbonate (50 mL). The organic phase was dried by anhydrous sodium sulphate and then by evaporation under reduced pressure. The resultant product was purified by column chromatography to obtain the product, which is a white solid (300 mg, Yield 64.8%).

2) Synthesis of 4-N—(N—(N—(N-(6-maleimido caproyl)-L-alanyl)-L-alanyl)-L-asparaginyl)-amino benzyl alcohol

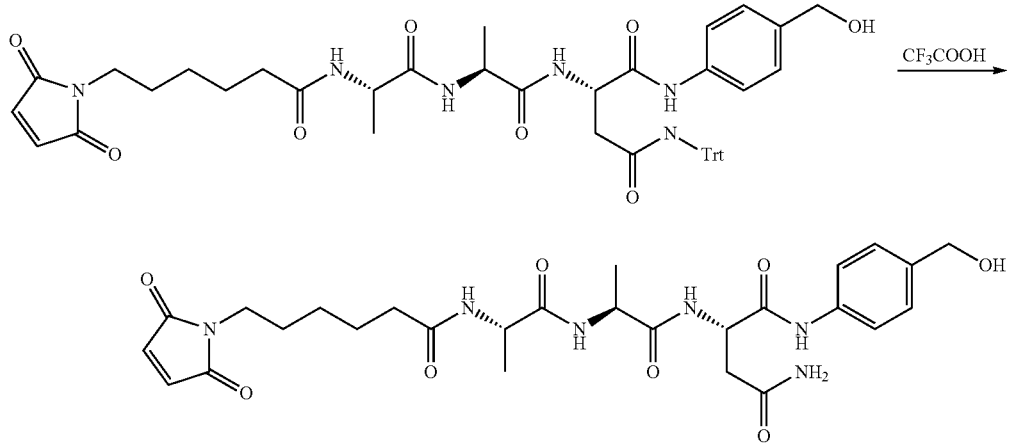

4-N—(N—(N—(N-(6-maleimido caproyl-L-alanyl)-L-alanyl)-N'-triphenylmethyl-L-asparaginyl)-amino benzyl alcohol (163 mg, 0.2 mmol) were dissolved in dichloromethane (5 mL). Trifluoroacetic acid (2 mL) were added. The resultant mixture was stirred at ambient temperature for 5 hours. The reaction solution was washed by water and then separated. The organic phase was dried by anhydrous sodium sulphate and the solvents were removed by evaporation under reduced pressure. The residual trifluoroacetic acid was removed by evaporation under high vacuum. The resultant crude product was purified by column chromatography to obtain a pale yellow solid (97 mg, Yield 85%).

3) Synthesis of 4-N—(N—(N—(N-(6-maleimido caproyl)-L-alanyl)-L-alanyl)-L-asparaginyl)-amino benzyl alcohol-p-nitrophenol-carbonic acid diester

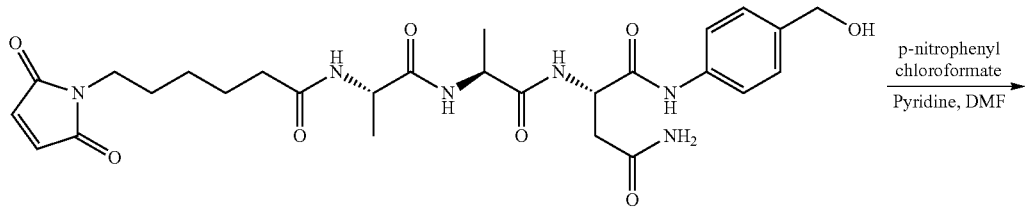

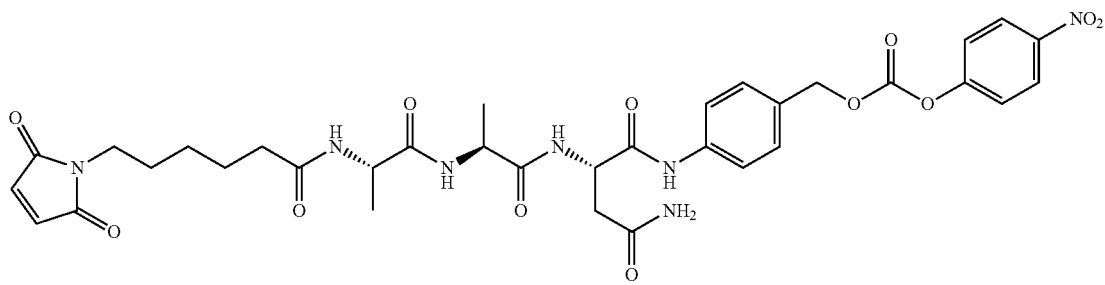

4-N—(N—(N—(N-(6-maleimido caproyl)-L-alanyl)-L-alanyl)-L-asparaginyl)-amino benzyl alcohol (814 mg, 1.0 mmol) were dissolved in dichloromethane (100 mL) and cooled to 0□ in an ice bath. p-nitrophenyl chloroformate (406 mg, 2.0 mmol) in a dichloromethane solution (20 mL) and pyridine (160 mg, 2.0 mmol) were subsequently dropped into the resultant mixture under protection by nitrogen gas. After dropping, the resultant mixture was warmed up to ambient temperature and then stirred overnight. The reaction solution was washed by water and separated. The organic phase was dried by anhydrous sodium sulphate and the solvents were removed by evaporation under reduced pressure. The resultant crude product was purified by column chromatography to obtain a white solid (597 mg, Yield 81%).

4) Synthesis of 4-N—(N—(N—(N-(6-maleimido caproyl)-L-alanyl)-L-alanyl)-L-asparaginyl)-amino benzyl alcohol-daunorubicin-carbamate (S5)

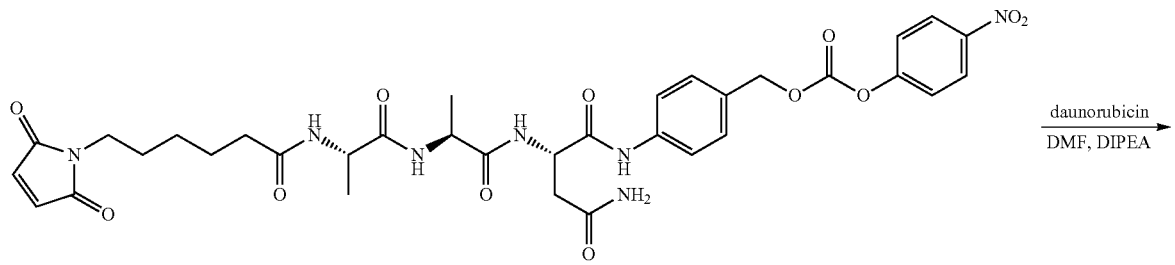

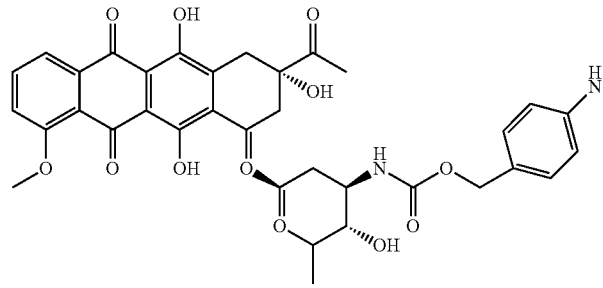
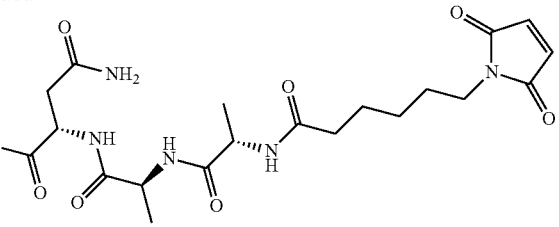

S5

4-N—(N—(N—(N-(6-maleimido caproyl)-L-alanyl)-L-alanyl)-L-asparaginyl)-amino benzyl alcohol-p-nitrophenol-carbonic acid diester (200 mg, 0.27 mmol) were dissolved in N,N-dimethylformamide (30 mL). Daunorubicin hydrochloride (152 mg, 0.27 mmol) were added. The resultant mixture was cooled to 5☐ and then N,N-diisopropyl ethylamine (0.1 mL, 0.6 mmol) in N,N-dimethylformamide (2 mL) solution were dropped into the mixture under protection by nitrogen gas. After dropping, the mixture was warmed up to ambient temperature and stirred for reaction overnight. The reaction solution was poured into methyl tert-butyl ether (600 mL), stirred for 0.5 hour and then filtered. The resultant red solid was purified by column chromatography to obtain a rid solid product S5 (164 mg, Yield 54%).

Example 7: Synthesis of 4-N—(N—(N—(N-(6-maleimido caproyl)-L-alanyl)-L-alanyl)-L-asparaginyl)-amino benzyl alcohol-MMAE-carbamate (S6)

4-N—(N—(N—(N-(6-maleimido caproyl)-L-alanyl)-L-alanyl)-L-asparaginyl)-amino benzyl alcohol-p-nitrophenol-carbonic acid diester (298 mg, 0.40 mmol) were dissolved in N,N-dimethylformamide (30 mL). MMAE (monomethyl auristatin) hydrochloride (305 mg, 0.40 mmol) were added. The resultant mixture was cooled to 5☐ and then N,N-diisopropyl ethylamine (0.1 mL, 0.6 mmol) in N,N-dimethylformamide (2 mL) solution under protection by nitrogen gas. After dropping, the mixture was warmed up to ambient temperature and stirred for reaction overnight. The reaction solution was poured into methyl tert-butyl ether (600 mL), stirred for 0.5 hour and then filtered. The resultant red solid was purified by column chromatography to obtain a rid solid product S6 (434 mg, Yield 82.4%).

The synthetic results of compounds 51, S2, S3, S4 and S5 are summarized in Table 1. The mass-to-charge ratios of 51, S2, S3, S4 and S5 detected by mass spectrum (MS) are 916, 885, 880, 1079 and 1513, respectively, which are consistent to their calculated mass-to-charge ratios, as shown in Table 1.

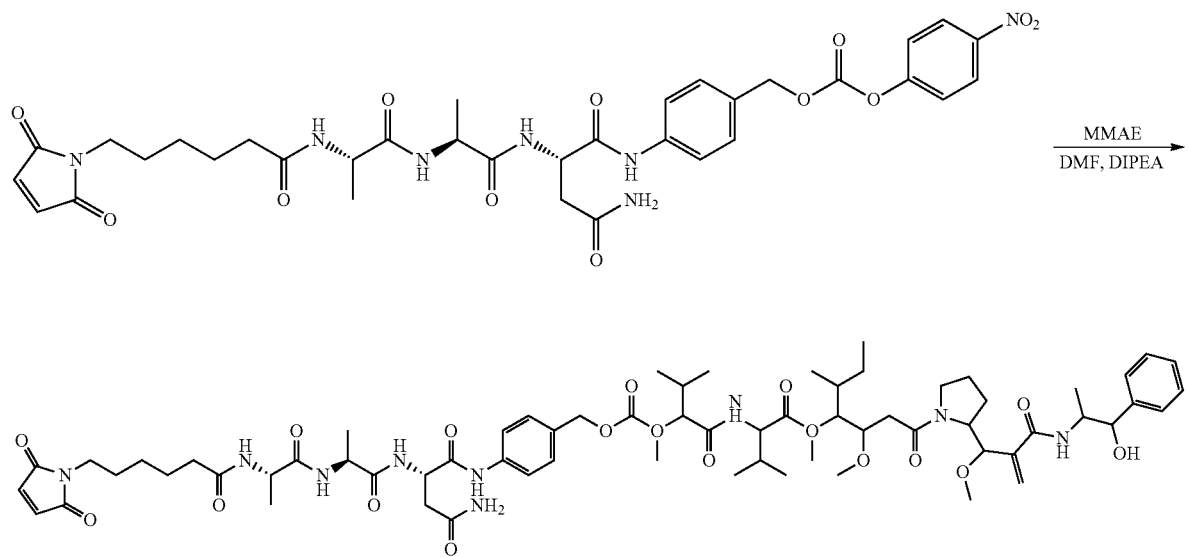

TABLE 1 the properties and MS data of S1-S5

| No. | $R_1$ | $R_1$ | $R_2$ | $R_3$ | $R_4$ | MS data | Character |
|---|---|---|---|---|---|---|---|
| S1 | 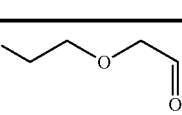 | Hydrophilic group | Thr | Ala | 10-hydroxyl camptothecin | 916 | Pale yellow powder |
| S2 | 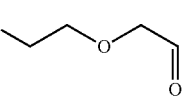 | Hydrophilic group | Ala | Ala | camptothecin | 885 | White solid |
| S3 | 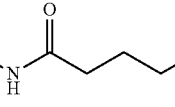 | Targeted group | Ala | Ala | capecitabine | 880 | Pale yellow soild |
| S4 | 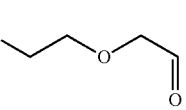 | Hydrophilic group | Thr | Ala | daunorubicin | 1079 | Red powder |
| S5 | 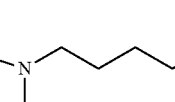 | Targeted group | Ala | Ala | daunorubicin | 1513 | Red powder |

Using different $R_2$ and $R_3$ merely results in the use of different starting materials when linking the amino acid. Different side chains of the amino acid $R_2$ and $R_3$ did not influence the synthesis. Consistent with the above methods, merely the corresponding $R_2$ amino acid and $R_3$ amino acid were used in the synthesis. The reaction for linking $R_4$ was also the same as the method mentioned above, except that the catalytic conditions and the reaction drugs were different in the tumor microenvironment.

Example 8

Conditions for linking the linking group for targeting a small molecule that is specifically activated in the tumor microenvironment to different $R_4$ compounds are different.

1) In the above compounds, method for linking $R_4$ via hydroxyl is different from the method for linking $R_4$ via amino.

Whether $R_1R_2R_3$-Asn-amino benzyl alcohol-p-nitrophenol-carbonic acid diester could be successfully linked to $R_6$ via amino depends on selection of $R_6$. For example, the reaction between $R_1R_2R_3$-Asn-amino benzyl alcohol-p-nitrophenol-carbonic acid diester and camptothecin is different from the reaction with MMAE, mainly in that the reaction with MMAE is taken place via the strong nucleophilicity of the amino group of MMAE (82.4%), while reaction of camptothecin is taken place via replacement of p-nitrophenol through nucleophilicity of the hydroxyl group of camptothecin. The nucleophilicity of hydroxyl is weaker than that of amino and is equal to or slightly weaker than p-nitrophenol, thus theoretically replacement of hydroxyl by p-nitrophenol cannot be carried out.

We found that only when adding HOBT into the reaction mixture as a catalyst, strictly controlling the temperature to the screened temperature and controlling the reaction time, a bound HOBT transition state that could easily be left was formed to thereby effectively exchange with hydroxyl of camptothecin and thus to produce less reaction impurities. The highest yield we obtained is 53.5%.

2) Whether the reaction between AA-Asn-amino benzyl alcohol-p-nitrophenol-carbonic acid diester and drug $R_5$ via amino could be successfully taken place fully depends on selection of $R_5$.

The steric hindrance of the amino group in $R_5$ and the substituent of $R_5$ have crucial effects on the linking reaction. The linking reaction between an aliphatic amino and $R_1$-$R_2$-$R_3$-Asn-amino benzyl alcohol-p-nitrophenol-carbonic acid diester could produce high yield (such as MMAE) at mild condition. However, for the aromatic amino, no reaction product is obtained because the nucleophilicity of the amino is reduced due to its lone paired electron and the conjugation of aromatic ring. By high-throughput screening and severe reaction conditions, for example the linking reaction between Nimustine and $R_1$-$R_2$-$R_3$-Asn-amino benzyl alcohol-p-nitrophenol-carbonic acid diester, we finally found that a small amount of products (yield 20%) could be obtained when using DMAP as a base and reacting at 80-85 □.

3) In the above compounds $R_1$ has different effects on linking of $R_4$.

Different $R_1$ groups have significant effect on the linking reaction conditions between $R_1$-$R_2$-$R_3$-Asn-amino benzyl alcohol-p-nitrophenol-carbonic acid diester and $R_4$. For example, linking reaction between 4-N—(N—(N—(N-(6-maleimido caproyl)-L-alanyl)-L-alanyl)-L-Asn)-amino benzyl alcohol-p-nitrophenol-carbonic acid diester and camptothecin did not produce a product. Therefore, different reactants and experimental conditions should be screened in order to obtain the product. For example, 4-N—(N—(N—(N-(2-(2-methoxyethoxy) acetyl-L-alanyl)-L-alanyl)-L-asparaginyl)-amino benzyl alcohol-p-nitrophenol-carbonic acid diester was used to react with camptothecin under a special temperature condition, thereby producing a corresponding product.

Example 9: Compounds Produced by Linking to the Cleavable Linker Specifically Activated in a Tumor Microenvironment and Cytotoxicity Change Thereof When $R_1$ is 2-(2-Methoxyethoxy)Acetyl, $R_2$ is Thr, and $R_3$ is Ala, the compounds comprising an $R_4$ indicated below linking to the cleavable linker could be screened by using similar catalysts used in the reactions for producing S1~S3: camptothecin (S7), 10-hydroxy camptothecin (S8), topotecan (S9), Floxuridine (S10), 5'-Deoxy-5-Fluorouridine (S11), cytarabine (S12), fludarabine (S13), etoposide (S14), Capecitabine (S15), gemcitabine (S16), vincristine (S17) and Epothilone B (S18), paclitaxel (S13'), Docetaxel (B13).

When $R_1$ is 2-(2-Methoxyethoxy)Acetyl, $R_2$ is Thr, and $R_3$ is Ala, compounds ($R_4$) that could be successfully linked to the cleavable linker which is specifically activated in a tumor microenvironment include: daunorubicin (S19), epirubicin (S20), fludarabine (S21), gemcitabine (S22), nimustine (S23), mitoxantrone (S24), methotrexate (S25), Cytarabine (S26), Melphalan (S27), Doxorubicin (S28), and Mitomycin (E13).

TABLE 2

The properties and MS data of the synthetic compounds

| No | Molecular ion peak of MS | Synthetic efficiency % | Cytoxicity reduced (Multiple) |
|---|---|---|---|
| S1 | 916 | 67 | 56 |
| S2 | 885 | 19 | 145 |
| S3 | 880 | 21 | 78 |
| S4 | 1079 | 42 | 345 |
| S5 | 1513 | 54 | 125 |
| S6 | 1238 | 82 | 35 |
| S7 | 954 | 56 | 432 |
| S8 | 969 | 34 | 144 |
| S9 | 1026 | 53 | 256 |
| S10 | 851 | 87 | 89 |
| S11 | 851 | 43 | 46 |
| S12 | 848 | 46 | 35 |
| S13 | 970 | 25 | 78 |
| S14 | 1193 | 46 | 463 |
| S15 | 964 | 45 | 235 |
| S16 | 868 | 32 | 124 |
| S17 | 1397 | 78 | 355 |
| S18 | 1126 | 34 | 233 |
| S19 | 1102 | 23 | 253 |
| S20 | 1118 | 45 | 39 |
| S21 | 940 | 54 | 352 |
| S22 | 838 | 22 | 121 |
| S23 | 863 | 67 | 234 |
| S24 | 1019 | 86 | 235 |
| S25 | 1029 | 43 | 644 |
| S26 | 818 | 34 | 123 |
| S27 | 879 | 57 | 79 |
| S28 | 1405 | 46 | 232 |
| S13' | 1433 | 34 | 356 |
| B13 | 1604 | 43 | 234 |
| E13 | 886 | 56 | 454 |

Toxicity detection method: a standard universal test program was used to perform the in vitro cytotoxicity test. 2500 HEK293 cells were cultured in a 96-well plate, and allowed to grow overnight. Cytotoxic compounds and their corresponding conjugated compounds were added into each well in different concentrations, cultivated with the cells at 37° C. for 72 hours, and then treated with MTT reagents. OD changes were read. The approximate multiples of the toxicity change were obtained by comparing the IC50 of the modified compounds to their corresponding cytotoxic compounds.

Example 10

Different compounds linking by the cleavable linker which is specifically activated in a tumor microenvironment have different activation efficiencies.

The structure-efficacy relationship between the linking group and the groups of the linked compound determines the activation effect. At 37□, 1 mg/ml of S1, S2, S3, S4, S5 and S6 were added into 10 μg/ml acidified asparagine endopeptidase solution or a homogenate from different tumor tissues (30 μg/ml), respectively. Reduction of reactant and increase of product were detected by HPLC, thereby comparing the activation efficiency of these compounds (the ratio between the amount of the compound released by cleaving by asparagine endopeptidase and the initial amount of the compound, higher activation efficiency indicating stronger activation efficiency). It was found that S1, S2, S3, S4 and S5 exhibited very high activation efficiency by the tumor tissue, while S6 had relatively low activation efficiency by the tumor tissue (Table 2). Our experimental results show that $R_1$ in S3, which is (N-hydroxylamino)-1,8-octandioic acid-1-monoacyl, could target and bind to metalloprotease MMP2 which is highly expressed in tumor, and $R_1$ in S5, which is 6-maleimido caproyl, could target and bind to cathepsin which is highly expressed in tumor. Thus, they have higher activation efficiency.

TABLE 3

Activation Efficiencies (%) of S1, S2, S3, S4, S5 and S6

| | Cells that produce tumor | S1 | S2 | S3 | S4 | S5 | S6 |
|---|---|---|---|---|---|---|---|
| asparagine endopeptidase | / | 88.4 | 87.5 | 84.8 | 84.3 | 83.3 | 24.5 |
| Human fibrosarcoma | HT-1080 | 78.3 | 75.6 | 94.9 | 78.4 | 98.4 | 24.3 |
| Human breast cancer | MDA-MB435 | 67.3 | 78.4 | 70.1 | 83.5 | 96.7 | 25.6 |
| Human ovarian cancer | SK-OV-3 | 78.3 | 74.6 | 94.3 | 78.4 | 97.4 | 23.5 |
| Human colon cancer | HT-29 | 63.7 | 78.3 | 81.7 | 83.5 | 78.4 | 22.4 |
| Human chronic leukemia | K562 | 46.6 | 63.7 | 93.2 | 64.5 | 73.5 | 28.4 |
| Human pancreatic cancer | Panc-1 | 78.4 | 68.4 | 91.6 | 67.3 | 97.4 | 17.3 |
| Human non-small cell lung cancer | A549 | 68.7 | 68.3 | 80.7 | 64.5 | 96.7 | 27.4 |
| Human prostate cancer | PC-3 | 78.5 | 75.4 | 98.3 | 78.3 | 97.3 | 13.2 |
| Human liver cancer | Hepg2 | 86.4 | 63.7 | 94.5 | 67.3 | 67.3 | 26.7 |
| Human renal cancer | OS-RC-2 | 84.5 | 53.6 | 67.4 | 78.5 | 98.3 | 20.4 |
| Human heart | / | 1.2 | 0.5 | 1.6 | 2.8 | 3.5 | 5.3 |

Example 11

Different compounds linking by a cleavable linker which is specifically activated in the tumor microenvironment have different activation efficiencies.

The structure-efficacy relationship between the linking group and the groups of the linked compound determines the activation effect. At 37□, 1 mg/ml of S7-S27 were added into 10 μg/ml acidified asparagine endopeptidase solution, respectively. Reduction of reactant and increase of product were detected by HPLC, thereby comparing the activation efficiency of these compounds. The results are shown in Table 3.

TABLE 4

Activation Efficiencies (%) of S7-S27

| Compound | | | | | | | |
|---|---|---|---|---|---|---|---|
| S7 | S8 | S9 | S10 | S11 | S12 | S13 | S14 |
| Activation Efficiencies (%) | | | | | | | |
| 75.7 | 65.5 | 86.4 | 95.4 | 66.2 | 73.6 | 79.6 | 85.3 |

| Compound | | | | | | | |
|---|---|---|---|---|---|---|---|
| S15 | S16 | S17 | S18 | S19 | S20 | S21 | S22 |
| Activation Efficiencies (%) | | | | | | | |
| 84.6 | 13.4 | 89.4 | 93.5 | 89.3 | 76.7 | 95.4 | 97.5 |

| Compound | | | | | |
|---|---|---|---|---|---|
| S23 | S24 | S25 | S26 | S27 | S28 |
| Activation Efficiencies (%) | | | | | |
| 91.5 | 90.7 | 74.4 | 78.5 | 73.5 | 66.5 |

From Table 4, it can be found that different compounds have different activation efficiencies by asparagine endopeptidase. The activation efficiencies of most of S7-S27 are all higher than 60%. S6 and S16 show very low activation efficiency, which is less than 30%. Asparagine endopeptidase activates at the linkage between asparaginyl and 4-amino benzyl alcohol. After cleaving by activation, 4-amino benzyl alcohol (4-aminobenzyl-OC(O)—) can be freely released, thereby releasing the drug, $R_4$—H. The active center of asparagine endopeptidase locates at the bottom of its globular depression. The cleavage site should be close to the active center. Thus, it is very important to determine whether there is a steric hindrance to the cleavage site produced by the linked compound and to change the polarity of the linking site. According to the above results, it is supposed that the steric hindrances and polarities of S6 and S16 may affect their activation, resulting that they have relatively low activation efficiencies while other compounds have relatively high activation efficiencies.

The results show that the cleavable linker which is specifically activated in a tumor microenvironment can link to and activate different compounds, in which the compounds may be classified into activatable compounds and un-activatable compounds based on their different steric hindrance.

Example 12: Study on Efficacy of S1, S2, S3, S4, S5, S6, S16, S22 and S28 Injections in Nude Mice Test purpose: to investigate the anti-tumor efficacy of S1, S2, S3, S4, S5, S6, S16, S22 and S28 via mouse tumor treatment model.

Test drug: S1, S2, S3, S4, S5, S6, S16, S22 and S28 injections, diluted to corresponding concentrations by physiological saline when testing.

Method and Results:

1. Animal: nude mice of 6-8 weeks old, all female.
2. Production of tumor model

1) Human breast cancer MDA-MB231 cells were purchased from American type culture collection (ATCC) and identified according the specification provided by ATCC. Cells were cultivated in Dulbecco's minimum essential medium (DMEM culture medium) containing 10% fetal bovine serum at 37° C. and 5% $CO_2$. The cells were passaged for every three days and cells within the 15th passage were used.

2) Production of tumor. $5 \times 10^6$ MDA-MB231 cells were subcutaneously injected to the back of the nude mice. Mice were randomly grouped after the tumor reached at least 100 $mm^3$. Then treatment began and the day on which the treatment began was day 1.

3) Course of treatment. According to the clinical application of S1, S2, S3, S4, S5, S6, S16, S22 and S28, drugs were intravenously injected (IV). A dose of 13.2 μmol/kg was used for S1, S2, S3, S4, S5, S6, S16, S22 and S28, camptothecin, capecitabine and daunorubicin, respectively. The drugs were administered once weekly for four weeks.

4) Grouping and test results are shown in Table 5.

TABLE 5

Effect of S1, S2, S3, S4, S5, S6, S16, S22 and S28 on treatment of tumor on nude mice

| Group | Number of animal | Size of Tumor ($mm^3$) | | Inhibitory rate on tumor (%) | |
|---|---|---|---|---|---|
| | | Day 10 | Day 24 | Day 10 | Day 24 |
| S1 group | 10 | 56.53 ± 14.36 | 124.44 ± 49.85 | 81 | 88 |
| camptothecin | 10 | 258.45 ± 57.43 | 847.46 ± 157.56 | 15 | 19 |
| S2 group | 10 | 59.35 ± 35.53 | 89.53 ± 65.45 | 81 | 91 |
| S3 group | 10 | 85.67 ± 36.42 | 0 | 72 | 100 |
| capecitabine | 10 | 225.53 ± 74.45 | 946.43 ± 275.86 | 26 | 9 |
| S4 group | 10 | 95.56 ± 57.54 | 64.68 ± 43.56 | 69 | 94 |
| S5 group | 10 | 63.67 ± 46.64 | 46.45 ± 19.43 | 79 | 95.5 |
| daunorubicin | 10 | 174.78 ± 78.43 | 864.01 ± 67.45 | 43 | 17 |
| S6 group | 10 | 235.5 ± 56.3 | 568.43 ± 245.56.67 | 23 | 45.3 |
| S16 group | 10 | 246.76 ± 45.56 | 840.64 ± 345.6 | 23 | 19.21 |
| S22 group | 10 | 0 | 0 | 100 | 100 |
| S28 group | 10 | 0 | 0 | 100 | 100 |

TABLE 5-continued

Effect of S1, S2, S3, S4, S5, S6, S16, S22 and S28 on treatment of tumor on nude mice

| Group | Number of animal | Size of Tumor (mm³) Day 10 | Size of Tumor (mm³) Day 24 | Inhibitory rate on tumor (%) Day 10 | Inhibitory rate on tumor (%) Day 24 |
|---|---|---|---|---|---|
| Control group (physiological saline) | 10 | 305.56 ± 75.75 | 1040.64 ± 298.65 | — | — |

5) Results and discussion: as shown in Table 5, S1, S2, S3, S4, S5, S22 and S28 exhibit strong inhibitory effect on tumor growth as compared to the control group, the camptothecin group, the capecitabine group and the daunorubicin group while S6 and S16 show less efficacy as they were not activated. These indicate that the conjugates could significantly improve the efficacy of the drugs and the treatment effect is determined by the cleaving efficiency. Comparing the structures of S6 with S4, S5 and S19~S27, it could be found that the amino of MMAE used for linking is positioned at the two adjacent hydrophobic valines in MMAE. After linking to 4-aminobenzyl-OC(O)—, the hydrophobic region of valine and the little peptide of S6 are presented to a position which is unfavorable in relation to the active center of asparagine endopeptidase, resulting in formation of steric hindrance and obstruction of the active center of asparagine endopeptidase to approach the cleavable bond. As a result, the efficiency of cleavage and activation is very low. The activation efficiency of S6 is lower than the AANVV polypeptide. The 4-aminobenzyl-OC(O)— linker is no effect in this compound. From the viewpoint of synthesis, it is more complicated to add the 4-aminobenzyl-OC(O)— linker than to form a peptide bond. On the contrary, the amino position for linking in S4, S5 and S19-S27 is not the amino group in their peptide, but it is the amino on the aromatic ring. We firstly discovered that the aromatic ring did not affect the polarity of the linker. Thus, use of the 4-aminobenzyl-OC(O)— linker could eliminate the steric hindrance due to direct linking to an amino group and favorable activation results could be produced. The activation efficiency is generally higher than the compounds having a direct linking and this property is not limited to the compounds containing an aromatic ring.

Example 13: A Comparative Study on the Different Cleavable Linkers of MMAE and Doxorubicin When R₁ is 2-(2-Methoxyethoxy)Acetyl, and R₃ is Ala, activation study and efficacy study were carried out by using compounds having different cleavable linker. The study methods are identical to those in Examples 10, 11 and 12. The in vitro activation efficiency was tested by asparagine endopeptidase and the tumor inhibition rate was tested by using human breast cancer MDA-MB231 model.

| No. | linker for the compounds | synthesis efficiency | Cleaving efficiency | Cytoxicity reduced (Multiples) | tumor inhibition rate (%) |
|---|---|---|---|---|---|
| S6:PEG-TAN-PABC-MMAE | 2-(2-methoxyethoxy)acetyl-Thr-Ala-Asn-4-amino benzyl alcohol | 84.5% | 25.6% | 35 | 45.4 |
| PEG-AAN-PABC-MMAE | 2-(2-methoxyethoxy)acetyl-Ala-Ala-Asn-4-amino benzyl alcohol | 63.4% | 14.4% | 22 | 34.4 |
| AC-AAN-PABC-MMAE | acetyl-Ala-Ala-Asn-4-amino benzyl alcohol | 36.5% | 3.4% | 15.5 | 16.7 |
| CBZ-AAN-PABC-MMAE | benzyloxy carbonyl-Ala-Ala-Asn-4-amino benzyl alcohol | 24.6% | 2.6% | 8.3 | 9.7 |
| S28:PEG-AAN-PABC-DOX | 2-(2-methoxyethoxy)acetyl-Ala-Ala-Asn-4-amino benzyl alcohol | 65.5% | 99.5% | 285.6 | 100 |
| PEG-AANL-DOX | 2-(2-methoxyethoxy)acetyl-AANL | 45.5% | 66.5% | 110.2 | 60.3 |

Example 14

Compounds S29-S43 were synthesized by the same method as S1, except that the amino acids used as starting material were different. In this Example, compounds having different amino acids were tested for their activation property and inhibitory rate on tumor. The test methods are identical to the methods in Examples 4, 6, 8, 12 and 13. The test results are shown in the following Table 7.

TABLE 7

The activation property and inhibitory rate on tumor for compounds S28-S43

| No. of Compound | R₂ | R₃ | Activation property (%) | Inhibitory rate on tumor (Day38) | Activation property (%) | Inhibitory rate on tumor (Day38) |
|---|---|---|---|---|---|---|
| S29 | Thr | Thr | 63.4% | 57.4% | 63.4%. | 57.4% |
| S30 | Thr | Val | 46.3% | 47.4% | 46.3% | 47.4% |
| S31 | Thr | Asn | 36.4% | 46.5% | 36.4% | 46.5% |
| S32 | Val | Ala | 68.4% | 56.5% | 68.4% | 56.5% |
| S33 | Val | Thr | 34.5% | 50.6% | 34.5% | 50.6% |
| S34 | Val | Val | 54.3% | 46.7% | 54.3% | 46.7% |

TABLE 7-continued

The activation property and inhibitory rate on tumor for compounds S28-S43

| No. of Compound | R$_2$ | R$_3$ | Activation property (%) | Inhibitory rate on tumor (Day38) | Activation property (%) | Inhibitory rate on tumor (Day38) |
|---|---|---|---|---|---|---|
| S35 | Val | Asn | 34.5% | 58.6% | 34.5% | 58.6% |
| S36 | Ile | Ala | 35.5% | 52.5% | 35.5% | 52.5% |
| S37 | Ile | Thr | 67.4% | 46.7% | 67.4% | 46.7% |
| S38 | Ile | Val | 38.5% | 46.3% | 38.5% | 46.3% |
| S39 | Ile | Asn | 46.6% | 48.4% | 46.6% | 48.4% |
| S40 | Ala | Ala | 69.4% | 80.5% | 69.4% | 80.5% |
| S41 | Ala | Thr | 78.3% | 64.6% | 78.3% | 64.6% |
| S42 | Ala | Val | 73.6% | 66.6% | 73.6% | 66.6% |
| S43 | Ala | Asn | 65.4% | 60.5% | 65.4% | 60.5% |

Results and discussion: As shown in Table 7, S29-S43 exhibit a certain activation property and inhibitory effect on tumor growth and metastasis. The results also demonstrate that in the compounds being highly activated, R$_2$ can be any of Thr, Val, Ile and Ala, and R$_3$ can be any of Ala, Thr, Val and Asn.

Example 15: Study on Efficacy of 51, S2, S3, S4, S5 and S6 in D121 Tumor Immune Model Test purpose: to investigate the anti-tumor efficacy of S1, S2, S3, S4, S5 and S6 in a D121 lung cancer model for immune treatment.

Test drug: S1, S2, S3, S4, S5, S6, camptothecin, capecitabine and daunorubicin, all used in 13.2 μmol/kg; PDL1 antibody, 5 μg/kg.

Animal: C57 mice of 6-8 weeks old, all female.

Production of Tumor Model:

1) D121 lung tumor cells were purchased from ATCC. Cells were cultivated in DMEM culture solution containing 10% fetal bovine serum at 37° C. and 5% $CO_2$. The cells were passaged for every three days and cells within the 15th passage were used.

2) Tumor immunization. $5 \times 10^5$ D121 lung cancer cells (purchased from ATCC) which were killed by irradiation were intraperitoneally injected to mice. The mice were injected for 3 times, once every two weeks. After immunization, mice were injected with tumor cells and the drugs were administered weekly for 4 weeks.

3) Production of tumor. At day 32, $10^6$ live lung tumor cells were subcutaneously injected to the back of the C57 mice immunized by tumor. Treatment began when the tumor grew to 0.3-0.4 cm.

4) Analysis on tumor CD8+ T cells. The tumor tissue was homogenated and individual cells in the tumor were filtered, separated and washed by buffer twice, then cultivated with the leucocyte common antigen CD45-PE and CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry.

5) Grouping and test results are shown in Table 8.

TABLE 8

Effect on inhibition of tumor and immune activation of S1, S2, S3, S4, S5, S6 and control

| Group | Number of animal | Size of tumor (mm$^3$) Day 18 | Inhibitory rate on tumor Day 18 | CD8: D45 (%) |
|---|---|---|---|---|
| Immune group, without D121 dead tumor cells | 8 | 1525.67 ± 314.6 | — | 6.8 |
| Immune group (Control group) | 8 | 1357.57 ± 275.78 |  | 13.5 |
| Immune group + S1 | 8 | 356.56 ± 74.78 | 73.74 | 17.4 |
| Immune group + camptothecin | 8 | 889.56 ± 148.56 | 34.47 | 13.2 |
| Immune group + S2 | 8 | 379.67 ± 214.45 | 72.03 | 17.7 |
| Immune group + S3 | 8 | 425.67 ± 126.67 | 68.64 | 18.4 |
| Immune group + capecitabine | 8 | 953.65 ± 245.43 | 29.75 | 13.6 |
| Immune group + S4 | 8 | 316.78 ± 109.98 | 76.67 | 16.8 |
| Immune group + S5 | 8 | 379.75 ± 125.64 | 72.03 | 17.4 |
| Immune group + daunorubicin | 8 | 1063.86 ± 317.56 | 21.63 | 13.2 |
| Immune group + S6 | 8 | 957.46 ± 257.87 | 29.47 | 13.0 |
| Immune group + S1 + PDL1-antibody | 8 | 81.78 ± 51.98 | 93.98 | 21.4 |
| Immune group + camptothecin + PDL1-antibody | 8 | 816.64 ± 268.56 | 39.85 | 14.4 |

6) Results and discussion. Treatment effects of S1, S2, S3, S4 and S5 on C57 mice were greatly improved as compared to the control group and the other treatment groups. The S6 group also has an improved treatment effect as compared to the daunorubicin group. S1 and PDL1-antibody show an excellent synergistic effect in promoting immunization and treatment. The results show that S1, S2, S3, S4 and S5 can inhibit tumor growth via improving immunization.

Example 16: Synthesis of Paclitaxel which is Specifically Activated in Tumor Microenvironment 1) Synthesis of (R)-2-(2-(R)-(benzyloxycarbonyl) amino) propionylamino)methyl propionate (I)

N-benzyloxycarbonyl-L Ala (100 g, 0.45 mol) were dissolved in N,N-dimethylformamide (3 L). 1-hydroxylbenzotriazole (72.6 g, 0.54 mol) and 1-ethyl-(3-dimethylaminopropyl) carbodiimide hydrochloride (103.3 g, 0.54 mol) were added when stirring. After reacting for 1 hour under stirring, the mixture was cooled in an ice bath and L-Ala methyl ester (46.2 g, 0.45 mol) and N,N-diisopropylethylamine (173.8 g, 1.34 mol) in the N,N-dimethylformamide solution (1 L) was dropped into the mixture. After dropping, the mixture was stirred under ambient temperature (25□) for 10 hours. The solvents were removed by evaporation under reduced pressure. The crude product was dissolved in dichloromethane (2 L) and washed subsequently by saturated ammonium chloride solution, water and saturated sodium chloride solution. The organic phase was dried by anhydrous sodium sulphate. After removing the solvents by evaporation under reduced pressure, the crude product was recrystallized to obtain a white solid I (101 g, Yield 73.1%). LC-MS: 309[M+1]+.

2) Synthesis of (R)-2-(2-(R)-(benzyloxycarbonyl) amino) propionylamino)propionic acid (II)

(R)-2-(2-(R)-(benzyloxycarbonyl)amino) propionylamino)methyl propionate (100 g, 0.34 mol) were dissolved in a mixed solution of tetrahydrofuran (2 L) and water (1 L). The mixture was cooled to 0□ and 1M lithium hydroxide solution (400 mL) were dropped into the mixture. The resultant mixture was stirred for reaction under ambient temperature (25□) for 10 hours. Concentrated hydrochloric acid was dropped to adjust the pH to be less than 6. Most of tetrahydrofuran were removed by rotary evaporation. The residual water phase was extracted by dichloromethane (1 L×3). The organic phase was dried by anhydrous sodium sulphate. A white solid II was obtained after vaporizing and drying under reduced pressure (88 g; Yield, 92.2%). LC-MS: 295 [M+1]+.

3) Synthesis of (R)-2-((9H-fluorene-9-yl) methoxycarbonylamino)-4-(triphenylmethylamino)-1-hydroxymethylphenyl succinic acid amide (III)

(R)-2-((9H-fluorene-9-yl) methoxycarbonylamino)-4-(triphenylmethylamino) butyrate (20 g, 0.03 mol), 2-(7-azabenzotriazol)-N,N,N',N'-tetramethyluronium hexafluorophosphate (HATU) (15 g, 0.04 mol), N,N-dimethylformamide (200 mL) were added into a 500 mL three-neck flask and stirred for 30 minutes. A solution of 4-amino benzyl alcohol (4.1 g, 0.03 mol) in N,N-dimethylformamide (5 mL), and N,N-diisopropyl ethylamine (8.7 g, 0.06 mol) were added separately under 0 □ and the mixture was stirred at ambient temperature (25□) for 3 hours. Most N,N-dimethylformamide were removed by rotary evaporation. The residue was dissolved in ethyl acetate (200 mL), washed subsequently by saturated ammonium chloride solution and saturated sodium chloride solution and dried by anhydrous sodium sulphate. After filtration, the solvent was removed by evaporation. The resultant crude product was pulping by n-hexane/ethyl acetate (5/1,300 mL) to obtain a white solid III (21.3 g, Yield 90%). LC-MS: 702 [M+1]+.

4) Synthesis of (R)-2-amino-4-(triphenylmethyl-amino)-1-hydroxymethylphenyl succinic acid amide (IV)

(R)-2-((9H-fluorene-9-yl) methoxycarbonylamino)-4-(triphenylmethylamino)-1-hydroxymethylphenyl succinic acid amide (13.0 g, 18 mmol) were dissolved in N,N-dimethylformamide (80 mL). Piperidine (30 mL) was added and then stirred at ambient temperature (25□) for 2 hours. The solvents were removed by evaporation under reduced pressure. And the resultant product was dried under high vacuum within a vacuum drying oven (100□) to remove a small quantity of piperidine. A pale yellow solid IV (8.43 g, yield: 95%) was obtained, which could be used in the next step without purification.

5) Synthesis of (R)-2-((R)-2-((R)-2-carboxybenzy-lamino) propionylamino) propionylamino-4-(triph-enylmethylamino)-1-hydroxymethylphenyl succinic acid amide (V)

(R)-2-((R)-2-(carboxybenzylamino) propionylamino) propionic acid (6.0 g, 20.4 mmol), benzotriazol-N,N,N',N'-tetramethyluronium hexafluorophosphate (HBTU, 11.6 g, 30.6 mmol) and N,N-dimethylformamide (50 mL) were added into a three-neck flask and stirred for 30 minutes in an ice bath. A solution of (R)-2-amino-4-(triphenylmethyl-amino)-1-hydroxymethylphenyl succinic acid amide in N,N-dimethylformamide (50 mL), and N,N-diisopropyleth-ylamine (7.89 g, 61.2 mmol) were added separately under 0° C. The resultant mixture was stirred for 17 hours at ambient temperature (25° C.). The solvents were removed by evaporation under reduced pressure. The residue was dissolved in acetyl acetate (200 mL), washed subsequently by saturated ammonium chloride solution (100 mL) and saturated sodium chloride solution (100 mL) and dried by anhydrous sodium sulphate. After filtration, the solvent was removed by evaporation. The resultant crude product was recrystallized to obtain a white solid V (15 g, Yield 97%). LC-MS: 756 [M+1]+.

6) Synthesis of (R)-2-((R)-2-((R)-aminopropio-nylamino) propionylamino-4-(triphenylmethyl-amino)-1-hydroxymethylphenyl succinic acid amide (VI)

(R)-2-((R)-2-((R)-2-carboxybenzylamino) propio-nylamino) propionylamino-4-(triphenylmethylamino)-1-hy-droxymethylphenyl succinic acid amide (5.0 g, 6.61 mmol) were dissolved in THF (150 mL). 10% Pd/C (1 g) was added. After introducing hydrogen gas, the resultant mixture was stirred for reaction under normal temperature (22° C.) for 5 hours. Pd/C was removed by filtration and washed by methanol (100 mL). The filtrates and the washing solutions were pooled. Most solvents were removed by rotary evaporation to obtain a crude product. After silica gel column chromatography (200-300 mesh, dichloromethane/methanol=20/1-10/1, 2.5 L), a white solid VI was obtained (2.0 g, Yield 49%). LC-MS: 622 [M+1]$^+$.

7) Synthesis of (R)-2-((R)-2-((R)-2-(methoxyethoxyacetylamino) propionylamino) propionylamino-4-(triphenylmethylamino)-1-hydroxymethylphenyl succinic acid amide (VII)

2-(2-methoxyethoxy) acetic acid (432 mg, 3.22 mmol) were dissolved in N,N-dimethylformamide (20 mL). Benzotriazol-N,N,N',N'-tetramethyluronium hexafluorophosphate (1.83 g, 4.83 mmol) were added and stirred for 30 minutes. Then (R)-2-((R)-2-((R)-aminopropionylamino) propionylamino(triphenylmethylamino)-1-hydroxymethylphenyl succinic acid amide (2.0 g, 3.22 mmol) and N,N-diisopropylethylamine (1.24 g, 9.61 mmol) in N,N-dimethylformamide (20 mL) were dropped into the resultant mixture. After dropping, the temperature was slowly raised to ambient temperature (25° C.) and then the mixture was stirred for 10 hours. Most of N,N-dimethylformamide were removed by evaporation under reduced pressure. The residue was dissolved in acetyl acetate (200 mL), washed subsequently by saturated ammonium chloride solution (150 mL) and saturated sodium chloride solution (150 mL) and dried by anhydrous sodium sulphate. After filtration, the solvent was removed by rotary evaporation. The resultant crude product was purified by silica gel column chromatography (200-300 mesh, dichloromethane/methanol=20/1-10/1, 2 L) to obtain a white solid VII (1.2 g, Yield 50%). LC-MS: 738 [M+1]$^+$.

8) Synthesis of (R)-2-((R)-2-((R)-2-(methoxyethoxyacetylamino) propionylamino) propionylamino-1-hydroxymethylphenyl succinic acid diamide (VIII)

(R)-2-((R)-2-((R)-2-(methoxyethoxyacetylamino) propionylamino) propionylamino-4-(triphenylmethylamino)-1-hydroxymethylphenyl succinic acid amide (VII) (1.0 g, 1.36 mmol) were dissolved in dichloromethane (10 mL). Trifluoroacetic acid (2 mL) were added and then the resultant mixture was stirred at ambient temperature (25° C.) for 5 hours. The reaction solution was washed by water (20 mL) and separated. The organic phase was dried by anhydrous sodium sulphate and the solvents were removed by evaporation under reduced pressure. The residual trifluoroacetic acid was removed by evaporation. The resultant crude product was purified by silica gel column chromatography (200-300 mesh, dichloromethane/methanol=15/1-8/1, 1.5 L) to obtain VIII (600 mg, Yield 89%). LC-MS: 496 [M+1]$^+$.

9) Synthesis of 4-((R)-2-((R)-2-((R)-2-(methoxyethoxyacetylamino) propionylamino) propionylamino-4-aminocarboxybutyryl)) aminobenzylp-nitrophenylcarbonate ester (IX)

(R)-2-((R)-2-((R)-2-(methoxyethoxyacetylamino) propionylamino) propionylamino-1-hydroxymethylphenyl Succinimide (500 mg, 1.01 mmol) were added into a 50 mL three-neck flask, dissolved in dichloromethane (10 mL). The resultant mixture was cooled to 0-5° C. p-nitrophenyl chloroformate (406 mg, 2.02 mmol) and pyridine (160 mg, 2.03 mmol) were subsequently dropped into the mixture under protection by nitrogen gas. After dropping, the resultant mixture was stirred at ambient temperature (25° C.) for 18 hours. The reaction solution was washed by water (10 mL) and separated. The organic phase was dried by anhydrous sodium sulphate and the solvents were removed by rotary evaporation. The resultant crude product was purified by silica gel column chromatography (200-300 mesh, dichloromethane/methanol=30/1-20/1, 1 L) to obtain IX (450 mg, Yield 67%). LC-MS: 661 [M+1]$^+$.

10) Synthesis of 2-(2-methoxyethoxy) acetylamino-L-Ala-L-Ala-L-Asn-p-amino-benzyl-paclitaxel (S1')

4-((R)-2-((R)-2-((R)-2-(methoxyethoxyacetylamino)propionylamino) propionylamino-4-amino-succinyl))aminobenzyl-paclitaxel-carbonic acid diester (250 mg, 0.293 mmol) and paclitaxel (194 mg, 0.293 mmol) were dissolved in anhydrous N,N-dimethylformamide (10 mL). The resultant mixture was cooled to 0□ and then 4-dimethyl pyridine (DMAP) (54 mg, 0.44 mmol) were added. The resultant mixture was stirred at ambient temperature (25□) for 18 hours. The reaction solution was poured into acetyl acetate (20 mL), the organic phase was combined and washed subsequently by water (30 mL) and dried by anhydrous sodium sulphate. The solvents were removed by rotary evaporation to obtain a crude product. The crude product was purified by silica gel column chromatography (200-300 mesh, dichloromethane/methanol=20/1-15/1, 500 mL) to obtain the target product S1 (150 mg, Yield 57%). LC-MS: 1375 [M+1]$^+$. The LC-MS result showed that the corresponding mass-to-charge ratio of elution peak 8.59 was 1375, which are consistent to its calculated mass-to-charge ratio of 1374.5.

S2', S3' and S4' were synthesized by making reference to S1', as shown in the below table, except that the acetic acids substituted by alkoxy group used in step 7 have different molecular weights. When synthesizing S2', 3, 6, 9, 12, 15, 18-hexaoxanonadecanoic acid was used to replace 2-(2-methoxyethoxy) acetic acid; in synthesis of S3', 3, 6, 9, 12, 15, 18, 21, 24, 27, 30, 33, 36-dodecaoxaheptatriacontanoic acid was used to replace 2-(2-methoxyethoxy) acetic acid; and in synthesis of S4', purchased long chain polyoxa fatty acid (customized from GL Biochem (Shanghai) Ltd., n=300) was used to replace 2-(2-methoxyethoxy) acetic acid. According to mass spectrum (MS) detection results, the mass-to-charge ratios of S2' and S3' are 1551 and 1816, respectively, which are consistent to their calculated molecular weights, 1550.6 and 1815.9. According to Matrix-Assisted Laser Desorption/Ionization Time of Flight Mass Spectrometry (MALDI-TOF-MS), S4's molecular weight is about 14524, which is consistent with its calculated molecular weight, 14524.7.

TABLE 9

| No. | n | Character | Molecular weight by MS | Fluorescence | Output (milligram) | Yield |
|-----|-----|--------------|------------------------|--------------|--------------------|-------|
| S1' | 1 | White powder | 1375 | None | 150 | 57% |
| S2' | 5 | White powder | 1551 | None | 178 | 48% |
| S3' | 11 | White powder | 1816 | None | 159 | 56% |
| S4' | 150 | White powder | 14524 | None | 525 | 38% |

Example 17: Synthesis of S10'-S24'

The synthetic method was similar to that for S1', except for the starting amino acids used for linking are different, as shown in Table 10. Corresponding $R_2$ amino acid and $R_3$ amino acid were dissolved in N,N-dimethylformamide, respectively. The same condensating agent, 1-ethyl-(3-dimethylaminopropyl) carbodiimide hydrochloride, was added and reactions were allowed to take place at 0-25□ for 0.5-2 hours. Then Asn was added and reaction was taken place at 0-25□ for 2-24 hours to obtain a tripeptide. As determined by mass spectrum (MS), the molecular weights of S10'-S24' (n=1) are shown in the following table, which are consistent with their calculated molecular weights.

TABLE 10

| No. | $R_2$ amino acid | $R_3$ amino acid | MS detection | Molecular weight | Character | Output (mg) | Yield |
|---|---|---|---|---|---|---|---|
| S10' | Ala | Thr | 1405 | 1405.03 | white powder | 97 | 67% |
| S11' | Ala | Val | 1403 | 1402.98 | white powder | 113 | 43% |
| S12' | Ala | Asn | 1418 | 1417.95 | white powder | 135 | 25% |
| S13' | Thr | Ala | 1405 | 1405.03 | white powder | 321 | 78% |
| S14' | Thr | Thr | 1435 | 1435.05 | white powder | 79 | 57% |
| S15' | Thr | Val | 1433 | 1433.08 | white powder | 41 | 24% |
| S16' | Thr | Asn | 1448 | 1448.05 | white powder | 135 | 57% |
| S17' | Val | Ala | 1403 | 1403.05 | white powder | 312 | 68% |
| S18' | Val | Thr | 1433 | 1433.08 | white powder | 112 | 45% |
| S19' | Val | Val | 1431 | 1431.11 | white powder | 68 | 36% |
| S20' | Val | Asn | 1446 | 1446.08 | white powder | 39 | 53% |
| S21' | Ile | Ala | 1417 | 1417.08 | white powder | 18 | 19% |
| S22' | Ile | Thr | 1447 | 1447.11 | white powder | 27 | 32% |
| S23' | Ile | Val | 1445 | 1445.14 | white powder | 74 | 34% |
| S24' | Ile | Asn | 1460 | 1460.11 | white powder | 47 | 51% |

Example 18: Solubility Comparison of Present Water-Soluble Paclitaxel for Targeted Activation in Tumor Microenvironment and Control Compounds on the Formulation of the Drug (1) Sample Treatment Compounds S1', S2', S3' and S4'(prepared in example 16) and various control compounds C1, C2, C3, C4, C5 and C6 were lyophilized (-70□), separately packing in a sterile room. Before animal test, S1', S2', S3' and S4' were dissolved by solvent 1 (injectable water) or solvent 2 (50% injectable water, 42%~49% propanediol, 1%~8% Tween80) in sterile room. S1', S2', S3' and S4' could completely dissolved in both solvent 1 and solvent 2, achieving a concentration of 10 mg/ml, and can be diluted by injectable water to the desired concentration. On the contrary, comparative compounds (C1, C2, C3, C4, C5) did not satisfy the formulating requirement, as shown in Table 11.

TABLE 11

Effect of absence of similar components in control compounds or linkage to Paclitaxel at its 7- or 2-position (i.e., linking the group to the OH at 7- or 2-position of Paclitaxel) on the solubility of the drug

| Compound | Solvent 1 | Solvent 2 |
|---|---|---|
| C1: AAN -group 2- Paclitaxel (linking at 2-position) | insoluble | insoluble |
| C2: group 1- AANL - Paclitaxel (linking at 2-position) | insoluble | insoluble |
| C3: AAN - Paclitaxel (linking at 2-position) | insoluble | insoluble |
| C4: group 1- AAN -group 2- Paclitaxel (linking at 7-position) | insoluble | insoluble |
| C5: group 1- AANL -group 2- Paclitaxel (linking at 2-position) | insoluble | insoluble |
| C6: group 1- AANK -group 2- Paclitaxel (linking at 2-position) | soluble | soluble |
| S1' | soluble | soluble |
| S2' | soluble | soluble |
| S3' | soluble | soluble |
| S4' | soluble | soluble | group 1: [chemical structure of an aldehyde-PEG group]

group 2: H$_2$N-[benzyl formate group]

In Table 11, AAN, AANL and AANK indicate the linkage formed by small peptides in the compounds, A is Ala, N is Asn, L is Leu and K is Lys. Solvent 1 is injectable water, solvent 2 contains 50% injectable water, 45%~49% propanediol, 1%~5% Tween80. The dissolution concentration is 10 mg/ml.

According to Table 11, solubility of the present Paclitaxel derivatives is significantly changed, with increased solubility in solvent 1 or 2. Change in solubility may greatly affect the formulation scheme of a drug. Solubility of comparative compounds (C1, C2, C3, C4, C5) did not satisfy the formulating requirement. As compared to the traditional Paclitaxel which is insoluble in water, S1', S2', S3' and S4' can be used to produce a soluble formulation. Their injection doses and efficacies can be improved and auxiliary materials that cause allergy generally used for Paclitaxel can be avoided, indicating that they have a promising innovation and prospect of use.

Example 19: Methods for Determining the Contents of S1', S2', S3' and S4' in Respective Products and their Content Ranges As detected by analytic HPLC (Agilent 1220 series, C8 column 5 μm, 4.6 mm ID×250 mm; the mobile phase is 0-95% acetonitrile (ACN)), the purities of S1', S2', S3' and S4' are all in the range of 95-99%.

Example 20: Activation Efficiency of Present Paclitaxel Derivatives for Targeted Activation in Tumor Microenvironment Solvent (50% injectable water, 45%-49% alcohol, 1%-5% Tween 80) was used to dissolve sample compound S1', S2', S3' and S4', and they were diluted for ten times to a concentration of 1 mg/ml. At 37□, sample compounds were added into 100 μg acidized tumor tissue homogenates (pH6.0) in a concentration of 1 mg/ml. The enzyme in tumor tissue homogenates could release Paclitaxel. Reduction of compounds and increase of Paclitaxel were detected by HPLC, thereby comparing the activation efficiency of the drugs by the tumor tissue. It was found that the current compounds S1', S2', S3' and S4' exhibited highest activation efficiency among the screened compounds.

TABLE 12

Activation ratio (%) of S1', S2', S3' and S4' in homogenates from different tumor tissues

| Different tumor tissues | Cells producing tumor | Activation ratio (%) in homogenates from different tumor tissues | | | |
|---|---|---|---|---|---|
| | | S1' | S2' | S3' | S4' |
| Human fibrosarcoma | HT-1080 | 74.7 | 75.4 | 67.9 | 74.6 |
| Human breast cancer | MDA-MB435 | 92.3 | 91.4 | 90.4 | 92.8 |
| Human ovarian cancer | SK-OV-3 | 88.4 | 84.6 | 79.3 | 63.8 |
| Human colon cancer | HT-29 | 79.4 | 89.9 | 91.4 | 90.6 |
| Human chronic leukemia | K562 | 64.7 | 73.3 | 70.2 | 74.2 |
| Human pancreatic cancer | Panc-1 | 94.8 | 93.8 | 91.5 | 93.1 |
| Human non-small cell lung cancer | A549 | 86.4 | 89.4 | 81.4 | 83.6 |
| Human prostate cancer | PC-3 | 97.3 | 98.4 | 96.3 | 93.5 |
| Human liver cancer | Hepg2 | 95.3 | 84.6 | 83.5 | 74.2 |
| Human renal cancer | OS-RC-2 | 86.4 | 91.5 | 86.4 | 90.5 |
| Human heart | | none | none | none | none |

Solvent (50% injectable water, 42%-49% alcohol, 1%-8% Tween 80) was used to dissolve sample compounds S1', S2', S3' and S4', and they were diluted for ten times to a concentration of 1 mg/ml. At 37□, sample compounds were added into 100 μg acidized human breast cancer (MDA-MB435) tumor tissue homogenates (pH6.0) in a concentration of 1 mg/ml. The enzyme in tumor tissue homogenates could release Paclitaxel. Reduction of compounds and increase of Paclitaxel were detected by HPLC, thereby comparing the activation efficiency of the drugs by the tumor tissue. Results were showed in table 13.

TABLE 13

Effect of absence of similar components in control compounds on activation of the drugs

| Compounds | activation efficiency (%) |
|---|---|
| C1: AAN-group 2-Paclitaxel (linking at 2-position) | 67.4 |
| C2: group 1-AAN-Paclitaxel (linking at 2-position) | 54.8 |
| C3: AAN-Paclitaxel (linking at 2-position) | 34.9 |
| C4: group 1-AAN-group 2-Paclitaxel (linking at 7-position) | 12.1 |
| C5: group 1-AANL-group 2-Paclitaxel (linking at 2-position) | 57.4 |
| C6: group 1-AANK-group 2-Paclitaxel (linking at 2-position) | 47.7 |
| S1' | 94.3 |
| S2' | 93.1 |
| S3' | 91.5 |
| S4' | 87.8 |

According to the results, different groups in the present Paclitaxel for targeted activation in tumor microenvironment have various effects on the activation of Paclitaxel drugs in tumor tissue. The mutual structure-efficacy of Paclitaxel with the groups linked determined the targeting and activation effects in tissues. Activation of S1', S2', S3' and S4' in different tumor types (10 kinds) proved their broad treatment spectrum (Table 13). Meanwhile, certain compounds produced in the screening were compared, and the activation efficiency in the same human breast cancer MDA-MB435 tissue was examined. It was proved that the respective group selection in S1', S2', S3' and S4' had relatively higher activation efficiency (Table 13).

The Paclitaxel derivatives for targeted activation in tumor microenvironment of the present disclosure were based on a great amount of synthetic experiments. In these experiments, we designed a lot of complicated compounds having different linking manners. Then the complicated compounds were linked to position 2 or 7 of Paclitaxel, that is, they were linked to Paclitaxel via the OH at position 2 or position 7. The resultant Paclitaxel derivatives were screened through activation efficiency in tumor tissues. The screened derivatives were further screened through inhibition of tumor for $R_2$, $R_3$ and n. The activated site that is specific to the tumor tissue locates between AAN and group 2. After cleaving by activation, group 2 can be freely released, thereby releasing Paclitaxel. Because the active center of asparagine endopeptidase locates at the bottom of its globular depression and the cleavage site should be close to the active center, it is very important if there is a steric hindrance to the cleavage site produced by the complicated compounds.

According to the screening results, it is presumed that linking of group 2 may effectively avoid steric hindrance produced by directly linking Paclitaxel, which thereby not affecting approach of asparagine endopeptidase. And, the structure-efficacy of group 1 may increase the polarity of the cleavage site, which allows the more water-soluble protease to be easily to approach the cleavage site and thereby to increase the cleaving efficiency. Linking to position 2 of Paclitaxel could obviously reduce steric hindrance produced by Paclitaxel to protease, expose more groups, each of which as a whole is hydrophilic, and increase cleaving efficiency and water solubility. Whereas an additional polar amino acid K or L would decrease the activation efficiency.

Example 21: Detection of Maximum Tolerated Dose (MTD) by Intravenous Injection of the Paclitaxel Derivatives for Targeted Activation in Tumor Microenvironment Test purpose: to investigate the acute toxicity of the present Paclitaxel derivatives via detecting MTD (maximum tolerated dose) by intravenous injection.

Test drugs: Solvent (50% injectable water, 42%-49% alcohol, 1%-8% Tween 80) was used to dissolve sample compounds S1', S2', S3' and S4', diluted to corresponding concentrations by physiological saline when testing, to prepare S1', S2', S3' and S4' injections.

Animal: the first class BALB/C mice purchased from SHANGHAI SLAC LABORATORY ANIMAL CO. LTD, weighing 19-21 g and all mice being female.

Method and results: 42 BALB/C mice were randomly divided into 7 groups according to their body weights, with 6 mice in each group. As shown in Table 14, the mice were intravenously injected with S1', S2', S3' and S4' for just one time in a dose of 0 mg/kg, 25 mg/kg, 50 mg/kg, 60 mg/kg, 70 mg/kg, 80 mg/kg, and 960 mg/kg. Control tests were performed by injecting 0.2 ml physiological saline or Paclitaxel (purchased from Youcare Pharmaceutical Group Co., Ltd). Animals were observed for 17 continuous days for presence or absence of the following behaviors on each day: pilo-erection, hair tousle and lackluster, lethargy, stoop and irritable reaction, and body weight and death were recorded. Blood samples were taken on the 3, 5 and 14 days for counting the whole blood cells. Animals were anatomized on day 14 to take the heart, liver, kidney, lung, spleen, and pancreas for HE staining.

TABLE 14

Comparison of mortality rates of test mice receiving different doses of S1', S2', S3' and S4' injections, physiological saline or Paclitaxel injection

| Group | | Dose (mg/kg) | Number of animal | Number of dead animal | Mortality rate (%) |
|---|---|---|---|---|---|
| 1 | physiological saline | 0 mg/kg | 10 | 0 | 0 |
| 2 | S1' | 125 mg/kg | 10 | 0 | 0 |
| 3 | S1' | 150 mg/kg | 10 | 0 | 0 |
| 4 | S1' | 175 mg/kg | 10 | 0 | 0 |
| 5 | S1' | 200 mg/kg | 10 | 1 | 10 |
| 6 | S2' | 125 mg/kg | 10 | 0 | 0 |
| 7 | S2' | 150 mg/kg | 10 | 0 | 0 |
| 8 | S2' | 175 mg/kg | 10 | 0 | 0 |
| 9 | S2' | 200 mg/kg | 10 | 1 | 10 |
| 10 | S3' | 125 mg/kg | 10 | 0 | 0 |
| 11 | S3' | 150 mg/kg | 10 | 0 | 0 |
| 12 | S3' | 175 mg/kg | 10 | 0 | 0 |
| 13 | S3' | 200 mg/kg | 10 | 1 | 10 |
| 14 | S4' | 125 mg/kg | 10 | 0 | 0 |
| 15 | S4' | 150 mg/kg | 10 | 0 | 0 |
| 16 | S4' | 175 mg/kg | 10 | 0 | 0 |
| 17 | S4' | 200 mg/kg | 10 | 0 | 10 |
| 18 | Paclitaxel | 25 mg/kg | 10 | 0 | 0 |
| 19 | Paclitaxel | 30 mg/kg | 10 | 1 | 10% |
| 20 | Paclitaxel | 35 mg/kg | 10 | 4 | 40% |
| 21 | Paclitaxel | 40 mg/kg | 10 | 8 | 90% |

Results and discussions: no pilo-erection, hair tousle and lackluster, lethargy, stoop, irritable reaction and death were observed in mice receiving 90 mg/kg S1', S2', S3' and S4' injections. As shown in Table 11, the MTD of the S1' and S2' injections were about 90 mg/kg, which is far beyond the MTD of Paclitaxel, 6 mg/kg. The MTD for intravenous administration of a test drug is an important reference index for drug toxicity. The results indicate that the toxicity of the Paclitaxel released by targeted activation is significantly reduced as compared with Paclitaxel.

Example 22: Study on Efficacy of S1', S2', S3' and S4' Injections in Nude Mice

Test purpose: to investigate the anti-tumor efficacy of S1', S2', S3' and S4' in mice model for tumor treatment.

Test drug: S1', S2', S3' and S4' injections (same as Example 21) and Paclitaxel injection (purchased from Youcare Pharmaceutical Group Co., Ltd), diluted to corresponding concentrations by physiological saline when testing.

Method and Results:

1. Animal: nude mice of 6-8 weeks old, all female (purchased from SHANGHAI SLAC LABORATORY ANIMAL CO. LTD).

2. Production of tumor model

1) Human prostate cancer PC-3 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ Panc-1 cells were subcutaneously injected to the back of the nude mice. Mice were randomly grouped after the tumor reached at least 100 $mm^3$. Then treatment began and the day on which the treatment began was day 1.

3) Course of treatment According to the clinical application of S1', S2', S3' and S4', drugs were intravenously injected (IV). S1', S2', S3' and S4' were administered in a dose of less than ⅙ MTD, i.e., 24 mg/kg, and Paclitaxel was administered in a dose of ⅓ MTD, i.e., 8 mg/kg. The control group was administered by physiological saline. Drugs were administered once weekly for four weeks.

4) Grouping and test results are shown in Table 15.

TABLE 15

Effect of S1', S2', S3' and S4', Paclitaxel and control group on tumor treatment in nude mice

| Group | Number of animal | Size of tumor ($mm^3$) | | inhibitory rate on tumor | |
|---|---|---|---|---|---|
| | | Day 10 | Day 24 | Day 10 | Day 24 |
| S1' group | 10 | 76.42 ± 14.96 | 84.62 ± 45.94 | 35.7% | 66.1% |
| S2' group | 10 | 60.17 ± 30.26 | 42.39 ± 62.24 | 36.4% | 83.01% |
| S3' group | 10 | 75.60 ± 28.54 | 74.39 ± 48.94 | 49.4% | 70.2% |
| S4' group | 10 | 73.35 ± 38.46 | 63.99 ± 47.13 | 42.9% | 81.5% |

TABLE 15-continued

Effect of S1', S2', S3' and S4', Paclitaxel and control group on tumor treatment in nude mice

| Group | Number of animal | Size of tumor (mm³) Day 10 | Size of tumor (mm³) Day 24 | inhibitory rate on tumor Day 10 | inhibitory rate on tumor Day 24 |
|---|---|---|---|---|---|
| Paclitaxel treatment group | 10 | 118.85 ± 36..47 | 249.54 ± 95.46 | 7.5% | 27.9% |
| Control group | 10 | 268.12 ± 55.64 | 346.1 ± 104.74. | / | / |

5) Results and discussions: As shown in Table 15, inhibition on tumor growth by S1', S2', S3' and S4' were greatly improved as compared with the groups treating by Paclitaxel using the same molar concentration and the control group.

Example 23: Study on Efficacy of S1', S2', S3' and S4' in D121 Tumor Immune Model Test purpose: to investigate the anti-tumor efficacy of S1', S2', S3' and S4' in a D121 lung cancer model for immune treatment.

Animal: C57 mice of 6-8 weeks old, all female (purchased from SHANGHAI SLAC LABORATORY ANIMAL CO. LTD).

Test drug: S1', S2', S3' and S4' injections (same as Example 21) and Paclitaxel injection (purchased from Youcare Pharmaceutical Group Co., Ltd), diluted to corresponding concentrations by physiological saline when testing.

Production of Tumor Model:

1) D121 lung tumor cells were purchased from ATCC. Cells were cultivated in DMEM culture solution containing 10% fetal bovine serum at 37° C. and 5% $CO_2$. The cells were passaged for every three days and cells within the 15th passage were used.

2) Tumor immunization. $5 \times 10^5$ D121 lung cancer cells (purchased from ATCC) which were killed by irradiation were intraperitoneally injected to mice. The mice were injected for 3 times, once every two weeks. After immunization, mice were injected with tumor cells and the drugs were administered weekly for 4 weeks. In table 16 below the immune group was immuned with D121 lung tumor cells and the group without dead D121 lung tumor cells was injected with physiological saline as controls.

3) Production of tumor. After immunization (4 weeks later), $10^6$ live lung tumor cells were subcutaneously injected to the back of the C57 mice immunized by tumor. Treatment began when the tumor grew to 0.3-0.4 cm. Tumor size (mm³) were noted and tumor inhibition rates were calculated.

4) Analysis on tumor CD8+ T cells. The tumor tissue was homogenated and individual cells in the tumor were filtered, separated and washed by buffer twice, then cultivated with the leucocyte common antigen CD45-PE and CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry.

5) Grouping and test results are shown in Table 16.

TABLE 16

Effect on inhibition of tumor and immune activation of S1', S2', S3' and S4', Paclitaxel and control

| Group | Number of animal | Size of tumor (mm³) Day 18 | inhibitory rate on tumor % Day 18 | CD8: CD45 (%) |
|---|---|---|---|---|
| Immune group, without D121 dead tumor cells | 8 | 1887.56 ± 323.4 | | 5.6 |
| Immune group (Control group) | 8 | 1574.46 ± 456.34 | control | 13.5 |
| Immune group + S1' | 8 | 237.60 ± 156.42 | 84.9% | 19.6 |
| Immune group + S2' | 8 | 331.57 ± 114.74 | 78.9% | 18.1 |
| Immune group + S3' | 8 | 357.63 ± 194.54 | 77.3% | 16.7 |
| Immune group + S4' | 8 | 304.55 ± 184.53 | 80.7% | 17.8 |
| Immune group + S1' + PDL1 antibody | 8 | 74.78 ± 27.25 | 95.3% | 24.4 |
| Immune group + Paclitaxel | 30 | 1210.28 ± 375.46 | 23.1% | 6.6 |
| Immune group + Paclitaxel + PDL1 antibody | 8 | 1334.90 ± 257.34 | 15.2% | 7.7 |

6) Results and discussion. As shown in table 13, treatment effects of S1', S2', S3' and S4' on C57 mice were greatly improved as compared to the control group and the other treatment groups. S1' and PDL1-antibody show an excellent synergistic effect in promoting immunization and treatment. They can inhibit tumor growth via improving immunization.

Example 24: Study on Efficacy of S1', S2', S3' and S4' in BALB/C Mice Model for Tumor Metastasis Test purpose: to investigate the anti-tumor efficacy of S1', S2', S3' and S4' in BALB/C mice model for treatment of tumor metastasis.

Test drug: S1', S2', S3' and S4' injections (same as Example 31) and Paclitaxel injection (purchased from Youcare Pharmaceutical Group Co., Ltd), diluted to corresponding concentrations by physiological saline when testing.

Method and Results:

1. Animal: the first class BALB/C mice of 6-8 weeks old, all female (purchased from SHANGHAI SLAC LABORATORY ANIMAL CO. LTD).

2. Production of tumor model 1) 4T1 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor metastasis. $10^6$ T1 cells were subcutaneously injected to the back of the BALB/C mice. Mice were randomly grouped after the tumor grew to about 1.5 cm. The subcutaneous tumor was removed by surgery and drug treatment began. Mice were killed after anesthesia on day 27. The whole lung was taken out and put into Bouin's solution for staining. The number of the tumor metastasized to lung was counted with anatomical microscope.

3) Course of treatment

According to the clinical application of S1', S2', S3' and S4', drugs were intravenously injected (IV). S1', S2', S3' and S4' were administered in a dose of ⅙ MTD, i.e., 12 mg/kg, and Paclitaxel was administered in a dose of ⅙ MTD, i.e., 4 mg/kg. The control group was administered by physiological saline. Drugs were administered once for every three days for 4 times.

4) Grouping and test results are shown in Table 17.

TABLE 17

Effects of S1', S2', S3' and S4', Paclitaxel and control on inhibition of tumor metastasis in BALB/C mice

| Group | Number of animal | Number of metastasized tumor | Inhibitory rate on metastasis |
|---|---|---|---|
| S1' Group | 10 | 2 ± 3 | 99.2% |
| S2' Group | 10 | 8 ± 7 | 94.1% |
| S3' Group | 10 | 13 ± 8 | 90.44% |
| S4' Group | 10 | 15 ± 16 | 89.0% |
| Paclitaxel treatment group | 10 | 128 ± 25 | 5.9% |
| Control group | 10 | 136.0 ± 46 | / |

5) Results and discussion. As shown in Table 17, the inhibitory effect on tumor metastasis of BALB/C mice was greatly improved after intraperitoneal injection of S1', S2', S3' and S4', as compared with the Paclitaxel group and the control group, indicating that this kind of drugs exhibits an excellent efficacy on anti-tumor metastasis.

Example 25: Study on Efficacy of S1' Injection in Multiple Tumor Models

Test purpose: to investigate the anti-tumor spectrum of S1' through multiple tumor models from mice Test drug: S1' injection (same as Example 21), diluted to corresponding concentrations by physiological saline when testing.

Method and Results:

1. Animal: nude mice of 6-8 weeks old, all female (purchased from SHANGHAI SLAC LABORATORY ANIMAL CO. LTD).

2. Production of tumor model

1) Corresponding tumor cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ corresponding cells were subcutaneously injected to the back of the nude mice. Mice were randomly grouped after the tumor reached at least 100 $mm^3$. Then treatment began and the day on which the treatment began was day 1.

3) Course of treatment. According to the clinical application of S1', S1' was administered in a dose of ⅙ MTD, i.v., 17.6 μmol/kg. The control group was administered by physiological saline. Animals were administered once weekly for three weeks.

4) Grouping and test results are shown in Table 18.

TABLE 18

Treatment effect of S1' in multiple tumor models

| Group | Tumor cell | inhibitory rate on tumor (Day 26) |
|---|---|---|
| Human breast cancer | MDA-MB435 | 90.7% |
| Human ovarian cancer | SK-OV-3 | 85.6% |
| Human colon cancer | HT-29 | 89.7% |
| Human chronic leukemia | K562 | 77.9% |
| Human colon caner | HT1080 | 94.3% |
| Human pancreatic cancer | Panc-1 | 88.59% |
| Human non-small cell lung cancer | A549 | 94.6% |
| Human liver cancer | Hepg2 | 84.3% |
| Human renal cancer | OS-RC-2 | 85.7% |

5) Results and discussion. As shown in Table 18, S1' shows an excellent efficacy in multiple tumor models, demonstrating that the anti-tumor drug has a wide anti-tumor spectrum.

Example 26: Activation Efficiency, Inhibitory Rate on Tumor and Inhibitory Rate on Metastasis of S10'~S24'

The activation efficiency, inhibitory rate on tumor and inhibitory rate on metastasis of S10'~S24' were examined respectively using methods same as that in example 20, 22 and 24. Results were showed in table 19.

TABLE 19 activation efficiency, inhibitory rate on tumor and on metastasis of S10'~S24'

| Compound No. | $R_2$ | $R_3$ | activation efficiency (%) | inhibitory rate on tumor (%)(Day 38) | inhibitory rate on metastasis (%) |
|---|---|---|---|---|---|
| S10' | Ala | Thr | 65.4%. | 65.6% | 75.3% |
| S11' | Ala | Val | 42.6% | 46.2% | 44.5% |
| S12' | Ala | Asn | 38.4% | 49.5% | 81.6% |
| S13' | Thr | Ala | 75.7% | 61.3% | 87.4% |
| S14' | Thr | Thr | 37.5% | 52.4% | 29.4% |
| S15' | Thr | Val | 54.6% | 45.8% | 39.3% |
| S16' | Thr | Asn | 33.2% | 68.3% | 56.8% |
| S17' | Val | Ala | 30.6% | 58.3% | 64.8% |
| S18' | Val | Thr | 65.8% | 69.8% | 80.1% |
| S19' | Val | Val | 38.5% | 55.2% | 68.3% |
| S20' | Val | Asn | 43.5% | 47.8% | 71.4% |
| S21' | Ile | Ala | 49.6% | 43.4% | 63.9% |
| S22' | Ile | Thr | 69.9% | 59.5% | 70.5% |
| S23' | Ile | Val | 57.5% | 65.2% | 45.5% |
| S24' | Ile | Asn | 49% | 47.48% | 54.2% |

In the present disclosure, other Paclitaxel derivatives for targeted activation in tumor microenvironment were synthesized, of which n is any integer between 1-300, $R_2$ is Ala, Thr, Val or Ile; $R_3$ is Ala, Thr, Val or Asn. And they were subjected to activation test as done in Examples 17, study on efficacy on tumor as done in Examples 23 and 24, study on efficacy of inhibiting metastasis as done in Example 25 and study on efficacy on multiple tumors as done in Example 26. Results showed that they had similar results to S1'-S4'. As demonstrated by the experiments, when n is in the range of 1-300, the inhibitory rate on tumor is slightly reduced as n increases. The activation activity also slightly decreases and mass of drugs in the same mole increases, as n increases. However, the metabolic half life of the drug also increases as n increases. Therefore, the entire efficacy is only slightly decreased and when n is in the range of 1-300, all compounds could produce similar technical effect to S1'-S4'.

Example 27: Synthesis of Water-Soluble Paclitaxel for Targeted Activation

1). Synthesis of Di-(2-Methoxyethoxyacetyl)-L-Lysine Ethyl Ester (I)

2-(2-methoxyethoxy) acetic acid (161 mg, 1.2 mmol) were dissolved N,N-dimethylformamide (10 mL) and cooled in an ice bath. 2-(7-azabenzotriazol)-N,N,N',N'-tetramethyluronium hexafluorophosphate (462 mg, 1.2 mmol), N,N-diisopropyl ethylamine (313 mg, 2.4 mmol) and L-lysine ethyl ester dihydrochloride (100 mg, 0.4 mmol) were added when stirring. After addition, the resultant mixture was stirred at ambient temperature overnight. The solvents were removed by evaporation under reduced pressure. The crude product was purified by reversed phase column to obtain I (128 mg, Yield 77.8%).

2). Synthesis of di (2-methoxyethoxyacetyl)-L-lysine (II)

Di (2-methoxyethoxyacetyl)-L-lysine ethyl ester (I) (122 mg, 0.3 mmol) were dissolved in tetrahydrofuran (15 mL). An aqueous solution of lithium hydroxide (39 mg, 0.9 mmol) was dropped into the resultant mixture after it was cooled to 0° C. The resultant mixture was stirred at ambient temperature for 2 hours and then cooled in an ice bath. Then pH was adjusted by concentrated hydrochloric acid to 2. Tetrahydrofuran was removed by evaporation. The resultant product was freeze-dried to produce a crude product II (112 mg, Yield 99%), which could be directly used in the next step without purification.

3). Synthesis of di (2-methoxyethoxyacetyl)-L-Lys-L-Ala-L-Ala-L-Asn (Trt)-4-amino benzyl alcohol (III)

Di (2-methoxyethoxyacetyl)-L-lysine (112 mg, 0.3 mmol) were dissolved in N,N-dimethylformamide (10 mL). 3-(Diethoxyphosphoryloxy)-1, 2, 3-benzotrizin-4-one (109 mg, 0.36 mmol), L-Ala-L-Ala-L-Asn (Trt)-4-amino benzyl alcohol (188 mg, 0.3 mmol) and N,N-diisopropyl ethylamine (117 mg, 0.9 mmol) were dropped into the resultant mixture after it was cooled to 0° C. After dropping, the resultant mixture was stirred at ambient temperature overnight. The solvents were removed by evaporation under reduced pressure. The crude product was purified by reversed phase column to obtain III (159 mg, Yield 54.0%).

4). Synthesis of di (2-methoxyethoxyacetyl)-L-Lys-L-Ala-L-Ala-L-Asn (Trt)-4-aminobenzyl-4-nitrophenyl carbonate (IV)

Di (2-methoxyethoxyacetyl)-L-Lys-L-Ala-L-Ala-L-Asn (Trt)-4-amino benzyl alcohol (167 mg, 0.17 mmol) dissolved in tetrahydrofuran (10 mL) was added into a three-neck flask. 4-nitrophenyl chloroformate (73 mg, 0.36 mmol) and pyridine (39 mg, 0.50 mmol) were dropped into the resultant mixture after it was cooled to 0□. The resultant mixture was stirred at ambient temperature overnight. The solvents were removed by evaporation under reduced pressure. The crude product was purified by reversed phase column to obtain IV (153 mg, Yield 78.5%).

5). Synthesis of di (2-methoxyethoxyacetyl)-L-Lys-L-Ala-L-Ala-L-Asn-4-aminobenzyl-4-nitrophenyl carbonate (V)

Di (2-methoxyethoxyacetyl)-L-Lys-L-Ala-L-Ala-L-Asn (Trt)-4-aminobenzyl-4-nitrophenyl carbonate (IV) (100 mg, 0.087 mmol) were dissolved in trifluoroacetic acid (1 mL). Two drops of water were added and then pumped by an oil pump immediately to obtain a crude product V (80 mg), which could be directly used in the next step without purification.

6). Synthesis of di (2-methoxyethoxyacetyl)-L-Ala-L-Ala-L-Asn-4-aminobenzyl-Paclitaxel (A1)

Di (2-methoxyethoxyacetyl)-L-Lys-L-Ala-L-Ala-L-Asn-4-aminobenzyl-4-nitrophenyl carbonate (80 mg, 0.088 mmol) and Paclitaxel (76 mg, 0.089 mmol) were dissolved by anhydrous N,N-dimethylformamide (10 mL) and cooled to 0□. DMAP (22 mg, 0.18 mmol) were added and then stirred at ambient temperature overnight. Again Paclitaxel (38 mg, 0.044 mmol) was added and the mixture was stirred overnight. The reaction solution was poured into ethyl acetate. The organic phases were pooled, washed by water, dried by anhydrous sodium sulphate. The solvents were removed by rotary evaporation. The crude product was purified by reverse phase column to obtain the target product A1 (25 mg, Yield 37.5%). According to the detection result by LC-MS, the mass-to-charge ratio of elution peak is 1619, which is consistent with its calculated molecular weight.

7

A2, A3 and A4 were synthesized by making reference to A1, except that the acetic acids substituted by alkoxy group used in step 7 have different molecular weights. When synthesizing A2, 3, 6, 9, 12, 15, 18-hexaoxanonadecanoic acid was used to replace 2-(2-methoxyethoxy) acetic acid, in synthesis of A3, 3, 6, 9, 12, 15, 18, 21, 24, 27, 30, 33, 36-dodecaoxaheptatriacontanoic acid was used to replace 2-(2-methoxyethoxy) acetic acid, and in synthesis of A4, polyoxa fatty acid was used to replace 2-(2-methoxyethoxy) acetic acid. According to mass spectrum (MS) detection results, the mass-to-charge ratios of A2, A3 and A4 are 1619, 1972 and 2500, respectively, which are consistent to their calculated molecular weights, 1619.71, 1972.13 and 2500.77. According to Matrix-Assisted Laser Desorption/Ionization Time of Flight Mass Spectrometry (MALDI-TOF-MS), A4's molecular weight is about 14739, which is consistent with its calculated molecular weight, 14739.59, as shown in the table 20 below.

TABLE 20

| No. | n | Character | Molecular weight by MS | Fluorescence | Output (milligram) | Yield |
|---|---|---|---|---|---|---|
| A1 | 1 | White powder | 1619 | None | 25 | 37.5% |
| A2 | 5 | White powder | 1972 | None | 245 | 43.3% |
| A3 | 11 | White powder | 2500 | None | 456 | 66.4% |
| A4 | 150 | White powder | 14739 | None | 645 | 34.6% |

Compounds A10-A24 (n=5) were also prepared in the present disclosure by similar method for synthesizing A2, except that the starting amino acids used for linking were different, as shown in Table 21. Corresponding $R_2$ amino acid and $R_3$ amino acid were dissolved in N,N-dimethylformamide. The same condensating agent, 1-ethyl-(3-dimethylaminopropyl) carbodiimide hydrochloride, was added respectively and reactions were allowed to take place at 0-25☐ for 0.5-2 hours. Then Asn was added and reaction was taken place at 0-25☐ for 2-24 hours. The resultant was purified to obtain a tripeptide. The tripeptide Ala-Ala-Asn was replaced to the synthesized intermediate to prepare A10-A24. Molecular weights of A10-A24, as detected by mass spectrum (MS), are shown in Table 21, which are consistent to their respective calculated molecular weights.

TABLE 21

| No. of Compound | $R_2$ | $R_3$ | Molecular weight by MS | Calculated molecular weight | Output (milligram) | Yield |
|---|---|---|---|---|---|---|
| A10 | Ala | Thr | 2002 | 2002.16 | 64 | 43% |
| A11 | Ala | Val | 2000 | 2000.11 | 58 | 42% |
| A12 | Ala | Asn | 2015 | 2015.08 | 43 | 27% |
| A13 | Thr | Ala | 2002 | 2002.16 | 48 | 38% |
| A14 | Thr | Thr | 2032 | 2032.18 | 45 | 37% |
| A15 | Thr | Val | 2030 | 2030.21 | 22 | 25% |
| A16 | Thr | Asn | 2045 | 2045.18 | 46 | 37% |
| A17 | Val | Ala | 2000 | 2000.18 | 57 | 23% |
| A18 | Val | Thr | 2030 | 2030.21 | 43 | 35% |
| A19 | Val | Val | 2028 | 2028.24 | 23 | 23% |
| A20 | Val | Asn | 2043 | 2043.21 | 46 | 64% |
| A21 | Ile | Ala | 2014 | 2014.21 | 75 | 19% |
| A22 | Ile | Thr | 2044 | 2044.24 | 43 | 4% |
| A23 | Ile | Val | 2042 | 2042.27 | 23 | 33% |
| A24 | Ile | Asn | 2057 | 2057.24 | 66 | 45% |

Example 28: Solubility Comparison of Present Water-Soluble Paclitaxel for Targeted Activation and Control Compounds on the Formulation of the Drug lyophilized (−70☐) compounds A1, A2, A3, A4 and various control compounds C1, C2, C3, C4, C5 and C6 were separately packing in a sterile room. Before animal test, A1, A2, A3 and A4 were dissolved by solvent 1 (injectable water) or solvent 2 (45% alcohol, 55% injectable water) in sterile room. A1, A2, A3 and A4 could completely dissolved in both solvent 1 and solvent 2, achieving a concentration of 10 mg/ml, and can be diluted by injectable water to the desired concentration. On the contrary, comparative compounds (C1, C2, C3, C4, C5 and C6) did not satisfy the formulating requirement, as shown in Table 22.

TABLE 22

Effect of absence of similar components in control compounds or linkage to Paclitaxel at its 7- or 2-position (i.e., linking the group to the OH at 7- or 2-position of Paclitaxel) on the solubility of the drug

| Compound | Solvent 1 | Solvent 2 |
|---|---|---|
| C1: AAN -group 2- Paclitaxel (linking at 2-position) | insoluble | insoluble |
| C2: group 1- AANL - Paclitaxel (linking at 2-position) | insoluble | insoluble |
| C3: AAN - Paclitaxel (linking at 2-position) | insoluble | insoluble |
| C4: group 1- AAN -group 2- Paclitaxel (linking at 7-position) | insoluble | insoluble |
| C5: group 1- AANL -group 2- Paclitaxel (linking at 2-position) | insoluble | insoluble |
| C6: group 1- AANK -group 2- Paclitaxel (linking at 2-position) | insoluble | insoluble |
| A1 | insoluble | soluble |
| A2 | soluble | soluble |
| A3 | soluble | soluble |
| A4 | soluble | soluble | group 1: 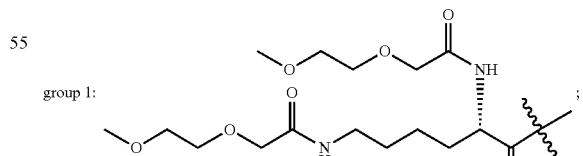

group 2: 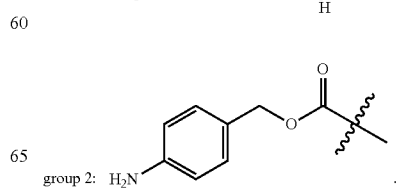

In Table 22, AAN, AANL and AANK indicate the linkage formed by small peptides in the compounds, A is Ala, N is Asn, L is Leu and K is Lys.

According to Table 22, Paclitaxel is insoluble in water, but its solubility is significantly changed after modification, with increased solubility in water. Change in solubility may greatly affect the formulation scheme of a drug. As compared to the traditional Paclitaxel which is insoluble in water, A1, A2, A3 and A4 can be used to produce a soluble formulation. A1, A2, A3 and A4 can directly dissolve in water, Thus, their injection doses and efficacies can be improved and auxiliary materials that cause allergy generally used for Paclitaxel can be avoided. This is a great progress in drug development, and indicates that the water-soluble Paclitaxel for targeted activation in tumor microenvironment has a promising innovation and prospect of use. On the contrary, comparative compounds (C1, C2, C3, C4, C5 and C6) did not satisfy the formulating requirement.

Example 29: Methods for Determining the Contents of A1, A2, A3 and A4 in Respective Products and their Content Ranges As detected by analytic HPLC (Agilent 1220 series, C8 column 5 μm, 4.6 mm ID×250 mm; the mobile phase is 0-95% acetonitrile (ACN)), the purities of A1, A2, A3 and A4 are all in the range of 95-99%.

Example 30: Activation Efficiency of Present Water-Soluble Paclitaxel Derivatives for Targeted Activation in Tumor Microenvironment Solvent (50% injectable water, 45%-49% alcohol, 1%-5% Tween 80) was used to dissolve sample compound A1, A2, A3 and A4, and they were diluted for ten times to a concentration of 1 mg/ml. At 370, sample compounds were added into 100 μg acidized tumor tissue homogenates (pH6.0) in a concentration of 1 mg/ml. The enzyme in tumor tissue homogenates could release Paclitaxel. Reduction of compounds and increase of Paclitaxel were detected by HPLC, thereby comparing the activation efficiency of the drugs by the tumor tissue. It was found that the current compounds A1, A2, A3 and A4 exhibited highest activation efficiency among the screened compounds.

TABLE 23

Activation ratio (%) of A1, A2, A3 and A4 in homogenates from different tumor tissues

| Different tumor tissues | Cells producing tumor | Activation ratio (%) in homogenates from different tumor tissues | | | |
|---|---|---|---|---|---|
| | | A1 | A2 | A3 | A4 |
| Human fibrosarcoma | HT-1080 | 77.7 | 78.4 | 70.3 | 77.2 |
| Human breast cancer | MDA-MB435 | 95.6 | 94.4 | 93.4 | 97.8 |
| Human ovarian cancer | SK-OV-3 | 91.4 | 88.6 | 82.8 | 66.4 |
| Human colon cancer | HT-29 | 82.4 | 92.9 | 94.6 | 93.6 |
| Human chronic leukemia | K562 | 67.7 | 76.3 | 73.2 | 77.2 |
| Human pancreatic cancer | Panc-1 | 97.8 | 93.8 | 94.5 | 96.1 |
| Human non-small cell lung cancer | A549 | 89.5 | 92.4 | 84.4 | 86.2 |
| Human prostate cancer | PC-3 | 100.3 | 101.4 | 99.3 | 96.5 |
| Human liver cancer | Hepg2 | 98.3 | 87.6 | 86.5 | 77.0 |
| Human renal cancer | OS-RC-2 | 89.2 | 94.5 | 89.4 | 93.5 |
| Human heart | | none | none | none | none |

The affect to drug activation of similar ingredients in control compounds was evaluated. Solvent (50% injectable water, 42%-49% alcohol, 1%-8% Tween 80) was used to dissolve sample compound A1, A2, A3 and A4, and they were diluted for ten times to a concentration of 1 mg/ml. At 37□, sample compounds were added into 100 μg acidized human breast cancer (MDA-MB435) tumor tissue homogenates (pH6.0) in a concentration of 1 mg/ml. The enzyme in tumor tissue homogenates could release Paclitaxel. Reduction of compounds and increase of Paclitaxel were detected by HPLC, thereby comparing the activation efficiency of the drugs by the tumor tissue. Results were showed in table 24.

TABLE 24

| Compounds | activation efficiency (%) |
|---|---|
| C1: AAN-group 2-Paclitaxel (linking at 2-position) | 64.4 |
| C2: group 1-AAN-Paclitaxel (linking at 2-position) | 51.9 |
| C3: AAN-Paclitaxel (linking at 2-position) | 32.7 |
| C4: group 1-AAN-group 2-Paclitaxel (linking at 7-position) | 11.6 |
| C5: group 1-AANL-group 2-Paclitaxel (linking at 2-position) | 54.4 |
| C6: group 1-AANK-group 2-Paclitaxel (linking at 2-position) | 43.3 |
| A1 | 95.1 |
| A2 | 96.3 |
| A3 | 94.5 |
| A4 | 84.3 |

According to the results, different groups in the present Paclitaxel for targeted activation in tumor microenvironment have various effects on the activation of Paclitaxel drugs in tumor tissue. The mutual structure-efficacy of Paclitaxel with the groups linked determined the targeting and activation effects in tissues. Activation of A1, A2, A3 and A4 in different tumor types (10 kinds) proved their broad treatment spectrum (Table 24). Meanwhile, certain compounds produced in the screening were compared, and the activation efficiency in the same human breast cancer MDA-MB435 tissue was examined. It was proved that the respective group selection in A1, A2, A3 and A4 had relatively higher activation efficiency (Table 24).

The Paclitaxel derivatives (A1~A4 and A10~A23) for targeted activation in tumor microenvironment of the present disclosure were based on a great amount of synthetic experiments. In these experiments, we designed a lot of complicated compounds having different linking manners. Then the complicated compounds were linked to position 2 or 7 of Paclitaxel, that is, they were linked to Paclitaxel via the OH at position 2 or position 7. The resultant Paclitaxel derivatives were screened through activation efficiency in tumor tissues. The screened derivatives were further screened through inhibition of tumor for $R_2$, $R_3$ and n. The activated site that is specific to the tumor tissue locates between AAN and group 2. After cleaving by activation, group 2 can be freely released, thereby releasing Paclitaxel. Because the active center of asparagine endopeptidase locates at the bottom of its globular depression and the cleavage site should be close to the active center, it is very important if there is a steric hindrance to the cleavage site produced by the complicated compounds.

According to the screening results, it is presumed that linking of group 2 may effectively avoid steric hindrance produced by directly linking Paclitaxel, which thereby not affecting approach of asparagine endopeptidase. And, the structure-efficacy of group 1 may increase the polarity of the cleavage site, which allows the more water-soluble protease to be easily to approach the cleavage site and thereby to increase the cleaving efficiency. Linking to position 2 of Paclitaxel could obviously reduce steric hindrance produced by Paclitaxel to protease, expose more groups, each of which as a whole is hydrophilic, and increase cleaving efficiency and water solubility. Whereas an additional polar amino acid K or L would decrease the activation efficiency.

Example 31: Detection of Maximum Tolerated Dose (MTD) by Intravenous Injection of the Water-Soluble Paclitaxel Derivatives for Targeted Activation in Tumor Microenvironment Test purpose: to investigate the acute toxicity of the present Paclitaxel derivatives via detecting MTD by intravenous injection.

Test drugs: Solvent (50% injectable water, 42%-49% alcohol, 1%-8% Tween 80) was used to dissolve sample compound A1, A2, A3 and A4, diluted to corresponding concentrations by physiological saline when testing, to prepare A1, A2, A3 and A4 injections.

Animal: the first class BALB/C mice purchased from SHANGHAI SLAC LABORATORY ANIMAL CO. LTD, weighing 19-21 g and all mice being female.

Method and results: 42 BALB/C mice were randomly divided into 7 groups according to their body weights, with 6 mice in each group. As shown in Table 21, the mice were intravenously injected with A1, A2, A3 and A4 for just one time in a dose of 0 mg/kg, 25 mg/kg, 50 mg/kg, 60 mg/kg, 70 mg/kg, 80 mg/kg, and 960 mg/kg. Control tests were performed by injecting 0.2 ml physiological saline or Paclitaxel (purchased from Youcare Pharmaceutical Group Co., Ltd). Animals were observed for 17 continuous days for presence or absence of the following behaviors on each day: pilo-erection, hair tousle and lackluster, lethargy, stoop and irritable reaction, and body weight and death were recorded. Blood samples were taken on the 3, 5 and 14 days for counting the whole blood cells. Animals were anatomized on day 14 to take the heart, liver, kidney, lung, spleen, and pancreas for HE staining.

TABLE 25

Comparison of mortality rates of test mice receiving different doses of A1, A2, A3 and A4 injections, physiological saline or Paclitaxel injection

| Group | | Dose (mg/kg) | Number of animal | Number of dead animal | Mortality rate (%) |
|---|---|---|---|---|---|
| 1 | physiological saline | 0 mg/kg | 10 | 0 | 0 |
| 2 | A1 | 125 mg/kg | 10 | 0 | 0 |
| 3 | A1 | 150 mg/kg | 10 | 0 | 0 |
| 4 | A1 | 175 mg/kg | 10 | 0 | 0 |
| 5 | A1 | 200 mg/kg | 10 | 0 | 0 |
| 6 | A2 | 125 mg/kg | 10 | 2 | 10 |
| 7 | A2 | 150 mg/kg | 10 | 0 | 0 |
| 8 | A2 | 175 mg/kg | 10 | 0 | 0 |
| 9 | A2 | 200 mg/kg | 10 | 0 | 0 |
| 10 | A3 | 125 mg/kg | 10 | 1 | 10 |
| 11 | A3 | 150 mg/kg | 10 | 0 | 0 |
| 12 | A3 | 175 mg/kg | 10 | 0 | 0 |
| 13 | A3 | 200 mg/kg | 10 | 0 | 0 |
| 14 | A4 | 125 mg/kg | 10 | 2 | 20 |
| 15 | A4 | 150 mg/kg | 10 | 0 | 0 |
| 16 | A4 | 175 mg/kg | 10 | 0 | 0 |
| 17 | A4 | 200 mg/kg | 10 | 0 | 0 |
| 18 | Paclitaxel | 25 mg/kg | 10 | 0 | 10 |
| 19 | Paclitaxel | 30 mg/kg | 10 | 0 | 0 |
| 20 | Paclitaxel | 35 mg/kg | 10 | 1 | 10% |
| 21 | Paclitaxel | 40 mg/kg | 10 | 4 | 40% |

Results and discussions: no pilo-erection, hair tousle and lackluster, lethargy, stoop, irritable reaction and death were observed in mice receiving 90 mg/kg A1, A2, A3 and A4 injections. As shown in Table 25, the MTD of the A1 and A2 injections were about 90 mg/kg, which is far beyond the MTD of Paclitaxel, 6 mg/kg. The MTD for intravenous administration of a test drug is an important reference index for drug toxicity. The results indicate that the toxicity of the Paclitaxel released by targeted activation is significantly reduced as compared with Paclitaxel.

Example 32: Study on Efficacy of A1, A2, A3 and A4 Injections in Nude Mice

Test purpose: to investigate the anti-tumor efficacy of A1, A2, A3 and A4 in mice model for tumor treatment.

Test drug: A1, A2, A3 and A4 injections (same as Example 31) and Paclitaxel injection (purchased from Youcare Pharmaceutical Group Co., Ltd), diluted to corresponding concentrations by physiological saline when testing.

Method and Results:

1. Animal: nude mice of 6-8 weeks old, all female.
2. Production of tumor model

1) Human prostate cancer PC-3 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ Panc-1 cells were subcutaneously injected to the back of the nude mice. Mice were randomly grouped after the tumor reached at least 100 mm$^3$. Then treatment began and the day on which the treatment began was day 1.

3) Course of treatment

According to the clinical application of A1, A2, A3 and A4, drugs were intravenously injected (IV). A1, A2, A3 and A4 were administered in a dose of less than ⅙ MTD, i.e., 24 mg/kg, and Paclitaxel was administered in a dose of ⅓ MTD, i.e., 8 mg/kg. The control group was administered by physiological saline. Drugs were administered once weekly for four weeks.

4) Grouping and test results are shown in Table 26.

TABLE 26

Effect of A1, A2, A3 and A4, Paclitaxel and control group on tumor treatment in nude mice

| Group | Number of animal | Size of tumor (mm³) | | inhibitory rate on tumor | |
|---|---|---|---|---|---|
| | | Day 10 | Day 24 | Day 10 | Day 24 |
| A1 group | 10 | 85.16 ± 58.4 | 89.78 ± 63.7 | 71.1% | 76.4% |
| A2 group | 10 | 55.19 ± 56.2 | 44.43 ± 47.9 | 81.3% | 88.3% |
| A3 group | 10 | 82.72 ± 69.4.4 | 81.83 ± 89.2 | 71.9% | 78.5% |

TABLE 26-continued

Effect of A1, A2, A3 and A4, Paclitaxel and control group on tumor treatment in nude mice

| Group | Number of animal | Size of tumor (mm³) Day 10 | Size of tumor (mm³) Day 24 | inhibitory rate on tumor Day 10 | inhibitory rate on tumor Day 24 |
|---|---|---|---|---|---|
| A4 group | 10 | 80.69 ± 68.2.4 | 67.09 ± 72.4 | 72.6% | 82.4% |
| Paclitaxel treatment group | 10 | 123.04 ± 125.3 | 252.49 ± 248.5 | 58.3% | 33.7% |
| Control group | 10 | 294.93 ± 275.8 | 380.71 ± 362.7 | / | / |

5) Results and discussions: As shown in Table 26, inhibition on tumor growth by A1, A2, A3 and A4 were greatly improved as compared with the groups treating by Paclitaxel using the same molar concentration and the control group.

Example 33: Study on Efficacy of A1, A2, A3 and A4 in D121 Tumor Immune Model

Test purpose: to investigate the anti-tumor efficacy of A1, A2, A3 and A4 in a D121 lung cancer model for immune treatment.

Animal: C57 mice of 6-8 weeks old, all female.

Test drug: A1, A2, A3 and A4 injections (same as Example 31) and Paclitaxel injection (purchased from Youcare Pharmaceutical Group Co., Ltd), diluted to corresponding concentrations by physiological saline when testing.

Production of Tumor Model:

1) D121 lung tumor cells were purchased from ATCC. Cells were cultivated in DMEM culture solution containing 10% fetal bovine serum at 37° C. and 5% $CO_2$. The cells were passaged for every three days and cells within the 15th passage were used.

2) Tumor immunization. $5 \times 10^5$ D121 lung cancer cells (purchased from ATCC) which were killed by irradiation were intraperitoneally injected to mice. The mice were injected for 3 times, once every two weeks. After immunization, mice were injected with tumor cells and the drugs were administered weekly for 4 weeks. In the table below the immune group was immuned with D121 lung tumor cells and the group without dead D121 lung tumor cells was injected with physiological saline as controls.

3) Production of tumor. After immunization (4 weeks later), $10^6$ live lung tumor cells were subcutaneously injected to the back of the C57 mice immunized by tumor. Treatment began when the tumor grew to 0.3-0.4 cm. Tumor size (mm³) were noted and tumor inhibition rates were calculated.

4) Analysis on tumor CD8+ T cells. The tumor tissue was homogenated and individual cells in the tumor were filtered, separated and washed by buffer twice, then cultivated with the leucocyte common antigen CD45-PE and CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry.

5) Grouping and test results are shown in Table 27.

TABLE 27

Effect on inhibition of tumor and immune activation of A1, A2, A3 and A4, Paclitaxel and control

| Group | Number of animal | Size of tumor (mm³) Day 18 | inhibitory rate on tumor % Day 18 | CD8: CD45 (%) |
|---|---|---|---|---|
| Immune group, without D121 dead tumor cells | 8 | 2076.316 ± 457.8 | | 6.7 |
| Immune group (Control group) | 8 | 1687.906 ± 341.6 | | 14.2 |
| Immune group + A1 | 8 | 261.36 ± 178.3 | 84.52 | 20.4 |
| Immune group + A2 | 8 | 375.727 ± 247.3 | 77.74 | 19.4 |
| Immune group + A3 | 8 | 360.393 ± 312.7 | 78.65 | 17.3 |
| Immune group + A4 | 8 | 324.005 ± 268.4 | 80.80 | 16.9 |
| Immune group + A1 + PDL1 antibody | 8 | 71.258 ± 113.9 | 95.78 | 23.4 |
| Immune group + Paclitaxel | 8 | 1342.308 ± 379.3.8 | 20.47 | 5.7 |
| Immune group + Paclitaxel + PDL1 antibody | 8 | 1468.39 ± 412.8 | 13.00 | 7.2 |

6) Results and discussion. As shown in table 27, treatment effects of A1, A2, A3 and A4 on C57 mice were greatly improved as compared to the control group and the other treatment groups. A1 and PDL1-antibody show an excellent synergistic effect in promoting immunization and treatment. They can inhibit tumor growth via improving immunization.

Example 34: Study on Efficacy of A1, A2, A3 and A4 in BALB/C Mice Model for Tumor Metastasis Test purpose: to investigate the anti-tumor efficacy of A1, A2, A3 and A4 in BALB/C mice model for treatment of tumor metastasis.

Test drug: A1, A2, A3 and A4 injections (same as Example 31) and Paclitaxel injection (purchased from Youcare Pharmaceutical Group Co., Ltd), diluted to corresponding concentrations by physiological saline when testing.

Method and Results:

1. Animal: BALB/C mice of 6-8 weeks old, all female.
2. Production of tumor model 1) 4T1 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor metastasis. $10^6$ T1 cells were subcutaneously injected to the back of the BALB/C mice. Mice were randomly grouped after the tumor grew to about 1.5 cm. The subcutaneous tumor was removed by surgery and drug treatment began. Mice were killed after anesthesia on day 27. The whole lung was taken out and put into Bouin's solution for staining. The number of the tumor metastasized to lung was counted with anatomical microscope.

3) Course of treatment

According to the clinical application of A1, A2, A3 and A4, drugs were intravenously injected (IV). A1, A2, A3 and A4 were administered in a dose of ⅙ MTD, i.e., 12 mg/kg, and Paclitaxel was administered in a dose of ⅙ MTD, i.e., 4 mg/kg. The control group was administered by physiological saline. Drugs were administered once for every three days for 4 times.

4) Grouping and test results are shown in Table 28.

TABLE 28

Effects of A1, A2, A3 and A4, Paclitaxel and control on inhibition of tumor metastasis in BALB/C mice

| Group | Number of animal | Number of metastasized tumor | Inhibitory rate on metastasis |
|---|---|---|---|
| A1 Group | 10 | 3 ± 4 | 97.9% |
| A2 Group | 10 | 9 ± 5 | 93.9% |
| A3 Group | 10 | 16 ± 9 | 89.1% |
| A4 Group | 10 | 12 ± 18 | 91.8% |
| Paclitaxel treatment group | 10 | 137 ± 32 | 6.8% |
| Control group | 10 | 147.0 ± 46 | / |

5) Results and discussion. As shown in Table 24, the inhibitory effect on tumor metastasis of BALB/C mice was greatly improved after intraperitoneal injection of A1, A2, A3 and A4, as compared with the Paclitaxel group and the control group, indicating that this kind of drugs exhibits an excellent efficacy on anti-tumor metastasis.

Example 35: Study on Efficacy of A1 Injection in Multiple Tumor Models

Test purpose: to investigate the anti-tumor spectrum of A1 through multiple tumor models from mice Test drug: A1 injection (same as Example 31), diluted to corresponding concentrations by physiological saline when testing.

Method and Results:
1. Animal: nude mice of 6-8 weeks old, all female.
2. Production of tumor model 1) Corresponding tumor cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ corresponding cells were subcutaneously injected to the back of the nude mice. Mice were randomly grouped after the tumor reached at least 100 $mm^3$. Then treatment began and the day on which the treatment began was day 1.

3) Course of treatment. According to the clinical application of A1, A1 was administered in a dose of ⅙ MTD, i.v., 17.6 μmol/kg. The control group was administered by physiological saline. Animals were administered once weekly for three weeks.

4) Grouping and test results are shown in Table 29.

TABLE 29

Treatment effect of A1 in multiple tumor models

| Group | Tumor cell | inhibitory rate on tumor (Day 26) |
|---|---|---|
| Human breast cancer | MDA-MB435 | 91.2% |
| Human ovarian cancer | SK-OV-3 | 84.4% |
| Human colon cancer | HT-29 | 87.5% |
| Human chronic leukemia | K562 | 76.9% |
| Human colon caner | HT1080 | 95.6% |
| Human pancreatic cancer | Panc-1 | 89.2% |
| Human non-small cell lung cancer | A549 | 95.3% |
| Human liver cancer | Hepg2 | 85.4% |
| Human renal cancer | OS-RC-2 | 86.6% |

5) Results and discussion. As shown in Table 29, A1 shows an excellent efficacy in multiple tumor models, demonstrating that the anti-tumor drug has a wide anti-tumor spectrum.

In other examples (A10~A24) of the present disclosure, activation efficiency, inhibitory rate on tumor and inhibitory rate on metastasis of the present water-soluble Paclitaxel derivatives for targeted activation with different amino acid structures were examined using methods same as that in example 30, 32 and 34. Results were showed in table 30.

TABLE 30 activation efficiency, inhibitory rate on tumor and on metastasis of A10-A24

| Compound No. | $R_2$ | $R_3$ | activation efficiency (%) | inhibitory rate on tumor (%) (Day 38) | inhibitory rate on metastasis (%) |
|---|---|---|---|---|---|
| A10 | Ala | Thr | 70.4 | 69.85 | 82.5 |
| A11 | Ala | Val | 46.86 | 50.82 | 48.95 |
| A12 | Ala | Asn | 42.24 | 53.79 | 89.76 |
| A13 | Thr | Ala | 83.27 | 67.1 | 96.14 |
| A14 | Thr | Thr | 41.25 | 57.64 | 32.34 |
| A15 | Thr | Val | 60.06 | 50.6 | 43.23 |
| A16 | Thr | Asn | 36.52 | 75.13 | 62.48 |
| A17 | Val | Ala | 33.66 | 64.13 | 71.28 |
| A18 | Val | Thr | 72.38 | 76.78 | 88.11 |
| A19 | Val | Val | 42.35 | 60.72 | 75.13 |
| A20 | Val | Asn | 47.85 | 52.58 | 78.54 |
| A21 | Ile | Ala | 54.56 | 47.74 | 70.29 |
| A22 | Ile | Thr | 76.89 | 65.45 | 77.55 |
| A23 | Ile | Val | 63.25 | 71.72 | 50.05 |
| A24 | Ile | Asn | 76.44 | 86.4 | 78.45 |

Results and discussion. As shown in Table 30, compounds A10~A24 could be activated and had some effects on inhibition of tumor growth and on metastasis, indicating the screening of inventors could optimize the activation and treatment of tumor. It should be understood that the above descriptions of preferred Examples are not intended to limit the subject invention. After reading the above details, it is apparent to the skilled artisan that amino acids at position $R_2$ and $R_3$ of the present drugs or compounds can be changed or replaced.

In some examples of the invention, other water-soluble Paclitaxel derivatives for targeted activation in tumor microenvironment were synthesized, of which n is any integer between 1-150, $R_2$ is Ala, Thr, Val or Ile; $R_3$ is Ala, Thr, Val or Asn. And they were subjected to activation test as done in Examples 28, study on efficacy on tumor as done in Examples 32 and 33, study on efficacy of inhibiting metastasis as done in Example 34 and study on efficacy on multiple tumors as done in Example 35. Results showed that they had similar results to A1-A4. As demonstrated by the experiments, when n is in the range of 1-300, the inhibitory rate on tumor is slightly reduced as n increases. The activation activity also slightly decreases and mass of drugs in the same mole increases, as n increases. However, the metabolic half life of the drug also increases as n increases. Therefore, the entire efficacy is only slightly decreased and when n is in the range of 1-150, all compounds could produce similar technical effect to A1-A4.

Example 36: Synthesis of Water-Soluble and Targeting Activated Docetaxel B1

1. Synthesis of di (2-methoxyethoxyacetyl)-L-lysine ethyl ester (I)

2-(2-methoxyethoxy) acetic acid (161 mg, 1.2 mmol) were dissolved N,N-dimethylformamide (10 mL) and cooled in an ice bath. 2-(7-azabenzotriazol)-N,N,N',N'-tetramethyluronium hexafluorophosphate (462 mg, 1.2 mmol), N,N-diisopropyl ethylamine (313 mg, 2.4 mmol) and L-lysine ethyl ester dihydrochloride (100 mg, 0.4 mmol) were added when stirring. After addition, the resultant mixture was stirred at ambient temperature overnight. The solvents were removed by evaporation under reduced pressure. The crude product was purified by reversed phase column to obtain I (128 mg, Yield 77.8%).

2. Synthesis of di (2-methoxyethoxyacetyl)-L-lysine (II)

Di (2-methoxyethoxyacetyl)-L-lysine ethyl ester (I) (122 mg, 0.3 mmol) were dissolved in tetrahydrofuran (15 mL). An aqueous solution of lithium hydroxide (39 mg, 0.9 mmol) was dropped into the resultant mixture after it was cooled to 0° C. The resultant mixture was stirred at ambient temperature for 2 hours and then cooled in an ice bath. Then pH was adjusted by concentrated hydrochloric acid to 2. Tetrahydrofuran was removed by evaporation. The resultant product was freeze-dried to produce a crude product II (112 mg, Yield 99%), which could be directly used in the next step without purification.

3. Synthesis of di (2-methoxyethoxyacetyl)-L-Lys-L-Ala-L-Ala-L-Asn (Trt)-4-amino benzyl alcohol (III)

Di (2-methoxyethoxyacetyl)-L-lysine (112 mg, 0.3 mmol) were dissolved in N,N-dimethylformamide (10 mL). 3-(Diethoxyphosphoryloxy)-1, 2, 3-benzotrizin-4-one (109 mg, 0.36 mmol), L-Ala-L-Ala-L-Asn (Trt)-4-amino benzyl alcohol (188 mg, 0.3 mmol) and N,N-diisopropyl ethylamine (117 mg, 0.9 mmol) were dropped into the resultant mixture after it was cooled to 0□. After dropping, the resultant mixture was stirred at ambient temperature overnight. The solvents were removed by evaporation under reduced pressure. The crude product was purified by reversed phase column to obtain III (159 mg, Yield 54.0%).

4. Synthesis of di (2-methoxyethoxyacetyl)-L-Lys-L-Ala-L-Ala-L-Asn (Trt)-4-aminobenzyl-4-nitrophenyl carbonate (IV)

Di (2-methoxyethoxyacetyl)-L-Lys-L-Ala-L-Ala-L-Asn (Trt)-4-amino benzyl alcohol (167 mg, 0.17 mmol) dissolved in tetrahydrofuran (10 mL) was added into a three-neck flask. 4-nitrophenyl chloroformate (73 mg, 0.36 mmol) and pyridine (39 mg, 0.50 mmol) were dropped into the resultant mixture after it was cooled to 0□. The resultant mixture was stirred at ambient temperature overnight. The solvents were removed by evaporation under reduced pressure. The crude product was purified by reversed phase column to obtain IV (153 mg, Yield 78.5%).

5. Synthesis of di (2-methoxyethoxyacetyl)-L-Lys-L-Ala-L-Ala-L-Asn-4-aminobenzyl-4-nitrophenyl carbonate (V)

Di (2-methoxyethoxyacetyl)-L-Lys-L-Ala-L-Ala-L-Asn (Trt)-4-aminobenzyl-4-nitrophenyl carbonate (IV) (100 mg, 0.087 mmol) were dissolved in trifluoroacetic acid (1 mL). Two drops of water were added and then pumped by an oil pump immediately to obtain a crude product V (80 mg), which could be directly used in the next step without purification.

6. Synthesis of di (2-methoxyethoxyacetyl)-L-Ala-L-Ala-L-Asn-4-aminobenzyl-Docetaxel (B1)

Di (2-methoxyethoxyacetyl)-L-Lys-L-Ala-L-Ala-L-Asn-4-aminobenzyl-4-nitrophenyl carbonate (1176 mg, 1.3 mmol) and Docetaxel (1293 mg, 1.6 mmol) were dissolved by anhydrous N,N-dimethylformamide (20 mL) and cooled to 0□. DMAP (318 mg, 2.6 mmol) were added and then stirred at ambient temperature overnight. The reaction solution was poured into dichloromethane. The organic phases were pooled, washed by water, dried by anhydrous sodium sulphate. The solvents were removed by rotary evaporation. The crude product was purified by reverse phase column to obtain the target product B1 (511 mg, Yield 25%). According to the detection result by mass spectrum (MS), the mass-to-charge ratio of B1 is 1573, which is consistent with its calculated molecular weight, 1573.69.

B2, B3 and B4 were synthesized by making reference to B1, except that the acetic acids substituted by alkoxy group used in step 1 have different molecular weights. When synthesizing B2, 3, 6, 9, 12, 15, 18-hexaoxanonadecanoic acid was used to replace 2-(2-methoxyethoxy) acetic acid, in synthesis of B3, 3, 6, 9, 12, 15, 18, 21, 24, 27, 30, 33, 36-dodecaoxaheptatriacontanoic acid was used to replace 2-(2-methoxyethoxy) acetic acid, and in synthesis of B4, polyoxa fatty acid was used to replace 2-(2-methoxyethoxy) acetic acid. According to mass spectrum (MS) detection results, the mass-to-charge ratios of B2 and B3 are 1926 and 2454, respectively, which are consistent to their calculated molecular weights, 1926.11 and 2454.74. According to Matrix-Assisted Laser Desorption/Ionization Time of Flight Mass Spectrometry (MALDI-TOF-MS), B4's molecular weight is about 14964, which is consistent with its calculated molecular weight, 14964.56, as shown in Table 31.

TABLE 31

Character, mass spectrum and fluorescence test results of B1-B4

| No. | n | Character | Molecular weight by MS | Fluorescence |
|---|---|---|---|---|
| B1 | 1 | White powder | 1573 | None |
| B2 | 5 | White powder | 1926 | None |
| B3 | 11 | White powder | 2454 | None |
| B4 | 150 | White powder | 14964 | None |

Example 37: Synthesis of B10-B24

B10-B24 were synthesized by a similar method for B1, except that the amino acids used for linking are different, as shown in Table 32.

Corresponding $R_2$ amino acid and $R_3$ amino acid were dissolved in N,N-dimethylformamide, respectively. The condensating agent, such as 1-ethyl-(3-dimethylaminopropyl) carbodiimide hydrochloride, was added and reactions were allowed to take place at 0-25☐ for 0.5-2 hours. Then Asn was added and reaction was taken place at 0-25☐ for 2-24 hours. The reaction solution was purified to obtain a tripeptide. The tripeptide was used to replace Ala-Ala-Asn as an intermediate to prepare B10-B24 according to Example 36. Molecular weights of B10-B24, as detected by mass spectrum, are shown in the following table, which are consistent to their respective calculated molecular weights.

TABLE 32

Character and mass spectrum results of B10-B24

| No. | $R_2$ | $R_3$ | Character | Molecular weight by MS | Calculated molecular weight |
|---|---|---|---|---|---|
| B10 | Ala | Thr | White powder | 1604 | 1603.72 |
| B11 | Ala | Val | White powder | 1602 | 1601.67 |
| B12 | Ala | Asn | White powder | 1617 | 1616.64 |
| B13 | Thr | Ala | White powder | 1604 | 1603.72 |
| B14 | Thr | Thr | White powder | 1634 | 1633.74 |
| B15 | Thr | Val | White powder | 1632 | 1631.77 |
| B16 | Thr | Asn | White powder | 1647 | 1646.74 |
| B17 | Val | Ala | White powder | 1602 | 1601.74 |
| B18 | Val | Thr | White powder | 1632 | 1631.77 |
| B19 | Val | Val | White powder | 1630 | 1629.80 |
| B20 | Val | Asn | White powder | 1645 | 1644.77 |
| B21 | Ile | Ala | White powder | 1616 | 1615.77 |
| B22 | Ile | Thr | White powder | 1646 | 1645.80 |
| B23 | Ile | Val | White powder | 1644 | 1643.83 |
| B24 | Ile | Asn | White powder | 1659 | 1658.80 |

Example 38: Effect of Different Groups in the Water-Soluble Docetaxel for Targeted Activation in Tumor Microenvironment on the Formulation of the Drug B1, B2, B3 and B4 and various control compounds were dried under vacuum, sterilized via gas sterilization, and separately packing in a sterile room. Before animal test, B1, B2, B3 and B4 were dissolved by solvent 1 (injectable water) or solvent 2 (30% alcohol, 70% injectable water) and diluted by injectable water to the desired concentration in sterile room. On the contrary, comparative compounds (C1', C2', C3', C4', C5', and C6') did not satisfy the formulating requirement, as shown in Table 33. Docetaxel is insoluble in water, but its solubility is significantly changed after modification, with increased solubility in water. Change in solubility may greatly affect the formulation scheme of a drug. As compared to the traditional Docetaxel which is insoluble in water, B1, B2, B3 and B4 can be used to produce a soluble formulation. Thus, their injection doses and efficacies can be improved and auxiliary materials that cause allergy generally used for Docetaxel can be avoided. This is a great progress in drug development, and indicates that the water-soluble Docetaxel for targeted activation in tumor microenvironment has a promising innovation and prospect of use.

TABLE 33

Solutility test of the screened drugs and Effect of absence of similar components in control compounds or linkage to Docetaxel at its 7- or 2-position (i.e., linking the group to the OH at 7- or 2-position of Docetaxel) on the solubility of the drugs

| Compounds | Solvent 1 | Solvent 2 |
|---|---|---|
| C1': AAN -group 2-Docetaxel (linking at 2-position) | insoluble | insoluble |
| C2': group 1- AANL -Docetaxel (linking at 2-position) | insoluble | insoluble |
| C3': AAN -Docetaxel (linking at 2-position) | insoluble | insoluble |
| C4': group 1- AAN -group 2-Docetaxel (linking at 7-position) | insoluble | insoluble |
| C5': group 1- AANL -group 2-Docetaxel (linking at 2-position) | insoluble | soluble |
| C6': group 1- AANK -group 2-Docetaxel (linking at 2-position) | insoluble | insoluble |
| B1 | insoluble | soluble |
| B2 | soluble | soluble |
| B3 | soluble | soluble |
| B4 | soluble | soluble |

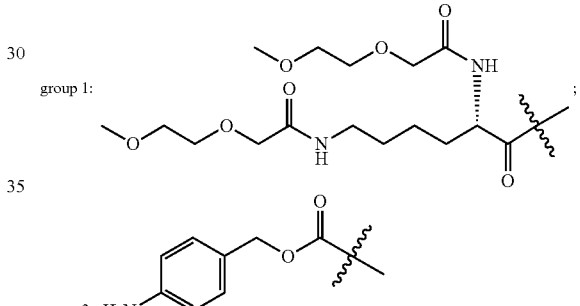

group 1:

group 2: $H_2N$

Group 1 and group 2 mentioned below are identical to the above group 1 and 2, respectively.

In Table 33, AAN, AANL and AANK indicate the linkage formed by a small peptide in the compounds, A is Ala, N is Asn, L is Leu and K is Lys.

The water-soluble Docetaxel derivatives for targeted activation in tumor microenvironment of the present disclosure were based on a great amount of synthetic experiments. In these experiments, we designed a lot of complicated compounds having different linking manners. Then the complicated compounds were linked to position 2 or 7 of Docetaxel, that is, they were linked to Docetaxel via the OH at position 2 or position 7. The resultant Docetaxel derivatives were screened through activation efficiency in the presence of tumor tissue or aspartate endopeptidase. The screened derivatives were further screened through inhibition of tumor for $R_2$, $R_3$ and n. The activated site that is specific to the tumor tissue locates between AAN and group 2. After cleaving by activation, group 2 can be freely released, thereby releasing Docetaxel. Because the active center of asparagine endopeptidase locates at the bottom of its globular depression and the cleavage site should be close to the active center, it is very important if there is a steric hindrance to the cleavage site produced by the complicated compound.

According to the screening results, it is presumed that linking of group 2 may effectively avoid steric hindrance produced by directly linking Docetaxel, which thereby not affecting approach of asparagine endopeptidase. And, the structure-efficacy of group 1 may increase the polarity of the cleavage site, which allows the more water-soluble protease to be easily to approach the cleavage site and thereby to increase the cleaving efficiency. Linking to position 2 of Docetaxel could obviously reduce steric hindrance produced by Docetaxel to protease, expose more groups, each of which as a whole is hydrophilic, and increase cleaving efficiency and water solubility.

Example 39: Methods for Determining the Contents of B1, B2, B3 and B4 and their Content Ranges As detected by analytic HPLC (Agilent 1220 series, C8 column 5 μm, 4.6 mm ID×250 mm; the mobile phase is 0-95% acetonitrile (ACN)), the purities of B1, B2, B3 and B4 are all in the range of 95-99%.

Example 40: Various Effects of Different Groups in Present Water-Soluble Docetaxel Derivatives for Targeted Activation in Tumor Microenvironment on the Activation of Paclitaxel Drugs in Tumor Tissue The mutual structure-efficacy of Docetaxel with the groups linked determined the targeting and activation effects in tissues. At 37□, sample compounds were added into 100 μg acidized tumor tissue homogenates in a concentration of 1 mg/ml. The enzyme in tumor tissue homogenates could release Docetaxel. Reduction of compounds and increase of Docetaxel were detected by HPLC, thereby comparing the activation efficiency of the drugs by the tumor tissue.

TABLE 34

Activation ratio (%) of B1, B2, B3 and B4 in homogenates from different tumor tissues

| Different tumor tissues | Cells producing tumor | B1 activation efficiency (%) | B2 activation efficiency (%) | B3 activation efficiency (%) | B4 activation efficiency (%) |
|---|---|---|---|---|---|
| Human fibrosarcoma | HT-1080 | 79.1 | 79.9 | 71.6 | 78.6 |
| Human breast cancer | MDA-MB435 | 93.5 | 90.3 | 95.1 | 89.9 |
| Human ovarian cancer | SK-OV-3 | 93.1 | 90.2 | 84.3 | 67.6 |
| Human colon cancer | HT-29 | 83.9 | 94.6 | 96.4 | 95.3 |
| Human chronic leukemia | K562 | 69.0 | 77.7 | 74.6 | 78.6 |
| Human pancreatic cancer | Panc-1 | 86.9 | 90.6 | 90.4 | 89.8 |
| Human non-small cell lung cancer | A549 | 91.2 | 94.1 | 86.0 | 87.8 |
| Human prostate cancer | PC-3 | 76.1 | 86.7 | 83.9 | 83.0 |
| Human liver cancer | Hepg2 | 76.3 | 89.2 | 88.1 | 78.4 |
| Human renal cancer | OS-RC-2 | 90.9 | 90.5 | 91.1 | 88.4 |
| Human heart | / | 12.2 | 8.3 | 2.5 | 4.4 |

TABLE 35

Effect of changes of similar components in control compounds or linkage to Docetaxel at its 7- or 2-position on activation efficiency of the drugs by MDA-MB231 tumor tissue

| Compounds | activation efficiency (%) |
|---|---|
| C1': AAN -group 2- Docetaxel (linking at 2-position) | 17.5 |
| C2': group 1- AANL - Docetaxel (linking at 2-position) | 46.6 |
| C3': AAN - Docetaxel (linking at 2-position) | 38.5 |
| C4': group 1- AAN -group 2- Docetaxel (linking at 7-position) | 16.3 |
| C5': group 1- AANL -group 2- Docetaxel (linking at 2-position) | 67.4 |
| C6': group 1- AANK -group 2- Docetaxel (linking at 2-position) | 56.6 |
| B1 | 93.4 |
| B2 | 91.6 |
| B3 | 90.6 |
| B4 | 88.5 |

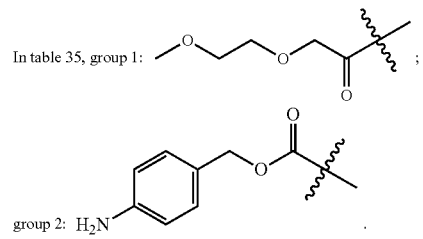

In table 35, group 1: (structure shown); group 2: $H_2N$- (structure shown)

As table 35 shows, activation efficiency of linkage to Docetaxel at its 2-position is far higher than that at 7-position.

According to the results, different groups in the present Docetaxel for targeted activation in tumor microenvironment have various effects on the activation of Docetaxel drugs in tumor tissue. The mutual structure-efficacy of Docetaxel with the groups linked determined the targeting and activation effects in tissues. Activation of B1, B2, B3 and B4 in different tumor types (10 kinds) proved their broad treatment spectrum (Table 36). Meanwhile, certain compounds produced in the screening were compared, and the activation efficiency in the same human breast cancer MDA-MB435 tissue was examined. It was proved that the respective group selection in B1, B2, B3 and B4 had relatively higher activation efficiency (Table 36).

Example 41: Detection of Maximum Tolerated Dose (MTD) by Intravenous Injection of the Drugs Test purpose: to investigate the acute toxicity of the present new formulations via detecting MTD by intravenous injection.

Test drugs: B1, B2, B3 and B4 injections, diluted to corresponding concentrations by physiological saline when testing.

Animal: the first class BALB/C mice, weighing 19-21 g and all mice being female.

Method and results: 210 BALB/C mice were randomly divided into 21 groups according to their body weights, with 10 mice in each group. As shown in Table 37, the mice were intravenously injected with B1, B2, B3 and B4 for just one time in a dose of 0 mg/kg, 125 mg/kg, 150 mg/kg, 175 mg/kg, and 200 mg/kg. Control tests were performed by injecting 0.2 ml physiological saline or Docetaxel. Animals were observed for 17 continuous days for presence or absence of the following behaviors on each day: pilo-erection, hair tousle and lackluster, lethargy, stoop and irritable reaction, and body weight and death were recorded. Blood samples were taken on the 3, 5 and 14 days for counting the whole blood cells. Animals were anatomized on day 14 to take the heart, liver, kidney, lung, spleen, and pancreas for HE staining.

TABLE 37

Comparison of mortality rates of test mice receiving different doses of B1, B2, B3 and B4 injections, physiological saline or Docetaxel injection

| Group | | Dose (mg/kg) | Number of animal | Number of dead animal | Mortality rate (%) |
|---|---|---|---|---|---|
| 1 | physiological saline | 0 mg/kg | 10 | 0 | 0 |
| 2 | B1 | 125 mg/kg | 10 | 0 | 0 |
| 3 | B1 | 150 mg/kg | 10 | 0 | 0 |
| 4 | B1 | 175 mg/kg | 10 | 0 | 0 |
| 5 | B1 | 200 mg/kg | 10 | 2 | 20 |
| 6 | B2 | 125 mg/kg | 10 | 0 | 0 |
| 7 | B2 | 150 mg/kg | 10 | 0 | 0 |
| 8 | B2 | 175 mg/kg | 10 | 0 | 0 |
| 9 | B2 | 200 mg/kg | 10 | 2 | 20 |
| 10 | B3 | 125 mg/kg | 10 | 0 | 0 |
| 11 | B3 | 150 mg/kg | 10 | 0 | 0 |
| 12 | B3 | 175 mg/kg | 10 | 0 | 0 |
| 13 | B3 | 200 mg/kg | 10 | 3 | 3 |
| 14 | B4 | 125 mg/kg | 10 | 0 | 0 |
| 15 | B4 | 150 mg/kg | 10 | 0 | 0 |
| 16 | B4 | 175 mg/kg | 10 | 0 | 0 |
| 17 | B4 | 200 mg/kg | 10 | 1 | 10 |
| 18 | Docetaxel | 25 mg/kg | 10 | 0 | 0 |
| 19 | Docetaxel | 30 mg/kg | 10 | 3 | 30% |
| 20 | Docetaxel | 35 mg/kg | 10 | 6 | 60% |
| 21 | Docetaxel | 40 mg/kg | 10 | 10 | 100% |

Results and discussions: no pilo-erection, hair tousle and lackluster, lethargy, stoop, irritable reaction and death were observed in mice receiving 175 mg/kg B1, B2, B3 and B4 injections. As shown in Table 37, the MTD of the B1 and B2 injections were about 150 mg/kg, which is far beyond the MTD of Docetaxel, 25 mg/kg. The MTD for intravenous administration of a test drug is an important reference index for drug toxicity. The results indicate that the toxicity of the Docetaxel released by targeted activation is significantly reduced as compared with Docetaxel.

Example 42: Study on Efficacy of the Present B1, B2, B3 and B4 Injections in Nude Mice Test purpose: to investigate the anti-tumor efficacy of B1, B2, B3 and B4 in mice model for tumor treatment.

Test drug: B1, B2, B3 and B4 injections and Docetaxel injection, diluted to corresponding concentrations by physiological saline when testing.

Method and Results:

1. Animal: nude mice of 6-8 weeks old, all female.

2. Production of tumor model

1) Human prostate cancer PC-3 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ Panc-1 cells were subcutaneously injected to the back of the nude mice. Mice were randomly grouped after the tumor reached at least 100 mm³. Then treatment began and the day on which the treatment began was day 1.

3) Course of treatment

According to the clinical application of B1, B2, B3 and B4, drugs were intravenously injected (IV). B1, B2, B3 and B4 were administered in a dose of less than ⅙ MTD, i.e., 25 mg/kg, and Docetaxel was administered in a dose of ⅓ MTD, i.e., 8.3 mg/kg. The control group was administered by physiological saline. Drugs were administered once weekly for four weeks.

4) Grouping and test results are shown in Table 38.

TABLE 38

Effect of B1, B2, B3 and B4, Docetaxel and control group on tumor treatment in nude mice

| Group | Number of animal | Size of tumor (mm³) | | inhibitory rate on tumor | |
|---|---|---|---|---|---|
| | | Day 10 | Day 24 | Day 10 | Day 24 |
| B1 group | 10 | 92.4 ± 59.66 | 128.45 ± 105.56 | 67.8 | 66.3 |
| B2 group | 10 | 67.35 ± 53.67 | 136.45 ± 57.45 | 76.5 | 64.2 |
| B3 group | 10 | 89.45 ± 78.67 | 178.45 ± 79.45 | 68.8 | 53.1 |
| B4 group | 10 | 68.88 ± 35.56 | 215.67 ± 103.45 | 76.0 | 43.4 |
| Docetaxel treatment group | 10 | 254.75 ± 146.55 | 263.65 ± 184.67 | 11.1 | 30.7 |
| Control group | 10 | 286.64 ± 214.45 | 684.25 ± 324.45 | / | / |

5) Results and discussions: As shown in Table 38, inhibition on tumor growth by B1, B2, B3 and B4 were greatly improved as compared with the groups treating by Docetaxel using the same molar concentration and the control group.

Example 43: Study on Efficacy of B1, B2, B3 and B4 in D121 Tumor Immune Model Test purpose: to investigate the anti-tumor efficacy of B1, B2, B3 and B4 in a D121 lung cancer model for immune treatment.

Test drugs: B1, B2, B3, B4, and Docetaxel were administered in a dose of 13.2 μmol/kg, and the dose of PDL1-antibody was 5 μg/kg.

Animal: C57 mice of 6-8 weeks old, all female.

Production of Tumor Model:

1) D121 lung tumor cells were purchased from ATCC. Cells were cultivated in DMEM culture solution containing 10% fetal bovine serum at 37° C. and 5% $CO_2$. The cells were passaged for every three days and cells within the 15th passage were used.

2) Tumor immunization. $5\times10^5$ D121 lung cancer cells (purchased from ATCC) which were killed by irradiation were intraperitoneally injected to mice. The mice were injected for 3 times, once every two weeks. After immunization, mice were injected with tumor cells and the drugs were administered weekly for 4 weeks.

3) Production of tumor. At day 32, $10^6$ live lung tumor cells were subcutaneously injected to the back of the C57 mice immunized by tumor. Treatment began when the tumor grew to 0.3-0.4 cm.

4) Analysis on tumor CD8+ T cells. The tumor tissue was homogenated and individual cells in the tumor were filtered, separated and washed by buffer twice, then cultivated with the leucocyte common antigen CD45-PE and T-lymphocyte antigen CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry. Increasement of the ratio indicates increased T lymphocyte cells and thus the animal immunity against the tumor was improved.

5) Grouping and test results are shown in Table 39.

6) Results and discussion. As shown in table 39, treatment effects of B1, B2, B3 and B4 on C57 mice were greatly improved as compared to the control group and the other treatment groups. B1 and PDL1-antibody show an excellent synergistic effect in promoting immunization and treatment. They can inhibit tumor growth via improving immunization.

Example 44: Study on Efficacy of B1, B2, B3 and B4 in BALB/C Mice Model for Tumor Metastasis Test purpose: to investigate the anti-tumor efficacy of B1, B2, B3 and B4 in BALB/C mice model for treatment of tumor metastasis.

Test drug: B1, B2, B3 and B4 injections and Docetaxel injection, diluted to corresponding concentrations by physiological saline when testing.

Method and Results:

1. Animal: BALB/C mice of 6-8 weeks old, all female.

2. Production of tumor model 1) 4T1 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor metastasis. $10^6$ T1 cells were subcutaneously injected to the back of the BALB/C mice. Mice were randomly grouped after the tumor grew to about 1.5 cm. The subcutaneous tumor was removed by surgery and drug treatment began. Mice were killed after anesthesia on day 27. The whole lung was taken out and put into Bouin's solution for staining. The number of the tumor metastasized to lung was counted with anatomical microscope.

3) Course of treatment

According to the clinical application of B1, B2, B3 and B4, drugs were intravenously injected (IV). B1, B2, B3 and B4 were administered in a dose of ⅙ MTD, i.e., 17.6 μmol/kg, and Docetaxel was administered in a dose of ⅙ MTD, i.e., 3 μmol/kg. The control group was administered by physiological saline. Drugs were administered once for every three days for 4 times.

TABLE 39

Effect on inhibition of tumor and immune activation of B1, B2, B3 and B4, Docetaxel and control

| Group | Number of animal | Size of tumor (mm³) Day 18 | inhibitory rate on tumor % Day 18 | CD8: CD45 (%) |
|---|---|---|---|---|
| Immune group, without D121 dead tumor cells | 8 | 1937.45 ± 368.45 | / | 4.6 |
| Immune group (Control group) | 8 | 1620.39 ± 389.23 | | 13.4 |
| Immune group + B1 | 8 | 271.36 ± 157.56 | 83.25 | 18.9 |
| Immune group + B2 | 8 | 375.727 ± 301.67 | 76.81 | 17.4 |
| Immune group + B3 | 8 | 350.393 ± 124.65 | 78.37 | 17.8 |
| Immune group + B4 | 8 | 324.005 ± 155.56 | 80.00 | 16.6 |
| Immune group + B1 + PDL1 antibody | 8 | 71.28 ± 35.59 | 95.60 | 23.6 |
| Immune group + Docetaxel | 8 | 1242.30 ± 359.48 | 23.33 | 5.4 |
| Immune group + Docetaxel + PDL1 antibody | 8 | 1068.39 ± 451.16 | 34.06 | 7.1 |

4) Grouping and test results are shown in Table 40.

TABLE 40

Effects of B1, B2, B3 and B4, Docetaxel and control on inhibition of tumor metastasis in nude BALB/C mice

| Group | Number of animal | Number of metastasized tumor | Inhibitory rate on metastasis |
|---|---|---|---|
| B1 Group | 10 | 5 ± 3 | 96.0 |
| B2 Group | 10 | 11 ± 7 | 91.3 |
| B3 Group | 10 | 17 ± 11 | 86.5 |
| B4 Group | 10 | 18 ± 16 | 85.7 |
| Docetaxel treatment group | 10 | 85 ± 17 | 32.5 |
| Control group | 10 | 126 ± 37 | / |

5) Results and discussion. As shown in Table 40, the inhibitory effect on tumor metastasis of BALB/C mice was greatly improved after intraperitoneal injection of B1, B2, B3 and B4, as compared with the Docetaxel group and the control group, indicating that this kind of drugs exhibits an excellent efficacy on anti-tumor metastasis.

Example 45: Study on Efficacy of B1 Injection in Multiple Tumor Models

Test purpose: to investigate the anti-tumor spectrum of B1 through multiple tumor models from mice Test drug: B1 injection, diluted to corresponding concentrations by physiological saline when testing.

Method and Results:
1. Animal: nude mice of 6-8 weeks old, all female.
2. Production of tumor model
1) Corresponding tumor cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.
2) Production of tumor. $5 \times 10^6$ corresponding cells were subcutaneously injected to the back of the nude mice. Mice were randomly grouped after the tumor reached at least 100 $mm^3$. Then treatment began and the day on which the treatment began was day 1.
3) Course of treatment. According to the clinical application of B1, B1 was administered in a dose of ⅙ MTD, i.v., 17.6 μmol/kg. The control group was administered by physiological saline. Animals were administered once weekly for three weeks.
4) Grouping and test results are shown in Table 41.

TABLE 41

Treatment effect of B1 in multiple tumor models

| Group | Tumor cell | inhibitory rate on tumor (Day 26) |
|---|---|---|
| Human breast cancer | MDA-MB435 | 78.84% |
| Human ovarian cancer | SK-OV-3 | 74.67% |
| Human colon cancer | HT-29 | 74.56% |
| Human chronic leukemia | K562 | 72.56% |
| Human colon caner | HT1080 | 84.46% |
| Human pancreatic cancer | Panc-1 | 73.56% |
| Human non-small cell lung cancer | A549 | 74.56% |
| Human liver cancer | Hepg2 | 81.56% |
| Human renal cancer | OS-RC-2 | 86.67% |

5) Results and discussion. As shown in Table 41, B1 shows an excellent efficacy in multiple tumor models, demonstrating that the anti-tumor drug has a wide anti-tumor spectrum.

In other examples of the present disclosure, activation efficiency, inhibitory rate on tumor and inhibitory rate on metastasis of the present water-soluble Docetaxel derivatives (B10~B24) for targeted activation with different amino acid structures were examined using methods same as that in example 40, 42 and 44. Results were showed in table 42.

TABLE 42 activation efficiency, inhibitory rate on tumor and on metastasis of B10-B24

| Compound No. | $R_2$ | $R_3$ | n | activation efficiency (%) | inhibitory rate on tumor (%) (Day 38) | inhibitory rate on metastasis (%) |
|---|---|---|---|---|---|---|
| B10 | Ala | Thr | 5 | 66.18 | 65.66 | 77.55 |
| B11 | Ala | Val | 5 | 44.05 | 47.77 | 46.01 |
| B12 | Ala | Asn | 5 | 39.71 | 50.56 | 84.37 |
| B13 | Thr | Ala | 5 | 78.27 | 63.07 | 90.37 |
| B14 | Thr | Thr | 5 | 38.78 | 54.18 | 30.40 |
| B15 | Thr | Val | 5 | 56.46 | 47.56 | 40.64 |
| B16 | Thr | Asn | 5 | 34.33 | 70.62 | 58.73 |
| B17 | Val | Ala | 5 | 31.64 | 60.28 | 67.00 |
| B18 | Val | Thr | 5 | 68.04 | 72.17 | 82.82 |
| B19 | Val | Val | 5 | 39.81 | 57.08 | 70.62 |
| B20 | Val | Asn | 5 | 44.98 | 49.43 | 73.83 |
| B21 | Ile | Ala | 5 | 51.29 | 44.88 | 66.07 |
| B22 | Ile | Thr | 5 | 72.28 | 61.52 | 72.90 |
| B23 | Ile | Val | 5 | 59.46 | 67.42 | 47.05 |
| B24 | Ile | Asn | 5 | 50.67 | 49.09 | 56.04 |

Results and discussion. As shown in Table 42, compounds B10~B24 could be activated and had some effects on inhibition of tumor growth and on metastasis, indicating the screening of inventors could optimize the activation and treatment of tumor. It should be understood that the above descriptions of preferred Examples are not intended to limit the subject invention. After reading the above details, it is apparent to the skilled artisan that amino acids at position $R_2$ and $R_3$ of the present drugs or compounds can be changed or replaced.

In some examples of the invention, other water-soluble Docetaxel derivatives for targeted activation in tumor microenvironment were synthesized, of which n is any integer between 1-150, $R_2$ is Ala, Thr, Val or Ile; $R_3$ is Ala, Thr, Val or Asn. And they were subjected to formulation test as done in Examples 38, MTD test as done in Example 41, study on efficacy on tumor as done in Examples 42 and 43, study on efficacy of inhibiting metastasis as done in Example 44 and study on efficacy on multiple tumors as done in Example 45. Similar results to B1-B4 were obtained. As demonstrated by the experiments, when n is in the range of 1-150, the inhibitory rate on tumor is slightly reduced as n increases. The activation activity also slightly decreases and mass of drugs in the same mole increases, as n increases. However, the metabolic half life of the drug also increases as n increases. Therefore, the entire efficacy is only slightly decreased and when n is in the range of 1-150, all compounds could produce similar technical effect to B1-B4.

Example 46: Synthesis of Docetaxel Derivatives for Targeted Activation in Tumor Microenvironment Step 1: Synthesis of Cbz-L-Ala-L-Ala-OMe (Carboxybenzyl-L-Ala-L-Ala-methyl ester) (I)

N-Carboxybenzyl-L-Ala (N-Cbz-L-Ala) (100 g, 0.45 mol) was dissolved in N,N-dimethylformamide (3 L). 1-hydroxylbenzotriazole (72.6 g, 0.54 mol) and 1-ethyl-(3-dimethylaminopropyl) carbodiimide hydrochloride (103.3 g, 0.54 mol) were added when stirring. After reaction for 1 hour, The mixture was cooled to 0□ and L-Ala methyl ester (46.2 g, 0.45 mol) and N,N-diisopropyl ethylamine (173.8 g, 1.34 mol) in N,N-dimethylformamide (1 L) were added when stirring and then the resultant mixture was stirred at ambient temperature for 10 hours. The solvents were removed by evaporation under reduced pressure. The crude product was dissolved in dichloromethane (2 L), washed subsequently by saturated ammonium chloride solution, water and saturated sodium chloride solution. The organic phase was dried by anhydrous sodium sulphate. After removing the solvents by evaporation under reduced pressure, the crude product was recrystallized to obtain a white solid I (101 g, Yield 73.1%).

Step 2: Synthesis of Cbz-L-Ala-L-Ala-OH (II)

Cbz-L-Ala-L-Ala-OMe (100 g, 0.34 mol) prepared in step 1) was dissolved in a mixed solution of tetrahydrofuran (2 L) and water (1 L). After cooling to 0□, 1M lithium hydroxide solution (400 mL) were added. The resultant mixture was stirred for reaction for 10 hours. Concentrated hydrochloric acid was dropped to adjust the pH to be less than 6 and tetrahydrofuran were removed by rotary evaporation. The residual water phase was extracted by dichloromethane (1 L×3). The organic phase was dried by anhydrous sodium sulphate. A white solid II was obtained after vaporizing and drying under reduced pressure (88 g; Yield, 92.2%).

Step 3: Synthesis of Fmoc-L-Asn (Trt)-L-4-amino benzyl alcohol (III)

Fmoc-L-Asn (Trt)-OH (fluorenylmethoxycarbonyl-triphenylmethyl-L-Asn) (20 g, 0.03 mol), 2-(7-azabenzotriazol)-N,N,N',N'-tetramethyluronium hexafluorophosphate (HATU) (15 g, 0.04 mol) and DMF (200 mL) were added into a three-neck flask and stirred for 30 minutes. After cooling to 0° C., a solution of 4-amino benzyl alcohol (4.1 g, 0.03 mol) in DMF (5 mL), and N,N-diisopropyl ethylamine (8.7 g, 0.06 mol) were separately added. The resultant mixture was stirred at ambient temperature for 3 hours. Then Most of DMF were removed by rotary evaporation. The residue was dissolved in ethyl acetate (200 mL), washed subsequently by saturated ammonium chloride solution and saturated sodium chloride solution and dried by anhydrous sodium sulphate. After filtration, the solvent was removed by evaporation. The resultant crude product was pulping to obtain a white solid III (21.3 g, Yield 90%).

Step 4: Synthesis of L-Asn (Trt)-L-4-amino benzyl alcohol (IV)

Fmoc-L-Asn (Trt)-L-4-amino benzyl alcohol (13.0 g, 18 mmol) prepared in step 3) was dissolved in N,N-dimethylformamide (80 mL). Piperidine (30 mL) was added and then stirred at ambient temperature for 2 hours. The solvents were removed by evaporation under reduced pressure. And the resultant product was dried under high vacuum within a vacuum drying oven to remove a small quantity of piperidine. A pale yellow solid IV was obtained, which could be use in the next step without purification.

Step 5: Synthesis of Cbz-L-Ala-L-Ala-L-Asn (Trt)-4-amino benzyl alcohol (V)

Cbz-L-Ala-L-Ala-OH (6.0 g, 20.4 mmol) prepared in step 2), benzotriazol-N,N,N',N'-tetramethyluronium hexafluorophosphate (HBTU, 11.6 g, 30.6 mmol) and DMF (50 mL) were added into a three-neck flask and stirred for 30 minutes in an ice bath. A solution of L-Asn (Trt)-4-amino benzyl alcohol in DMF (50 mL), and N,N-diisopropylethylamine (7.89 g, 61.2 mmol) were added separately under 0° C. The resultant mixture was stirred overnight at ambient temperature. The solvents were removed by evaporation under reduced pressure. The residue was dissolved in acetyl acetate (200 mL), washed subsequently by saturated ammonium chloride solution and saturated sodium chloride solution and dried by anhydrous sodium sulphate. After filtration, the solvent was removed by evaporation. The resultant crude product was recrystallized to obtain a white solid V (15 g, Yield 97%).

Step 6: Synthesis of L-Ala-L-Ala-L-Asn (Trt)-4-amino benzyl alcohol (VI)

Cbz-L-Ala-L-Ala-L-Asn(Trt)-4-amino benzyl alcohol (5.0 g, 6.61 mmol) prepared in step 5) were dissolved in THF (150 mL). 10% Pd/C (1 g) was added. After introducing hydrogen gas, the resultant mixture was stirred for reaction under normal temperature and normal pressure for 5 hours. Pd/C was removed by filtration and washed by methanol. The filtrates and the washing solutions were pooled. Most solvents were removed by rotary evaporation to obtain a crude product. After column chromatography, a white solid VI was obtained (2.0 g, Yield 49%).

Step 7: Synthesis of 2-(2-methoxyethoxy) acetyl-L-Ala-L-Ala-L-Asn (Trt)-4-amino benzyl alcohol (VII)

2-(2-methoxyethoxy) acetic acid (432 mg, 3.22 mmol) were dissolved in N,N-dimethylformamide (20 mL). Benzotriazol-N,N,N',N'-tetramethyluronium hexafluorophosphate (1.83 g, 4.83 mmol) were added and stirred for 30 minutes. Then L-Ala-L-Ala-L-Asn (Trt)-4-amino benzyl alcohol (2.0 g, 3.22 mmol) prepared in step 6) and N,N-diisopropylethylamine (1.24 g, 9.61 mmol) in N,N-dimethylformamide (20 mL) were dropped into the resultant mixture. After dropping, the temperature was slowly raised to ambient temperature and then the mixture was stirred for 10 hours. Most of DMF were removed by evaporation under reduced pressure. The residue was dissolved in acetyl acetate (200 mL), washed subsequently by saturated ammonium chloride solution and saturated sodium chloride solution and dried by anhydrous sodium sulphate. After filtration, the solvent was removed by rotary evaporation. The resultant crude product was purified by silica gel column chromatography to obtain a white solid VII (1.2 g, Yield 50%).

Step 8: Synthesis of 2-(2-methoxyethoxy) acetyl-L-Ala-L-Ala-L-Asn-4-amino benzyl alcohol (VIII)

2-(2-methoxyethoxy) acetyl-L-Ala-L-Ala-L-Asn (Trt)-4-amino benzyl alcohol (1.0 g, 1.36 mmol) prepared in step 7) were dissolved in dichloromethane (10 mL). Trifluoroacetic acid (2 mL) were added and then the resultant mixture was stirred at ambient temperature for 5 hours. The reaction solution was washed by water and separated. The organic phase was dried by anhydrous sodium sulphate and the solvents were removed by evaporation under reduced pressure. The residual trifluoroacetic acid was removed by evaporation under high vacuum. The resultant crude product was purified by column chromatography to obtain X (600 mg, Yield 89%).

Step 9: Synthesis of 2-(2-methoxyethoxy) acetyl-L-Ala-L-Ala-L-Asn-4-aminobenzyl-4-nitrophenyl carbonate (IX)

A solution of 2-(2-methoxyethoxy) acetyl-L-Ala-L-Ala-L-Asn-4-amino benzyl alcohol (500 mg, 1.01 mmol) in dichloromethane (10 mL) was added into a three-neck flask. P-nitrophenyl chloroformate (406 mg, 2.02 mmol) and pyridine (160 mg, 2.03 mmol) in a dichloromethane solution were subsequently dropped into the mixture in an ice bath under protection by nitrogen gas. After dropping, the resultant mixture was stirred at ambient temperature overnight. The reaction solution was washed by water and separated. The organic phase was dried by anhydrous sodium sulphate and the solvents were removed by rotary evaporation. The resultant crude product was purified by column chromatography to obtain IX (450 mg, Yield 67%).

Step 10: Synthesis of 2-(2-methoxyethoxy) acetyl-L-Ala-L-Ala-L-Asn-4-amino benzyl-Docetaxel (C1)

2-(2-methoxyethoxy) acetyl-L-Ala-L-Ala-L-Asn-4-aminobenzyl-4-nitrophenyl carbonate (880 mg, 1.3 mmol) prepared in step 9) and Docetaxel (1.3 g, 1.6 mmol) were dissolved by anhydrous N,N-dimethylformamide (20 mL) and cooled to 0□. DMAP (326 mg, 2.6 mmol) were added and then stirred at ambient temperature overnight. The reaction solution was poured into dichloromethane. The organic phases were pooled, washed by water, dried by anhydrous sodium sulphate. The solvents were removed by rotary evaporation to obtain a crude product. The crude product was purified by column chromatography to obtain the target product D1 (340 mg, Yield 49.2%).

D2, D3 and D4 were synthesized by making reference to D1, except that the acetic acids substituted by alkoxy group used in step 7 have different molecular weights. When synthesizing D2, 3, 6, 9, 12, 15, 18-hexaoxanonadecanoic acid was used to replace 2-(2-methoxyethoxy) acetic acid, in synthesis of D3, 3, 6, 9, 12, 15, 18, 21, 24, 27, 30, 33, 36-dodecaoxaheptatriacontanoic acid was used to replace 2-(2-methoxyethoxy) acetic acid, and in synthesis of D4, polyoxa fatty acid was used to replace 2-(2-methoxyethoxy) acetic acid. According to mass spectrum (MS) detection results, the mass-to-charge ratios of D1, D2 and D3 are 1329, 1505, and 1770, respectively, which are consistent to their calculated molecular weights, 1329.40, 1505.61, and 1769.93. According to Matrix-Assisted Laser Desorption/Ionization Time of Flight Mass Spectrometry (MALDI-TOF-MS), D4's molecular weight is about 14497, which is consistent with its calculated molecular weight, 14497.31, as shown in Table 43.

sterilization, and separately packing in a sterile room. Before animal test, D1, D2, D3 and D4 were dissolved by solvent 1 (injectable water) or solvent 2 (45% alcohol, 55% injectable water) and diluted by injectable water to the desired concentration in sterile room. On the contrary, comparative compounds (C1', C2', C3', C4', C5', and C6') did not satisfy the formulating requirement, as shown in Table 44. Docetaxel is insoluble in water, but its solubility is significantly changed after modification, with increased solubility in water. Change in solubility may greatly affect the formulation scheme of a drug. As compared to the traditional Docetaxel which is insoluble in water, D1, D2, D3 and D4 can be used to produce a soluble formulation. Thus, their injection doses and efficacies can be improved and auxiliary materials that cause allergy generally used for Docetaxel can be avoided. This is a great progress in drug development, and indicates that the Docetaxel for targeted activation in tumor microenvironment has a promising innovation and prospect of use.

TABLE 44

Effect of absence of similar components in control compounds or linkage to Docetaxel at its 7- or 2-position (i.e., linking the group to the OH at 7- or 2-position of Docetaxel) on the solubility of the drug

| Compound | Solvent 1 | Solvent 1 |
|---|---|---|
| C1': AAN -group 2-Docetaxel (linking at 2-position) | insoluble | insoluble |
| C2': group 1- AANL -Docetaxel (linking at 2-position) | insoluble | insoluble |
| C3': AAN -Docetaxel (linking at 2-position) | insoluble | insoluble |
| C4': group 1- AAN -group 2-Docetaxel (linking at 7-position) | insoluble | insoluble |
| C5': group 1- AANL -group 2-Docetaxel (linking at 2-position) | insoluble | soluble |
| C6': group 1- AANK -group 2-Docetaxel (linking at 2-position) | insoluble | insoluble |
| D1 | insoluble | soluble |
| D2 | insoluble | soluble |
| D3 | soluble | soluble |
| D4 | soluble | soluble |

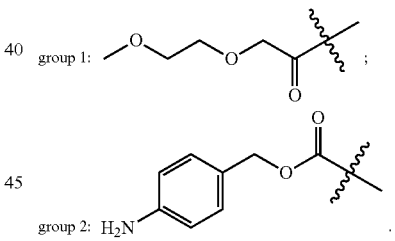

group 1:

group 2:

TABLE 43

Character, mass spectrum and fluorescence test results of C1-C4

| No. | n | Character | Molecular weight by mass spectrum | fluorescence | Output (milligram) | Yield |
|---|---|---|---|---|---|---|
| D1 | 1 | White powder | 1329 | None | 340 | 49.2% |
| D2 | 5 | White powder | 1505 | None | 157 | 49% |
| D3 | 11 | White powder | 1770 | None | 365 | 46% |
| D4 | 300 | White powder | 14497 | None | 345 | 28% |

Example 47: Effect of Different Groups in the Docetaxel for Targeted Activation in Tumor Microenvironment on the Formulation of the Drug Different groups in the Docetaxel for targeted activation in tumor microenvironment show great effect on the formulation of the drug. D1, D2, D3, D4 and various control compounds were dried under vacuum, sterilized via gas Group 1 and group 2 mentioned below are identical to the above group 1 and 2, respectively.

In Table 44, AAN, AANL and AANK indicate the linkage formed by a small peptide in the compounds, A is Ala, N is Asn, L is Leu and K is Lys.

Group 1 in the Docetaxel for targeted activation in tumor microenvironment is significantly important for the activation and efficacy of the entire drug. When group 1 is absent, the solubility and activation efficiency are greatly affected.

Group 2 in the Docetaxel for targeted activation in tumor microenvironment is significantly important for the activation and efficacy of the entire drug. When group 2 is absent, the activation efficiency and the blockage of toxicity are greatly affected.

The Docetaxel derivatives for targeted activation in tumor microenvironment of the present disclosure were based on a great amount of synthetic experiments. In these experiments, we designed a lot of complicated compounds having different linking manners. Then the complicated compounds were linked to position 2 or 7 of Docetaxel, that is, they were linked to Docetaxel via the OH at position 2 or position 7. The resultant Docetaxel derivatives were screened through activation efficiency in the presence of tumor tissue or aspartate endopeptidase. The screened derivatives were further screened through inhibition of tumor for $R_2$, $R_3$ and n. The activated site that is specific to the tumor tissue locates between AAN and group 2. After cleaving by activation, group 2 can be freely released, thereby releasing Docetaxel. Because the active center of asparagine endopeptidase locates at the bottom of its globular depression and the cleavage site should be close to the active center, it is very important if there is a steric hindrance to the cleavage site produced by the complicated compound.

According to the screening results, it is presumed that linking of group 2 may effectively avoid steric hindrance produced by directly linking Docetaxel, which thereby not affecting approach of asparagine endopeptidase. And, the structure-efficacy of group 1 may increase the polarity of the cleavage site, which allows the more water-soluble protease to be easily to approach the cleavage site and thereby to increase the cleaving efficiency. Linking to position 2 of Docetaxel could obviously reduce steric hindrance produced by Docetaxel to protease, expose more groups, each of which as a whole is hydrophilic, and increase cleaving efficiency and water solubility.

Example 48: Methods for Determining the Contents of D1, D2, D3 and D4 in Respective Products and their Content Ranges As detected by analytic HPLC (Agilent 1220 series, C8 column 5 µm, 4.6 mm ID×250 mm; the mobile phase is 0-95% acetonitrile (ACN)), the purities of D1, D2, D3 and D4 are all in the range of 95-99%.

Example 49: Various Effects of Different Groups in Present Docetaxel Derivatives for Targeted Activation in Tumor Microenvironment on the Activation of Paclitaxel Drugs in Tumor Tissue Different groups in present Docetaxel derivatives for targeted activation in tumor microenvironment have different effects on the activation of Paclitaxel drugs in tumor tissue. The mutual structure-efficacy of Docetaxel with the groups linked determined the targeting and activation effects in tissues. In the experiments, at 37□, compounds were added into proteases in 100 µg acidized tumor tissue homogenates in a concentration of 1 mg/ml. The tumor tissue homogenates could release Docetaxel. Reduction of compound and increase of Docetaxel were detected by HPLC, thereby comparing the activation efficiency of the drug by the tumor tissue. It was found that the linker linking to the screening compound exhibited highest activation efficiency. Activation in different tumor types also indicates that the drugs have a broad treatment spectrum (table 45). Meanwhile certain compounds produced in the screening were compared and their activation efficiency in same tissue was analyzed. It is proved the chemical group selection for D1 has the highest activation efficiency (table 45), and the activation efficiency of D2~D4 in different tumor tissue homogenates is close to D1.

TABLE 45

Activation ratio (%) of D1, D2, D3 and D4 in homogenates from different tumor tissues

| Different tumor tissues | Cells producing tumor | Activation ratio (%) in homogenates from different tumor tissues | | | |
|---|---|---|---|---|---|
| | | D1 | D2 | D3 | D4 |
| Human fibrosarcoma | HT-1080 | 77.23 | 67.86 | 71.11 | 67.14 |
| Human breast cancer | MDA-MB435 | 83.07 | 82.26 | 81.36 | 83.52 |
| Human ovarian cancer | SK-OV-3 | 79.56 | 86.14 | 71.37 | 57.42 |
| Human colon cancer | HT-29 | 71.46 | 80.91 | 82.26 | 81.54 |
| Human chronic leukemia | K562 | 68.23 | 65.97 | 63.18 | 66.78 |
| Human pancreatic cancer | Panc-1 | 85.32 | 84.42 | 82.35 | 83.79 |
| Human non-small cell lung cancer | A549 | 77.76 | 80.46 | 83.26 | 75.24 |
| Human prostate cancer | PC-3 | 87.57 | 88.56 | 86.67 | 84.15 |
| Human liver cancer | Hepg2 | 85.77 | 76.14 | 75.15 | 66.78 |
| Human renal cancer | OS-RC-2 | 77.76 | 82.35 | 77.76 | 81.45 |

TABLE 46

Effect of changes of similar but different components in control compounds or linkage to Docetaxel at its 7- or 2-position on activation efficiency of the drugs by MDA-MB231 tumor tissue

| Compounds | activation efficiency(%) |
|---|---|
| C1': AAN-group 2-Docetaxel (linking at 2-position) | 23.2 |
| C2': group 1-AANL-Docetaxel (linking at 2-position) | 50.4 |
| C3': AAN-Docetaxel (linking at 2-position) | 34.4 |
| C4': group 1-AAN-group 2-Docetaxel (linking at 7-position) | 16.8 |
| C5': group 1-AANL-group 2-Docetaxel (linking at 2-position) | 39.7 |
| C6': group 1-AANK-group 2-Docetaxel (linking at 2-position) | 57.4 |
| D1 | 91.5 |
| D2 | 91.1 |
| D3 | 90.8 |
| D4 | 89.5 |

As table 46 shows, activation efficiency of linkage to Docetaxel at its 2-position is higher than that at 7-position.

According to the results, different groups in the present Docetaxel for targeted activation in tumor microenvironment have various effects on the activation of Docetaxel drugs in tumor tissue. The mutual structure-efficacy of Docetaxel with the groups linked determined the targeting and activation effects in tissues.

Example 50: Detection of Maximum Tolerated Dose (MTD) by Intravenous Injection of the Test Drugs Test purpose: to investigate the acute toxicity of the new drug formulations via detecting MTD by intravenous injection.

Test drugs: D1, D2, D3 and D4 injections, diluted to corresponding concentrations by physiological saline when testing.

Animal: the first class BALB/C mice, weighing 19-21 g and all mice being female.

Method and results: 210 BALB/C mice were randomly divided into 21 groups according to their body weights, with 10 mice in each group. As shown in Table 47, the mice were intravenously injected with D1, D2, D3 and D4 for just one time in a dose of 0 mg/kg, 125 mg/kg, 150 mg/kg, 175 mg/kg, and 200 mg/kg. Control tests were performed by injecting 0.2 ml physiological saline or Docetaxel. Animals were observed for 17 continuous days for presence or absence of the following behaviors on each day: pilo-erection, hair tousle and lackluster, lethargy, stoop and irritable reaction, and body weight and death were recorded. Blood samples were taken on the 3, 5 and 14 days for counting the whole blood cells. Animals were anatomized on day 14 to take the heart, liver, kidney, lung, spleen, and pancreas for HE staining.

TABLE 47

Comparison of mortality rates of test mice receiving different doses of D1, D2, D3 and D4 injections, physiological saline or Docetaxel injection

| Group | injections | Dose (mg/kg) | Number of animal | Number of dead animal | Mortality rate (%) |
|---|---|---|---|---|---|
| 1 | physiological saline | 0 mg/kg | 10 | 0 | 0 |
| 2 | D1 | 125 mg/kg | 10 | 0 | 0 |
| 3 | D1 | 150 mg/kg | 10 | 0 | 0 |
| 4 | D1 | 175 mg/kg | 10 | 0 | 0 |
| 5 | D1 | 200 mg/kg | 10 | 1 | 10 |
| 6 | D2 | 125 mg/kg | 10 | 0 | 0 |
| 7 | D2 | 150 mg/kg | 10 | 0 | 0 |
| 8 | D2 | 175 mg/kg | 10 | 0 | 0 |
| 9 | D2 | 200 mg/kg | 10 | 2 | 20 |
| 10 | D3 | 125 mg/kg | 10 | 0 | 0 |
| 11 | D3 | 150 mg/kg | 10 | 0 | 0 |
| 12 | D3 | 175 mg/kg | 10 | 0 | 0 |
| 13 | D3 | 200 mg/kg | 10 | 1 | 10 |
| 14 | D4 | 125 mg/kg | 10 | 0 | 0 |
| 15 | D4 | 150 mg/kg | 10 | 0 | 0 |
| 16 | D4 | 175 mg/kg | 10 | 0 | 0 |
| 17 | D4 | 200 mg/kg | 10 | 0 | 10 |
| 18 | Docetaxel | 25 mg/kg | 10 | 0 | 0 |
| 19 | Docetaxel | 30 mg/kg | 10 | 2 | 20% |
| 20 | Docetaxel | 35 mg/kg | 10 | 5 | 50% |
| 21 | Docetaxel | 40 mg/kg | 10 | 10 | 100% |

Results and discussions: no pilo-erection, hair tousle and lackluster, lethargy, stoop, irritable reaction and death were observed in mice receiving 150 mg/kg D1, D2, D3 and D4 injections. As shown in Table 47, the MTD of the D1 and D2 injections were about 150 mg/kg, which is far beyond the MTD of Docetaxel, 25 mg/kg. The MTD for intravenous administration of a test drug is an important reference index for drug toxicity. The results indicate that the toxicity of the Docetaxel released by targeted activation is significantly reduced as compared with Docetaxel.

Example 51: Study on Efficacy of D1, D2, D3 and D4 Injections in Nude Mice

Test purpose: to investigate the anti-tumor efficacy of D1, D2, D3 and D4 in mice model for tumor treatment.

Test drug: D1, D2, D3 and D4 injections and Docetaxel injection, diluted to corresponding concentrations by physiological saline when testing.

Method and Results:

1. Animal: nude mice of 6-8 weeks old, all female.

2. Production of tumor model

1) Human prostate cancer PC-3 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ PC-3 cells were subcutaneously injected to the back of the nude mice. Mice were randomly grouped after the tumor reached at least 100 $mm^3$. Then treatment began and the day on which the treatment began was day 1.

3) Course of treatment

According to the clinical application of D1, D2, D3 and D4, drugs were intravenously injected (IV). D1, D2, D3 and D4 were administered in a dose of less than ⅙ MTD, i.e., 25 mg/kg, and Docetaxel was administered in a dose of ⅓ MTD, i.e., 8.3 mg/kg. The control group was administered by physiological saline. Drugs were administered once weekly for four weeks.

4) Grouping and test results are shown in Table 48.

TABLE 48

Effect of E1, E2, E3, E4, Docetaxel and control group on tumor treatment in nude mice

| Group | Number of animal | Size of tumor ($mm^3$) Day 10 | Size of tumor ($mm^3$) Day 24 | inhibitory rate on tumor Day 10 | inhibitory rate on tumor Day 24 |
|---|---|---|---|---|---|
| D1 group | 10 | 86.45 ± 26.42 | 143.34 ± 44.42 | 75.0 | 80.5 |
| D2 group | 10 | 78.53 ± 36.89 | 113.52 ± 41.88 | 77.3 | 84.5 |
| D3 group | 10 | 67.43 ± 28.93 | 157.45 ± 64.74 | 80.5 | 78.6 |
| D4 group | 10 | 78.56 ± 36.74 | 167.33 ± 63.65 | 77.3 | 77.2 |
| Docetaxel treatment group | 10 | 168.66 ± 79.43 | 313.75 ± 157.42 | 51.3 | 57.3 |
| Control group | 10 | 346.4 ± 121.78 | 734.45 ± 216.56 | / | / |

5) Results and discussions: As shown in Table 48, inhibition on tumor growth by D1, D2, D3 and D4 were greatly improved as compared with the groups treating by Docetaxel using the same molar concentration and the control group.

Example 52: Study on Efficacy of D1, D2, D3 and D4 in D121 Tumor Immune Model

Test purpose: to investigate the anti-tumor efficacy of D1, D2, D3 and D4 in a D121 lung cancer model for immune treatment.

Test drug: D1, D2, D3, D4 and Docetaxel, all used in 13.2 μmol/kg; PDL1 antibody, 5 μg/kg.

Animal: C57 mice of 6-8 weeks old, all female.

Production of Tumor Model:

1) D121 lung tumor cells were purchased from ATCC. Cells were cultivated in DMEM culture solution containing 10% fetal bovine serum at 37° C. and 5% $CO_2$. The cells were passaged for every three days and cells within the 15th passage were used.

2) Tumor immunization. $5 \times 10^5$ D121 lung cancer cells (purchased from ATCC) which were killed by irradiation were intraperitoneally injected to mice. The mice were injected for 3 times, once every two weeks. After immunization, mice were injected with tumor cells and the drugs were administered weekly for 4 weeks.

3) Production of tumor. At day 32, $10^6$ live D121 lung tumor cells were subcutaneously injected to the back of the C57 mice immunized by tumor. Treatment began when the tumor grew to 0.3-0.4 cm.

4) Analysis on tumor CD8+ T cells. The tumor tissue was homogenated and individual cells in the tumor were filtered, separated and washed by buffer twice, then cultivated with the leucocyte common antigen CD45-PE and T-lymphocyte antigen CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry. Increasement of the ratio indicates increased T lymphocyte cells and thus the animal immunity against the tumor was improved.

5) Grouping and test results are shown in Table 49.

TABLE 49

Effect on inhibition of tumor and immune activation of D1, D2, D3, D4, Docetaxel and control

| Group | Number of animal | Size of tumor (mm³) Day 18 | inhibitory rate on tumor % Day 18 | CD8: CD45 (%) |
|---|---|---|---|---|
| Immune group, without D121 dead tumor cells | 8 | 1673.56 | | 6.4 |
| Immune group (Control group) | 8 | 1425.56 | | 12.6 |
| Immune group + D1 | 8 | 324.45 | 77.2 | 18.5 |
| Immune group + D2 | 8 | 312.43 | 78.1 | 17.3 |
| Immune group + D3 | 8 | 323.56 | 77.3 | 17.7 |
| Immune group + D4 | 8 | 246.85 | 82.7 | 16.3 |
| Immune group + D1 + PDL1 antibody | 8 | 136.43 | 90.4 | 23.6 |
| Immune group + Docetaxel | 30 | 1268.64 | 11.0 | 6.9 |
| Immune group + Docetaxel + PDL1 antibody | 8 | 846.67 | 40.6 | 9.4 |

6) Results and discussion. Treatment effects of D1, D2, D3 and D4 on C57 mice were greatly improved as compared to the control group and the other treatment groups. D1 and PDL1-antibody show an excellent synergistic effect in promoting immunization and treatment. They can inhibit tumor growth via improving immunization.

Example 53: Study on Efficacy of D1, D2, D3 and D4 in BALB/C Mice Model for Tumor Metastasis Test purpose: to investigate the anti-tumor efficacy of D1, D2, D3 and D4 in BALB/C mice model for treatment of tumor metastasis.

Test drug: D1, D2, D3 and D4 injections and Docetaxel injection, diluted to corresponding concentrations by physiological saline when testing.

Method and Results:

1. Animal: BALB/C mice of 6-8 weeks old, all female.

2. Production of tumor model 1) 4T1 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor metastasis. $10^6$ T1 cells were subcutaneously injected to the back of the BALB/C mice. Mice were randomly grouped after the tumor grew to about 1.5 cm. The subcutaneous tumor was removed by surgery and drug treatment began. Mice were killed after anesthesia on day 27. The whole lung was taken out and put into Bouin's solution for staining. The number of the tumor metastasized to lung was counted with anatomical microscope.

3) Course of treatment

According to the clinical application of D1, D2, D3 and D4, drugs were intravenously injected (IV). D1, D2, D3 and D4 were administered in a dose of ⅙ MTD, i.e., 25 mg/kg, and Docetaxel was administered in a dose of ⅙ MTD, i.e., 4.2 mg/kg. The control group was administered by physiological saline. Drugs were administered once for every three days for 4 times.

4) Grouping and test results are shown in Table 50.

TABLE 50

Effects of D1, D2, D3, D4, Docetaxel and control on inhibition of tumor metastasis in BALB/C mice

| Group | Number of animal | Number of metastasized tumor | Inhibitory rate on metastasis |
|---|---|---|---|
| D1 Group | 10 | 5 ± 3 | 95.2 |
| D2 Group | 10 | 13 ± 8 | 97.3 |
| D3 Group | 10 | 17 ± 13 | 93.0 |
| D4 Group | 10 | 19 ± 13 | 90.8 |
| Docetaxel treatment group | 10 | 156 ± 24 | 89.7 |
| Control group | 10 | 185 ± 35 | / |

5) Results and discussion. As shown in Table 50, the inhibitory effect on tumor metastasis of BALB/C mice was greatly improved after intraperitoneal injection of D1, D2, D3 and D4, as compared with the Docetaxel group and the control group, indicating that this kind of drugs exhibits an excellent efficacy on anti-tumor metastasis.

Example 54: Study on Efficacy of C1 in Multiple Tumor Models

Test purpose: to investigate the anti-tumor spectrum of C1 through multiple tumor models from mice Test drug: C1 injection, diluted to corresponding concentrations by physiological saline when testing.

Method and Results:

1. Animal: nude mice of 6-8 weeks old, all female.
2. Production of tumor model

1) Corresponding tumor cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ corresponding cells were subcutaneously injected to the back of the nude mice. Mice were randomly grouped after the tumor reached at least 100 mm$^3$. Then treatment began and the day on which the treatment began was day 1.

3) Course of treatment. According to the clinical application of D1, D1 was administered in a dose of ⅙ MTD, i.e., 25 mg/kg. The control group was administered by physiological saline. Animals were administered once weekly for three weeks.

4) Grouping and test results are shown in Table 51.

TABLE 51

Treatment effect of D1 in multiple tumor models

| Group | Tumor cell | inhibitory rate on tumor (Day 26) |
|---|---|---|
| Human breast cancer | MDA-MB435 | 93.5% |
| Human ovarian cancer | SK-OV-3 | 82.9% |
| Human colon cancer | HT-29 | 68.6% |
| Human chronic leukemia | K562 | 84.6% |
| Human colon caner | HT1080 | 94.6% |
| Human pancreatic cancer | Panc-1 | 89.4% |
| Human non-small cell lung cancer | A549 | 90.4% |
| Human liver cancer | Hepg2 | 75.7% |
| Human renal cancer | OS-RC-2 | 87.7% |

5) Results and discussion. As shown in Table 51, D1 shows an excellent efficacy in multiple tumor models, demonstrating that the drug has a wide anti-tumor spectrum.

Compounds D10-D24 were also prepared in the present disclosure by similar method for synthesizing D1, except that the starting amino acids used for linking were different, as shown in Table 52. Corresponding $R_2$ amino acid and $R_3$ amino acid were dissolved in N,N-dimethylformamide. The same condensating agent, 1-ethyl-(3-dimethylaminopropyl) carbodiimide hydrochloride, was added respectively and reactions were allowed to take place at 0-25° C. for 0.5-2 hours. Then Asn was added and reaction was taken place at 0-25° C. for 2-24 hours to obtain a tripeptide. Molecular weights of D10-D24 (n=1), as detected by mass spectrum (MS), are shown in Table 47, which are consistent to their respective calculated molecular weights.

Activation property, inhibitory rate on tumor and inhibitory rate on metastasis of Docetaxel for targeted activation in tumor microenvironment having different amino acid structures were tested by the same methods as described in Examples 49, 51 and 53. The results are shown in Table 47. Since results from Examples 49, 51 and 53 indicate that n is preferably in the range of 1-11, at which range the drugs have the same treatment effects, n in D10-D24 is selected as 1 except that $R_2$ and $R_3$ are different.

TABLE 52

Activation property, inhibitory rate on tumor and inhibitory rate on metastasis of D10-D24 for targeted activation in tumor microenvironment

| No. of Compound | $R_2$ | $R_3$ | Character | Molecular weight by MS | Calculated molecular weight | activation efficiency (%) | inhibitory rate on tumor (%) (Day 38) | inhibitory rate on metastasis (%) |
|---|---|---|---|---|---|---|---|---|
| D10 | Ala | Thr | White powder | 1360 | 1359.72 | 65.4% | 65.6% | 75.3% |
| D11 | Ala | Val | White powder | 1358 | 1357.67 | 42.6% | 46.2% | 44.5% |
| D12 | Ala | Asn | White powder | 1373 | 1372.64 | 38.4% | 49.5% | 81.6% |
| D13 | Thr | Ala | White powder | 1360 | 1359.72 | 75.7% | 61.3% | 87.4% |
| D14 | Thr | Thr | White powder | 1390 | 1389.74 | 37.5% | 52.4% | 29.4% |
| D15 | Thr | Val | White powder | 1388 | 1387.77 | 54.6% | 45.8% | 39.3% |
| D16 | Thr | Asn | White powder | 1403 | 1402.74 | 33.2% | 68.3% | 56.8% |
| D17 | Val | Ala | White powder | 1358 | 1357.74 | 30.6% | 58.3% | 64.8% |
| D18 | Val | Thr | White powder | 1388 | 1387.77 | 65.8% | 69.8% | 80.1% |
| D19 | Val | Val | White powder | 1386 | 1385.80 | 38.5% | 55.2% | 68.3% |
| D20 | Val | Asn | White powder | 1401 | 1400.77 | 43.5% | 47.8% | 71.4% |

TABLE 52-continued

Activation property, inhibitory rate on tumor
and inhibitory rate on metastasis of D10-D24
for targeted activation in tumor microenvironment

| No. of Compound | $R_2$ | $R_3$ | Character | Molecular weight by MS | Calculated molecular weight | activation efficiency (%) | inhibitory rate on tumor (%) (Day 38) | inhibitory rate on metastasis (%) |
|---|---|---|---|---|---|---|---|---|
| D21 | Ile | Ala | White powder | 1372 | 1371.77 | 49.6% | 43.4% | 63.9% |
| D22 | Ile | Thr | White powder | 1402 | 1401.80 | 69.9% | 59.5% | 70.5% |
| D23 | Ile | Val | White powder | 1400 | 1399.83 | 57.5% | 65.2% | 45.5% |
| D24 | Ile | Asn | White powder | 1415 | 1414.80 | 49% | 47.48% | 54.2% |

Results and discussion: As shown in Table 52, compounds D10~D24 could be activated and had some effects on inhibition of tumor growth and on metastasis, indicating the screening of inventors could optimize the activation and treatment of tumor.

In some other examples of the invention, other Docetaxel derivatives for targeted activation in tumor microenvironment were synthesized, of which n is any integer between 1-300, $R_2$ is Ala, Thr, Val or Ile; $R_3$ is Ala, Thr, Val or Asn. And they were subjected to formulation test, MTD test, study on efficacy on tumor, study on efficacy of inhibiting metastasis and study on efficacy on multiple tumors. Similar results to D1-D4 were obtained. As demonstrated by the experiments, when n is in the range of 1-300, the inhibitory rate on tumor is slightly reduced as n increases. The activation activity also slightly decreases and mass of drugs in the same mole increases, as n increases. However, the metabolic half life of the drug also increases as n increases. Therefore, the entire efficacy is only slightly decreased and when n is in the range of 1-300, all compounds could produce similar technical effect to D1-D4.

Example 55: Synthesis of Mitomycin Targeting to Tumor Microenvironment

1) Synthesis of Fmoc-L-Ala-L-Ala-OMe (fluorenylmethoxycarbonyl-L-Ala-L-Ala-methyl ester) (I)

Fmoc-L-Ala-OH (fluorenylmethoxycarbonyl-L-Ala) (33 g, 0.1 mol) was dissolved in N,N-dimethylformamide (1 L). A solution of 1-hydroxylbenzotriazole (20.2 g, 0.15 mol), 1-ethyl-(3-dimethylaminopropyl) carbodiimide hydrochloride (34 g, 0.15 mol) and L-Ala methyl ester (13.9 g, 0.1 mol) and N,N-diisopropyl ethylamine (25.8 g, 0.2 mol) in N,N-dimethylformamide (500 mL) were added when stirring and then the resultant mixture was stirred at ambient temperature for 10 hours. The solvents were removed by evaporation under reduced pressure. The crude product was dissolved in dichloromethane (2 L), washed subsequently by saturated ammonium chloride solution, water and saturated sodium chloride solution. The organic phase was dried by anhydrous sodium sulphate. The organic phase was dried by anhydrous sodium sulphate. After removing the solvents by evaporation under reduced pressure, the crude product was recrystallized to obtain a white solid I (30 g, Yield 75.1%).

2) Synthesis of Fmoc-L-Ala-L-Ala-OH (fluorenylmethoxycarbonyl-L-Ala-L-Ala) (II)

Fmoc-L-Ala-L-Ala-OMe (40 g, 0.1 mol) was dissolved in a mixed solution of tetrahydrofuran (2 L) and water (1 L). After cooling, 1M lithium hydroxide solution (400 mL) were added. The resultant mixture was stirred for reaction for 10 hours. Concentrated hydrochloric acid was dropped to adjust the pH to be less than 6 and tetrahydrofuran were removed by evaporation under reduced pressure. The residual water phase was extracted by dichloromethane (1 L×3). The organic phase was dried by anhydrous sodium sulphate. A white solid II was obtained after vaporizing and drying under reduced pressure (36 g; Yield, 94%).

3) Synthesis of Fmoc-L-Asn (Trt)-L-4-amino benzyl alcohol (III)

Fmoc-L-Asn (Trt)-OH (fluorenylmethoxycarbonyl-triphenylmethyl-L-Asn) (20 g, 0.03 mol), 2-(7-azabenzotriazol)-N,N,N',N'-tetramethyluronium hexafluorophosphate (HATU) (15 g, 0.04 mol) and DMF (200 mL) were added into a three-neck flask and stirred for 30 minutes. A solution of 4-amino benzyl alcohol (4.1 g, 0.03 mol) in DMF (5 mL), and N,N-diisopropyl ethylamine (8.7 g, 0.06 mol) were separately added. The resultant mixture was stirred at ambient temperature for 3 hours. Then the solvents were removed by evaporation under reduced pressure. The residue was dissolved in ethyl acetate (200 mL), washed subsequently by saturated ammonium chloride solution and saturated sodium chloride solution and dried by anhydrous sodium sulphate. After filtration, the solvent was removed by evaporation. The resultant crude product was pulping to obtain a white solid III (21.3 g, Yield 90%).

4) Synthesis of L-Asn (Trt)-L-4-amino benzyl alcohol (IV)

Fmoc-L-Asn (Trt)-L-4-amino benzyl alcohol (13 g, 18 mmol) was dissolved in N,N-dimethylformamide (80 mL). Piperidine (30 mL) was added and then stirred at ambient temperature for 2 hours. The solvents were removed by evaporation under reduced pressure. And the resultant product was dried under high vacuum within a vacuum drying oven to remove a small quantity of piperidine. A pale yellow solid IV was obtained, which could be use in the next step without purification.

5) Synthesis of Fmoc-L-Ala-L-Ala-L-Asn (Trt)-4-amino benzyl alcohol (V)

Fmoc-L-Ala-L-Ala-OH (5.4 g, 14 mmol), benzotriazol-N,N,N',N'-tetramethyluronium hexafluorophosphate (HBTU, 8 g, 21 mmol) and DMF (50 mL) were added into a three-neck flask and stirred for 30 minutes in an ice bath under protection by nitrogen gas. A solution of L-Asn (Trt)-4-amino benzyl alcohol (6.7 g, 14 mmol) in DMF (50 mL), and N,N-diisopropylethylamine (5.5 g, 42 mmol) were added separately under 0° C. The resultant mixture was stirred overnight at ambient temperature. The solvents were removed by evaporation under reduced pressure. The residue was dissolved in acetyl acetate (200 mL), washed subsequently by saturated ammonium chloride solution and saturated sodium chloride solution and dried by anhydrous sodium sulphate. After filtration, the solvent was removed by evaporation. The resultant crude product was pulped to obtain a white solid V (18.5 g, Yield 78%).

6) Synthesis of L-Ala-L-Ala-L-Asn (Trt)-4-amino benzyl alcohol (VI)

Fmoc-L-Asn (Trt)-L-4-amino benzyl alcohol (864 mg, 1 mmol) were dissolved in N,N-dimethylformamide (30 mL). Piperidine (10 mL) was added and then stirred at ambient temperature for 2 hours. The solvents were removed by evaporation under reduced pressure. A pale yellow solid IV was obtained, which could be use in the next step without purification.

7) Synthesis of 2-(2-methoxyethoxy) acetyl-L-Ala-L-Ala-L-Asn (Trt)-4-amino benzyl alcohol (VII)

2-(2-methoxyethoxy) acetic acid (134 mg, 1 mmol) were dissolved in N,N-dimethylformamide (5 mL). After cooling to 0° C., 3-(Diethoxyphosphoryloxy)-1, 2, 3-benzotrizin-4-one (DEPBT, 450 mg, 1.5 mmol) were added and stirred for 30 minutes. Then L-Ala-L-Ala-L-Asn (Trt)-4-amino benzyl alcohol (621 mg, 1 mmol) and N,N-diisopropyl ethylamine (387 mg, 3 mmol) were added. The reaction temperature was slowly raised to ambient temperature in the dark and then stirred for 5 hours. The reaction solution was poured into 200 mL aqueous acetic acid solution and extracted by dichloromethane. The organic phases were pooled, washed by water and dried by anhydrous sodium sulphate. The solvents were removed by evaporation under reduced pressure to obtain an orange red crude product. The crude product was purified by silica gel column chromatography to obtain a white powder VII (479 mg, Yield 65%).

8) Synthesis of 2-(2-methoxyethoxy) acetyl-L-Ala-L-Ala-L-Asn (Trt)-4-aminobenzyl-4-nitrophenyl carbonate (VIII)

2-(2-methoxyethoxy) acetyl-L-Ala-L-Ala-L-Asn (Trt)-4-amino benzyl alcohol (1.9 g, 2.6 mmol) were added into a three-neck flask and dissolved in dichloromethane (10 mL). A solution of 4-nitrophenyl chloroformate (1 g, 5.2 mmol) and pyridine (400 mg, 5.2 mmol) in dichloromethane were dropped. The resultant mixture was stirred at ambient temperature overnight. The reaction solution was washed by water and separated. The organic phase was dried by anhydrous sodium sulphate. The solvents were removed by evaporation under reduced pressure. The crude product was purified by silica gel column chromatography to obtain VIII (1.8 g, Yield 80%).

9) Synthesis of 2-(2-methoxyethoxy) acetyl-L-Ala-L-Ala-L-Asn-4-aminobenzyl-4-nitrophenyl carbonate (IX)

2-(2-methoxyethoxy) acetyl-L-Ala-L-Ala-L-Asn (Trt)-4-aminobenzyl-4-nitrophenyl carbonate was dissolved in dichloromethane (2 mL). Trifluoroacetic acid (2 mL) were added and then stirred at ambient temperature for 2 hours. The reaction solution was washed by water and separated. The organic phase was dried by anhydrous sodium sulphate. The solvents were removed by evaporation under reduced pressure. The crude product was purified by column chromatography to obtain IX (625 mg, Yield 47%).

10) Synthesis of 2-(2-methoxyethoxy) acetyl-L-Ala-L-Ala-L-Asn-4-amino benzyl mitomycin (E1)

2-(2-methoxyethoxy) acetyl-L-Ala-L-Ala-L-Asn-4-aminobenzyl-4-nitrophenyl carbonate (400 mg, 0.6 mmol) was dissolved in N,N-dimethylformamide (10 mL). Mitomycin C (200 mg, 0.6 mmol), 1-hydroxy benzotriazole (HOBT, 17 mg, 0.12 mmol) and N,N-diisopropyl ethylamine (156 mg, 1.2 mmol) were added. The temperature was raised to ambient temperature and then the resultant mixture was stirred 10 hours. The solvents were removed by evaporation under reduced pressure. The residue was dissolved in dichloromethane (200 mL), washed subsequently by saturated ammonium chloride solution and saturated sodium chloride solution and dried by anhydrous sodium sulphate. After filtration, the solvent was removed by evaporation. The resultant crude product was purified by column chromatography to obtain a pale yellow solid, which was the target compound E1 (237 mg, Yield 46%).

E2, E3 and E4 were synthesized by making reference to E1, except that the acetic acids substituted by alkoxy group used in step 7 have different molecular weights. When synthesizing E2, 3, 6, 9, 12, 15, 18-hexaoxanonadecanoic acid was used to replace 2-(2-methoxyethoxy) acetic acid, in synthesis of E3, 3, 6, 9, 12, 15, 18, 21, 24, 27, 30, 33, 36-dodecaoxaheptatriacontanoic acid was used to replace 2-(2-methoxyethoxy) acetic acid, and in synthesis of E4, polyoxa fatty acid was used to replace 2-(2-methoxyethoxy) acetic acid. According to mass spectrum (MS) detection results, the mass-to-charge ratios of E1, E2 and E3 are 855, 1032, and 1296, respectively, which are consistent to their calculated molecular weights, 855.85, 1032.06, and 1296.37. According to Matrix-Assisted Laser Desorption/Ionization Time of Flight Mass Spectrometry (MALDI-TOF-MS), E4's molecular weight is about 14032, which is consistent with its calculated molecular weight, 14023.76, as shown in Table 53.

TABLE 53

Character, mass spectrum and fluorescence test results of E1-E4

| No. | n | Character | Molecular weight by mass spectrum | fluorescence |
|---|---|---|---|---|
| E1 | 1 | White powder | 855 | None |
| E2 | 5 | White powder | 1032 | None |
| E3 | 11 | White powder | 1296 | None |
| E4 | 150 | White powder | 14023 | None |

Example 56: Injections for E1, E2, E3 and E4

E1, E2, E3 and E4 were dried under vacuum, sterilized via gas sterilization, and separately packing in a sterile room. Before animal test, E1 was dissolved by injectable water containing 50% alcohol and diluted by injectable water to the desired concentration. E2, E3 and E4 could be directly diluted by injectable water to the desired concentrations.

Example 57: Methods for Determining the Contents of E1, E2, E3 and E4 in Respective Products and their Content Ranges As detected by analytic HPLC (Agilent 1220 series, C8 column 5 μm, 4.6 mm ID×250 mm; the mobile phase is 0-95% acetonitrile (ACN)), the purities of E1, E2, E3 and E4 are all in the range of 95-99%.

Example 58: Activation of Mitomycin for Targeted Activation in Tumor Microenvironment in Different Tumor Tissues At 37° C., compounds were added into proteases in 100 μg acidized tumor tissue homogenates in a concentration of 1 mg/ml. The tumor tissue homogenates could release mitomycin. Reduction of compound and increase of mitomycin were detected by HPLC, thereby comparing the activation efficiency of the drug by the tumor tissue. It was found that the current compounds linking to the screened compounds exhibited highest activation efficiency. Activation in different tumor types also indicates that the drugs have a broad treatment spectrum. See Table 54.

TABLE 54

Activation ratio (%) of E1, E2, E3 and E4 in homogenates from different tumor tissues

| Different tumor tissues | Cells producing tumor | Activation ratio (%) in homogenates from different tumor tissues | | | |
|---|---|---|---|---|---|
| | | E1 | E2 | E3 | E4 |
| Human fibrosarcoma | HT-1080 | 83.6 | 85.7 | 81.3 | 85.4 |
| Human breast cancer | MDA-MB435 | 97.3 | 90.6 | 96.3 | 78.8 |
| Human ovarian cancer | SK-OV-3 | 93.5 | 97.6 | 98.3 | 91.7 |
| Human colon cancer | HT-29 | 94.2 | 96.1 | 98.1 | 93.0 |
| Human chronic leukemia | K562 | 74.5 | 68.4 | 61.8 | 62.1 |
| Human pancreatic cancer | Panc-1 | 89.4 | 84.6 | 83.1 | 89.7 |
| Human non-small cell lung cancer | A549 | 97.4 | 96.4 | 89.4 | 84.2 |
| Human prostate cancer | PC-3 | 78.9 | 86.4 | 74.8 | 89.9 |
| Human liver cancer | Hepg2 | 94.6 | 94.8 | 97.8 | 91.5 |
| Human renal cancer | OS-RC-2 | 99.7 | 94.5 | 97.6 | 99.1 |

Example 59: Detection of Maximum Tolerated Dose (MTD) by Intravenous Injection of the Test Drugs Test purpose: to investigate the acute toxicity of the new drug formulations via detecting MTD by intravenous injection.

Test drugs: E1, E2, E3 and E4 injections, diluted to corresponding concentrations by physiological saline when testing.

Animal: the first class BALB/C mice, weighing 19-21 g and all mice being female.

Method and results: 210 BALB/C mice were randomly divided into 21 groups according to their body weights, with 10 mice in each group. As shown in Table 55, the mice were intravenously injected with E1, E2, E3 and E4 for just one time in a dose of 0 mg/kg, 50 mg/kg, 70 mg/kg, 90 mg/kg, and 110 mg/kg. Control tests were performed by injecting 0.2 ml physiological saline or mitomycin. Animals were observed for 17 continuous days for presence or absence of the following behaviors on each day: pilo-erection, hair tousle and lackluster, lethargy, stoop and irritable reaction, and body weight and death were recorded. Blood samples were taken on the 3, 5 and 14 days for counting the whole blood cells. Animals were anatomized on day 14 to take the heart, liver, kidney, lung, spleen, and pancreas for HE staining.

TABLE 55

Comparison of mortality rates of test mice receiving different doses of E1, E2, E3 and E4 injections, physiological saline or mitomycin injection

| Group | | Dose (mg/kg) | Number of animal | Number of dead animal | Mortality rate (%) |
|---|---|---|---|---|---|
| 1 | physiological saline | 0 mg/kg | 10 | 0 | 0 |
| 2 | E1 | 50 mg/kg | 10 | 0 | 0 |
| 3 | E1 | 70 mg/kg | 10 | 0 | 0 |
| 4 | E1 | 90 mg/kg | 10 | 0 | 0 |
| 5 | E1 | 110 mg/kg | 10 | 1 | 10 |
| 6 | E2 | 50 mg/kg | 10 | 0 | 0 |
| 7 | E2 | 70 mg/kg | 10 | 0 | 0 |
| 8 | E2 | 90 mg/kg | 10 | 0 | 0 |
| 9 | E2 | 110 mg/kg | 10 | 1 | 10 |
| 10 | E3 | 50 mg/kg | 10 | 0 | 0 |
| 11 | E3 | 70 mg/kg | 10 | 0 | 0 |
| 12 | E3 | 90 mg/kg | 10 | 0 | 0 |
| 13 | E3 | 110 mg/kg | 10 | 1 | 10 |
| 14 | E4 | 50 mg/kg | 10 | 0 | 0 |
| 15 | E4 | 70 mg/kg | 10 | 0 | 0 |
| 16 | E4 | 90 mg/kg | 10 | 0 | 0 |
| 17 | E4 | 110 mg/kg | 10 | 0 | 10 |
| 18 | mitomycin | 6 mg/kg | 10 | 0 | 0 |
| 19 | mitomycin | 7 mg/kg | 10 | 1 | 10% |
| 20 | mitomycin | 8 mg/kg | 10 | 4 | 40% |
| 21 | mitomycin | 9 mg/kg | 10 | 9 | 90% |

Results and discussions: no pilo-erection, hair tousle and lackluster, lethargy, stoop, irritable reaction and death were observed in mice receiving 90 mg/kg E1, E2, E3 and E4 injections. As shown in Table 55, the MTD of the E1 and E2 injections were about 90 mg/kg, which is far beyond the MTD of mitomycin, 6 mg/kg. The MTD for intravenous administration of a test drug is an important reference index for drug toxicity. The results indicate that the toxicity of the mitomycin released by targeted activation is significantly reduced as compared with mitomycin.

Example 60: Study on Efficacy of E1, E2, E3 and E4 Injections on Panc-1 Cells in Nude Mice Test purpose: to investigate the anti-tumor efficacy of E1, E2, E3 and E4 in mice model for tumor treatment.

Test drug: E1, E2, E3 and E4 injections and mitomycin injection, diluted to corresponding concentrations by physiological saline when testing.

Method and Results:

1. Animal: nude mice of 6-8 weeks old, all female.
2. Production of tumor model

1) Panc-1 cells were purchased from American type culture collection (ATCC) and identified according to the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ Panc-1 cells were subcutaneously injected to the back of the nude mice. Mice were randomly grouped after the tumor reached at least 100 $mm^3$. Then treatment began and the day on which the treatment began was day 1.

3) Course of treatment

According to the clinical application of E1, E2, E3 and E4, drugs were intravenously injected (IV). E1, E2, E3 and E4 were administered in a dose of ⅙ MTD, i.e., 15 mg/kg, and mitomycin was administered in a dose of ⅓ MTD, i.e., 2 mg/kg. The control group was administered by physiological saline. Drugs were administered once weekly for four weeks.

4) Grouping and test results are shown in Table 56.

TABLE 56

Effect of E1, E2, E3, E4, mitomycin and control group on tumor treatment in nude mice

| Group | Number of animal | Size of tumor (mm³) | | inhibitory rate on tumor | |
|---|---|---|---|---|---|
| | | Day 10 | Day 24 | Day 10 | Day 24 |
| E1 group | 10 | 76.42 ± 14.96 | 84.62 ± 45.94 | 35.7% | 66.1% |
| E2 group | 10 | 60.17 ± 30.26 | 42.39 ± 62.24 | 36.4% | 83.01% |
| E3 group | 10 | 75.60 ± 28.54 | 74.39 ± 48.94 | 49.4% | 70.2% |
| E4 group | 10 | 73.35 ± 38.46 | 63.99 ± 47.13 | 42.9% | 81.5% |
| Mitomycin treatment group | 10 | 118.85 ± 36.47 | 249.54 ± 95.46 | 7.5% | 27.9% |
| Control group | 10 | 128.5 ± 16.7 | 346.1 ± 104.74. | / | / |

5) Results and discussions: As shown in Table 56, inhibition on tumor growth by E1, E2, E3 and E4 were greatly improved as compared with the groups treating by mitomycin using the same molar concentration and the control group.

Example 61: Study on Efficacy of E1, E2, E3 and E4 Injections on HT1080 Cells in Nude Mice Test purpose: to investigate the anti-tumor efficacy of E1, E2, E3 and E4 in mice model for tumor treatment.

Test drug: E1, E2, E3 and E4 injections and mitomycin injection, diluted to corresponding concentrations by physiological saline when testing.

Method and Results:

1. Animal: nude mice of 6-8 weeks old, all female.

2. Production of tumor model

1) HT1080 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ HT1080 cells were subcutaneously injected to the back of the nude mice. Mice were randomly grouped after the tumor reached at least 100 mm³. Then treatment began and the day on which the treatment began was day 1.

3) Course of treatment

According to the clinical application of E1, E2, E3 and E4, drugs were intravenously injected (IV). E1, E2, E3 and E4 were administered in a dose of ⅙ MTD, i.e., 15 mg/kg, and mitomycin was administered in a dose of ⅓ MTD, i.e., 2 mg/kg. The control group was administered by physiological saline. Drugs were administered once weekly for four weeks.

4) Grouping and test results are shown in Table 57.

TABLE 57

Effect of E1, E2, E3, E4, mitomycin and control group on tumor treatment in nude mice

| Group | Number of animal | Size of tumor (mm³) | | inhibitory rate on tumor | |
|---|---|---|---|---|---|
| | | Day 13 | Day 26 | Day 13 | Day 26 |
| E1 Group | 10 | 438.15 ± 47.96 | 331.57 ± 114.74 | 51.9% | 78.9% |
| E2 Group | 10 | 378.11 ± 68.46 | 137.60 ± 156.42 | 58.5% | 91.3% |
| E3 Group | 10 | 439.82 ± 69.62 | 357.63 ± 194.54 | 51.7% | 77.3% |
| E4 Group | 10 | 426.74 ± 46.63 | 304.55 ± 184.53 | 53.2% | 80.7% |
| Mitomycin treatment group | 10 | 876.48 ± 78.29 | 1410.28 ± 375.46 | 3.7% | 10.4% |
| Control group | 10 | 910.42 ± 96.15 | 1574.46 ± 456.34 | / | / |

5) Results and discussions: As shown in Table 57, inhibition on tumor growth by E1, E2, E3 and E4 were greatly improved as compared with the groups treating by mitomycin using the same molar concentration and the control group.

Example 62: Study on Efficacy of E1, E2, E3 and E4 in BALB/C Mice Model for Tumor Metastasis Test purpose: to investigate the anti-tumor efficacy of E1, E2, E3 and E4 in BALB/C mice model for treatment of tumor metastasis.

Test drug: E1, E2, E3 and E4 injections and mitomycin injection, diluted to corresponding concentrations by physiological saline when testing.

Method and Results:
1. Animal: BALB/C mice of 6-8 weeks old, all female.
2. Production of tumor model 1) 4T1 cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor metastasis. $10^6$ T1 cells were subcutaneously injected to the back of the BALB/C mice. Mice were randomly grouped after the tumor grew to about 1.5 cm. The subcutaneous tumor was removed by surgery and drug treatment began. Mice were killed after anesthesia on day 27. The whole lung was taken out and put into Bouin's solution for staining. The number of the tumor metastasized to lung was counted with anatomical microscope.

3) Course of treatment

According to the clinical application of E1, E2, E3 and E4, drugs were intravenously injected (IV). E1, E2, E3 and E4 were administered in a dose of 1/6 MTD, i.e., 15 mg/kg, and mitomycin was administered in a dose of 1/6 MTD, i.e., 1 mg/kg. The control group was administered by physiological saline. Drugs were administered once for every three days for 4 times.

4) Grouping and test results are shown in Table 58.

TABLE 58

Effects of E1, E2, E3, E4, mitomycin and control on inhibition of tumor metastasis in BALB/C mice

| Group | Number of animal | Number of metastasized tumor | Inhibitory rate on metastasis |
|---|---|---|---|
| E1 Group | 10 | 2 ± 3 | 99.2% |
| E2 Group | 10 | 8 ± 7 | 94.1% |
| E3 Group | 10 | 13 ± 8 | 90.44% |
| E4 Group | 10 | 15 ± 16 | 89.0% |
| Mitomycin treatment group | 10 | 128 ± 25 | 5.9% |
| Control group | 10 | 136.0 ± 46 | / |

5) Results and discussion. As shown in Table 58, the inhibitory effect on tumor metastasis of BALB/C mice was greatly improved after intraperitoneal injection of E1, E2, E3 and E4, as compared with the mitomycin group and the control group, indicating that this kind of drugs exhibits an excellent efficacy on anti-tumor metastasis.

Example 63: Study on Efficacy of E1, E2, E3 and E4 in D121 Tumor Immune Model

Test purpose: to investigate the anti-tumor efficacy of E1, E2, E3 and E4 in a D121 lung cancer model for immune treatment.

Test drug: E1, E2, E3, E4 and mitomycin, all used in 13.2 μmol/kg; PDL1 antibody, 5 μg/kg.

Animal: C57 mice of 6-8 weeks old, all female.

Production of Tumor Model:

1) D121 lung tumor cells were purposed from ATCC. Cells were cultivated in DMEM culture solution containing 10% fetal bovine serum at 37° C. and 5% $CO_2$. The cells were passaged for every three days and cells within the 15th passage were used.

2) Tumor immunization. $5 \times 10^5$ D121 lung cancer cells (purchased from ATCC) which were killed by irradiation were intraperitoneally injected to mice. The mice were injected for 3 times, once every two weeks. After immunization, mice were injected with tumor cells and the drugs were administered weekly for 4 weeks.

3) Production of tumor. At day 32, $10^6$ live lung tumor cells were subcutaneously injected to the back of the C57 mice immunized by tumor. Treatment began when the tumor grew to 0.3-0.4 cm.

4) Analysis on tumor CD8+ T cells. The tumor tissue was homogenated and individual cells in the tumor were filtered, separated and washed by buffer twice, then cultivated with the leucocyte common antigen CD45-PE and CD8-FITC marked antibodies for 1 hour at ambient temperature. The cells were washed by phosphate buffer containing 1% fetal bovine serum twice and then analyzed for the ratio of the T lymphocyte antigen (CD8) positive cells in the leucocyte common antigen (CD45) positive cells by flow cytometry. Increasement of the ratio indicates increased T lymphocyte cells and thus the animal immunity against the tumor was improved.

5) Grouping and test results are shown in Table 59.

TABLE 59

Effect on inhibition of tumor and immune activation of E1, E2, E3, E4, mitomycin and control

| Group | Number of animal | Size of tumor ($mm^3$) Day 18 | inhibitory rate on tumor % Day 18 | CD8: CD45 (%) |
|---|---|---|---|---|
| Immune group, without D121 dead tumor cells | 8 | 1887.56 ± 323.4 | | 5.2 |
| Immune group (Control group) | 8 | 1574.46 ± 467.34 | | 13.1 |
| Immune group + E1 | 8 | 237.60 ± 358.57 | 83.27 | 18.4 |
| Immune group + E2 | 8 | 331.57 ± 124.45 | 83.87 | 19.7 |
| Immune group + E3 | 8 | 357.63 ± 157.32 | 79.55 | 16.3 |
| Immune group + E4 | 8 | 304.55 ± 216.47 | 74.85 | 18.4 |
| Immune group + E1 + PDL1 antibody | 8 | 74.78 ± 32.74 | 90.94 | 23.6 |
| Immune group + mitomycin | 8 | 1210.28 ± 368.45 | 28.62 | 6.7 |
| Immune group + mitomycin + PDL1 antibody | 8 | 1334.90 ± 274.78 | 7.75 | 7.4 |

6) Results and discussion. Treatment effects of E1, E2, E3 and E4 on C57 mice were greatly improved as compared to the control group and the other treatment groups. E1 and PDL1-antibody show an excellent synergistic effect in promoting immunization and treatment. They can inhibit tumor growth via improving immunization.

Example 64: Study on Efficacy of E1 Injection in Multiple Tumor Models

Test purpose: to investigate the anti-tumor spectrum of E1 through multiple tumor models from mice Test drug: E1 injection, diluted to corresponding concentrations by physiological saline when testing.

Method and Results:
1. Animal: nude mice of 6-8 weeks old, all female.
2. Production of tumor model 1) Corresponding tumor cells were purchased from American type culture collection (ATCC) and identified according the specification provided by ATCC. Cells were cultivated in DMEM culture solution containing 10% fetal bovine serum at 37° C. and 5% $CO_2$. The cells were passaged for every three days and cells within the 15th passage were used.

2) Production of tumor. $5 \times 10^6$ corresponding cells were subcutaneously injected to the back of the nude mice. Mice were randomly grouped after the tumor reached at least 100 $mm^3$. Then treatment began and the day on which the treatment began was day 1.

3) Course of treatment. According to the clinical application of E1, E1 was administered in a dose of ⅙ MTD, i.e., 15 mg/kg. The control group was administered by physiological saline. Animals were administered once weekly for three weeks.

4) Grouping and test results are shown in Table 60.

TABLE 60

Treatment effect of E1 in multiple tumor models

| Group | Tumor cell | inhibitory rate on tumor (Day 26) |
|---|---|---|
| Human breast cancer | MDA-MB435 | 86.3% |
| Human ovarian cancer | SK-OV-3 | 84.5% |
| Human colon cancer | HT-29 | 86.7% |
| Human chronic leukemia | K562 | 77.3% |
| Human colon caner | HT1080 | 95.4% |
| Human pancreatic cancer | Panc-1 | 86.5% |
| Human non-small cell lung cancer | A549 | 95.3% |
| Human liver cancer | Hepg2 | 85.7% |
| Human renal cancer | OS-RC-2 | 81.3% |

5) Results and discussion. As shown in Table 60, E1 shows an excellent efficacy in multiple tumor models, demonstrating that the drug has a wide anti-tumor spectrum.

Example 65: Study on Inhibition of Scar and Choroidal Neovascularization (CNV) by E1, E2, E3 and E3 Eye Drops Animal: C57 mice of 16 weeks old, all female and 8 animals in each group.

Production and treatment of scar. After fixed irradiation through photocoagulation by 150 mW laser, E1, E2, E3 and E4 were dropped daily. Two weeks later, eye tissues were taken from 4 animals of each group for immunohistochemical (HE) staining. For another 4 animals, they were subjected to fixed irradiation through photocoagulation by 50 mW laser and then to treatment. 48 hours later, their eye tissues were taken, homogenated, filtered to isolate individual cells in the scar and choroidal neovascularization (CNV) tissues. The cells were washed by buffer twice and stained by biotin-conjugated anti-F4/80 (biotin-labeled precursor cell antigen from macrophage) and FITC-conjugated anti-CD45 (isothiocyanate fluorescein labeled leucocyte common antigen) at ambient temperature for 1 hour. Then the cells were washed by PBS containing 1% fetal bovine serum twice and then analyzed for the ratio of the macrophage precursor antigen positive cells in the leucocyte common antigen (CD45) positive cells by flow cytometry. Reduction in the ratio indicates decrease of the macrophage precursor antigen positive cells, demonstrating that the macrophages associated with the disease in the animal were inhibited. The results are shown in Table 61.

TABLE 61

Study on inhibition of scar and choroidal neovascularization (CNV) by E1, E2, E3 and E3 eye drops

| Group | Number of animal | Maximal scar radius observed by pathological staining (pixel) | CDF4/80CD45 (%) |
|---|---|---|---|
| Control group | 8 | 1246 ± 335 | 16.2 ± 3.2 |
| E1 | 8 | 332 ± 124 | 7.1 ± 1.4 |
| E2 | 8 | 348 ± 146 | 7.7 ± 1.7 |
| E3 | 8 | 369 ± 185 | 8.3 ± 2.4 |
| E4 | 8 | 484 ± 252 | 9.2 ± 2.1 |
| mitomycin | 8 | 953 ± 249 | 14.6 ± 2.4 |

Results and discussion. E1, E2, E3 and E4 have greatly improved treatment effect on scar radius and inhibition of macrophage as compared to the control group and the mitomycin group.

E10-E24 were synthesized by a similar method for E1, except that the amino acids used for linking are different, as shown in Table 62.

Specifically, corresponding $R_2$ amino acid and $R_3$ amino acid were dissolved in N,N-dimethylformamide, respectively. The condensating agent, such as 1-ethyl-(3-dimethylaminopropyl) carbodiimide hydrochloride, was respectively added and reactions were allowed to take place at 0-25° C. for 0.5-2 hours. Then Asn was added and reaction was taken place at 0-25° C. for 2-24 hours. The reaction solution was purified to obtain a tripeptide. The tripeptide was used to replace Ala-Ala-Asn as an intermediate to prepare E10-E24 according to the procedures of Example 55. Molecular weights of E10-E24, as detected by mass spectrum, are shown in Table 57, which are consistent to their respective calculated molecular weights.

TABLE 62

Character and mass spectrum results of E10-E24

| No. of Compound | $R_2$ | $R_3$ | Character | Molecular weight by MS | Calculated molecular weight |
|---|---|---|---|---|---|
| E10 | Ala | Thr | light blue | 886 | 885.88 |
| E11 | Ala | Val | light blue | 884 | 883.83 |
| E12 | Ala | Asn | light blue | 899 | 898.80 |
| E13 | Thr | Ala | light blue | 886 | 885.88 |
| E14 | Thr | Thr | light blue | 916 | 915.90 |
| E15 | Thr | Val | light blue | 914 | 913.93 |
| E16 | Thr | Asn | light blue | 929 | 928.90 |
| E17 | Val | Ala | light blue | 884 | 883.90 |
| E18 | Val | Thr | light blue | 914 | 913.93 |
| E19 | Val | Val | light blue | 912 | 911.96 |
| E20 | Val | Asn | light blue | 927 | 926.93 |
| E21 | Ile | Ala | light blue | 898 | 897.93 |
| E22 | Ile | Thr | light blue | 928 | 927.96 |
| E23 | Ile | Val | light blue | 926 | 925.99 |
| E24 | Ile | Asn | light blue | 941 | 940.96 |

Compounds E10-E24 were subjected to MTD test as done in Example 59, study on efficacy on tumor as done in Examples 60 and 61, study on efficacy of inhibiting metastasis as done in Example 62 and study on efficacy on multiple tumors as done in Example 64. Results show that they have similar results to E1-E4. As demonstrated by the experiments, when n is in the range of 1-300, the inhibitory rate on tumor is slightly reduced as n increases. The activation activity also slightly decreases and mass of drugs in the same mole increases, as n increases. However, the metabolic half life of the drug also increases as n increases. Therefore, the entire efficacy is only slightly decreased and Example 66: Comparison Study on Toxicity, Efficacy and Immunological Property of Legutaxel (S1') in Tumor Model

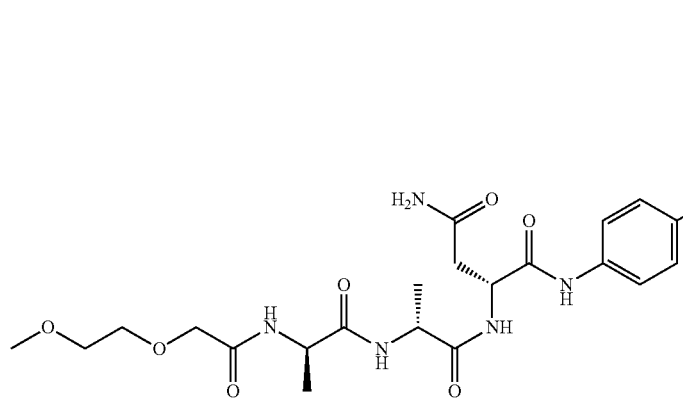
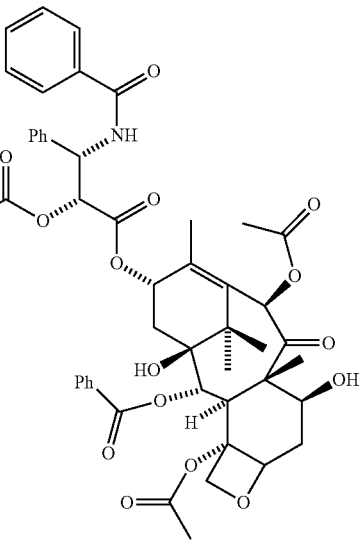

Test purpose: to investigate the efficacy and anti-tumor immunological property of the product.

Methods and Results:

Mice were injected with Legutaxel at tail vein weekly for 3 times. According to the results of toxicity experiments observed over 21 days, no death were observed in the experiments with a dose of 140, 150 and 160 mg/kg/day. Therefore, Legutaxel's dose could at least reach 160 mg/kg/day during treatment.

Figure 1B:
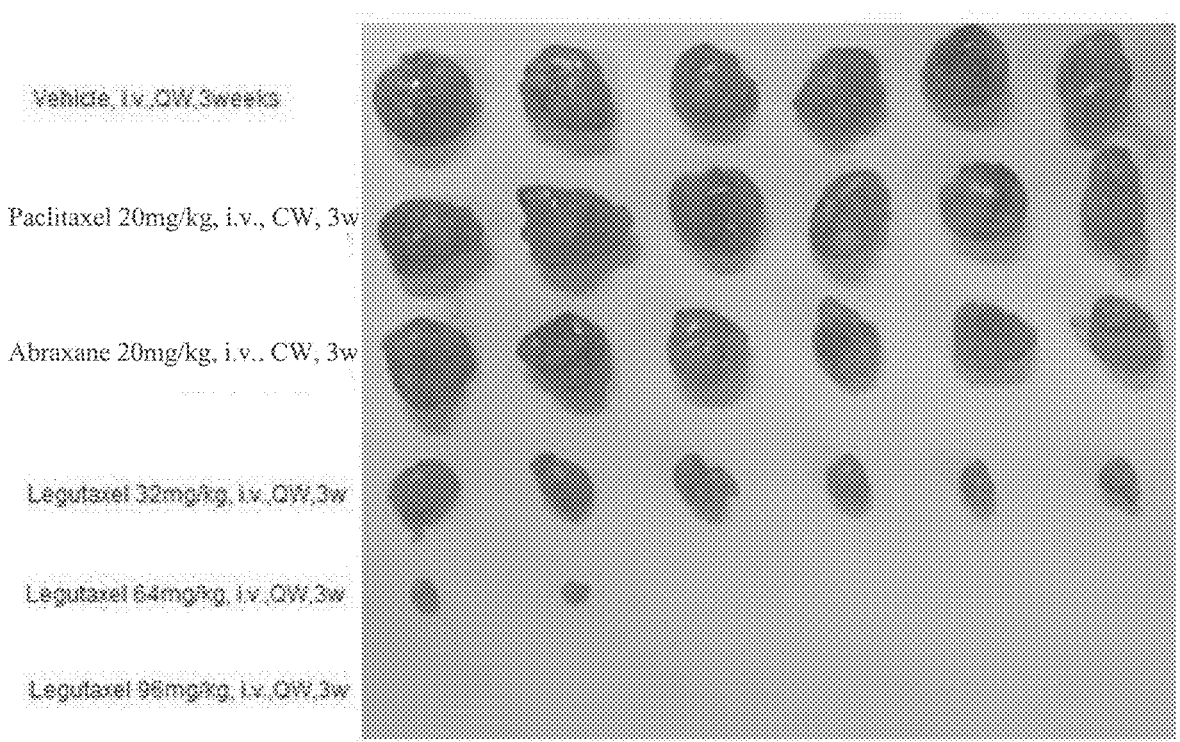

Comparative experiments for a high dose of Legutaxel, Abraxane and Paclitaxel were performed in HT1080 model, which were used at an equal molar dose and at an equal toxic dose. The treatment results show significantly different treatment efficacy. Death occurred after the third treatment with Paclitaxel injection, as shown in FIGS. 1A and 1B.

Figure 2:
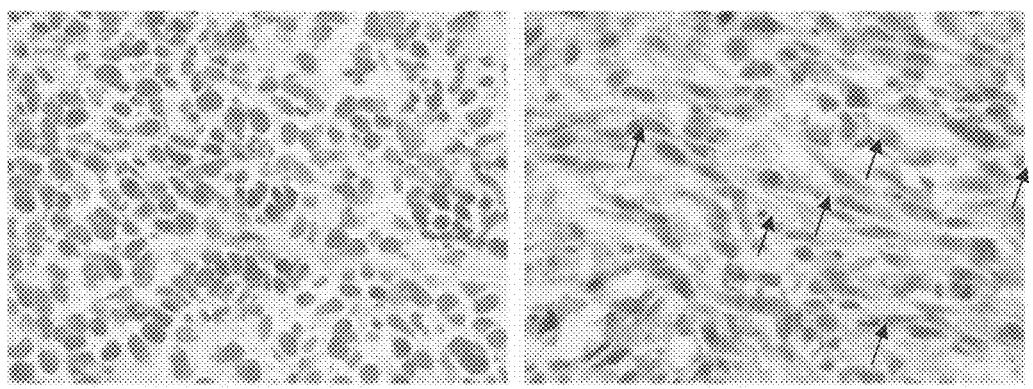
FIG. 2 shows the experimental results obtained from immunological stimulation test for Paclitaxel and Legutaxel, demonstrating that more toxic CD8 T cells (shown by the arrows in the right panel) were permeated from the tumor tissue treated by Lagutaxel.
Figure 3A:
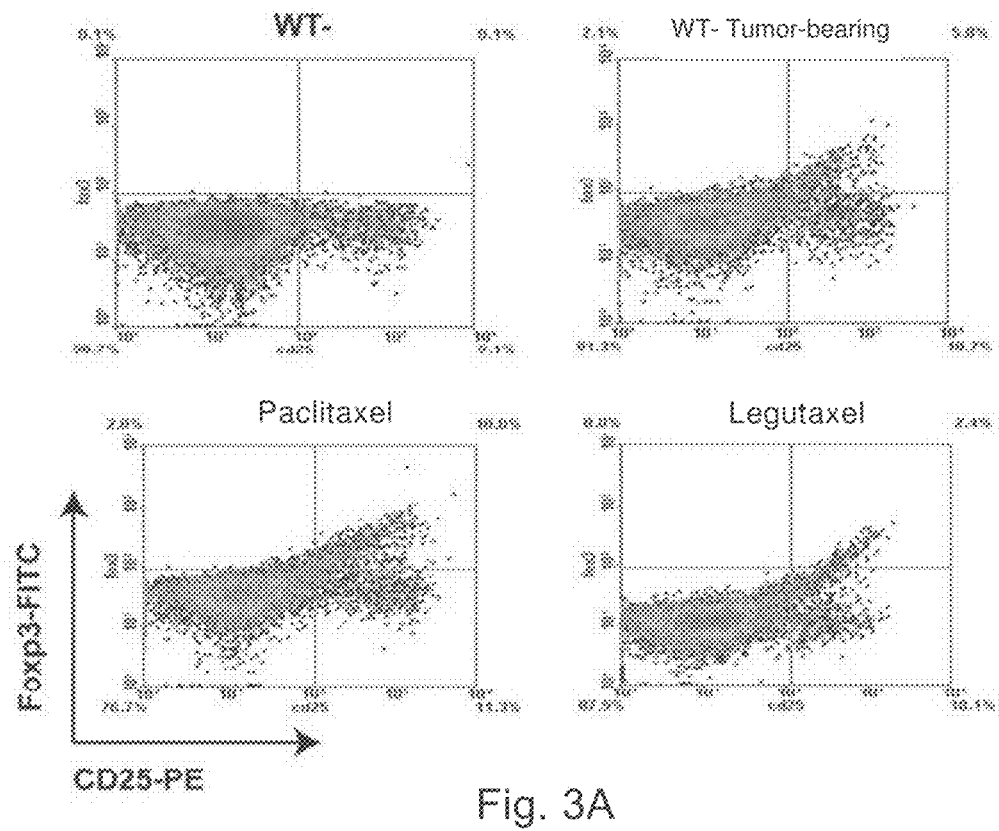
FIGS. 3A and 3B show the experimental results obtained from immunological stimulation test for Paclitaxel and Legutaxel.
Figure 3B:
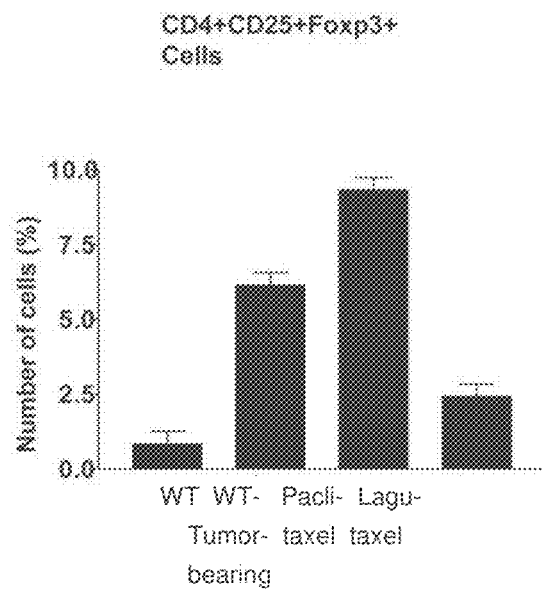

We further studied the immunological stimulation property of Legutaxel. As demonstrated by the immunological detection of mice receiving tumor treatment, we found that the indexes for tumor-derived immunosuppressive T cells (T reg: CD4+, CD25+, Foxp3+) obtained from the tumor-bearing group and in the treatment group by Paclitaxel were greatly increased. On the contrary, the index for tumor-derived immunosuppressive T cells in treatment group by Legutaxel decreased due to targeted chemotherapy (see panels in FIGS. 3A and 3B). Meanwhile, more toxic CD8 T cells (in FIG. 2, the CD8+ positive cells are in brown, as shown by the arrows) were permeated from the tumor tissue. From this lung cancer treatment model, it can be demonstrated that Legutaxel exhibits strong immunological stimulation.

In the treatment of solid tumors, traditional chemotherapeutic drug, paclitaxel, could impair human immunity and thereby inducing drug resistance, which are crucial obstacles preventing cancer patients from being cured. Our experiments showed that traditional chemotherapeutic drugs, such as paclitaxel, also greatly impair leucocyte. However, Legutaxel can only be activated in the tumor site, thus it can avoid damage to immune system that caused by traditional chemotherapeutic drugs. More importantly, Legutaxel could stimulate an anti-tumor immunization, thus it can be used synergistically with immune therapy to completely cure cancer.

Although the contents of the invention have been detailedly introduced via the above preferred Examples, it should be understood that the above descriptions are not intended to limit the subject invention. From examples of S1 to S27, it can be found that the cleavage linker that is specifically activated in tumor microenvironment and is used for targeting a small molecule can be used to link and activate different compounds. Thus, it is apparent that drugs or compounds at position $R_4$ can be changed or replaced. From the Examples in which $R_1$ is H, a hydrophilic group or a targeting group, it can be found that replacing or changing the group at the $R_1$ position is also obvious. Therefore, the protection scope of the subject invention should be defined by the appending claims.

The invention claimed is:

1. A compound of formula (III) or (IV) comprising a cleavable linker, wherein the cleavable linker is —$R_2$-$R_3$-Asn-4-aminobenzyl-OC(O)—:

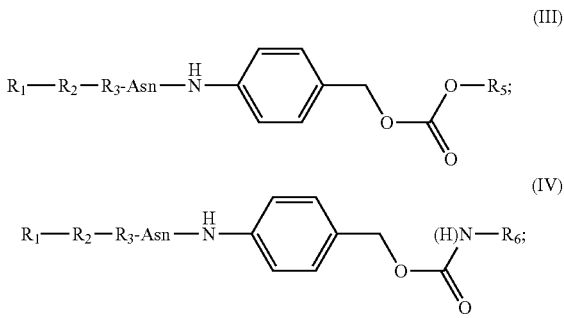

wherein $R_1$ is selected from the group consisting of 6-maleimide-$C_{1-10}$ alkylcarbonyl, hydroyxlaminocarbonyl-$C_{1-10}$ alkylcarbonyl, $C_{1-4}$ alkoxyl-($C_{1-4}$ alkoxyl)$_n$-$C_{1-6}$alkylcarbonyl, and

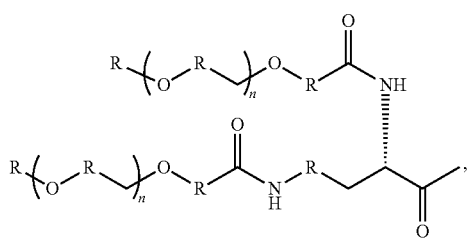

wherein each R is independently a $C_{1-4}$ alkylene, and each n is independently any integer between 1 and 300;

$R_2$ is an amino acid moiety selected from the group consisting of Ala, Thr, Val and Ile;

$R_3$ is an amino acid moiety selected from the group consisting of Ala, Thr, Val and Asn;

$R_2$ links to $R_3$ through an amide bond, $R_3$ links to Asn through an amide bond, and Asn links to —NH— through its carbonyl;

$R_5$ is an active moiety of an anticancer drug containing a hydroxyl group ($R_5$—OH), wherein the anticancer drug is selected from the group consisting of Camptothecin, 10-Hydroxyl Camptothecin, Topotecan, Floxuridine, 5'-Deoxy-5-Fluorouridine, Cytarabine, Etoposide, Fludarabine, Capecitabine, Vincristine, Epothilone B, Paclitaxel and Docetaxel, wherein Paclitaxel and Docetaxel link to the cleavable linker through the hydroxyl group at position 2 when the anticancer drug is Paclitaxel or Docetaxel;

$R_6$ is an active moiety of an anticancer drug containing an amino group ($R_6$—$NH_2$), wherein the anticancer drug is selected from the group consisting of Daunorubicin, Epirubicin, Methotrexate, Fludarabine, Gemcitabine, Cytarabine, Melphalan, Nimustine, Mitoxantrone, Doxorubicin and Mitomycin;

the cleavable linker is characterized in that it is cleavable by contact with an asparagine endopeptidase, and the compound is characterized by release of $R_5$ or $R_6$ through a cleavage of the cleavable linker by contact with the asparagine endopeptidase.

2. The compound of claim 1, wherein $R_1$ is selected from the group consisting of $C_{1-4}$ alkoxyl-$(C_{1-4}$ alkoxyl$)_n$-$C_{1-6}$ alkylcarbonyl, and

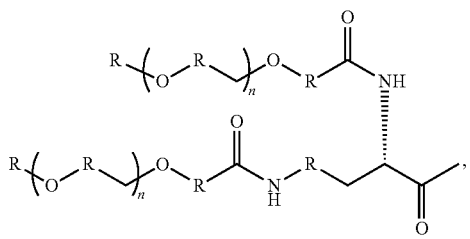

wherein each R is independently a $C_{1-4}$ alkylene, and each n is independently any integer between 1 and 300.

3. The compound of claim 2, wherein said each n is independently any integer between 1 and 150.

4. The compound of claim 1, wherein the compound has a structure as set forth in any of the following formulae (V), (VI), (VII), (VIII), and (IX):

(V)

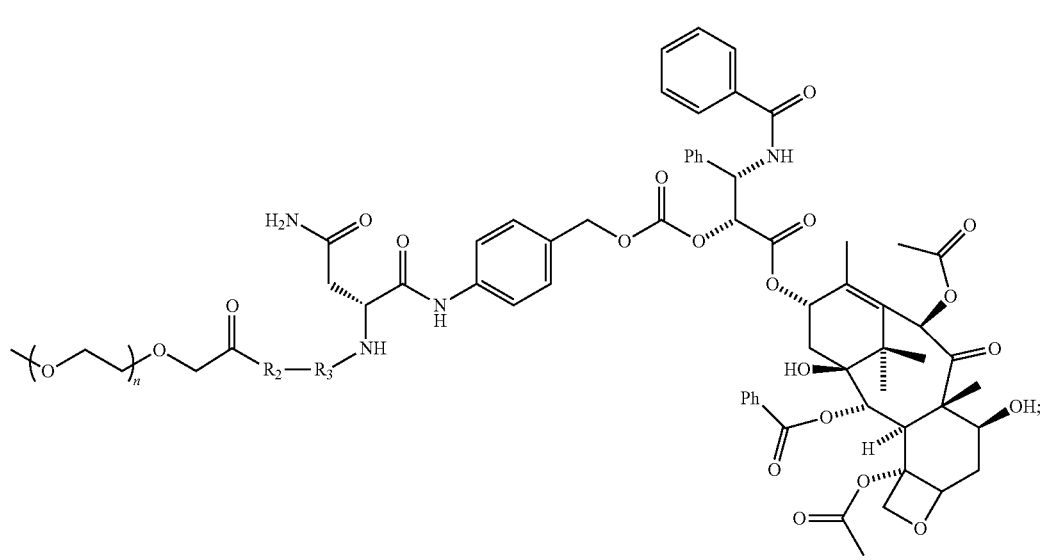

-continued
(VI)
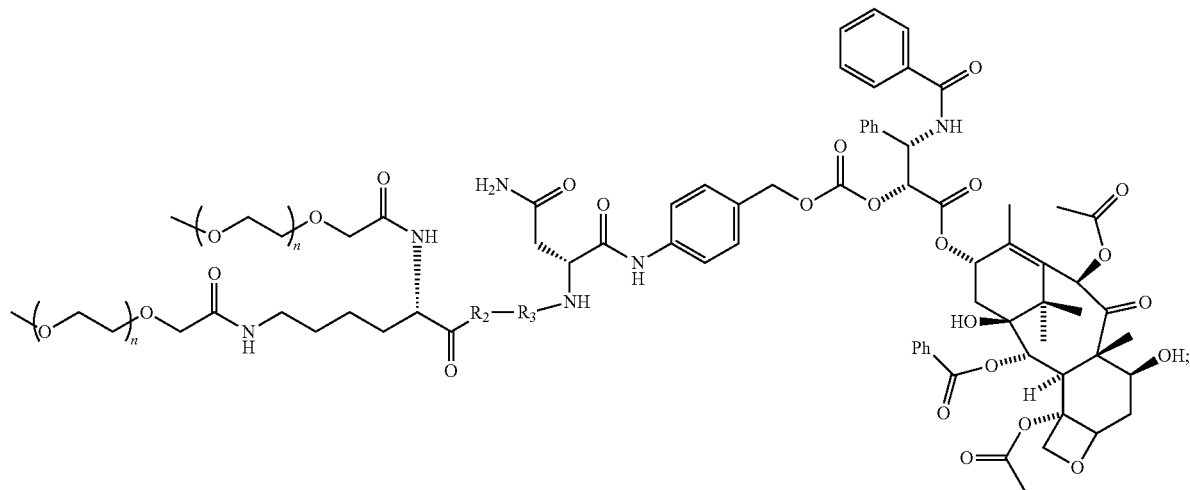
(VII)
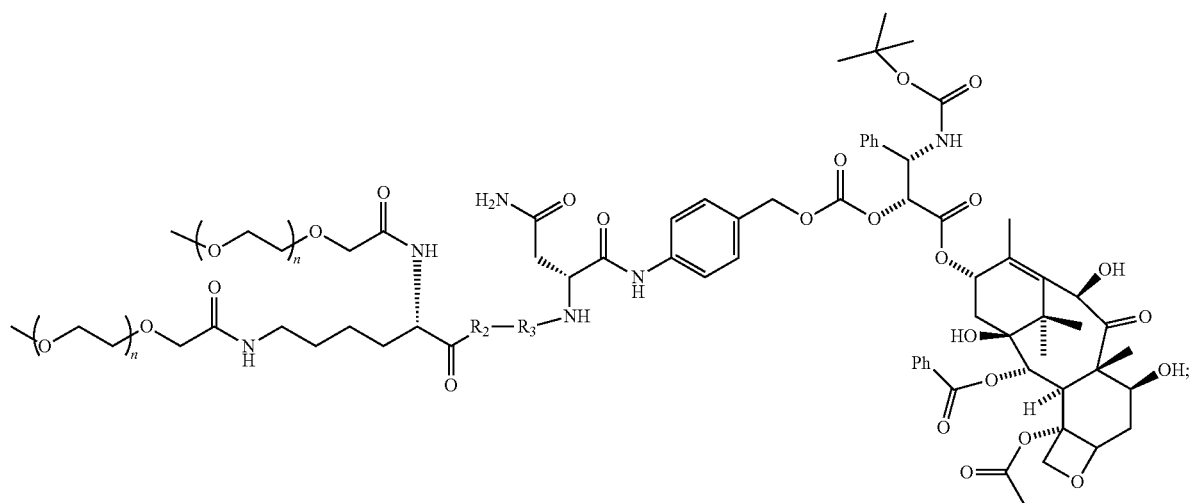
(VIII)
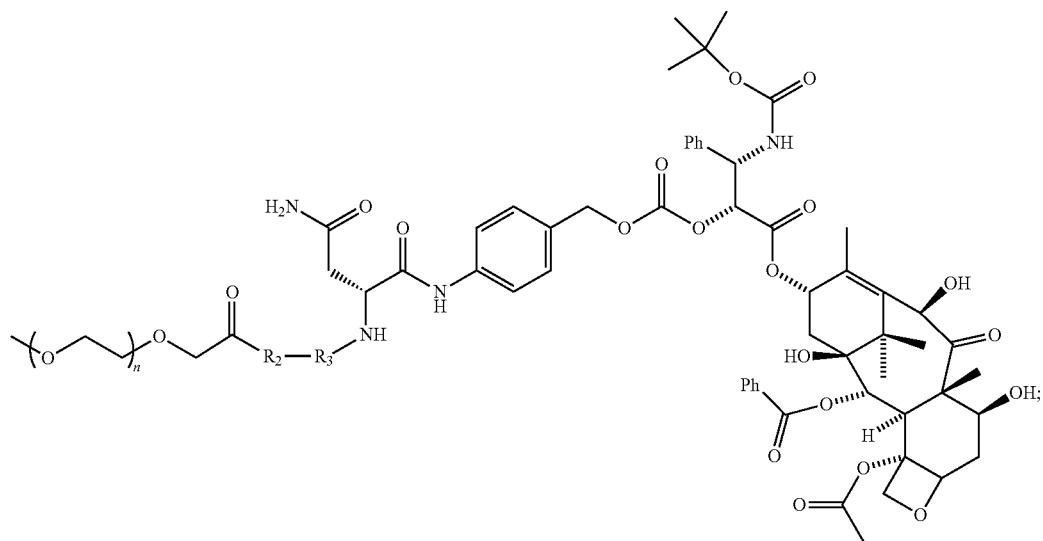

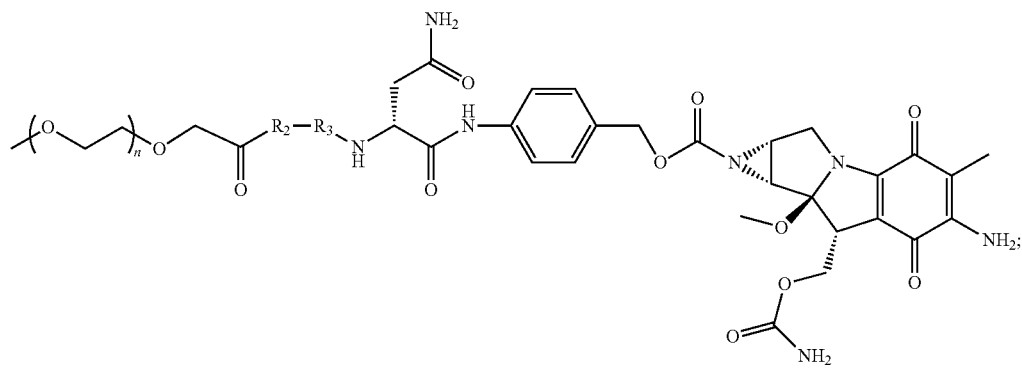
(IX)
wherein
each n is independently any integer between 1 and 300;
R₂ is Ala, Thr, Val or Ile; and
R₃ is Ala, Thr, Val or Asn.
5. The compound of claim 4, wherein said each n is independently any integer between 1 and 150.
6. The compound of claim 1, wherein the compound is selected from the group consisting of:
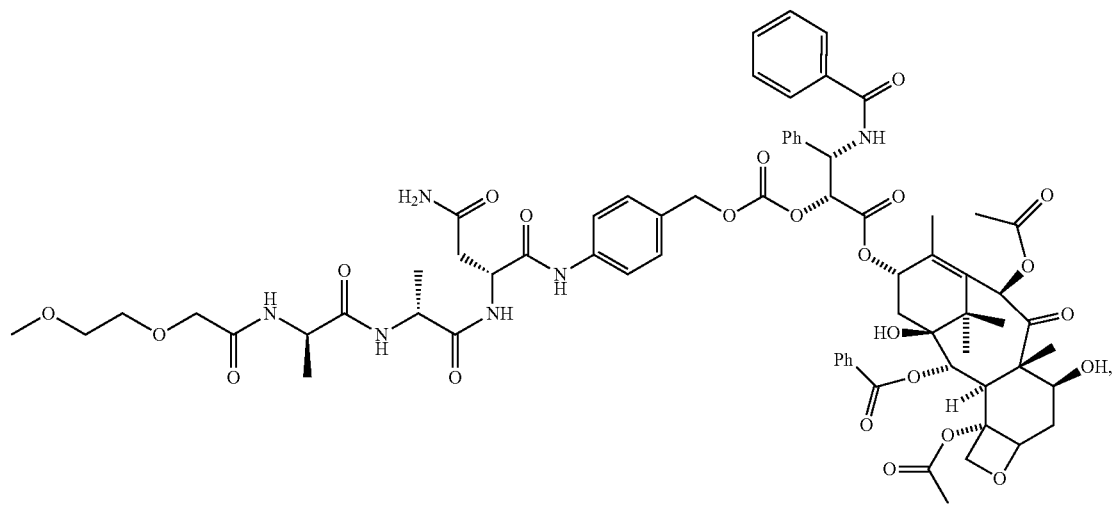
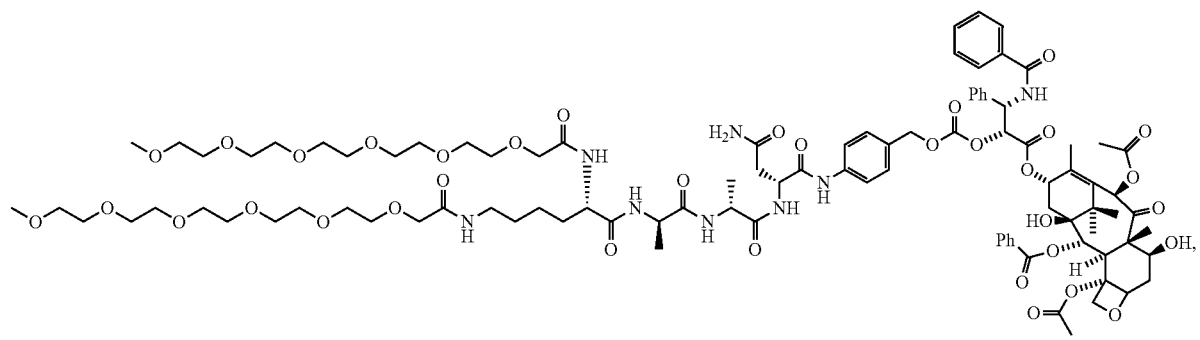

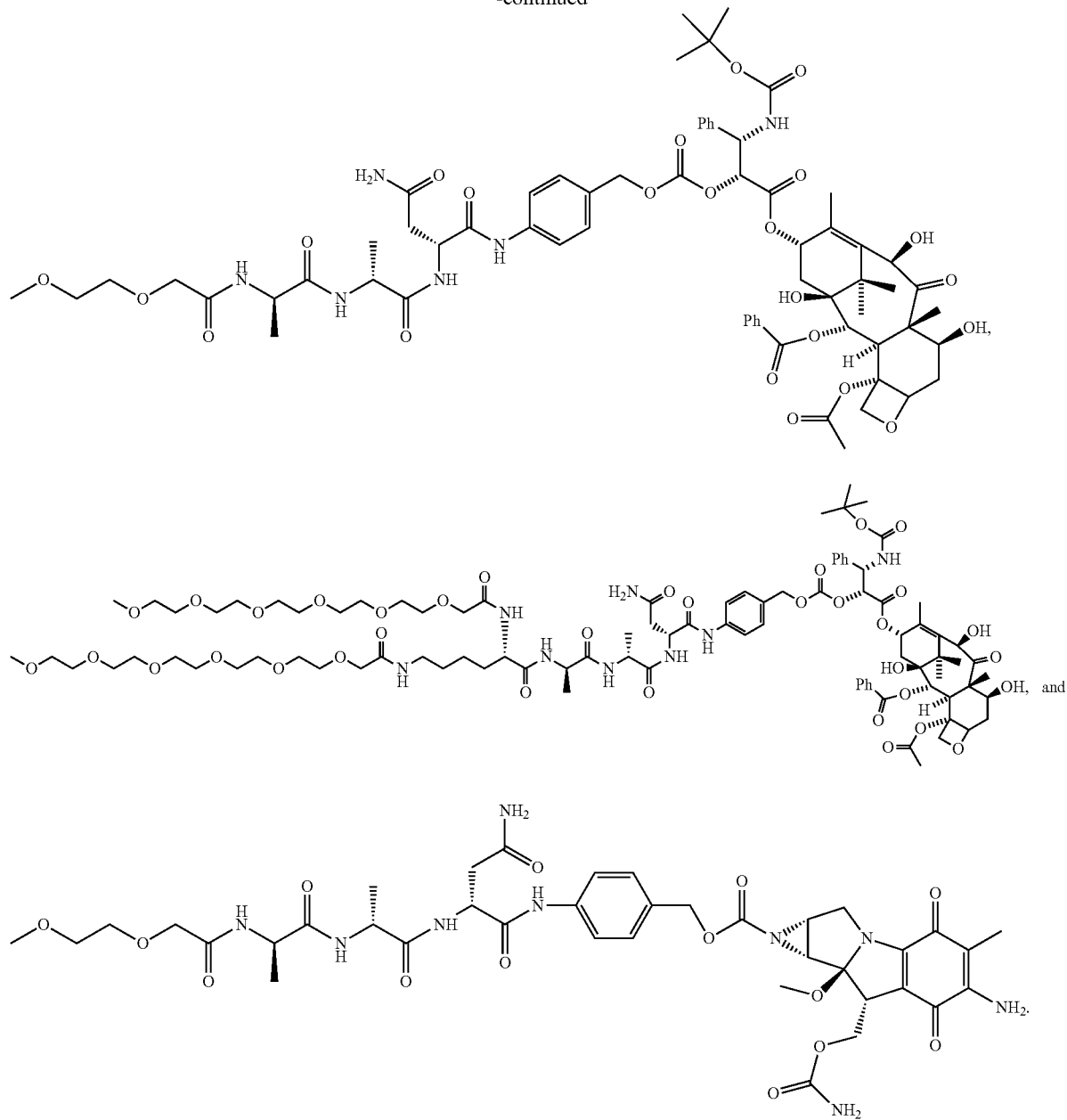
7. The compound of claim 1, wherein the compound is selected from the group consisting of:
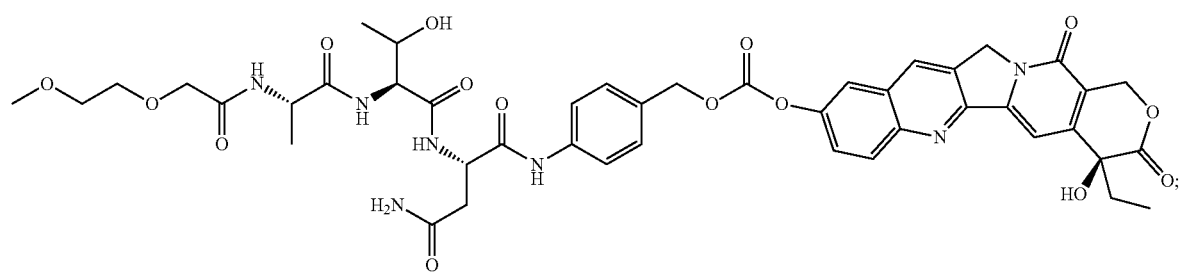

-continued
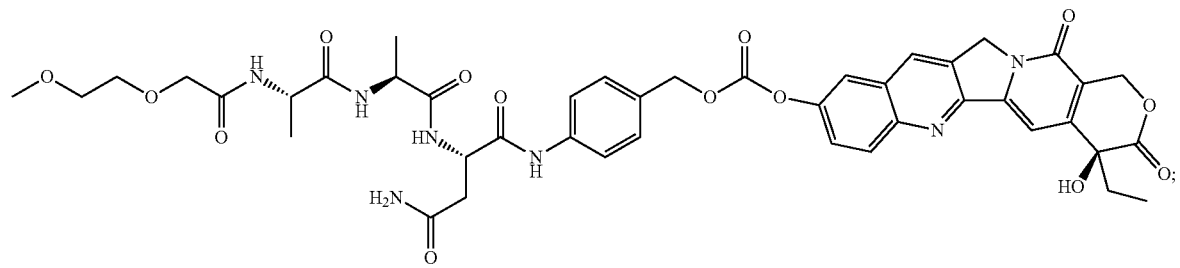
S2
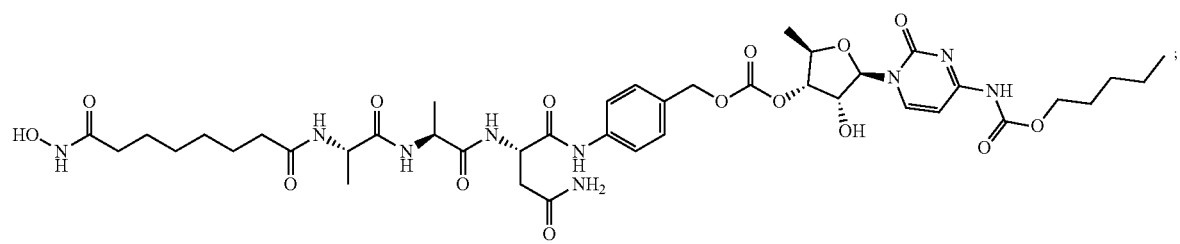
S3
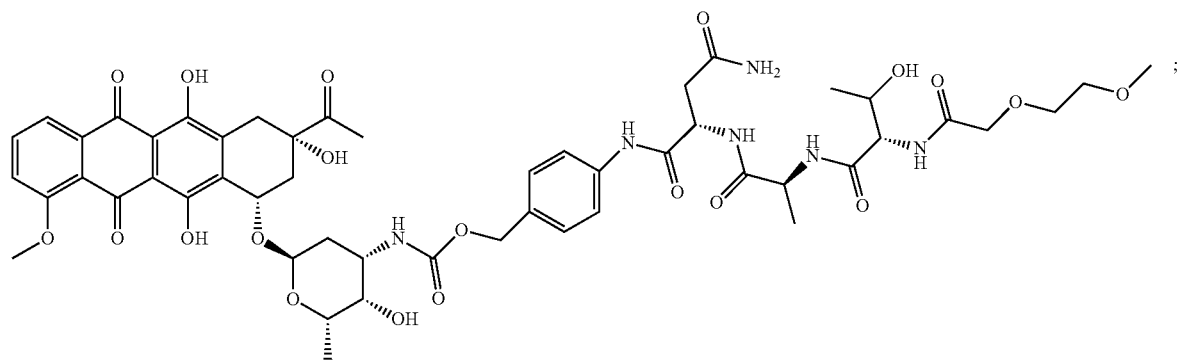
S4
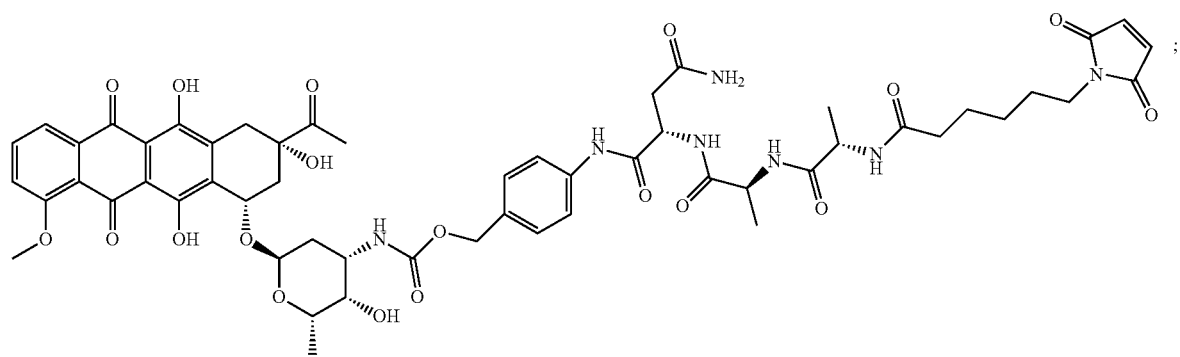
S5
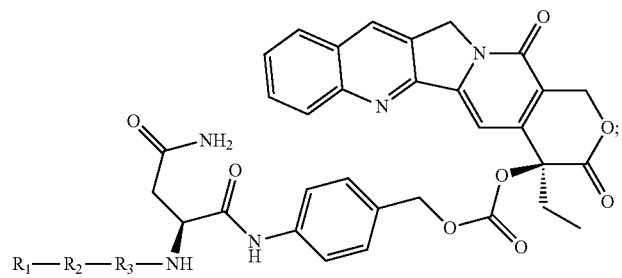
S7

-continued
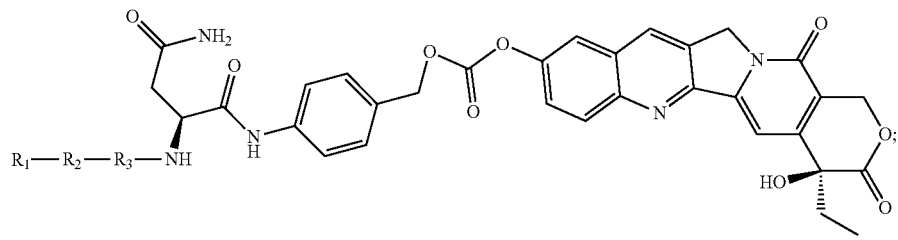
S8
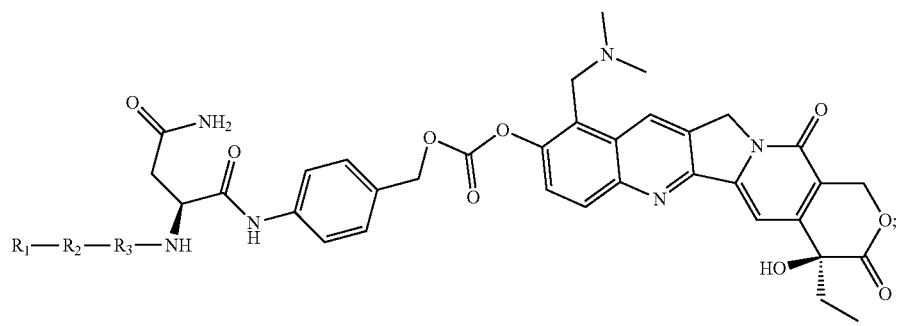
S9
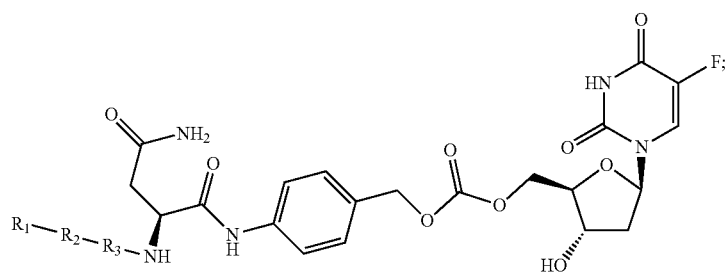
S10
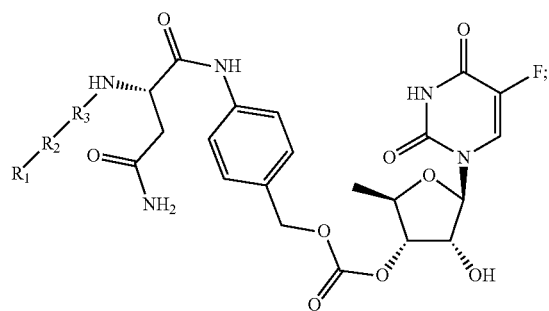
S11
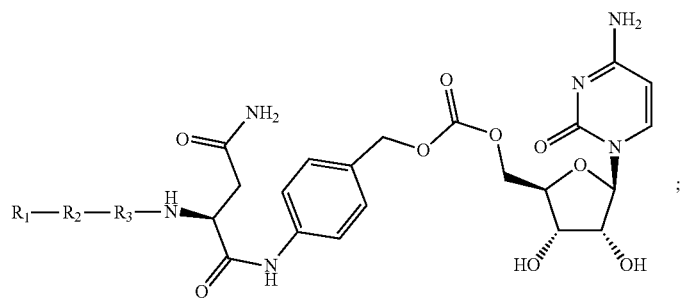
S12

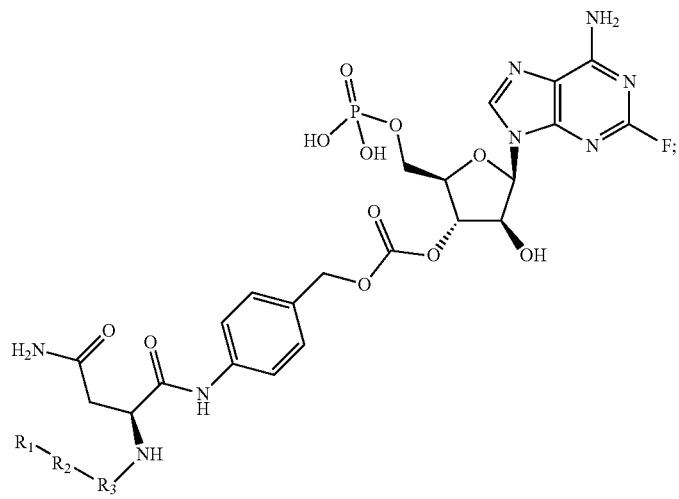
S13
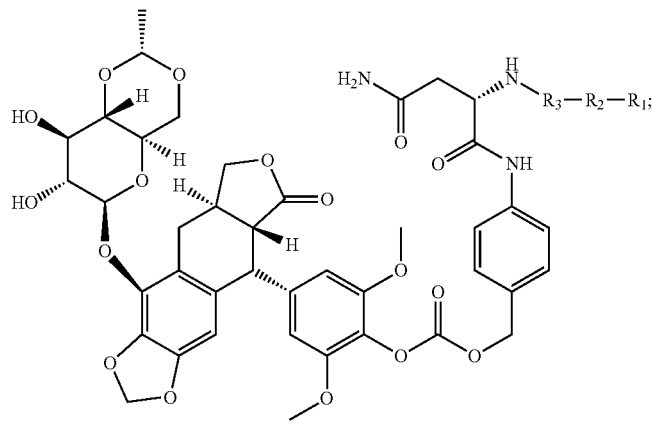
S14
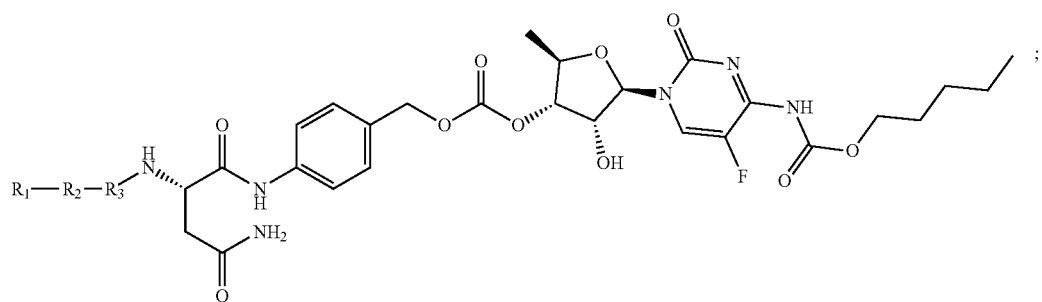
S15
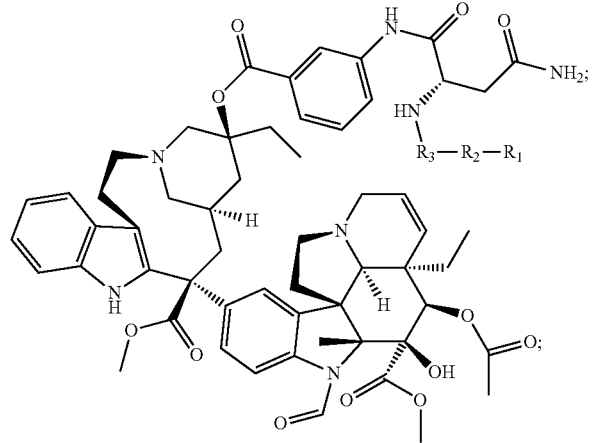
S17

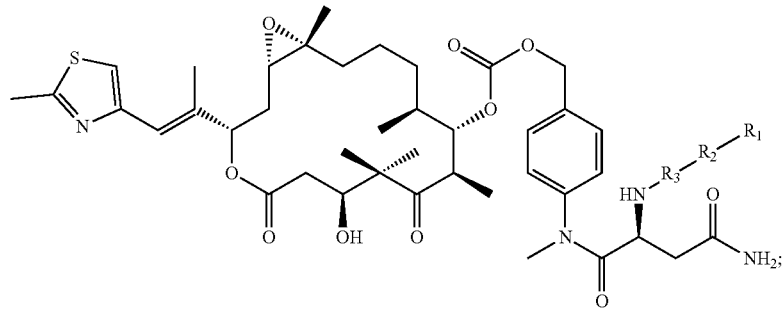
S18
wherein, in compounds S7-S15 and S17-S18, $R_1$ is 2-(2-methoxyethoxy)acetyl, $R_2$ is Thr, $R_3$ is Ala;
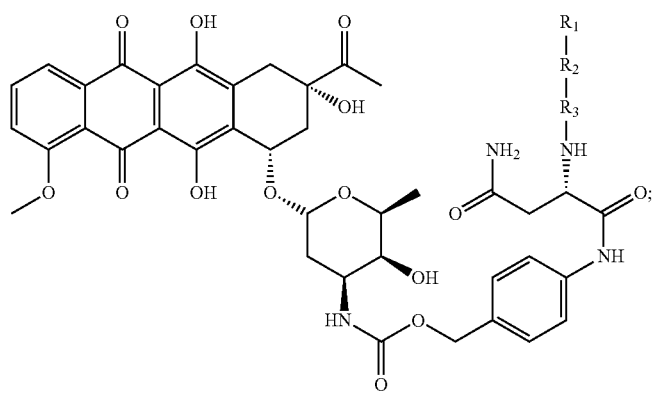
S19
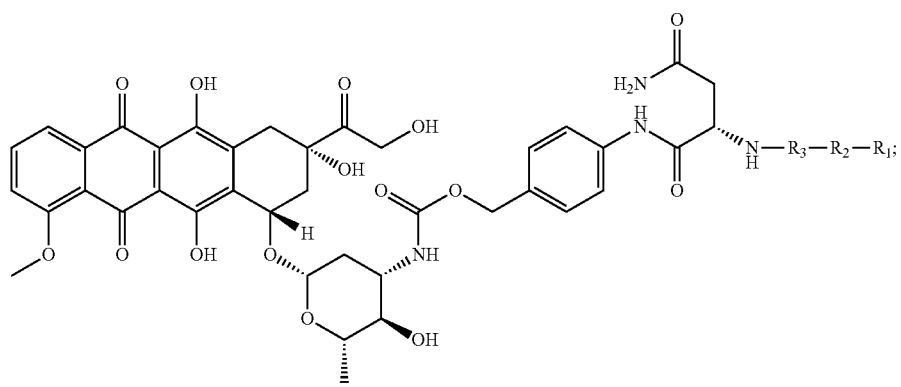
S20
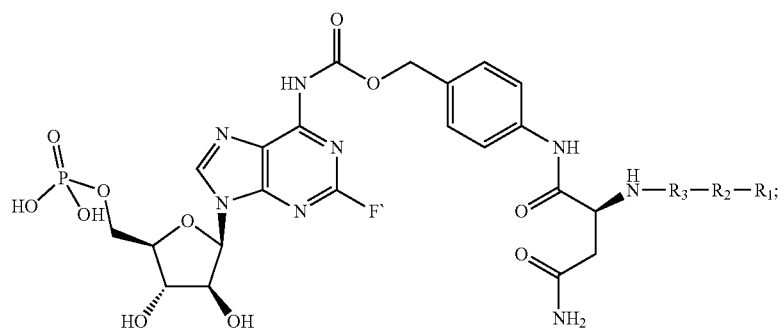
S21

-continued
S22
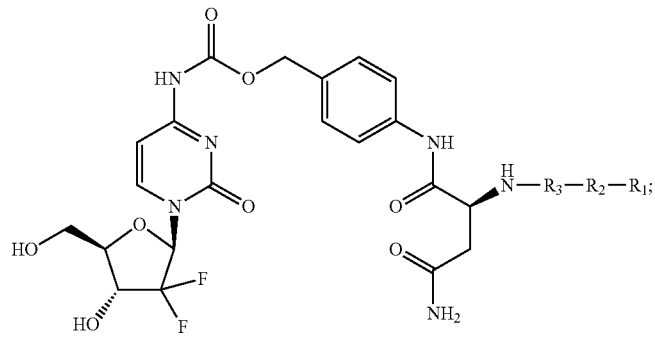
S23
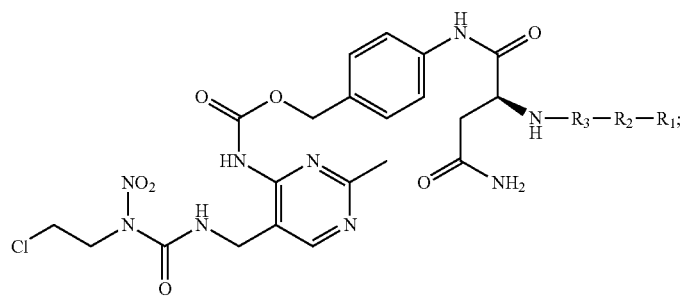
S24
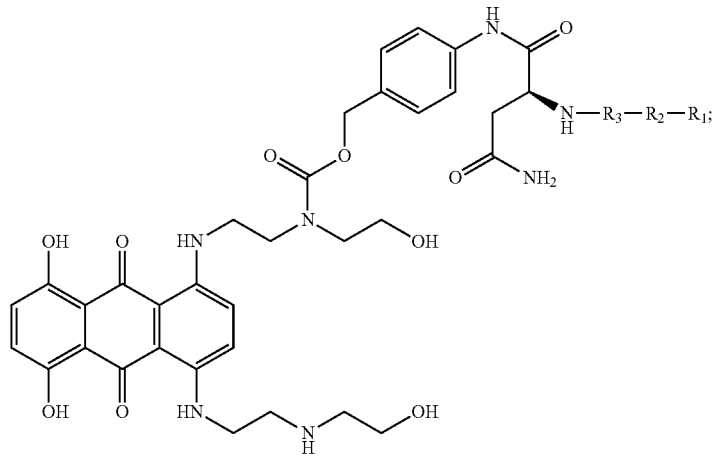
S25
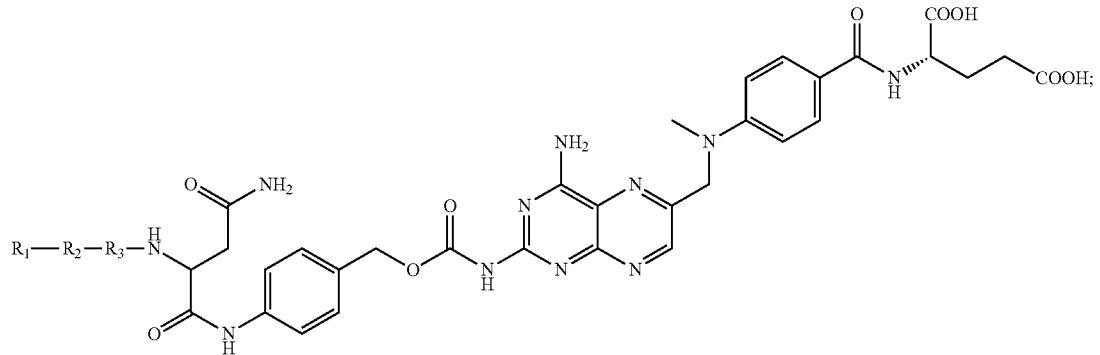

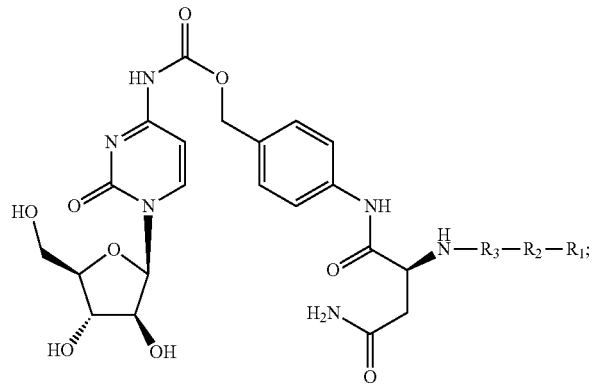
S26
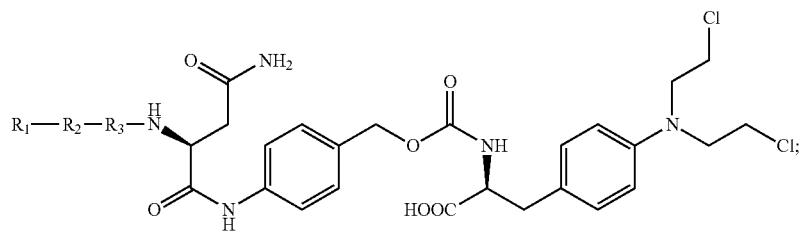
S27
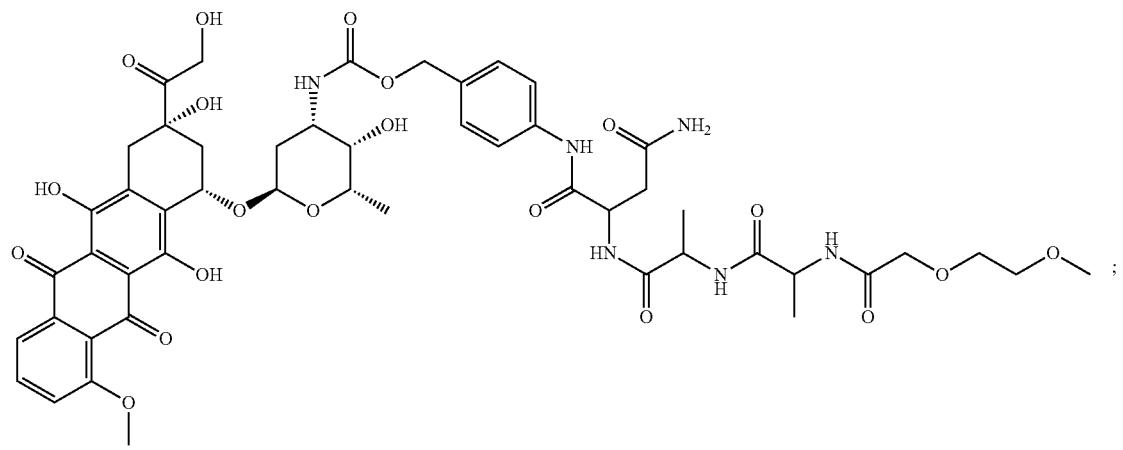
S28
wherein, in compounds S19-S28, $R_1$ is 2-(2-methoxyethoxy)acetyl, $R_2$ and $R_3$ are Ala;
S29-S43 represented by a formula
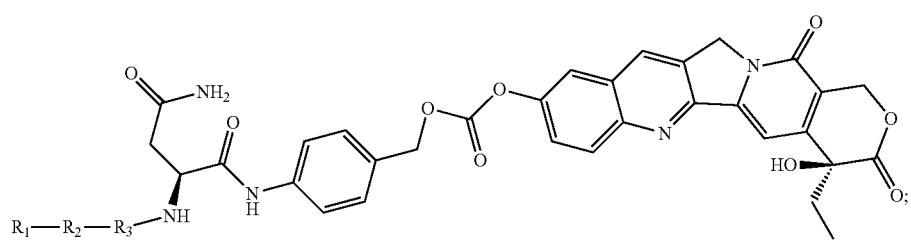

wherein, in compounds S29-S43, $R_1$ is 2-(2-methoxyethoxy)acetyl, and $R_2$ and $R_3$ are shown below:
| No. of Compound | $R_2$ | $R_3$ |
|---|---|---|
| S29 | Thr | Thr |
| S30 | Thr | Val |
| S31 | Thr | Asn |
| S32 | Val | Ala |
| S33 | Val | Thr |
| S34 | Val | Val |
| S35 | Val | Asn |
-continued
| No. of Compound | $R_2$ | $R_3$ |
|---|---|---|
| S36 | Ile | Ala |
| S37 | Ile | Thr |
| S38 | Ile | Val |
| S39 | Ile | Asn |
| S40 | Ala | Ala |
| S41 | Ala | Thr |
| S42 | Ala | Val |
| S43 | Ala | Asn |
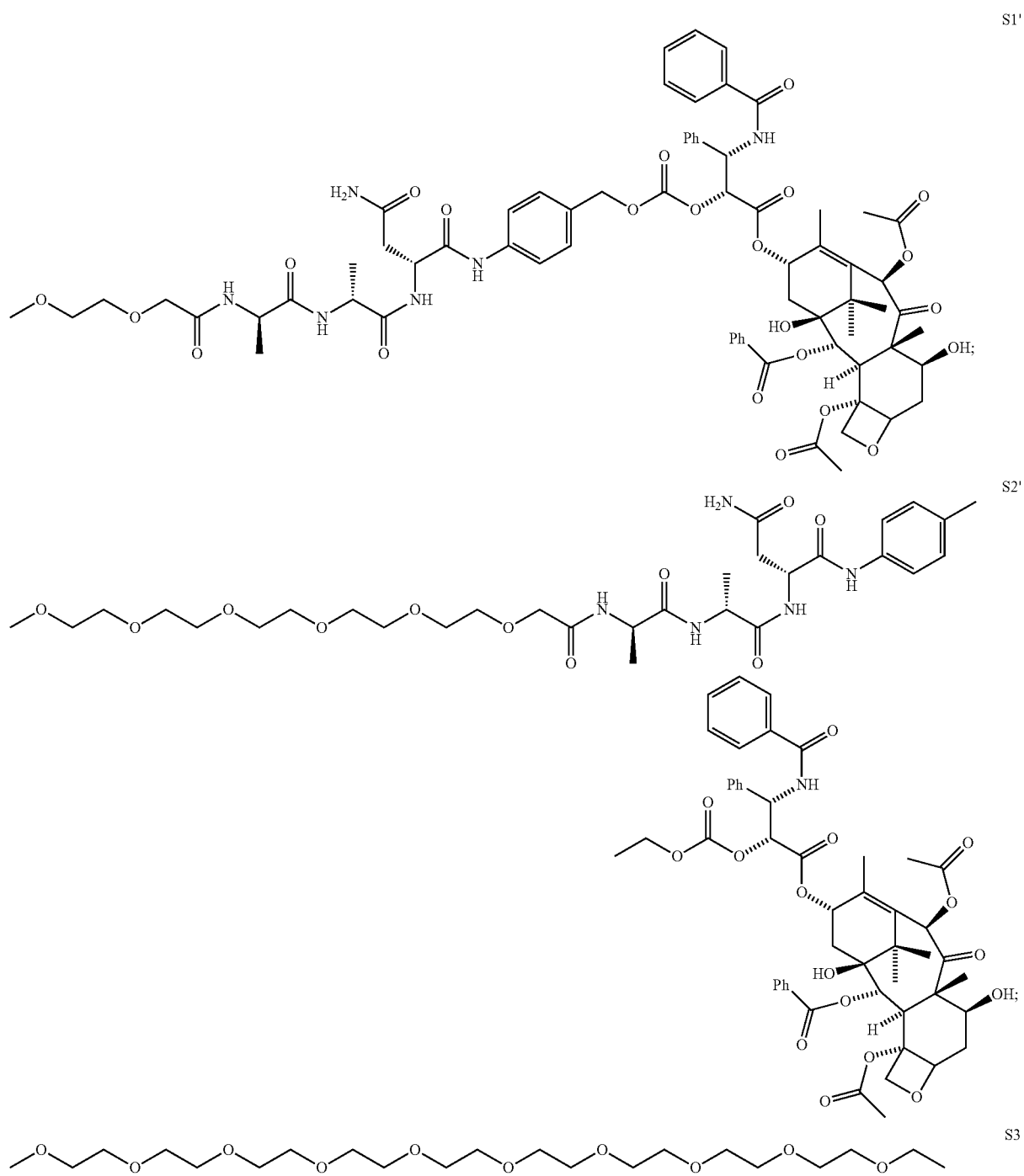

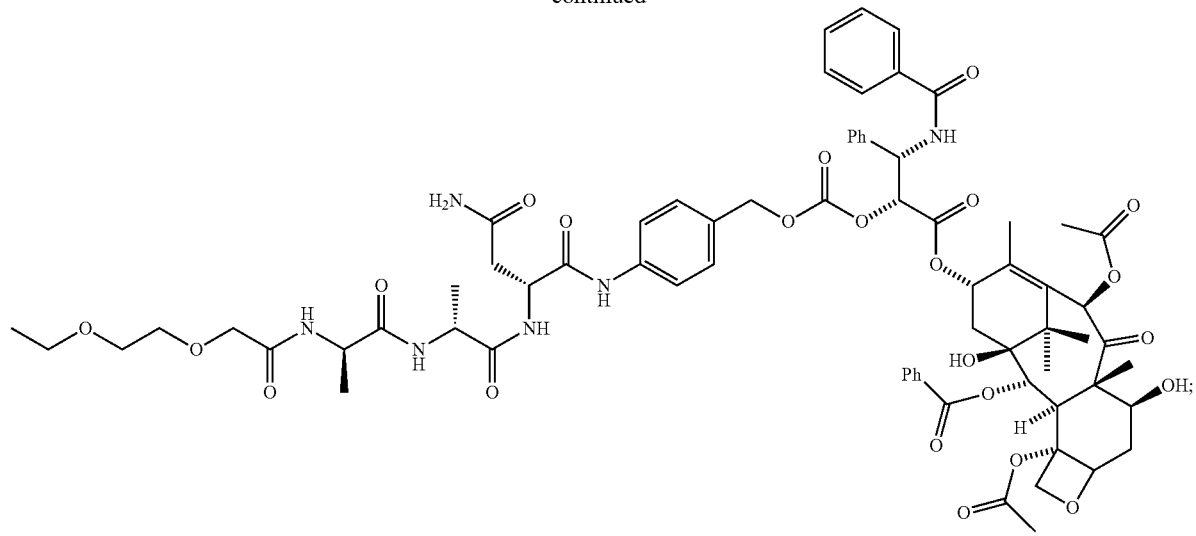
S4
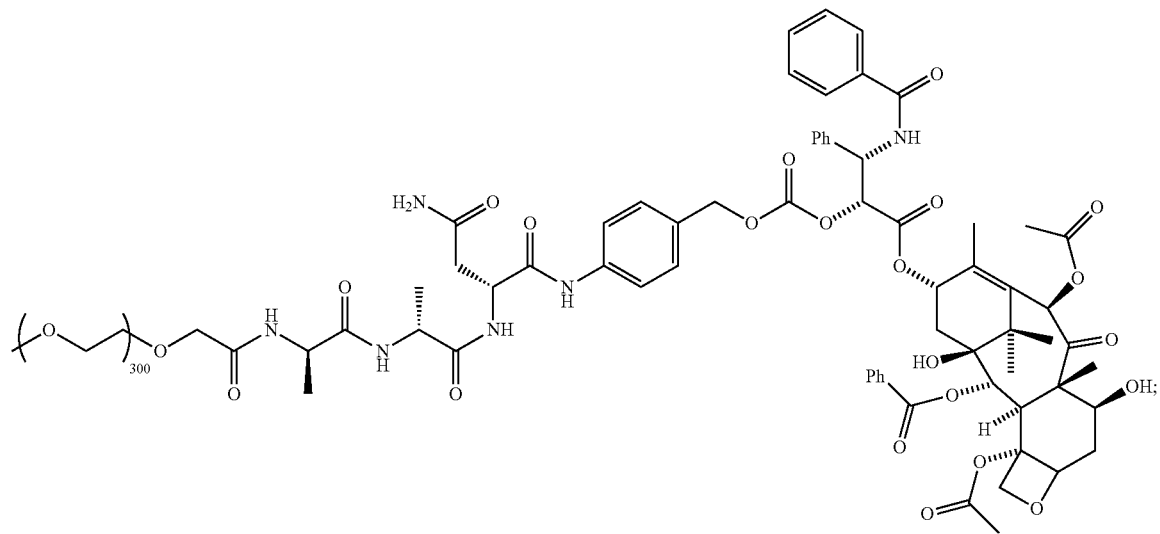
S10'-S24' represented by formula
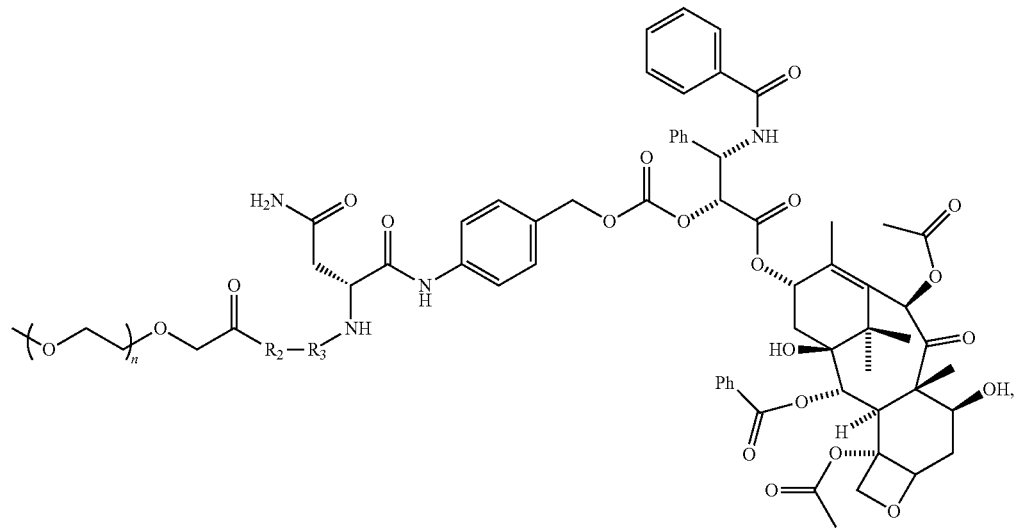

in which n is 1 and $R_2$ and $R_3$ are shown as follows:

| No. of Compound | $R_2$ | $R_3$ |
|---|---|---|
| S10' | Ala | Thr |
| S11' | Ala | Val |
| S12' | Ala | Asn |
| S13' | Thr | Ala |
| S14' | Thr | Thr |
| S15' | Thr | Val |
| S16' | Thr | Asn |
| S17' | Val | Ala |
| S18' | Val | Thr |
| S19' | Val | Val |
| S20' | Val | Asn |
| S21' | Ile | Ala |
| S22' | Ile | Thr |
| S23' | Ile | Val |
| S24' | Ile | Asn |

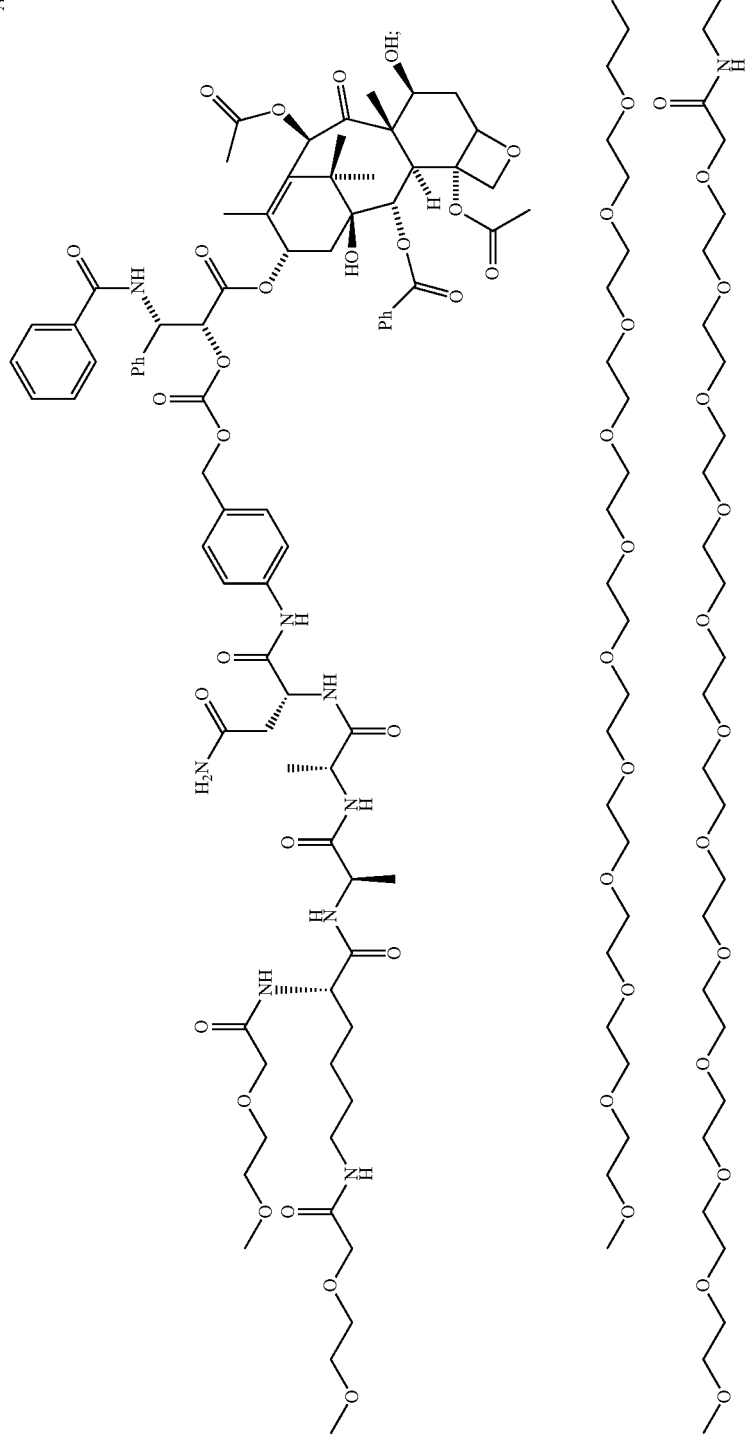

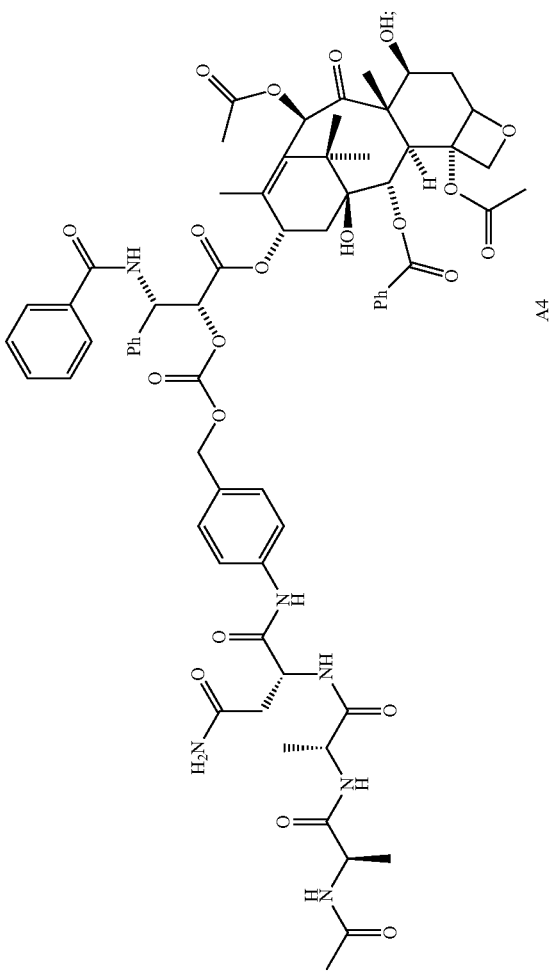
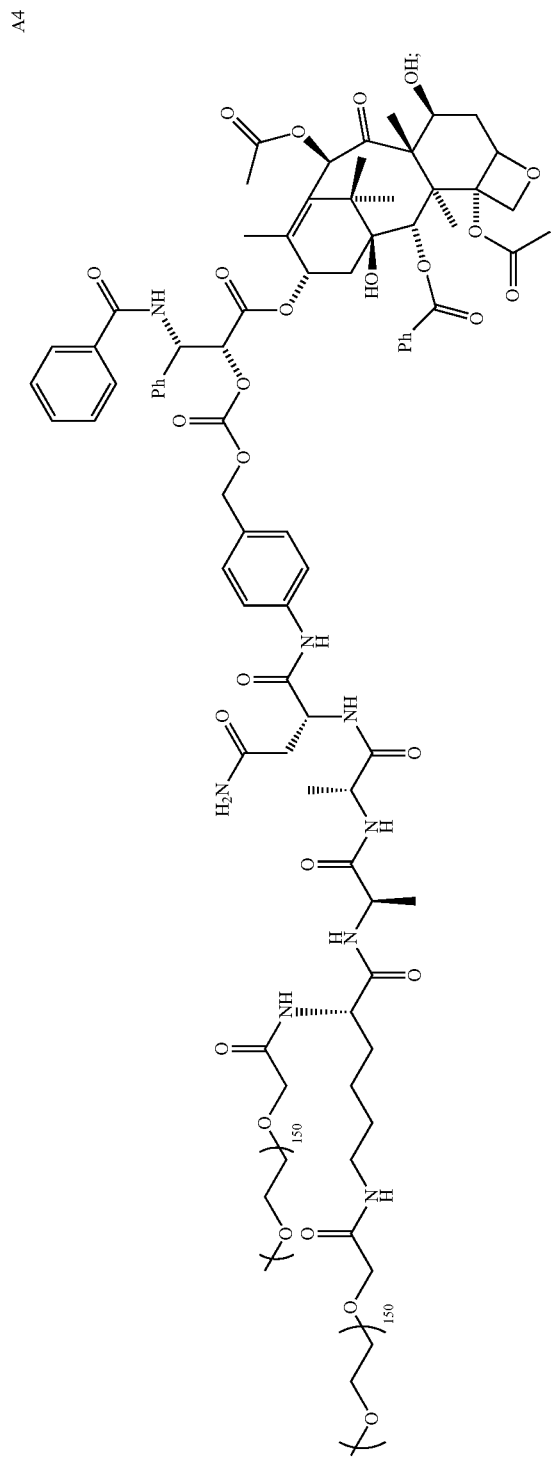

A10-A24 represented by formula
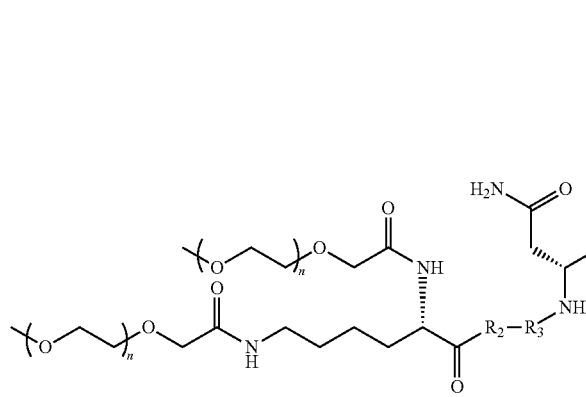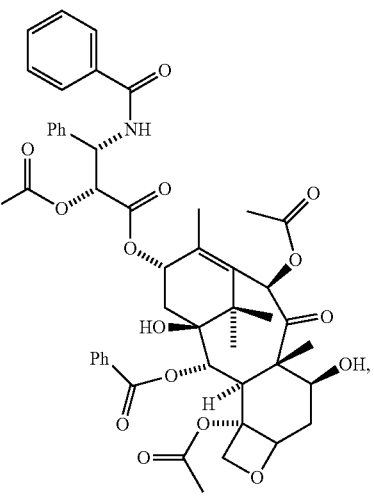
wherein n is 5 and R₂ and R₃ are shown in the following table:
| No. of Compound | R₂ | R₃ |
|---|---|---|
| A10 | Ala | Thr |
| A11 | Ala | Val |
| A12 | Ala | Asn |
| A13 | Thr | Ala |
| A14 | Thr | Thr |
| A15 | Thr | Val |
| A16 | Thr | Asn |
| A17 | Val | Ala |
| A18 | Val | Thr |
| A19 | Val | Val |
| A20 | Val | Asn |
| A21 | Ile | Ala |
| A22 | Ile | Thr |
| A23 | Ile | Val |
| A24 | Ile | Asn |

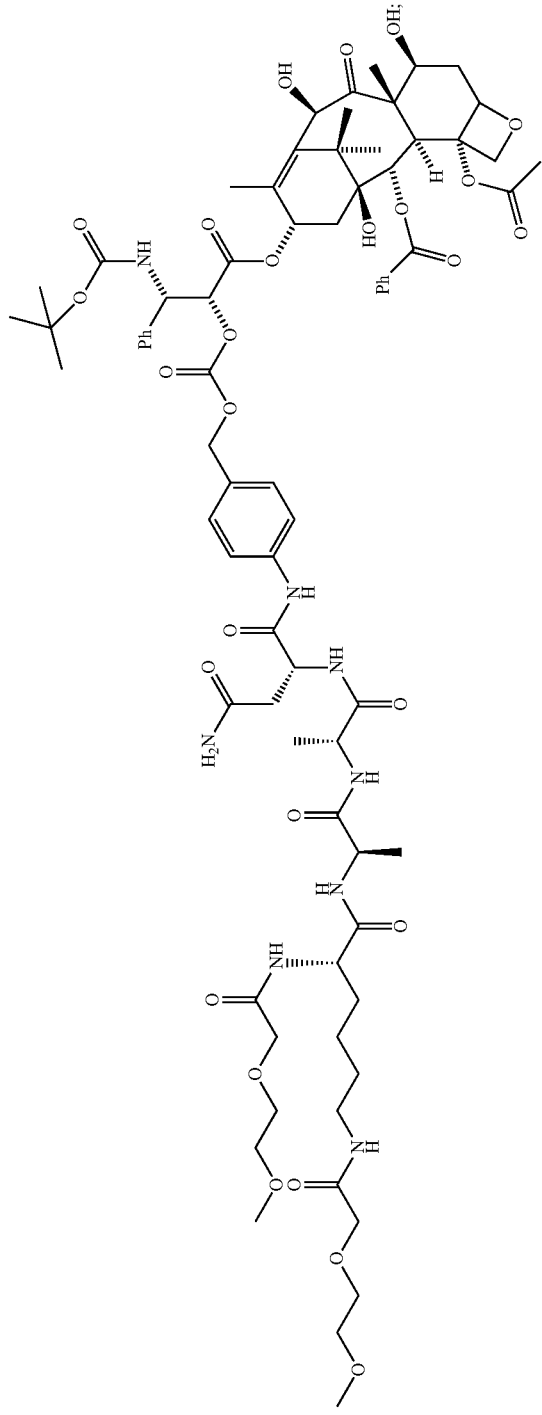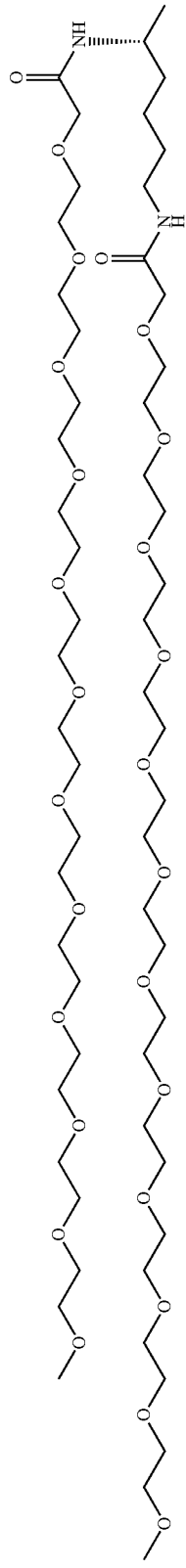

B4
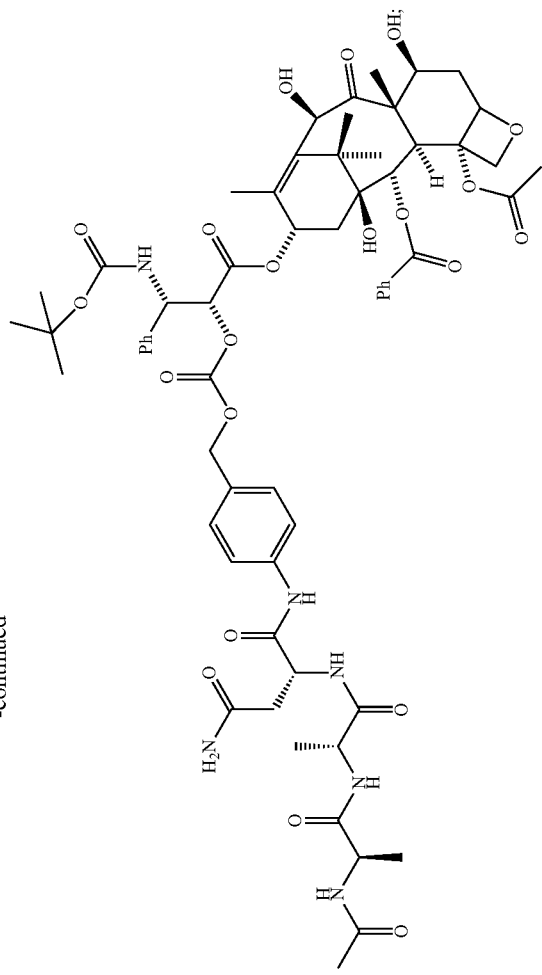
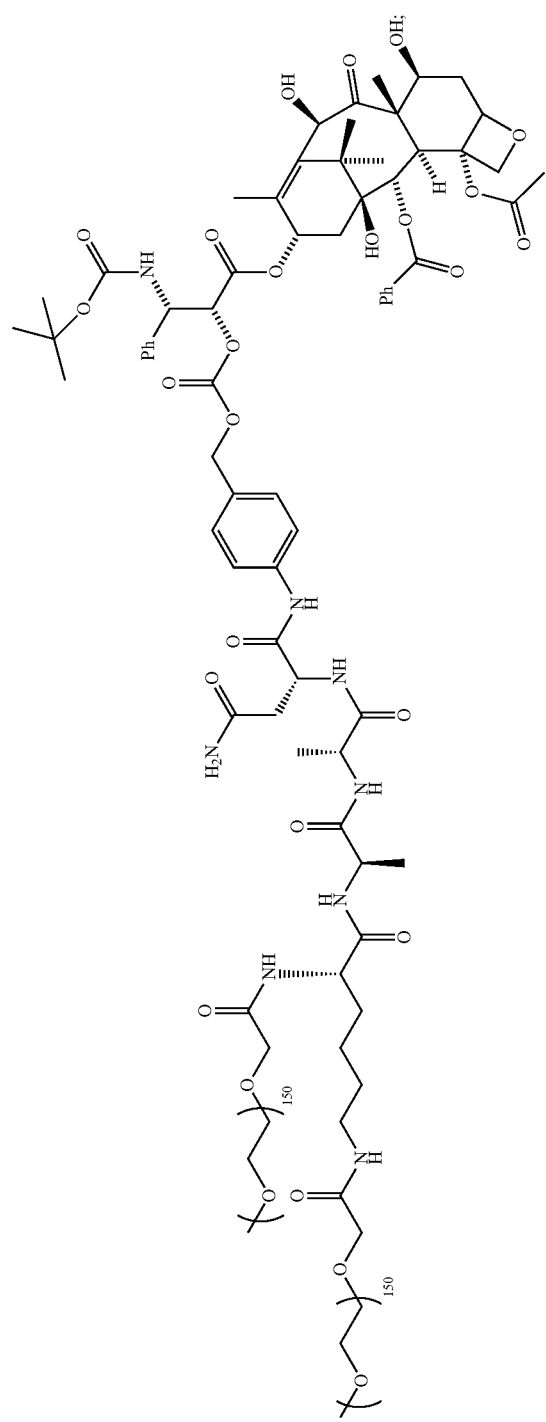

B10-B24 represented by
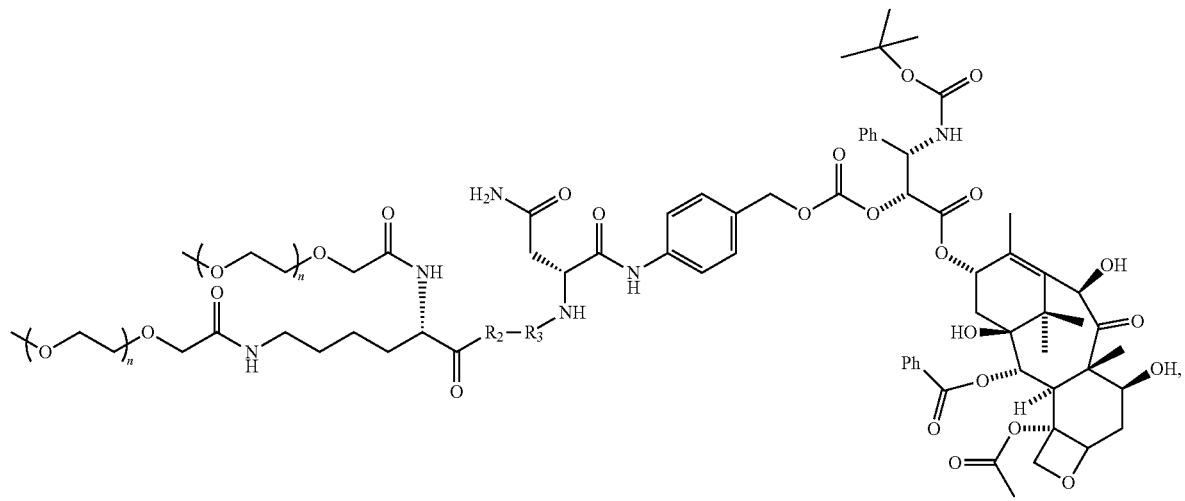
in which n, R₂ and R₃ are shown as follows:
| No. of Compound | R₂ | R₃ | n |
|---|---|---|---|
| B10 | Ala | Thr | 5 |
| B11 | Ala | Val | 5 |
| B12 | Ala | Asn | 5 |
| B13 | Thr | Ala | 5 |
| B14 | Thr | Thr | 5 |
| B15 | Thr | Val | 5 |
| B16 | Thr | Asn | 5 |
| B17 | Val | Ala | 5 |
| B18 | Val | Thr | 5 |
| B19 | Val | Val | 5 |
| B20 | Val | Asn | 5 |
| B21 | Ile | Ala | 5 |
| B22 | Ile | Thr | 5 |
| B23 | Ile | Val | 5 |
| B24 | Ile | Asn | 5 |

D2
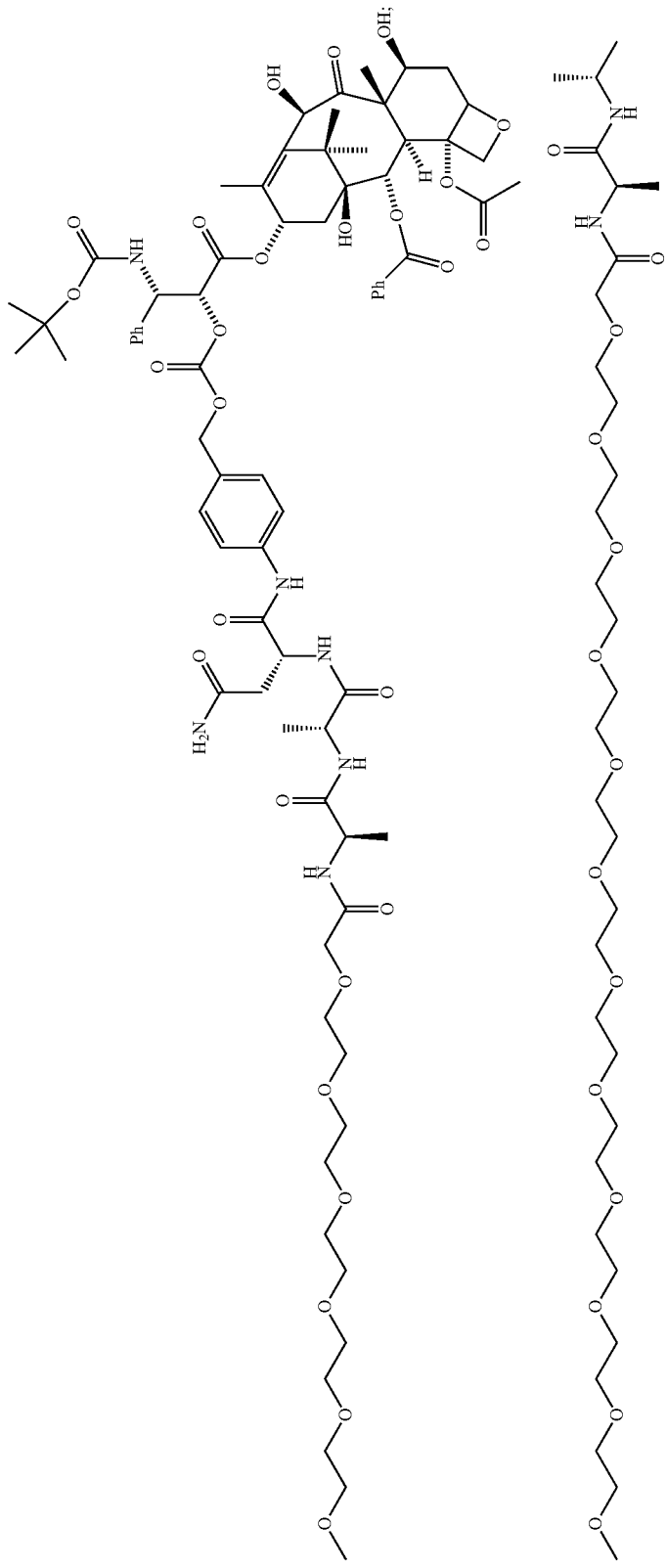
D3
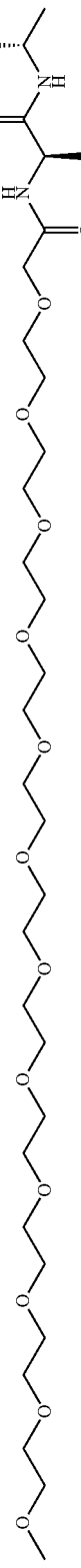

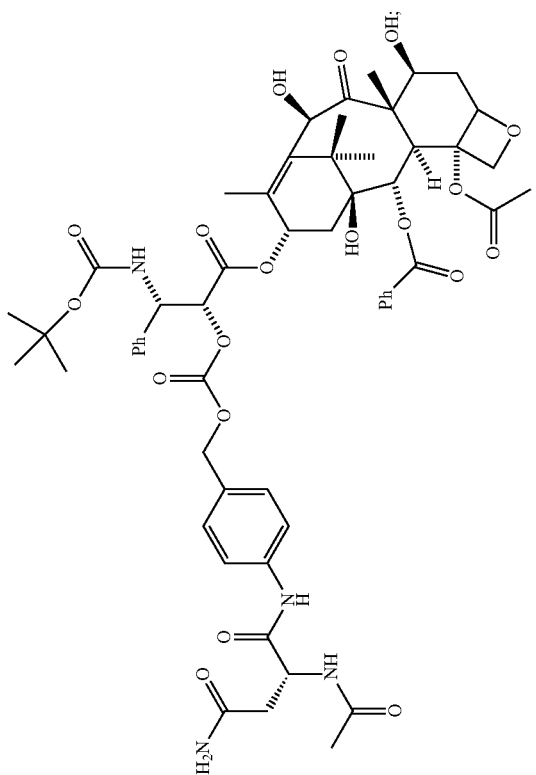
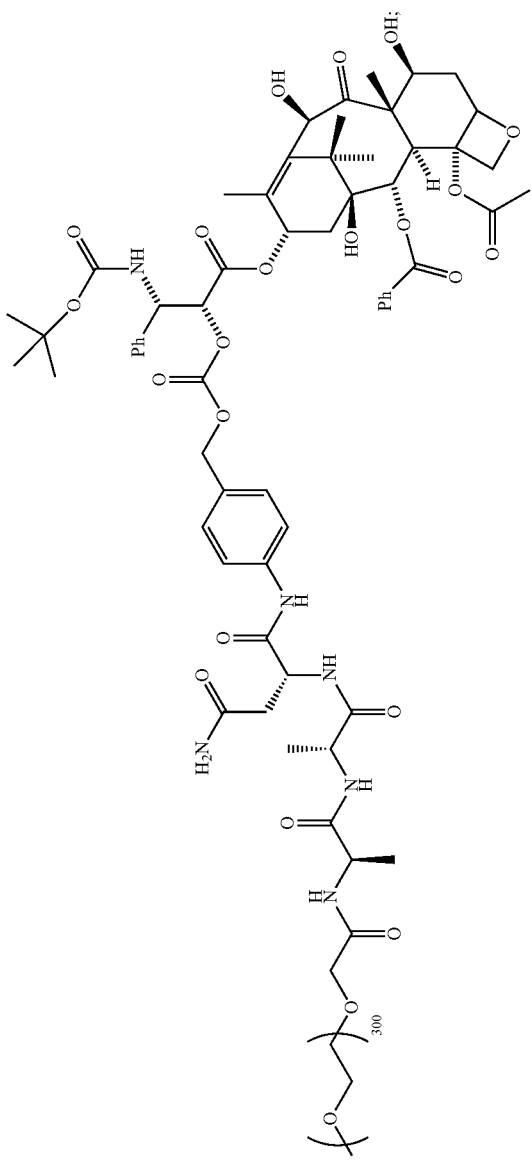

D10-D24 represented by
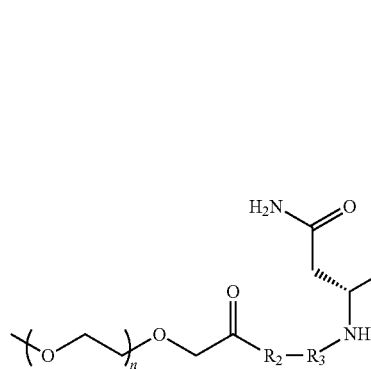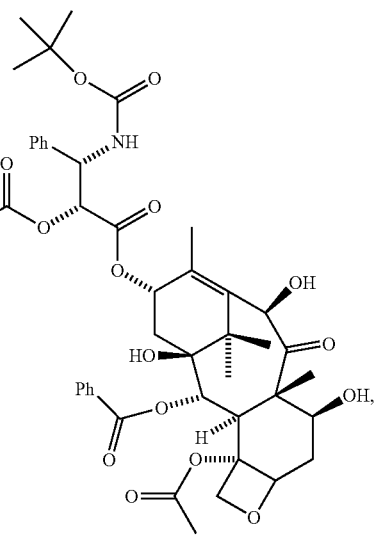
in which n, R₂ and R₃ are shown as follows:
| No. of Compound | R₂ | R₃ | n |
|---|---|---|---|
| D10 | Ala | Thr | 1 |
| D11 | Ala | Val | 1 |
| D12 | Ala | Asn | 1 |
| D13 | Thr | Ala | 1 |
| D14 | Thr | Thr | 1 |
| D15 | Thr | Val | 1 |
| D16 | Thr | Asn | 1 |
| D17 | Val | Ala | 1 |
| D18 | Val | Thr | 1 |
| D19 | Val | Val | 1 |
| D20 | Val | Asn | 1 |
| D21 | Ile | Ala | 1 |
| D22 | Ile | Thr | 1 |
| D23 | Ile | Val | 1 |
| D24 | Ile | Asn | 1 |

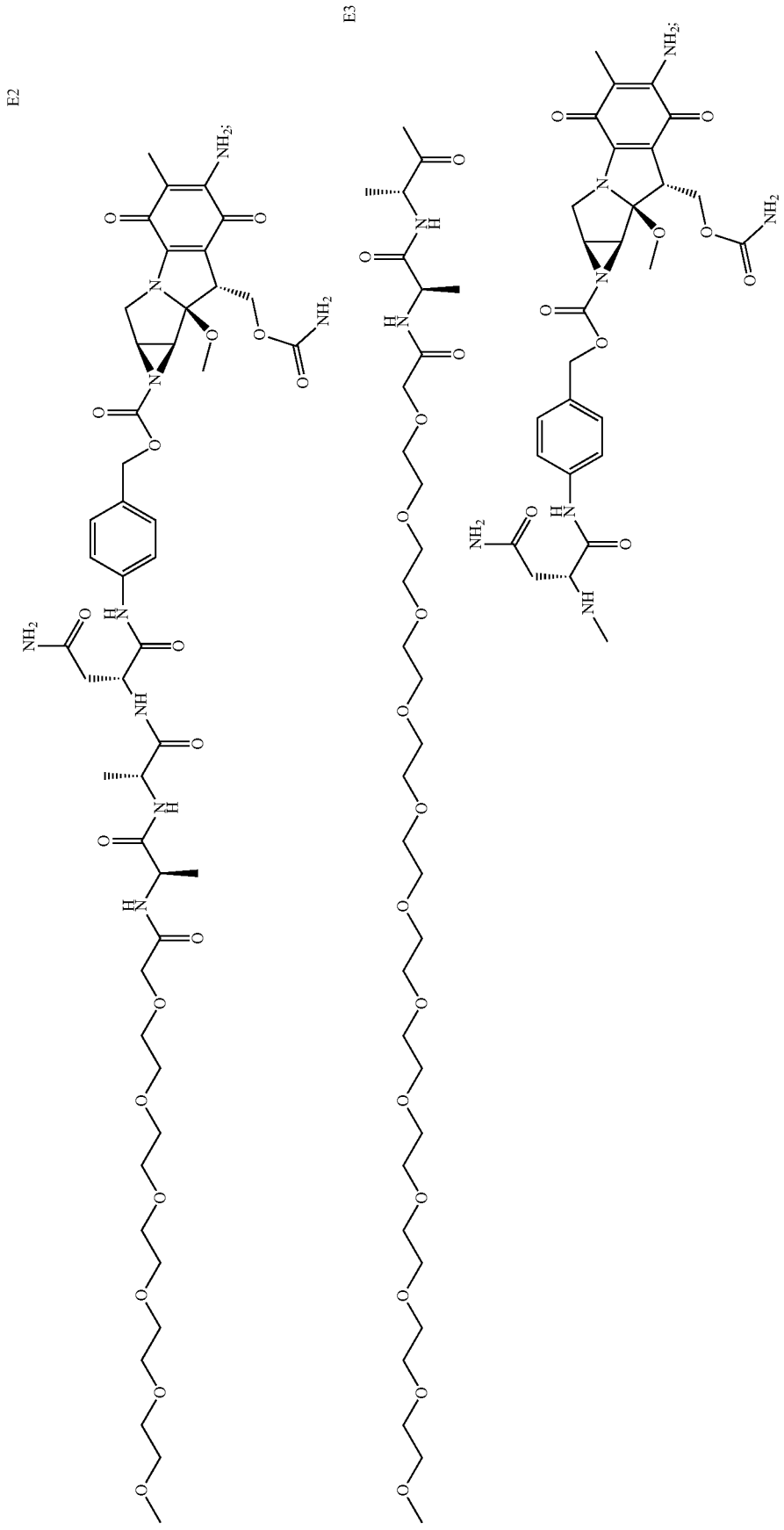

E4
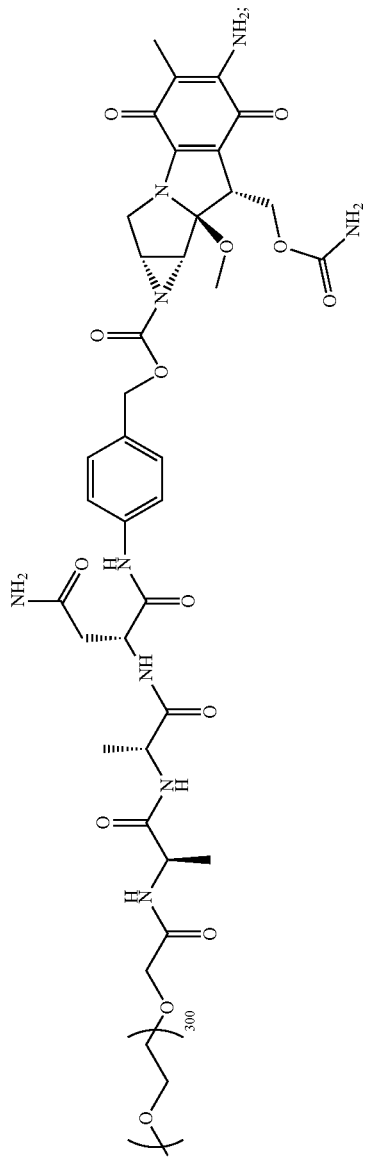

E10-E24 represented by formula

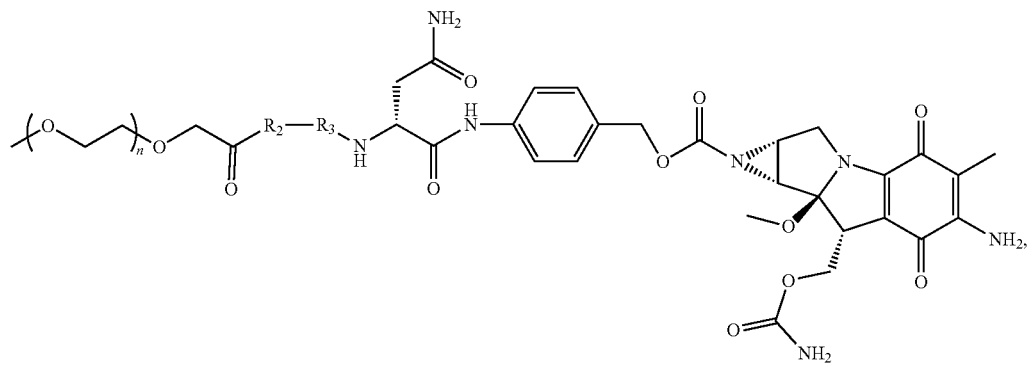

in which n, $R_2$ and $R_3$ are shown as follows:

| No. of Compound | $R_2$ | $R_3$ | n |
|---|---|---|---|
| E10 | Ala | Thr | 1 |
| E11 | Ala | Val | 1 |
| E12 | Ala | Asn | 1 |
| E13 | Thr | Ala | 1 |
| E14 | Thr | Thr | 1 |
| E15 | Thr | Val | 1 |
| E16 | Thr | Asn | 1 |
| E17 | Val | Ala | 1 |
| E18 | Val | Thr | 1 |
| E19 | Val | Val | 1 |
| E20 | Val | Asn | 1 |
| E21 | Ile | Ala | 1 |
| E22 | Ile | Thr | 1 |
| E23 | Ile | Val | 1 |
| E24 | Ile | Asn | 1. |

8. The compound of claim 1, wherein $R_2$ is Thr, $R_3$ is Ala; or $R_2$ is Val, $R_3$ is Ala; or $R_2$ is Ile, $R_3$ is Ala; or both $R_2$ and $R_3$ are Ala.

9. The compound of claim 1, wherein $R_1$ is 2-(2-Methoxyethoxy)acetyl, 6-maleimide caproyl or N-hydroxylamino-1,8-octandioic acid-1-monoacyl.

10. A pharmaceutical composition comprising the compound of claim 1 or a pharmaceutically acceptable salt thereof and a pharmaceutically acceptable carrier or excipient.

11. The pharmaceutical composition of claim 10, wherein $R_1$ is selected from the group consisting of $C_{1-4}$ alkoxyl-$(C_{1-4}$ alkoxyl$)_n$-$C_{1-6}$ alkylcarbonyl, and

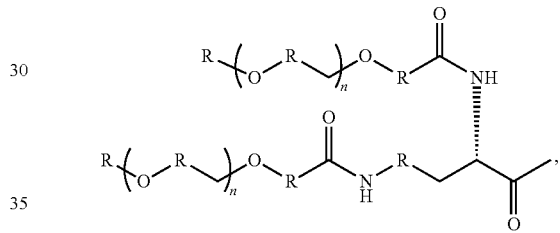

wherein each R is independently a $C_{1-4}$ alkylene, and each n is independently any integer between 1 and 300.

12. The pharmaceutical composition of claim 11, wherein said each n is independently any integer between 1 and 150.

13. The pharmaceutical composition of claim 10, wherein the compound has a structure as set forth in any of the following formulae (V), (VI), (VII), (VIII), and (IX):

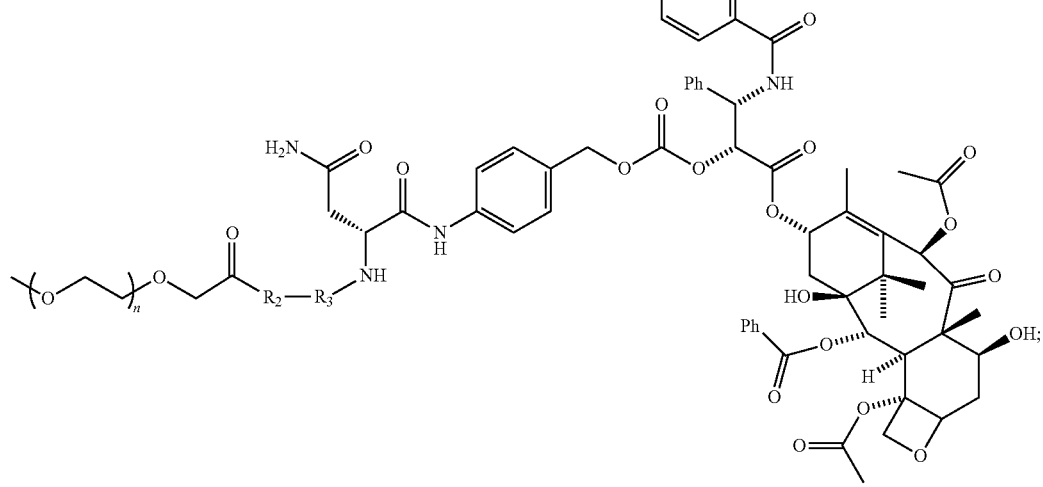

(V)

-continued
(VI)
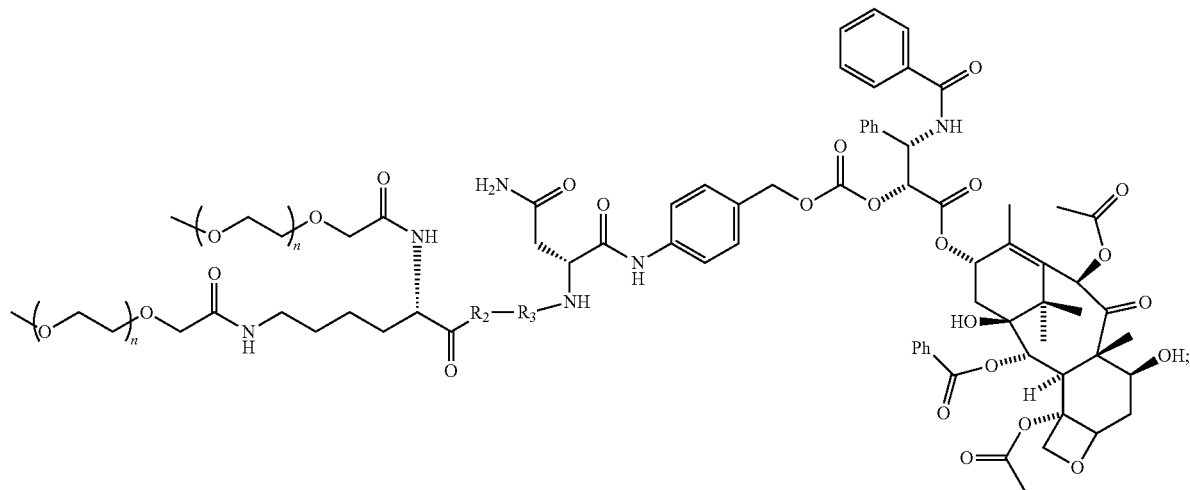
(VII)
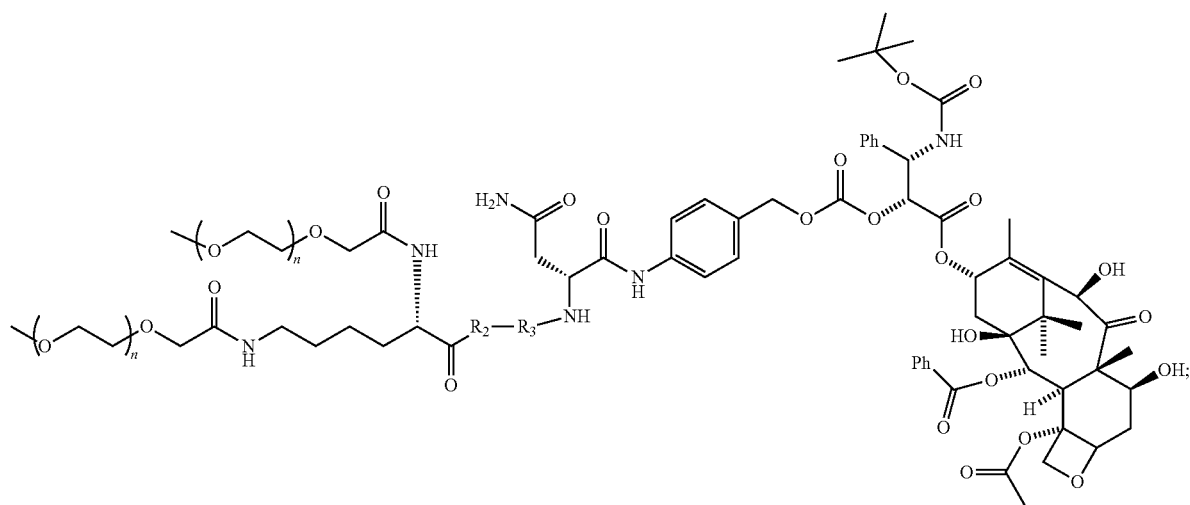
(VIII)
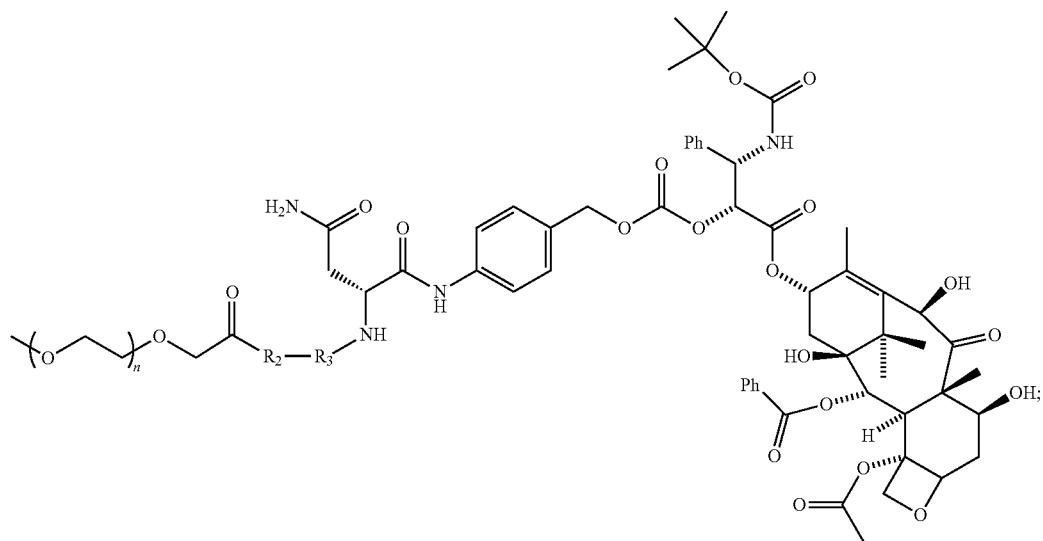

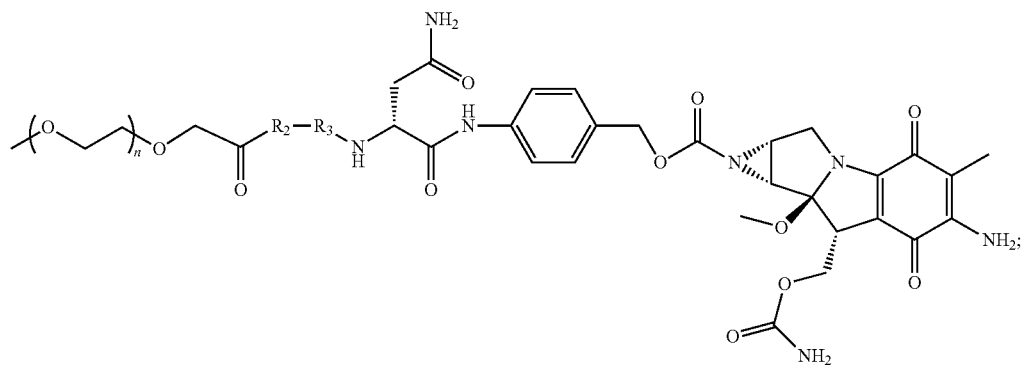
(IX)
wherein
each n is independently any integer between 1 and 300;
R₂ is Ala, Thr, Val or Ile; and
R₃ is Ala, Thr, Val or Asn.
14. The pharmaceutical composition of claim 13, wherein said each n is independently any integer between 1 and 150.
15. The pharmaceutical composition of claim 10, wherein the compound is selected from the group consisting of:
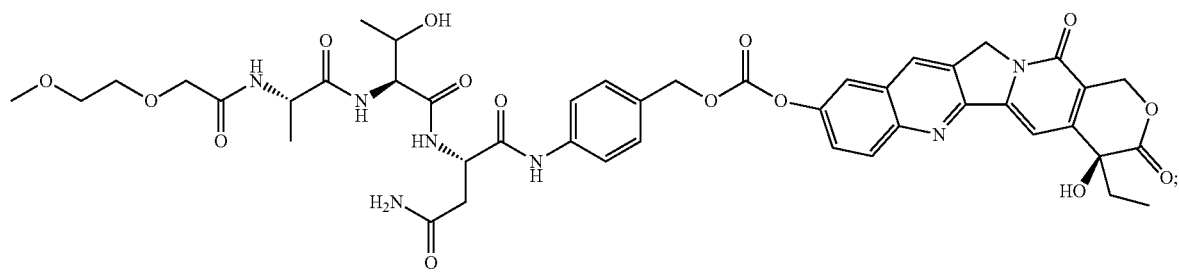
S1
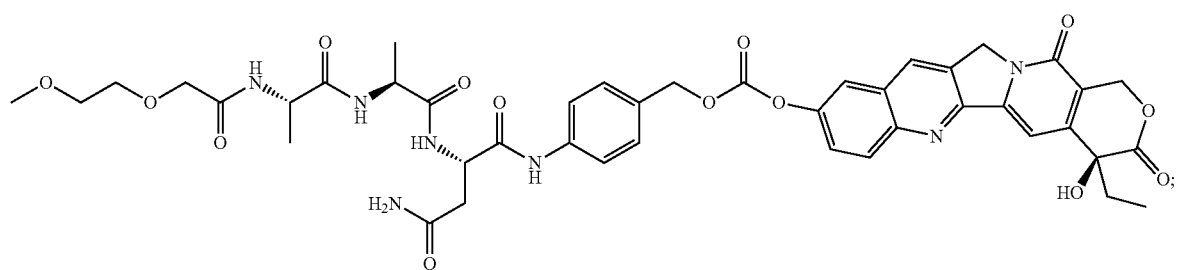
S2
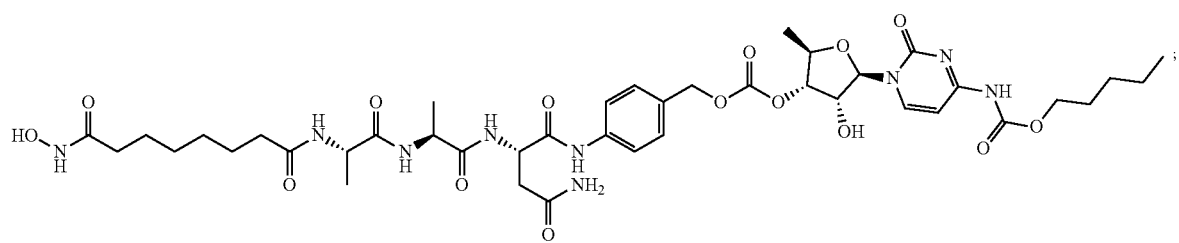
S3

-continued
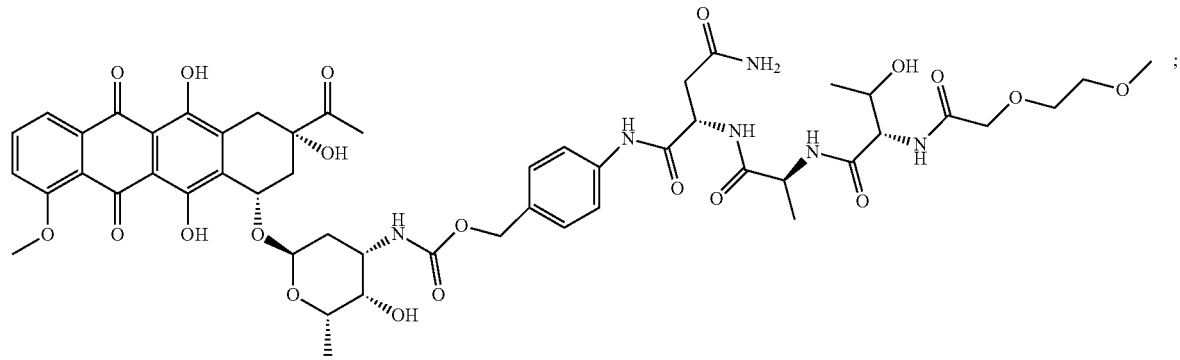
S4
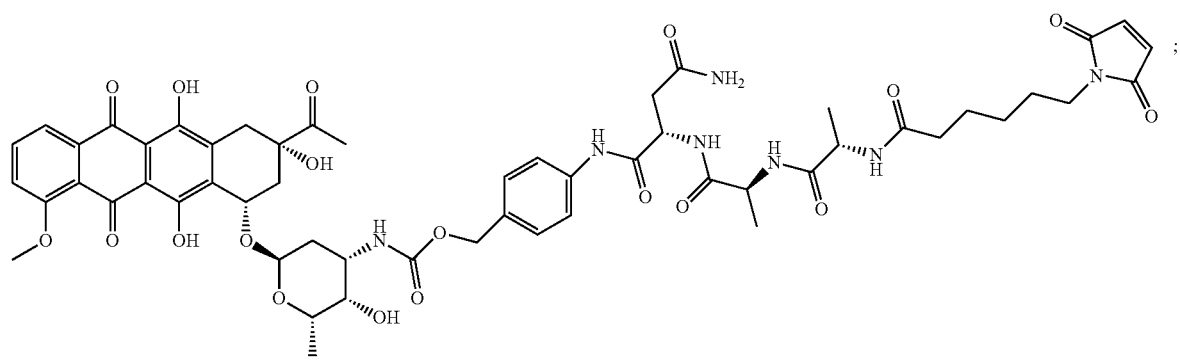
S5
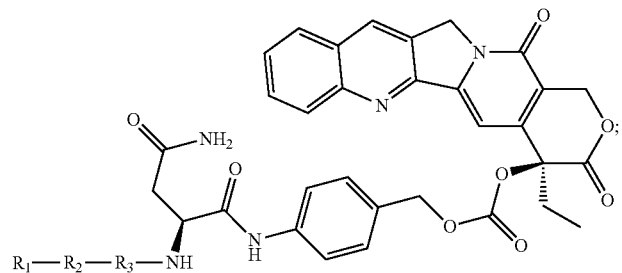
S7
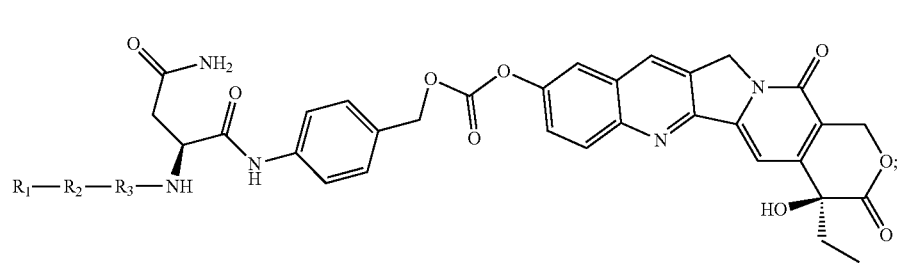
S8
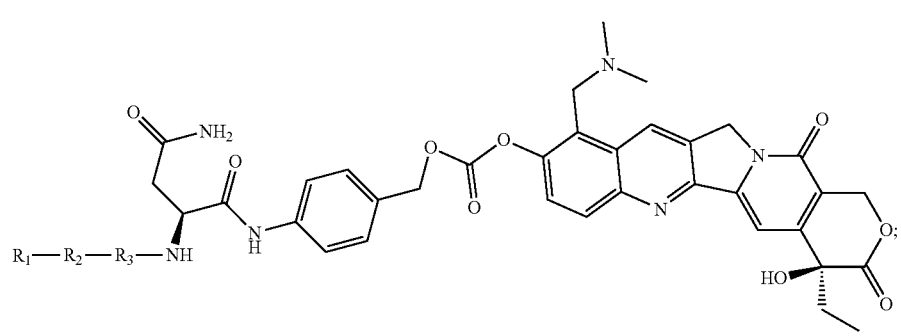
S9

-continued
S10
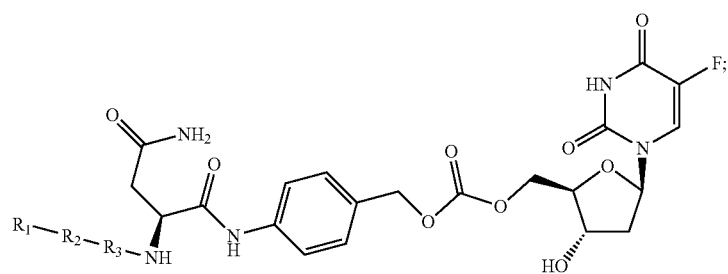
S11
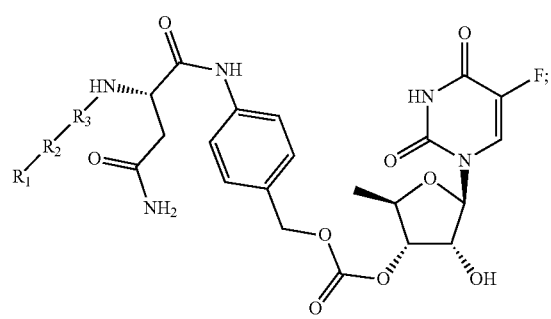
S12
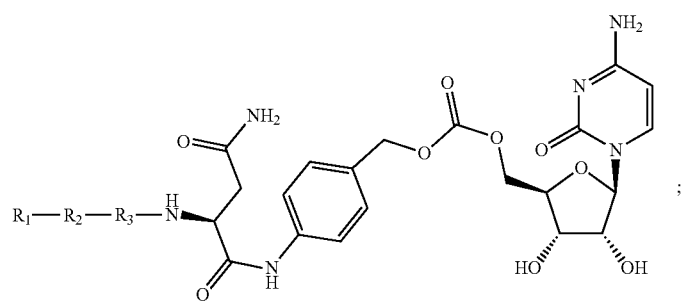
S13
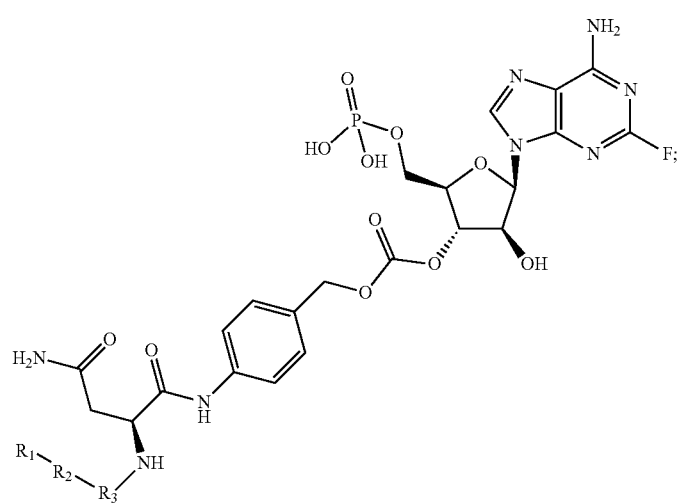

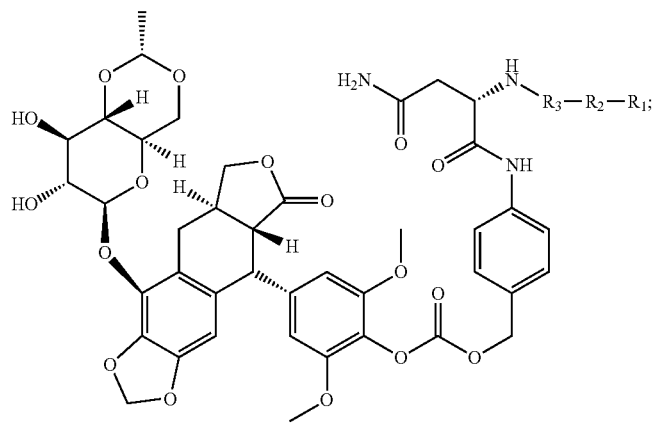
S14
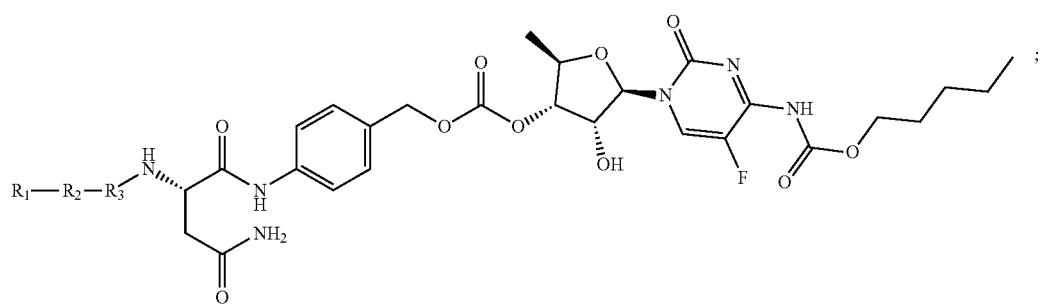
S15
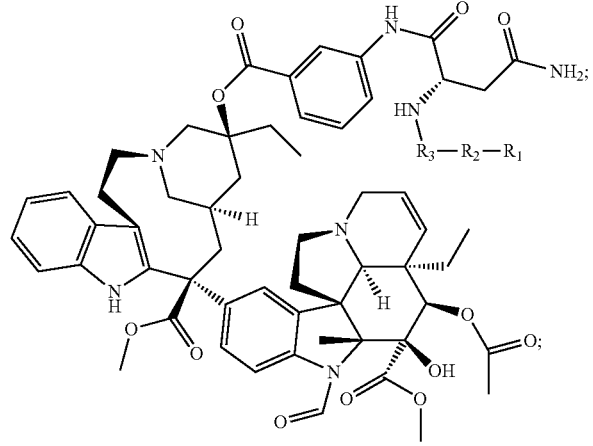
S17
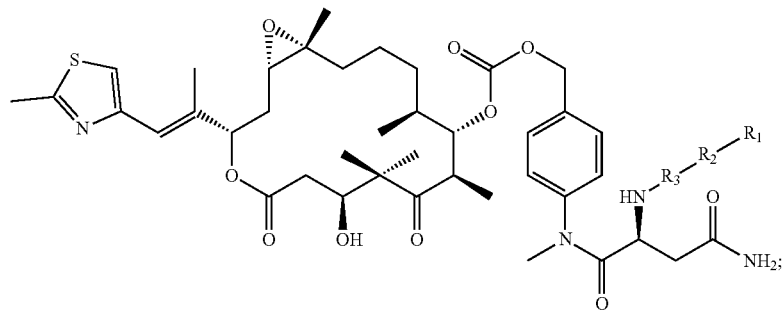
S18 wherein, in compounds S7-S15 and S17-S18, $R_1$ is 2-(2-methoxyethoxy)acetyl, $R_2$ is Thr, $R_3$ is Ala;
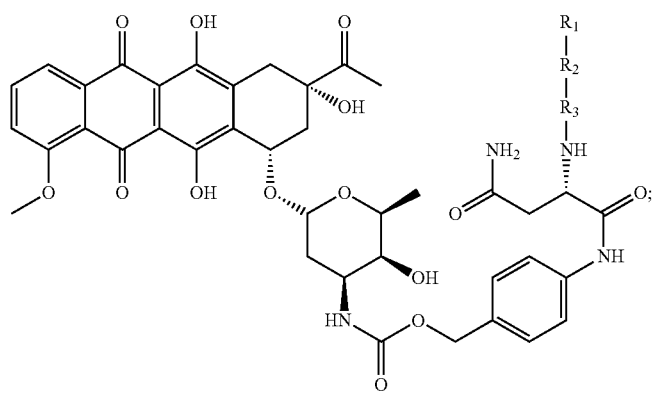
S19
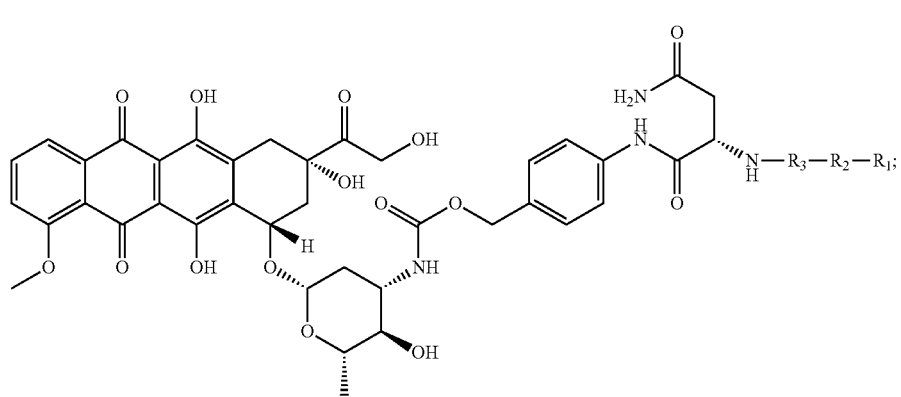
S20
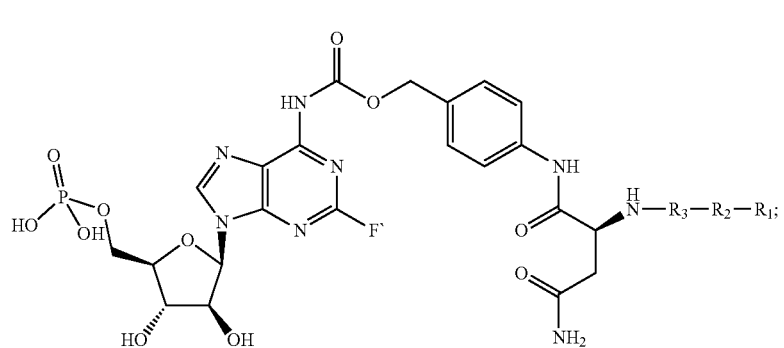
S21
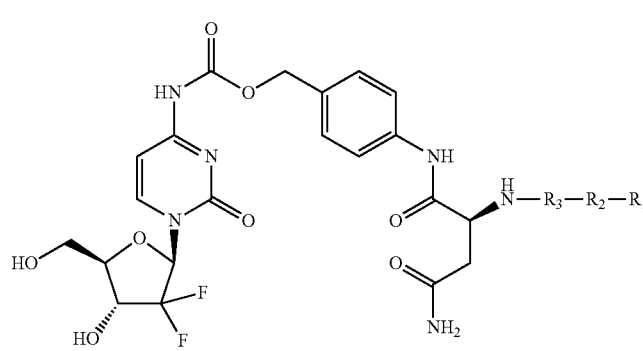
S22

-continued
S23
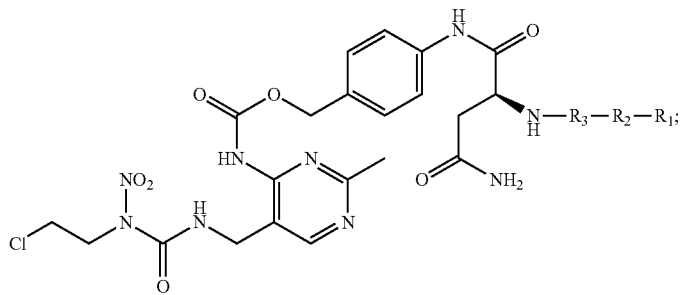
S24
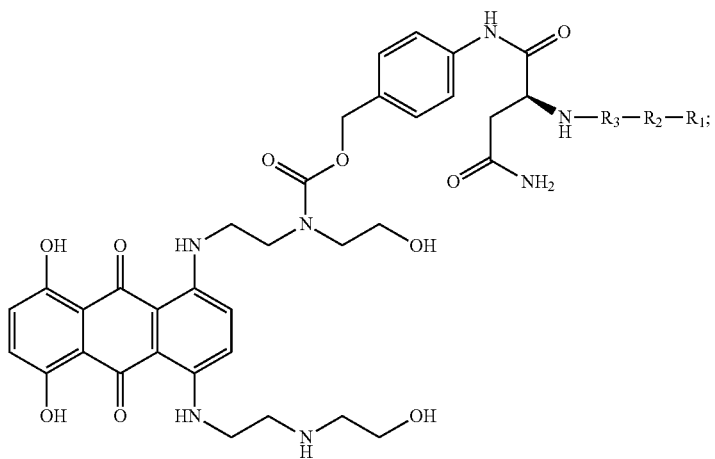
S25
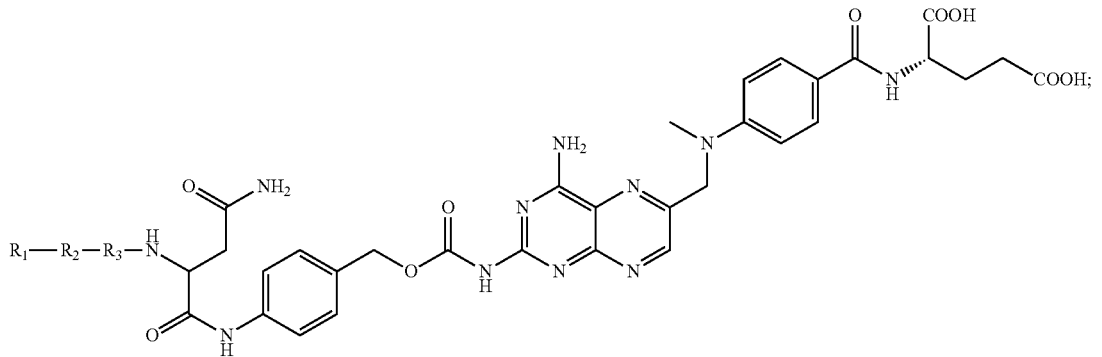
S26
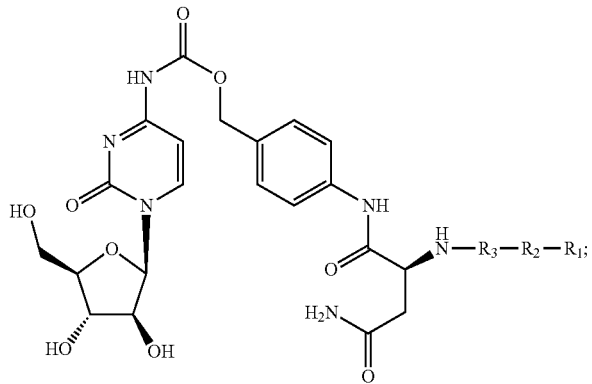

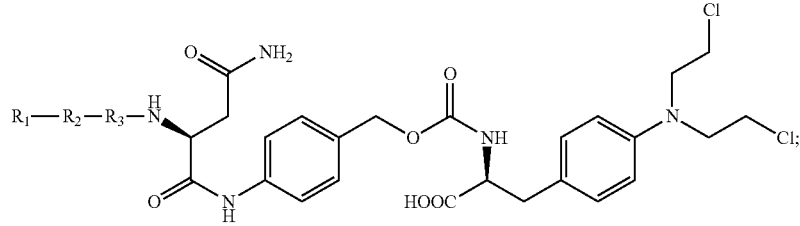
S27
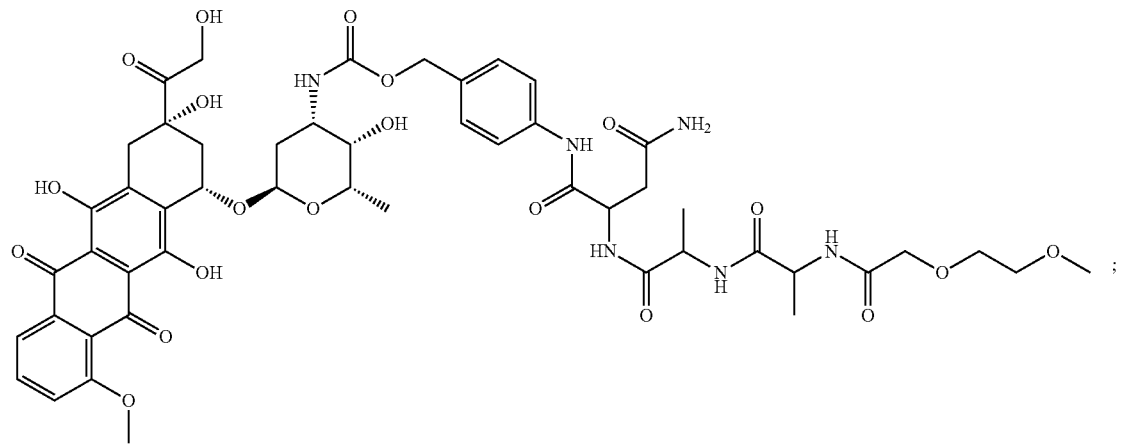
S28
wherein, in compounds S19-S28, $R_1$ is 2-(2-methoxyethoxy)acetyl, $R_2$ and $R_3$ are Ala;
S29-S43 represented by a formula
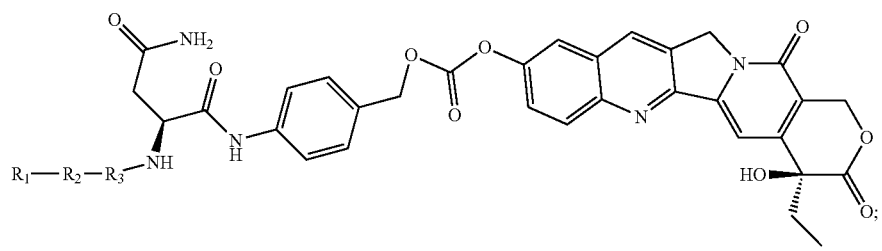
wherein, in compounds S29-S43, $R_1$ is 2-(2-methoxyethoxy)acetyl, and $R_2$ and $R_3$ are shown below:
| No. of Compound | $R_2$ | $R_3$ |
|---|---|---|
| S29 | Thr | Thr |
| S30 | Thr | Val |
| S31 | Thr | Asn |
| S32 | Val | Ala |
| S33 | Val | Thr |
| S34 | Val | Val |
| S35 | Val | Asn |
| S36 | Ile | Ala |
| S37 | Ile | Thr |
| S38 | Ile | Val |
| S39 | Ile | Asn |
| S40 | Ala | Ala |
| S41 | Ala | Thr |
| S42 | Ala | Val |
| S43 | Ala | Asn |

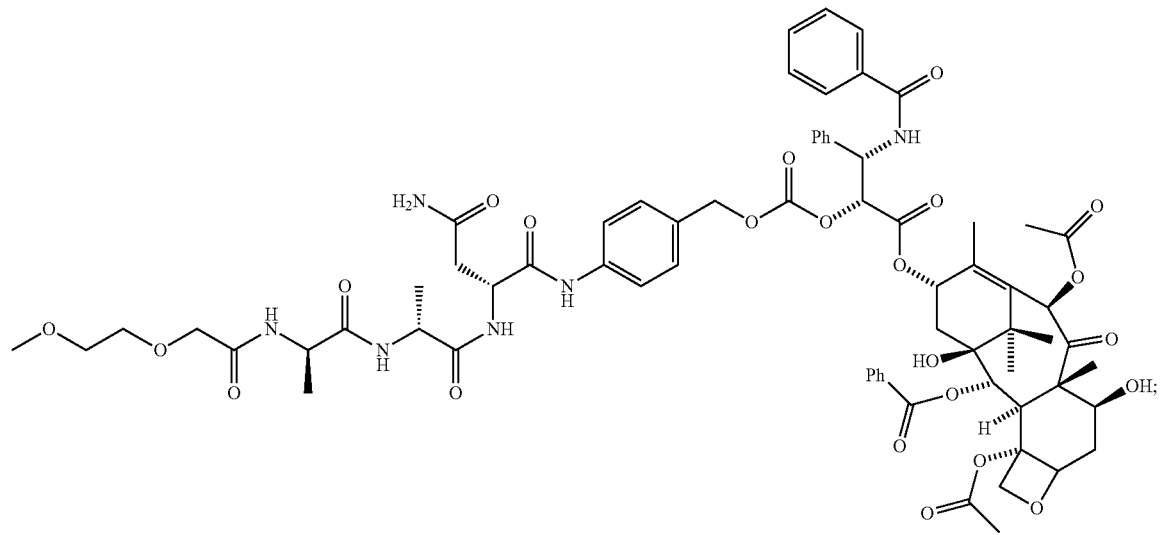
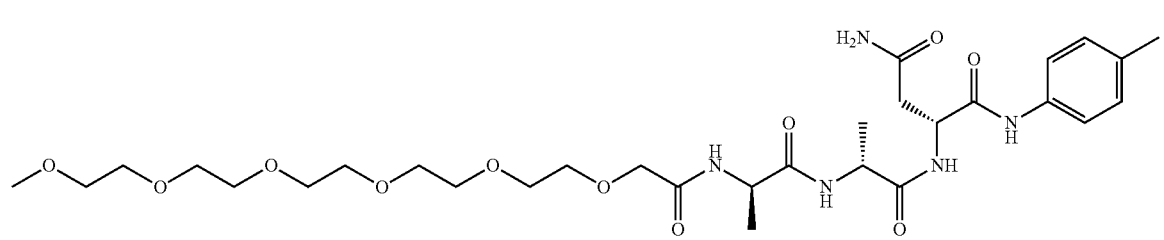
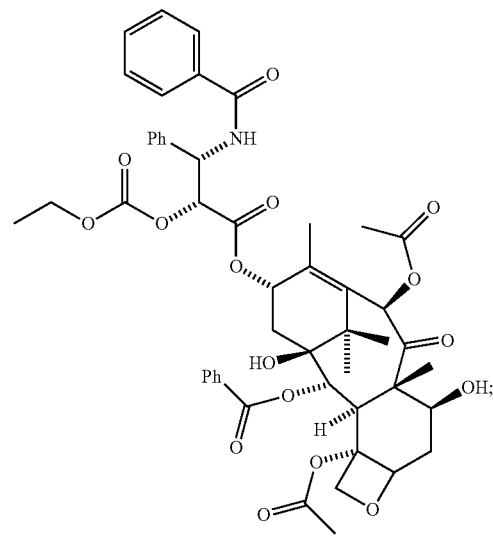
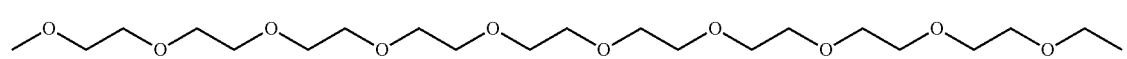

-continued
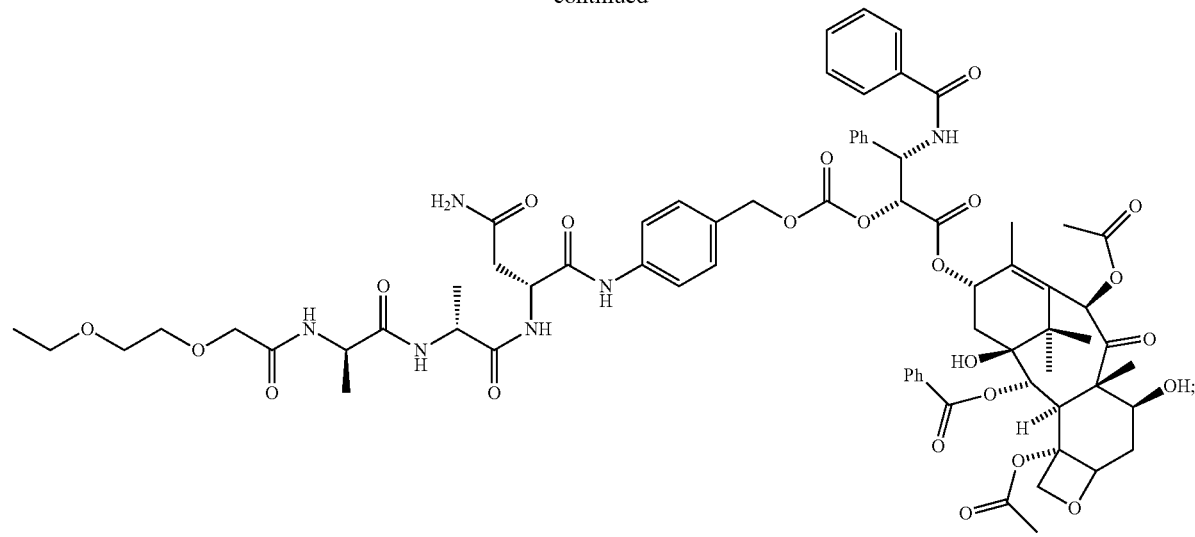
S4
S10'-S24' represented by formula
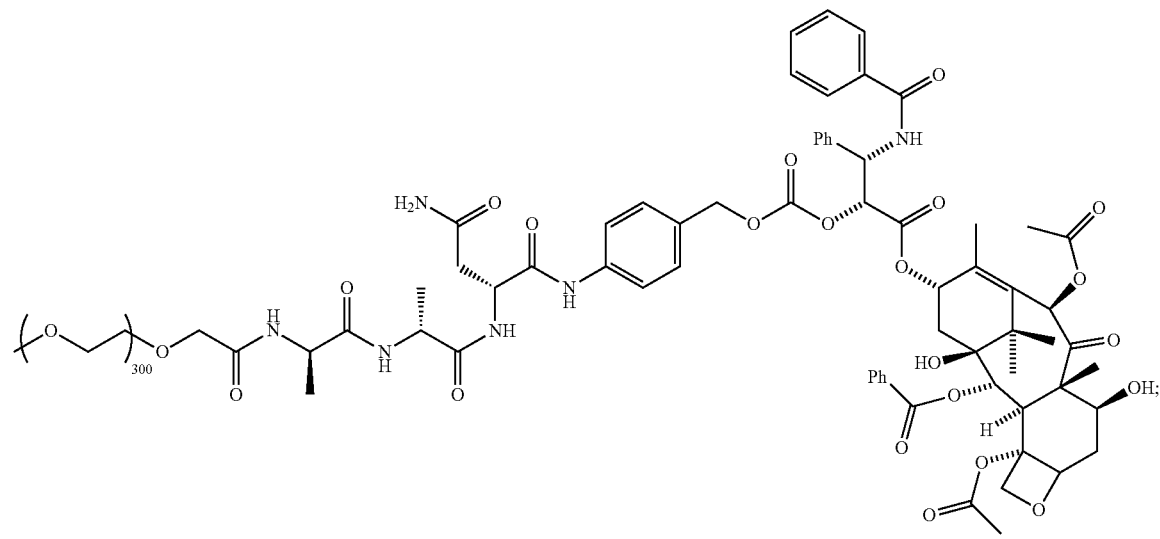
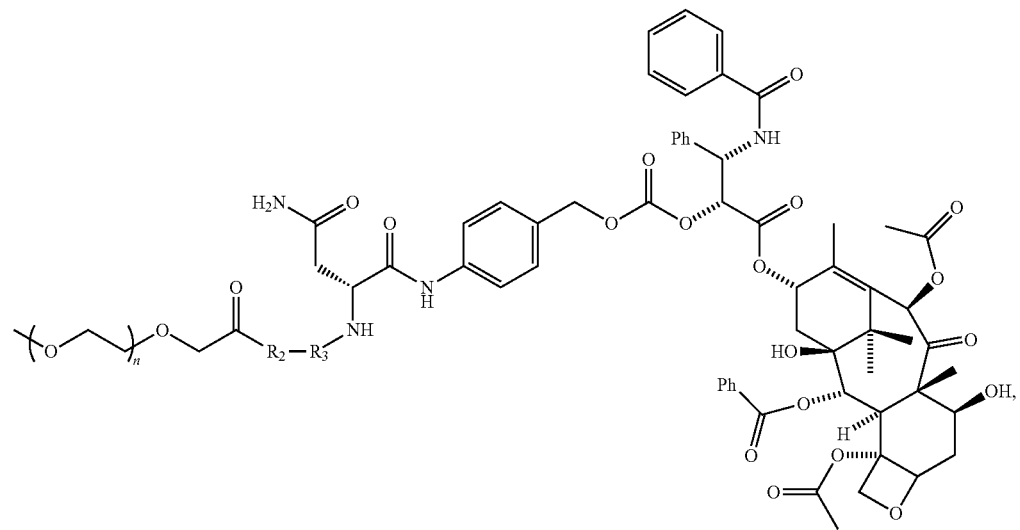

217
in which n is 1 and $R_2$ and $R_3$ are shown as follows:
| No. of Compound | $R_2$ | $R_3$ |
|---|---|---|
| S10' | Ala | Thr |
| S11' | Ala | Val |
| S12' | Ala | Asn |
| S13' | Thr | Ala |
| S14' | Thr | Thr |
| S15' | Thr | Val |
| S16' | Thr | Asn |
| S17' | Val | Ala |
218
-continued
| No. of Compound | $R_2$ | $R_3$ |
|---|---|---|
| S18' | Val | Thr |
| S19' | Val | Val |
| S20' | Val | Asn |
| S21' | Ile | Ala |
| S22' | Ile | Thr |
| S23' | Ile | Val |
| S24' | Ile | Asn |
A1
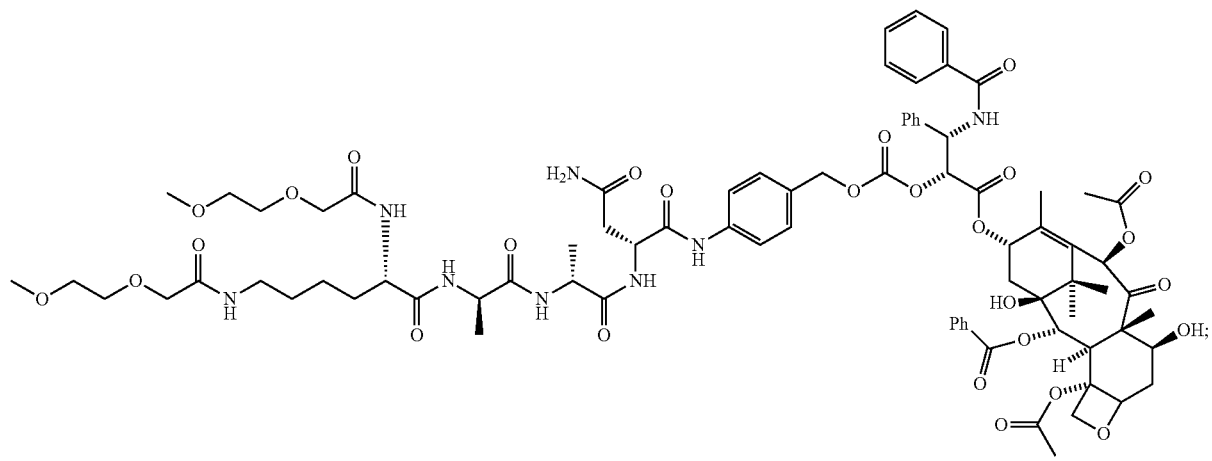
A2
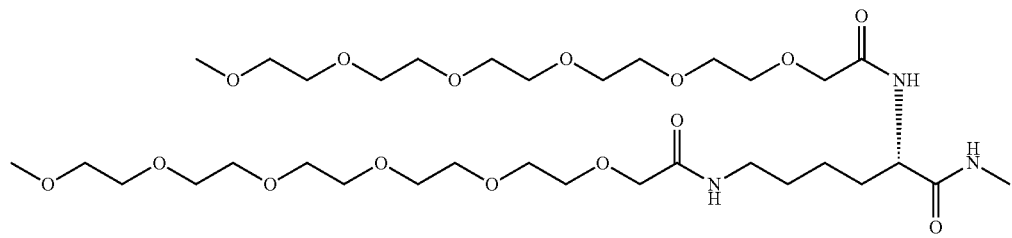
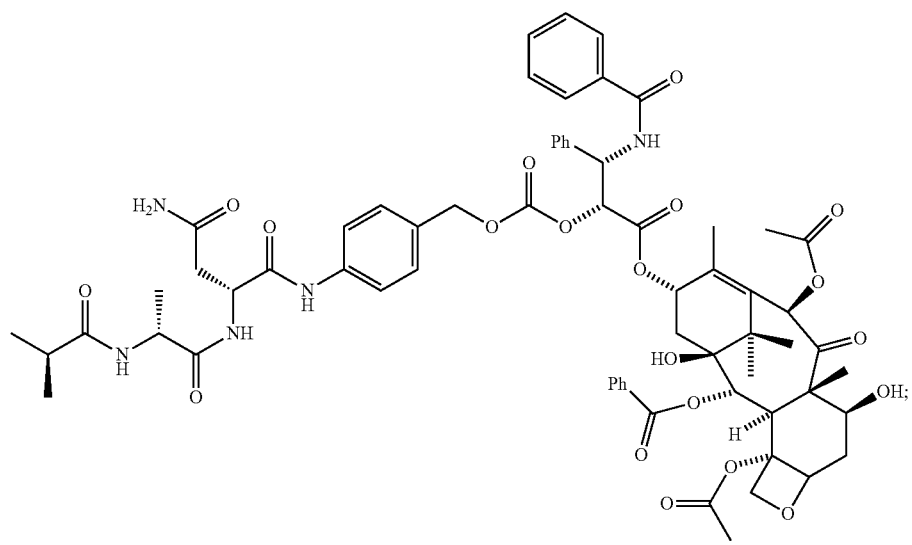

-continued
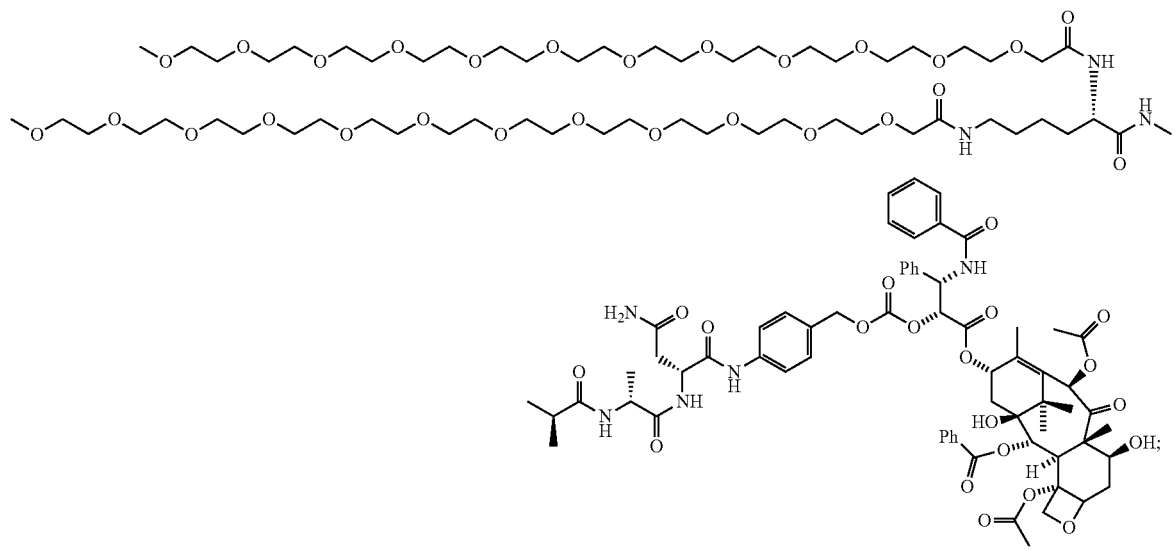
A3
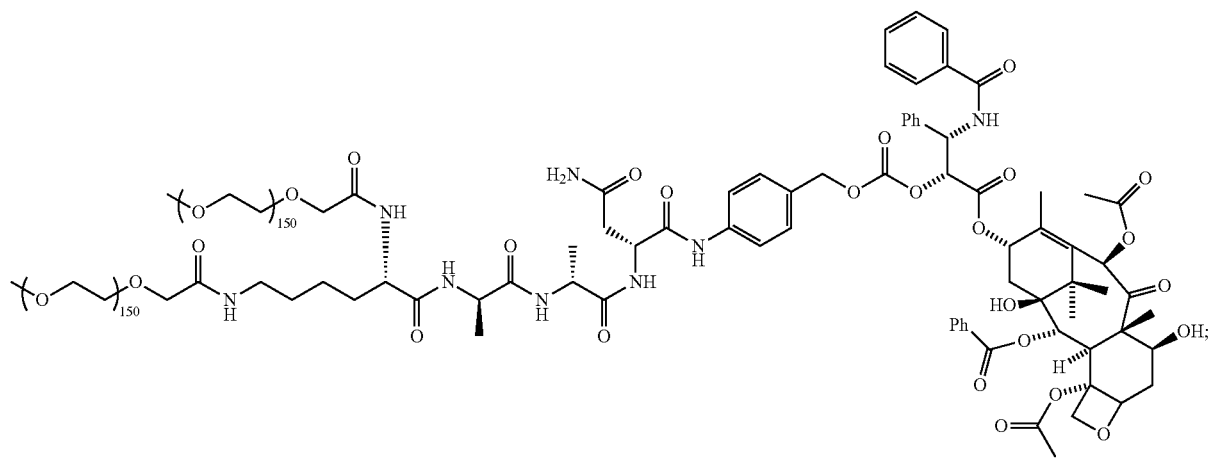
A4
A10-A24 represented by formula
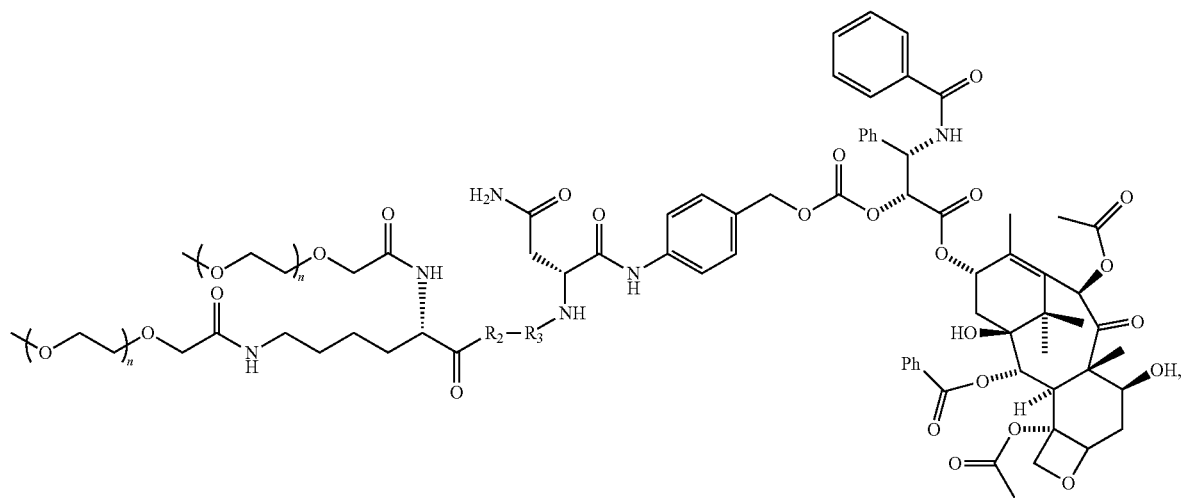

wherein n is 5 and $R_2$ and $R_3$ are shown in the following table:
| No. of Compound | $R_2$ | $R_3$ |
|---|---|---|
| A10 | Ala | Thr |
| A11 | Ala | Val |
| A12 | Ala | Asn |
| A13 | Thr | Ala |
| A14 | Thr | Thr |
| A15 | Thr | Val |
| A16 | Thr | Asn |
| A17 | Val | Ala |
| A18 | Val | Thr |
| A19 | Val | Val |
| A20 | Val | Asn |
| A21 | Ile | Ala |
| A22 | Ile | Thr |
| A23 | Ile | Val |
| A24 | Ile | Asn |
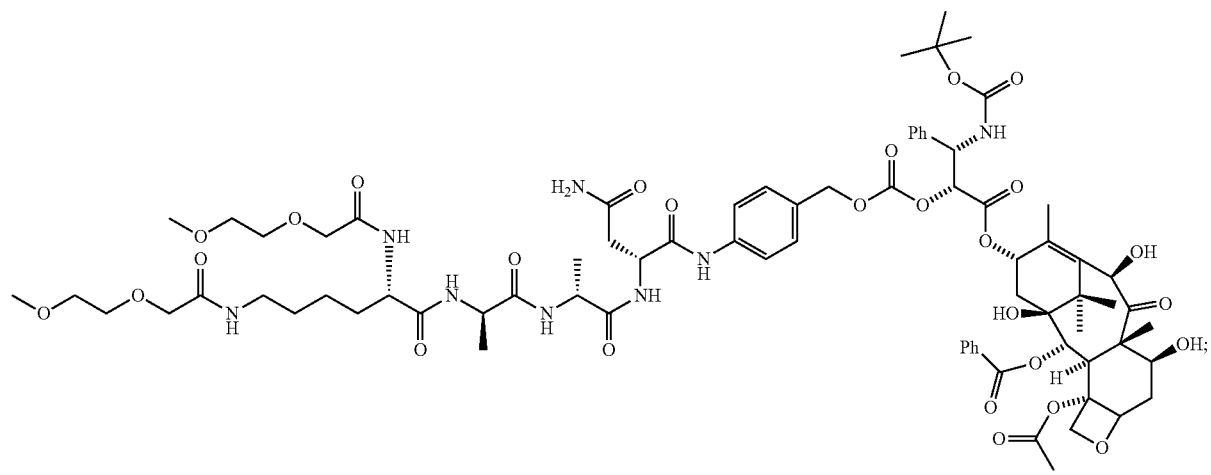
B1
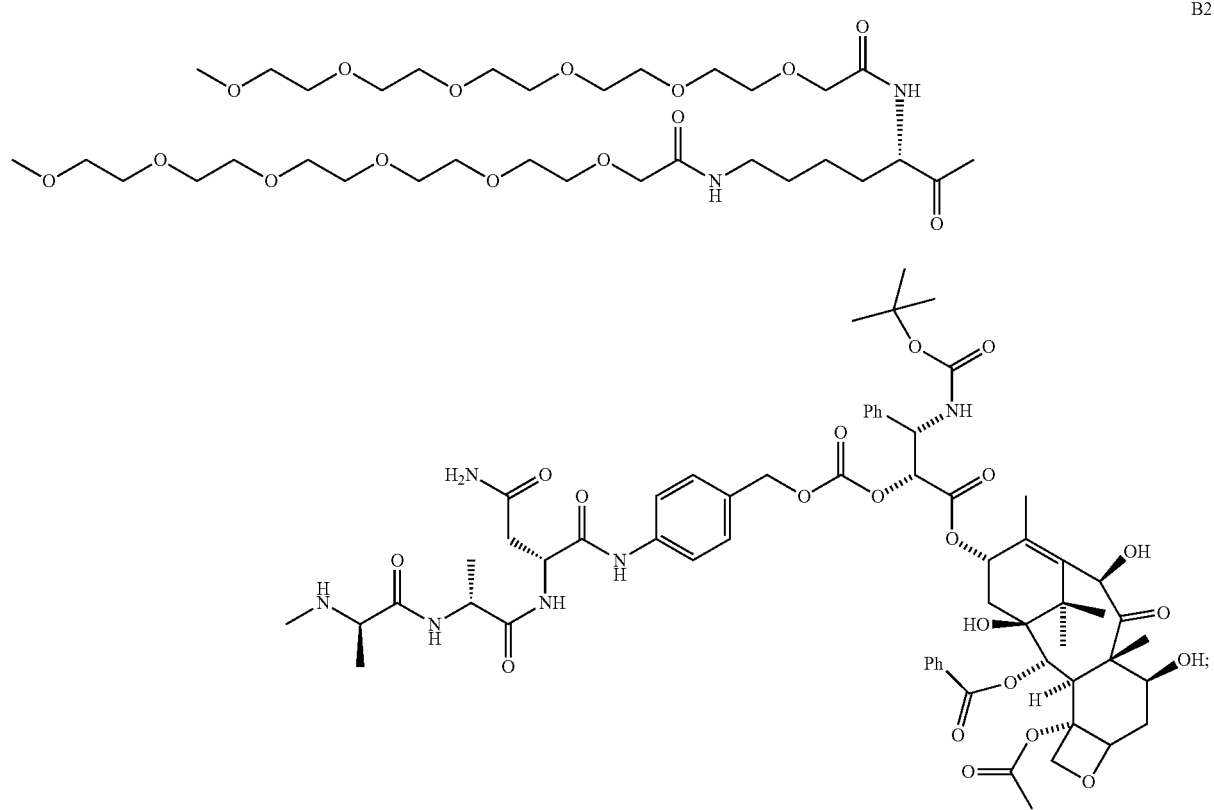
B2

-continued
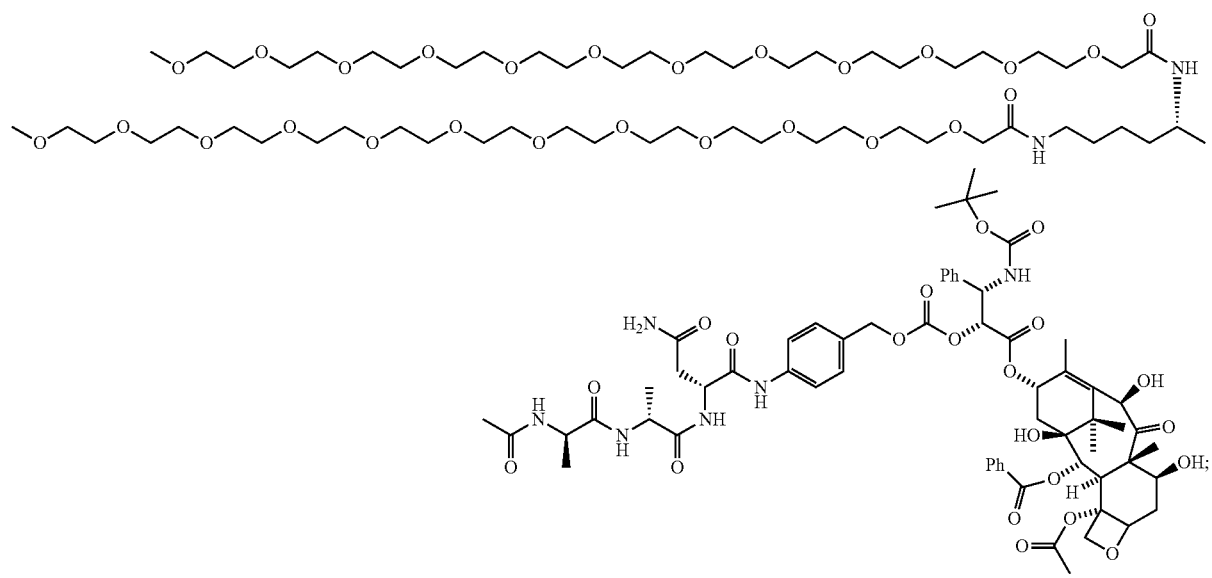
B3
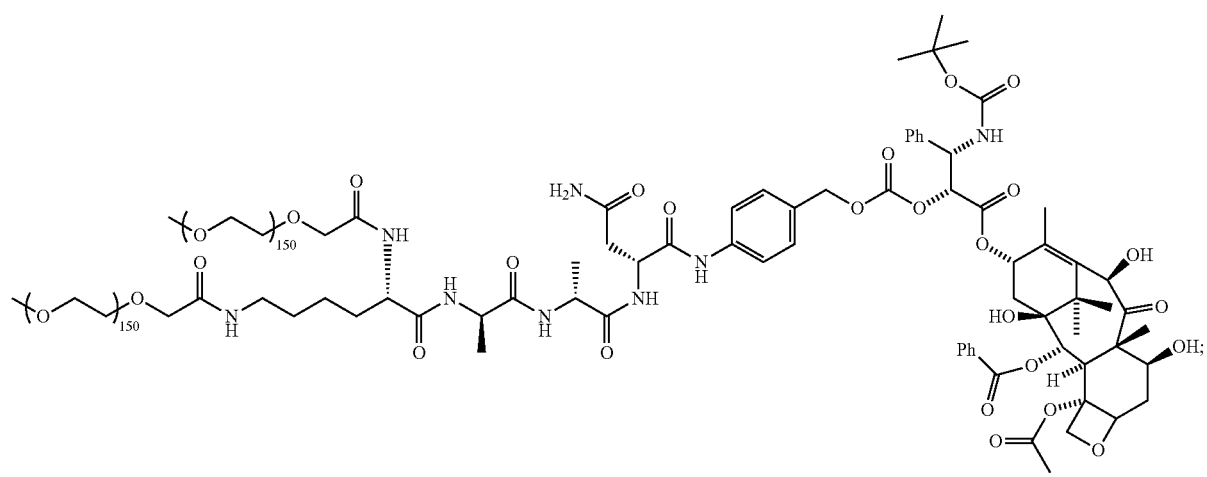
B4
B10-B24 represented by
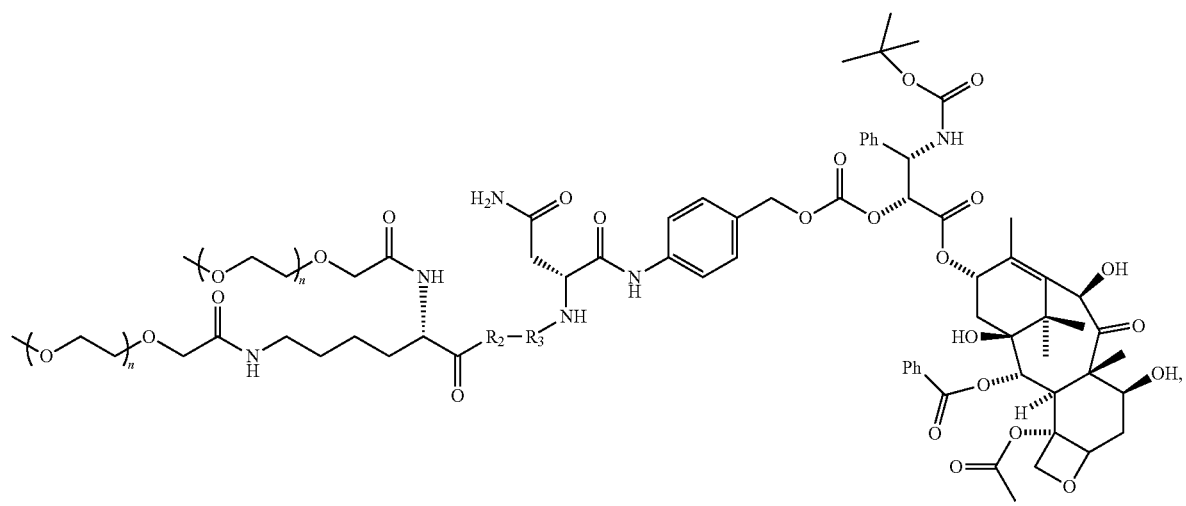

in which n, $R_2$ and $R_3$ are shown as follows:
| No. of Compound | $R_2$ | $R_3$ | n |
|---|---|---|---|
| B10 | Ala | Thr | 5 |
| B11 | Ala | Val | 5 |
| B12 | Ala | Asn | 5 |
| B13 | Thr | Ala | 5 |
| B14 | Thr | Thr | 5 |
| B15 | Thr | Val | 5 |
| B16 | Thr | Asn | 5 |
| B17 | Val | Ala | 5 |
| B18 | Val | Thr | 5 |
| B19 | Val | Val | 5 |
| B20 | Val | Asn | 5 |
| B21 | Ile | Ala | 5 |
| B22 | Ile | Thr | 5 |
| B23 | Ile | Val | 5 |
| B24 | Ile | Asn | 5 |
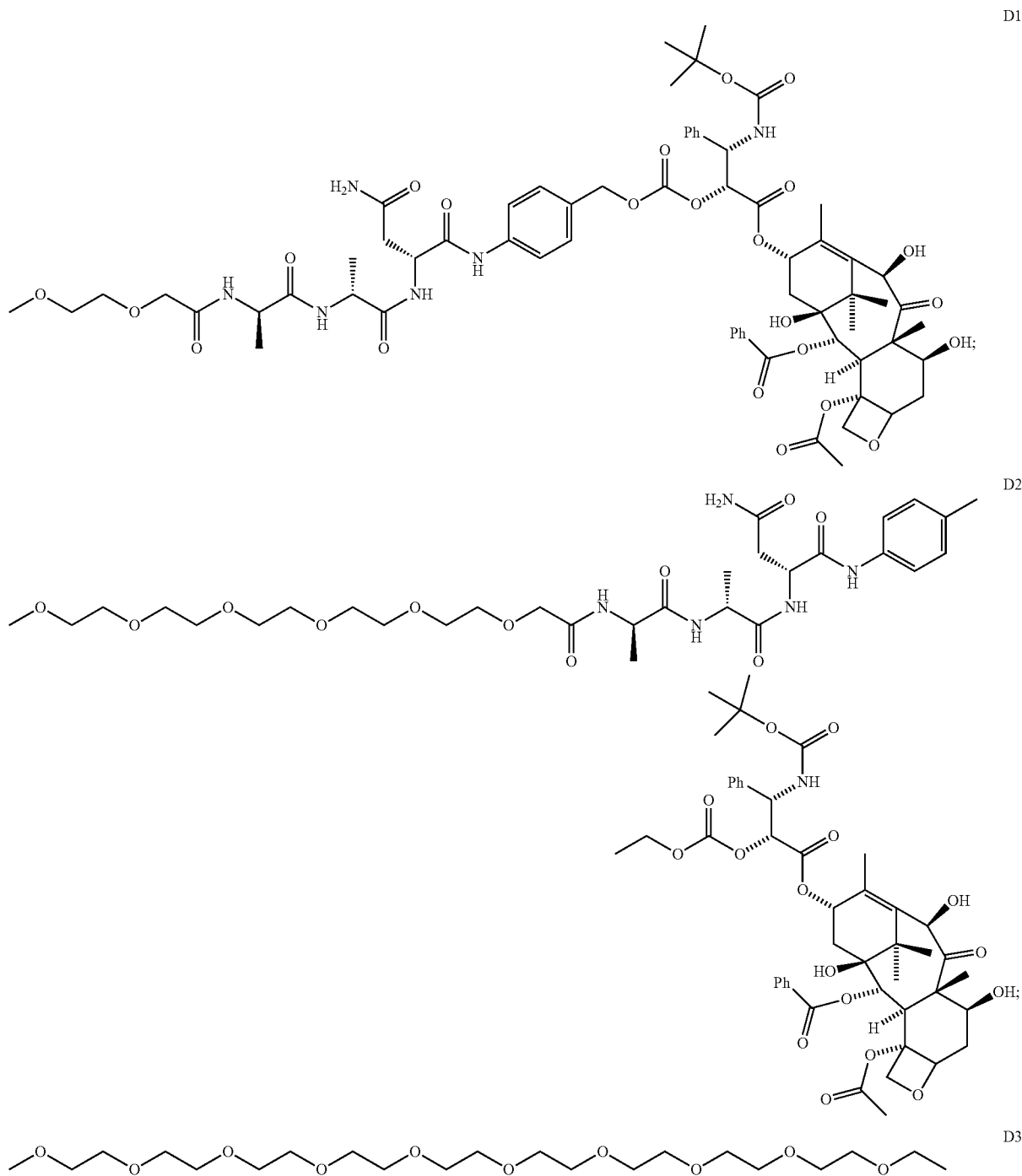

-continued
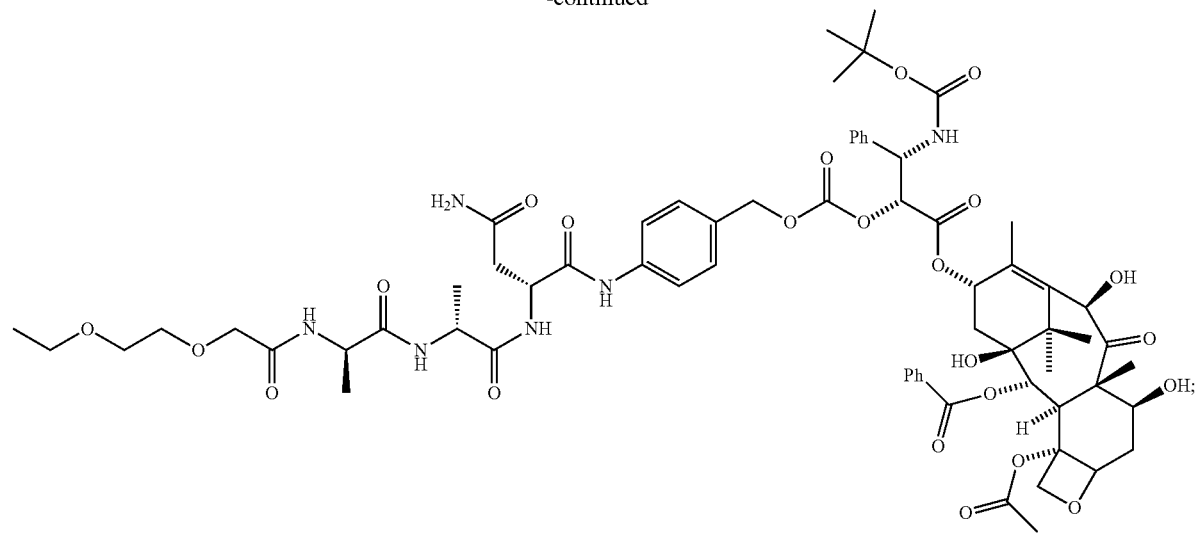
D4
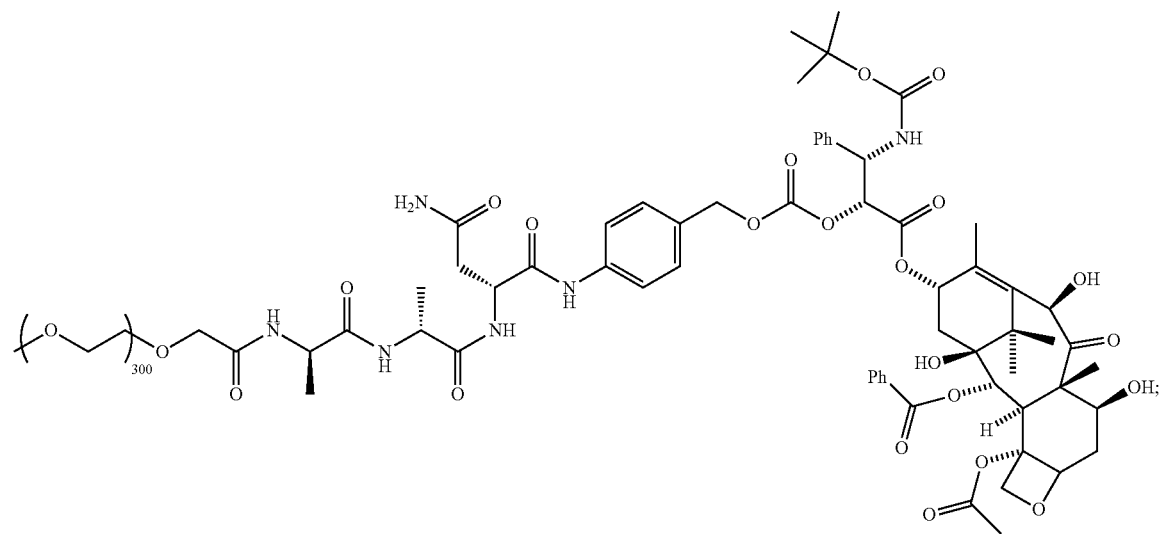
D10-D24 represented by
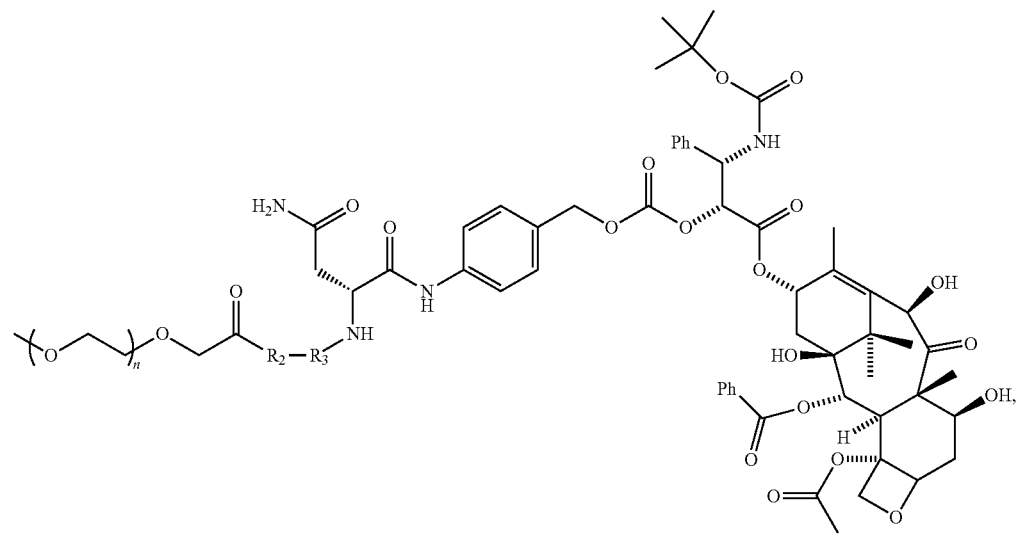

in which n, $R_2$ and $R_3$ are shown as follows:

| No. of Compound | $R_2$ | $R_3$ | n |
|---|---|---|---|
| D10 | Ala | Thr | 1 |
| D11 | Ala | Val | 1 |
| D12 | Ala | Asn | 1 |
| D13 | Thr | Ala | 1 |
| D14 | Thr | Thr | 1 |
| D15 | Thr | Val | 1 |
| D16 | Thr | Asn | 1 |
| D17 | Val | Ala | 1 |
| D18 | Val | Thr | 1 |
| D19 | Val | Val | 1 |
| D20 | Val | Asn | 1 |
| D21 | Ile | Ala | 1 |
| D22 | Ile | Thr | 1 |
| D23 | Ile | Val | 1 |
| D24 | Ile | Asn | 1 |

231
E1
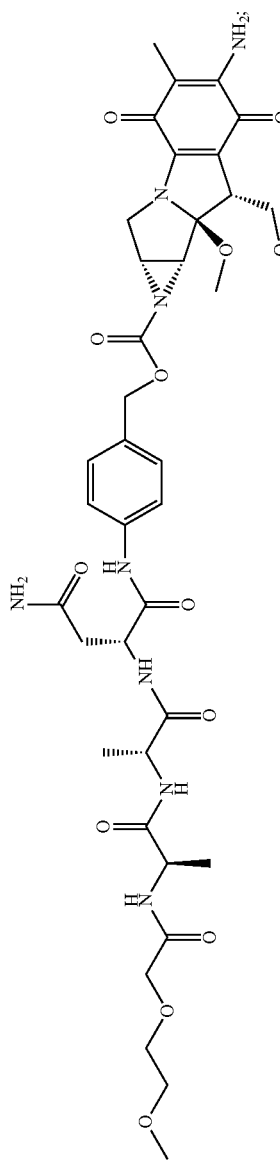
232
E2  E3
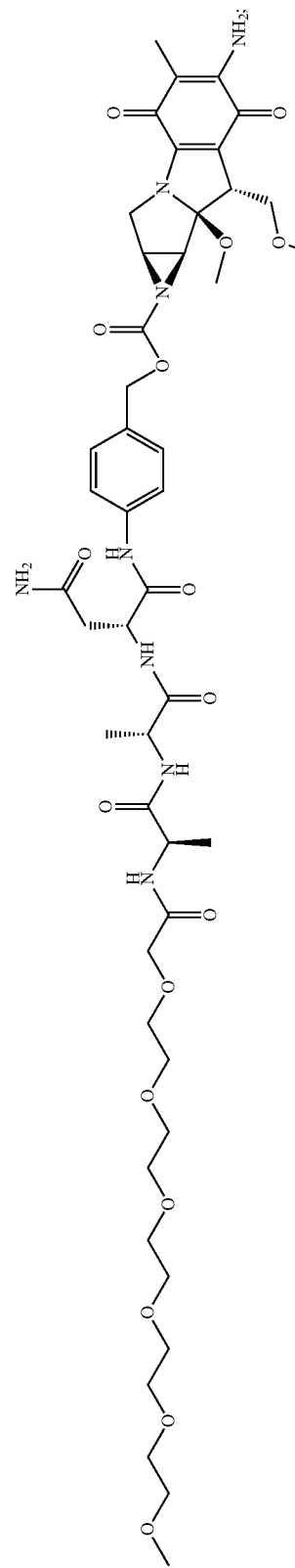 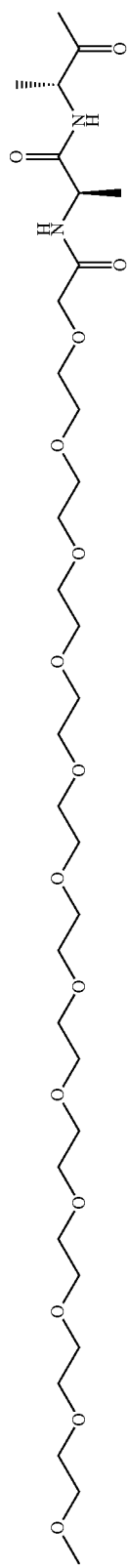

E4
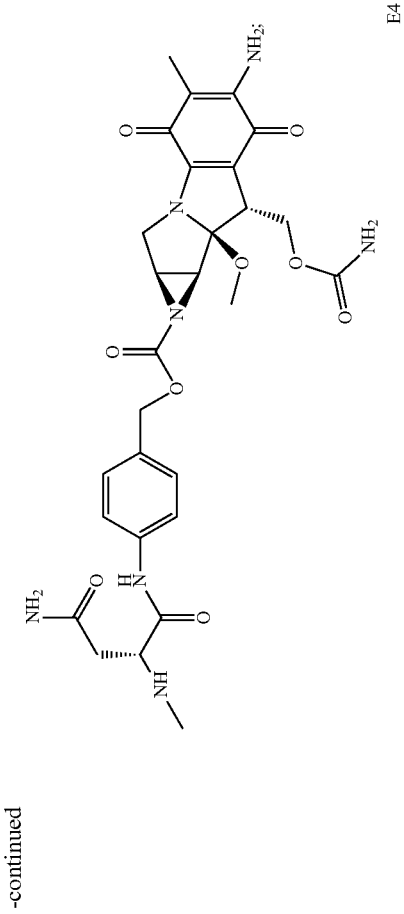
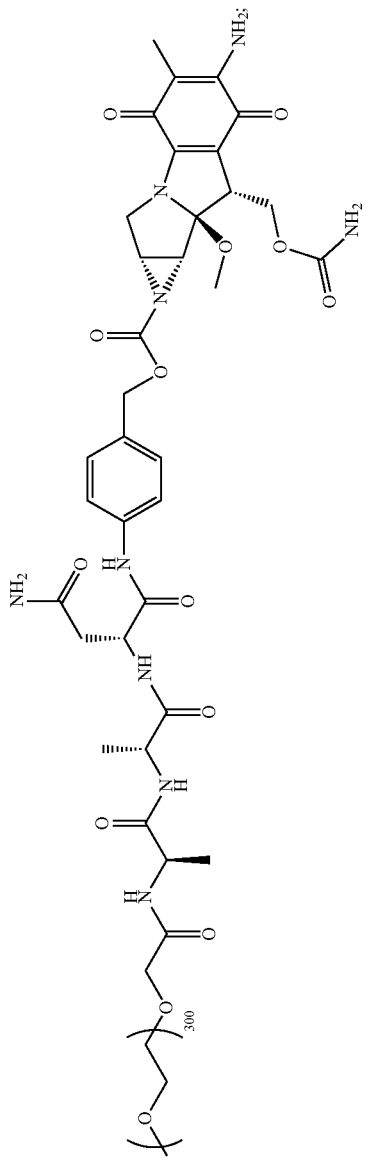

E10-E24 represented by formula
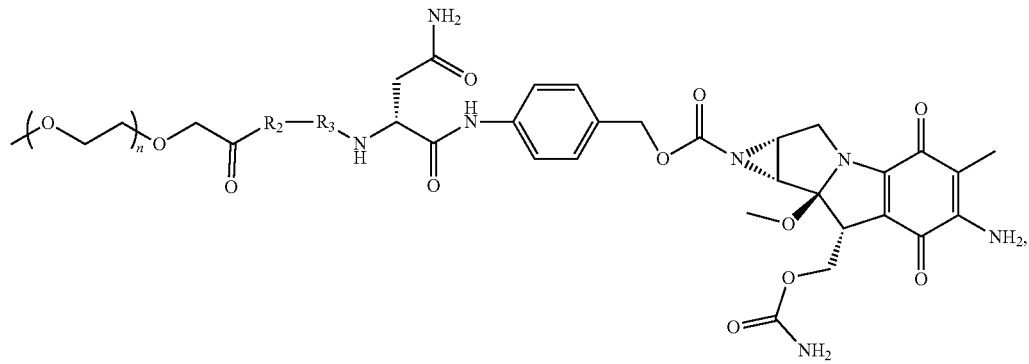
in which n, $R_2$ and $R_3$ are shown as follows:
| No. of Compound | $R_2$ | $R_3$ | n |
|---|---|---|---|
| E10 | Ala | Thr | 1 |
| E11 | Ala | Val | 1 |
| E12 | Ala | Asn | 1 |
| E13 | Thr | Ala | 1 |
| E14 | Thr | Thr | 1 |
| E15 | Thr | Val | 1 |
| E16 | Thr | Asn | 1 |
| E17 | Val | Ala | 1 |
| E18 | Val | Thr | 1 |
| E19 | Val | Val | 1 |
| E20 | Val | Asn | 1 |
| E21 | Ile | Ala | 1 |
| E22 | Ile | Thr | 1 |
| E23 | Ile | Val | 1 |
| E24 | Ile | Asn | 1. |
* * * * *

UNITED STATES PATENT AND TRADEMARK OFFICE
CERTIFICATE OF CORRECTION

PATENT NO. : 10,682,371 B2
APPLICATION NO. : 15/505861
DATED : June 16, 2020
INVENTOR(S) : Chen Liu et al.

It is certified that error appears in the above-identified patent and that said Letters Patent is hereby corrected as shown below:

On the Title Page

Item (71), Applicant: Line 1, delete "Biolg" and insert -- Biology --.

Item (73), Assignee: Line 1, delete "Biolg" and insert -- Biology --.

Item (73), Assignee: Line 3, delete "Shanghai (CN)" and insert -- Pudong, Shanghai (CN) --.

Item (74), Attorney: Line 1, delete "Knobbe, Martens, Olson & Bear LLP" and insert -- Knobbe, Martens, Olson & Bear, LLP --.

On page 2, in Column 2, item (56), Other Publications, Line 12, delete "Dipentide" and insert -- Dipeptide --.

On page 2, in Column 2, item (56), Other Publications, Line 13, delete "Biooranic" and insert -- Bioorganic --.

In the Specification

In Column 4, Line 43, delete "S10' ~S24'," and insert -- S10'~S24', --.

In Column 5, Line 5 (approx.), delete "III" and insert -- (III) --.

In Column 6, Line 5 (approx.), delete "IV" and insert -- (IV) --.

In Column 11, Line 49, delete "$R_4$" and insert -- $R_1$ --.

In Column 12, Line 3, delete "Lagutaxel." and insert -- Legutaxel. --.

Signed and Sealed this
Twenty-fourth Day of November, 2020

Andrei Iancu
*Director of the United States Patent and Trademark Office*

In Column 18, Lines 48-63, delete " 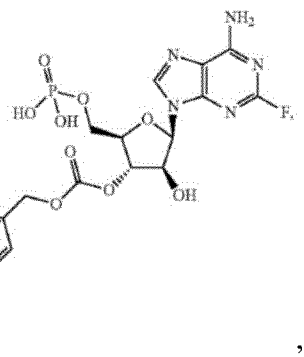 " and insert
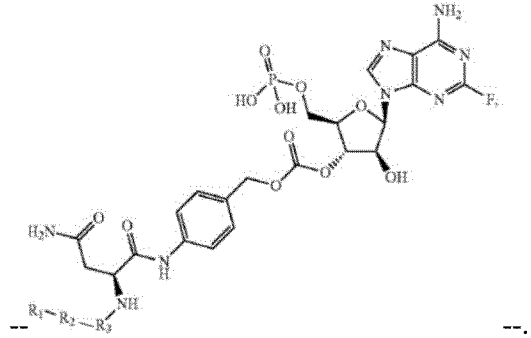
--.
In Column 19, Lines 50-61 (approx.), delete " 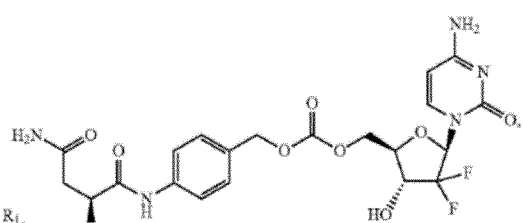 " and insert
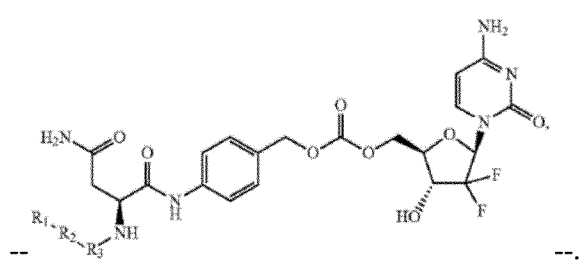
--.
In Column 21, Line 24 (approx.), delete "maleimide caproyl" and insert -- maleimido caproyl --.

CERTIFICATE OF CORRECTION (continued)
U.S. Pat. No. 10,682,371 B2

In Column 27, Line 1 (approx.), delete

" 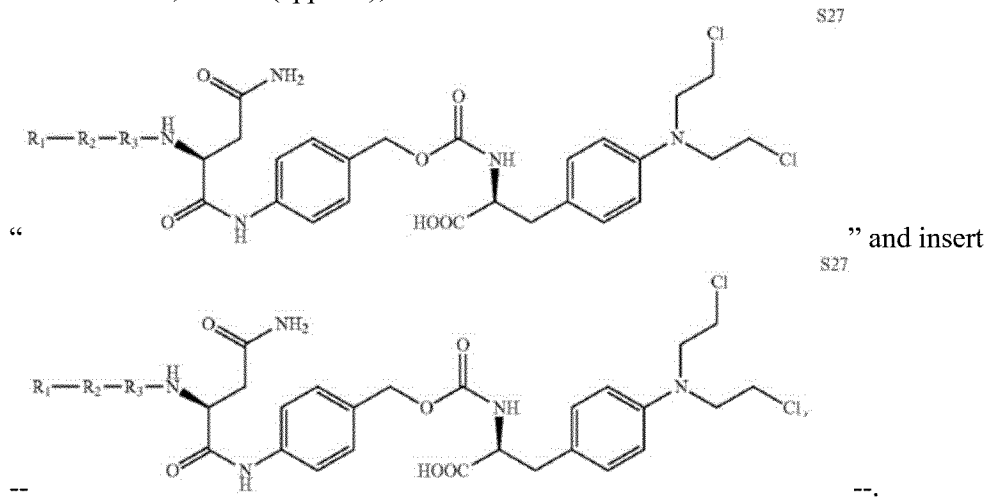 " and insert

-- --.

In Column 27, Line 37, delete "Doxorubcin" and insert -- Doxorubicin --.

In Columns 33 and 34, Line 8 (approx.), delete

" 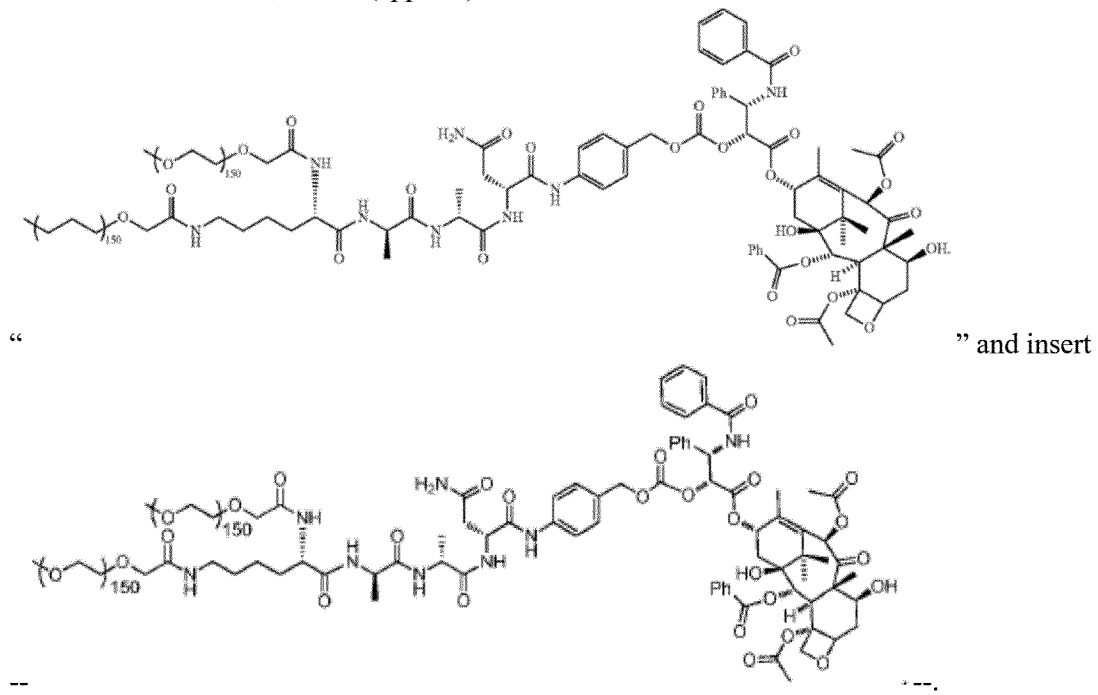 " and insert

-- --.

In Column 47, Line 47, delete "(XI)" and insert -- (IX) --.

In Column 49, Line 57, delete "R$_4$" and insert -- R$_1$ --.

In Column 51, Line 15, delete "hydroxylpropyl" and insert -- hydroxypropyl --.

In Column 54, Line 65, delete "diisopropylethylamine" and insert -- diisopropyl ethylamine --.

CERTIFICATE OF CORRECTION (continued)
U.S. Pat. No. 10,682,371 B2

In Column 54, Lines 59-60 (approx.), delete "1-hydroxyl-benzotriazole" and insert -- 1-hydroxyl benzotriazole --.

In Column 55, Lines 20-21, delete "[Lithium hydroxide]" and insert -- [Lithium hydroxide] --.

In Column 58, Line 20 (approx.), delete "diisopropylethylamine" and insert -- diisopropyl ethylamine --.

In Column 58, Line 32 (approx.), delete "asparaginyl)" and insert -- asparaginyl --.

In Column 58, Line 34 (approx.), delete "$H_2$ Pd/C" and insert -- $H_2$, Pd/C --.

In Column 59, Line 16 (approx.), delete "asparaginyl)" and insert -- asparaginyl --.

In Column 60, Line 20 (approx.), delete "asparaginyl)" and insert -- asparaginyl --.

In Column 60, Line 21 (approx.), delete "diisopropylethylamine" and insert -- diisopropyl ethylamine --.

In Column 61, Line 1, delete "(N" and insert -- N --.

In Column 61, Line 32, delete "(N" and insert -- N --.

In Column 61, Line 35, delete "5□." and insert -- 5□, --.

In Column 62, Line 38 (approx.), delete "(N" and insert -- N --.

In Column 63, Line 1, delete "(N" and insert -- N --.

In Column 64, Line 7, delete "(N" and insert -- N --.

In Column 64, Line 37 (approx.), delete "(N" and insert -- N --.

In Column 65, Line 13, delete "(N" and insert -- N --.

In Column 65, Line 19, delete "1-hydroxylbenzotriazole" and insert -- 1-hydroxyl benzotriazole --.

In Column 66, Line 55, delete "(N" and insert -- N --.

In Column 66, Line 58, delete "diisopropylethylamine" and insert -- diisopropyl ethylamine --.

In Column 66, Line 67, delete "a rid" and insert -- a red --.

In Column 67, Line 2, delete "(N" and insert -- N --.

CERTIFICATE OF CORRECTION (continued)
U.S. Pat. No. 10,682,371 B2

In Column 67, Lines 37-38 (approx.), delete "1-hydroxyl-benzotriazole" and insert -- 1-hydroxyl benzotriazole --.

In Column 69, Line 1, delete "(N" and insert -- N --.

In Column 70, Line 39 (approx.), delete "bath." and insert -- bath, --.

In Column 71, Line 33, delete "a rid" and insert -- a red --.

In Column 72, Line 32, delete "a rid" and insert -- a red --.

In Column 72, Line 38, delete "51," and insert -- S1, --.

In Column 72, Line 39, delete "51," and insert -- S1, --.

In Columns 73 and 74, Table 1, Line 5 (approx.), delete "soild" and insert -- solid --.

In Column 73, Line 49, delete "$R_1R_2R_3$-Asn" and insert -- $R_1$-$R_2$-$R_3$-Asn --.

In Column 73, Line 52, delete "$R_1R_2R_3$-Asn" and insert -- $R_1$-$R_2$-$R_3$-Asn --.

In Column 74, Line 62, delete "(N" and insert -- N --.

In Column 75, Line 3, delete "Cytoxicity" and insert -- Cytotoxicity --.

In Column 75, Table 2, Line 2, delete "Cytoxicity" and insert -- Cytotoxicity --.

In Column 76, Table 2- continued, Line 2, delete "Cytoxicity" and insert -- Cytotoxicity --.

In Columns 79 and 80, Line 24 (approx.), delete "Cytoxicity" and insert -- Cytotoxicity --.

In Columns 79 and 80, Line 27 (approx.), delete "MMAE)" and insert -- MMAE --.

In Column 79, Line 45, delete "4-aminobenzyl-OC(O)-" and insert -- 4-amino benzyl-OC(O)- --.

In Column 79, Line 53 (approx.), delete "-aminobenzyl-OC(O)-" and insert -- 4-amino benzyl-OC(O)- --.

In Column 79, Lines 55-56 (approx.), delete "4-aminobenzyl-OC(O)-" and insert -- 4-amino benzyl-OC(O)- --.

In Column 79, Line 61 (approx.), delete "4-aminobenzyl-OC(O)-" and insert -- 4-amino benzyl-OC(O)- --.

In Column 81, Line 29, delete "51," and insert -- S1, --.

In Column 83, Line 14, delete "propionylamino)" and insert -- propionylamino --.

In Column 83, Lines 17-18 (approx.), delete "1-hydroxyl-benzotriazole" and insert -- 1-hydroxyl benzotriazole --.

In Column 83, Lines 22-23 (approx.), delete "diisopropylethylamine" and insert -- diisopropyl ethylamine --.

In Column 83, Line 37, delete "propionylamino)" and insert -- propionylamino --.

In Column 83, Lines 39-40, delete "propionylamino)" and insert -- propionylamino --.

In Column 85, Line 4 (approx.), delete "((R)" and insert -- (R) --.

In Column 85, Line 12 (approx.), delete "((R)" and insert -- (R) --.

In Column 85, Line 15 (approx.), delete "diisopropylethylamine" and insert -- diisopropyl ethylamine --.

In Column 85, Line 31 (approx.), delete "((R)" and insert -- (R) --.

In Column 85, Line 36 (approx.), delete "((R)" and insert -- (R) --.

In Column 85, Line 54 (approx.), delete "aminobenzylp-" and insert -- aminobenzyl-p- --.

In Column 85, Line 56 (approx.), delete "((R)" and insert -- (R) --.

In Column 86, Lines 21-22 (approx.), delete "amino-benzyl" and insert -- amino benzyl --.

In Column 86, Line 47 (approx.), delete "amino-benzyl" and insert -- amino benzyl --.

In Column 87, Line 1, delete "524'" and insert -- S24' --.

In Column 87, Line 46, delete "Tween80)" and insert -- Tween 80) --.

In Column 88, Line 58, delete "Tween80." and insert -- Tween 80. --.

In Column 88, Line 65, delete "Paclitaxel" and insert -- Paclitaxel, --.

In Column 88, Line 66, delete "51'," and insert -- S1', --.

In Column 95, Line 56 (approx.), delete "mice" and insert -- mice. --.

In Column 96, Table 18, Line 8, delete "caner" and insert -- cancer --.

In Column 98, Line 5, delete "aminobenzyl" and insert -- amino benzyl --.

In Column 98, Line 20, delete "aminobenzyl" and insert -- amino benzyl --.

In Column 98, Line 24, delete "aminobenzyl" and insert -- amino benzyl --.

In Column 98, Line 32 (approx.), delete "aminobenzyl" and insert -- amino benzyl --.

In Column 98, Line 35 (approx.), delete "aminobenzyl" and insert -- amino benzyl --.

In Column 98, Line 58 (approx.), delete "Polyoxa" and insert -- Polyglycol --.

In Column 101, Line 8, delete "Paclitaxel" and insert -- Paclitaxel, --.

In Column 101, Line 36, delete "370," and insert -- 37□, --.

In Column 107, Line 52 (approx.), delete "mice" and insert -- mice. --.

In Column 108, Table 29, Line 8, delete "caner" and insert -- cancer --.

In Column 112, Table 33, Line 1, delete "Solutility" and insert -- Solubility --.

In Column 119, Line 28, delete "mice" and insert -- mice. --.

In Column 119, Table 41, Line 8, delete "caner" and insert -- cancer --.

In Column 122, Line 4, delete "diisopropylethylamine" and insert -- diisopropyl ethylamine --.

In Column 122, Line 40, delete "diisopropylethylamine" and insert -- diisopropyl ethylamine --.

In Column 123, Line 2, delete "aminobenzyl" and insert -- amino benzyl --.

In Column 123, Lines 21-22 (approx.), delete "amino-benzyl" and insert -- amino benzyl --.

In Column 123, Line 40, delete "Polyoxa" and insert -- Polyglycol --.

In Column 131, Line 5, delete "mice" and insert -- mice. --.

In Column 132, Table 51-continued, Line 6, delete "caner" and insert -- cancer --.

In Column 133, Line 48 (approx.), delete "1-hydroxylbenzotriazole" and insert -- 1-hydroxyl benzotriazole --.

In Column 135, Line 5, delete "diisopropylethylamine" and insert -- diisopropyl ethylamine --.

In Column 135, Line 66, delete "aminobenzyl" and insert -- amino benzyl --.

In Column 136, Lines 10-11, delete "amin-obenzyl" and insert -- amino benzyl --.

In Column 136, Line 32, delete "Polyoxa" and insert -- Polyglycol --.

In Column 142, Line 59, delete "mice" and insert -- mice. --.

In Column 143, Table 60, Line 8, delete "caner" and insert -- cancer --.

In the Claims

In Column 146, Line 65, Claim 1, delete "hydroyxlaminocarbonyl" and insert -- hydroxylaminocarbonyl --.

In Columns 155-156, Line 2 (approx.), Claim 7, delete

" 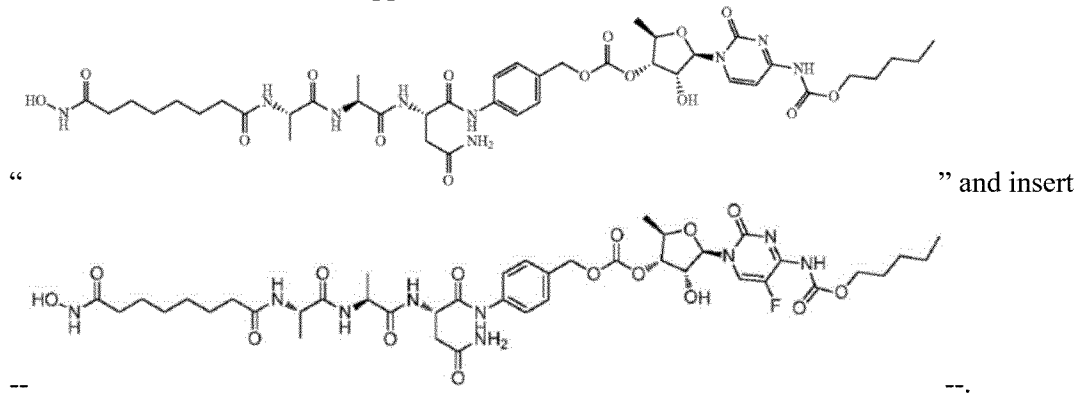 " and insert

-- --.

In Columns 161 and 162, Line 6 (approx.), Claim 7, delete

" 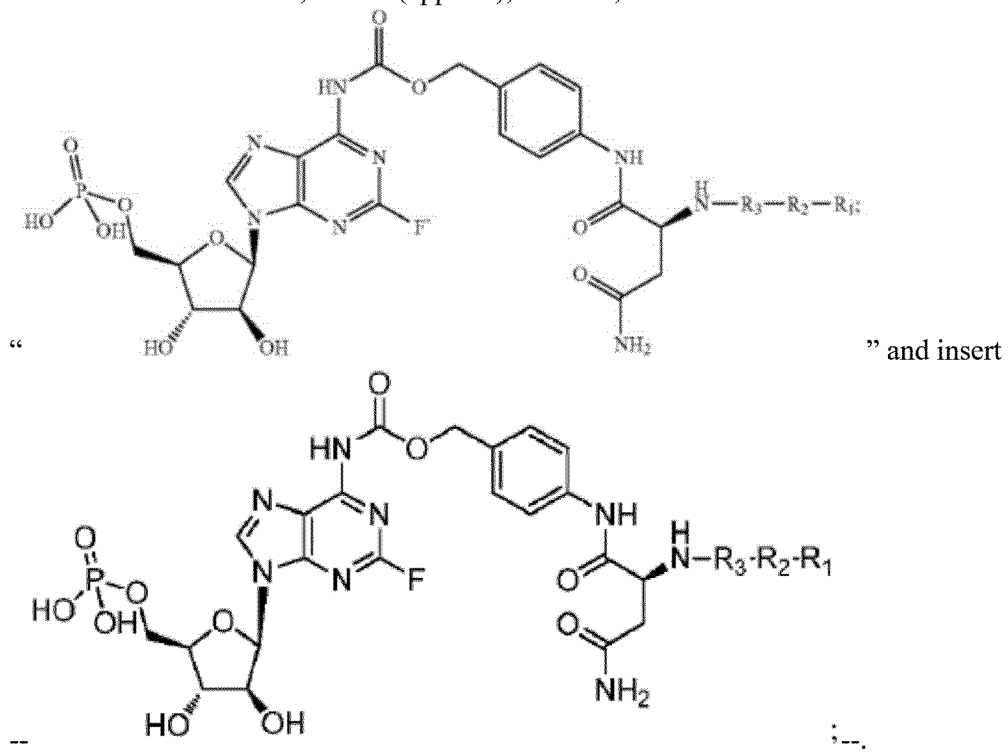 " and insert

-- ; --.

CERTIFICATE OF CORRECTION (continued)
U.S. Pat. No. 10,682,371 B2

In Column 168, Line 15 (approx.), Claim 7, delete "S3" and insert -- S3' --.

In Column 170, Line 1, Claim 7, delete "S4" and insert -- S4' --.

In Column 176, Line 2 (approx.), Claim 7, delete

" 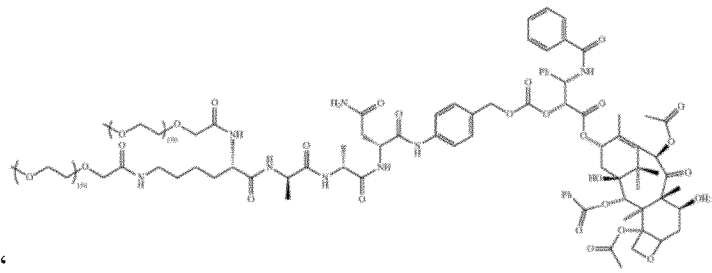 " and insert

-- 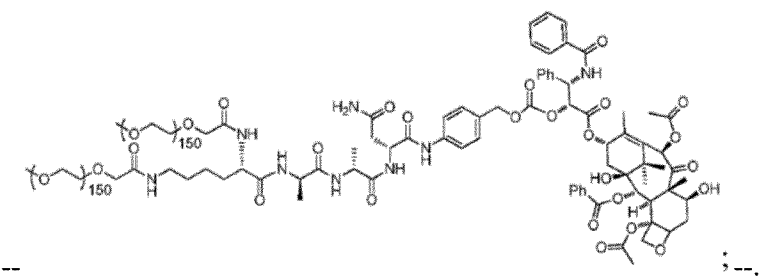 ;--.

In Column 191, Line 1 (approx.), Claim 7, delete

" 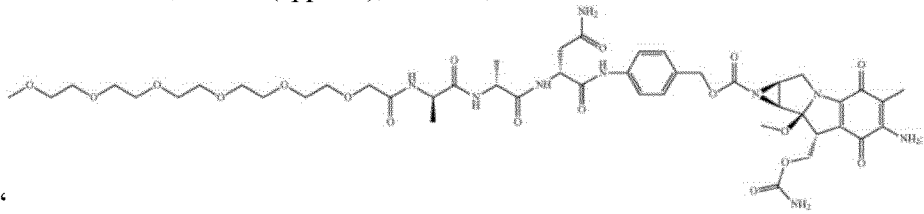 " and insert

-- 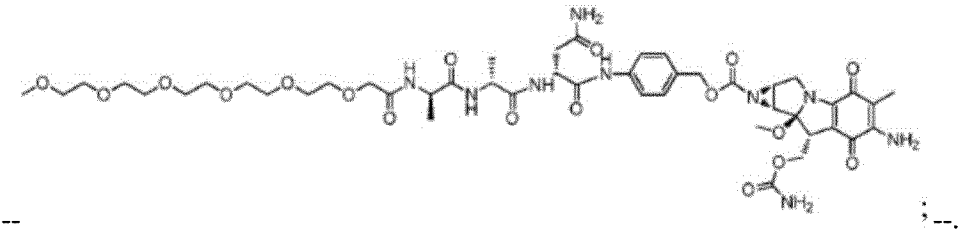 ;--.

In Column 192, Line 3 (approx.), Claim 7, delete

" 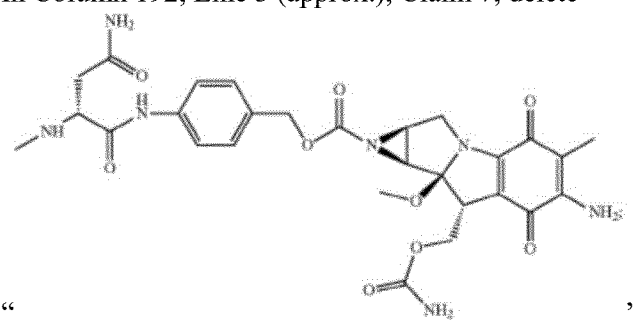 " and insert

CERTIFICATE OF CORRECTION (continued)
U.S. Pat. No. 10,682,371 B2

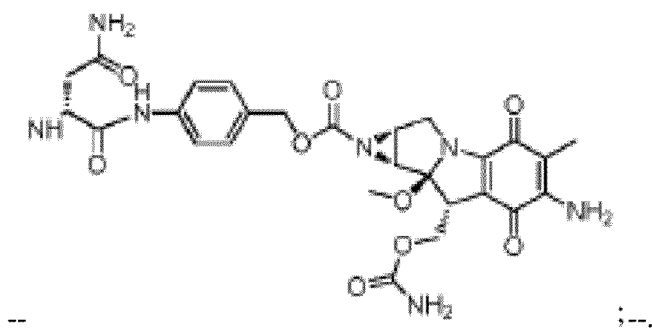

-- ;--.

In Column 195, Line 28 (approx.), Claim 7, delete "EIS" and insert -- E15 --.

In Columns 213 and 214, Line 1 (approx.), after compound "S2'" insert -- S2'; --.

In Columns 213 and 214, Line 4 (approx.), Claim 15, delete "S3" and insert -- S3' --.

In Columns 215 and 216, Line 1, Claim 15, delete "S4" and insert -- S4' --.

In Column 232, Line 2 (approx.), Claim 15, delete

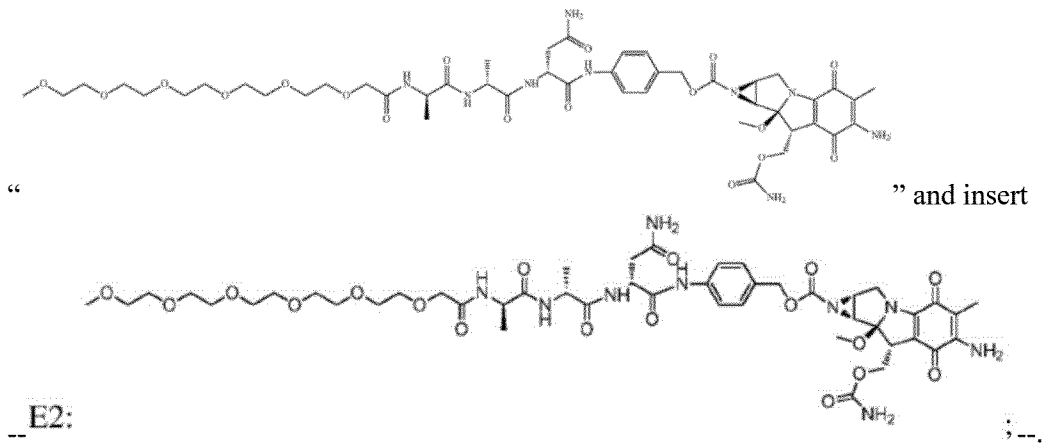

" and insert

--E2: ;--.

CERTIFICATE OF CORRECTION (continued)
U.S. Pat. No. 10,682,371 B2

In Column 233, Line 1 (approx.), Claim 15, delete " 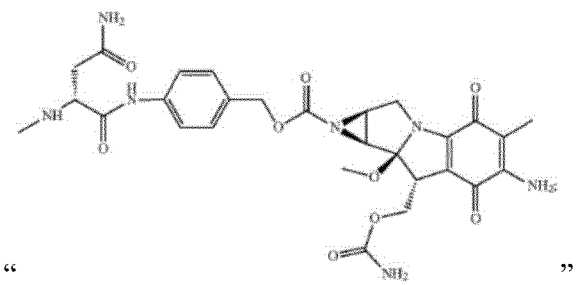 "

and insert -- 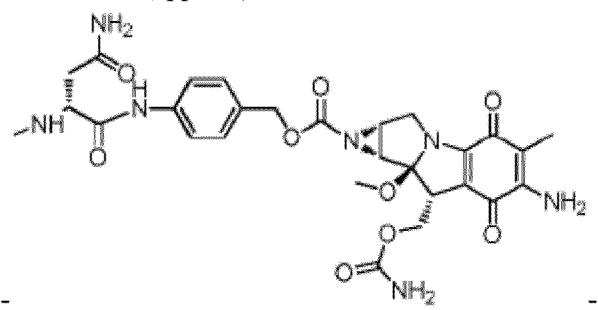 --.